US009518122B2

(12) United States Patent
Theuer et al.

(10) Patent No.: US 9,518,122 B2
(45) Date of Patent: *Dec. 13, 2016

(54) ENDOGLIN ANTIBODIES
(71) Applicant: Tracon Pharmaceuticals, Inc., San Diego, CA (US)
(72) Inventors: Charles Theuer, Carlsbad, CA (US); Maximiliano Vasquez, Palo Alto, CA (US)
(73) Assignee: Tracon Pharmaceuticals, Inc., San Diego, CA (US)
( * ) Notice: Subject to any disclaimer, the term of this patent is extended or adjusted under 35 U.S.C. 154(b) by 0 days.

This patent is subject to a terminal disclaimer.

(21) Appl. No.: 14/838,006
(22) Filed: Aug. 27, 2015
(65) Prior Publication Data
US 2016/0009811 A1  Jan. 14, 2016

Related U.S. Application Data

(60) Continuation of application No. 14/054,446, filed on Oct. 15, 2013, now Pat. No. 9,150,652, which is a continuation of application No. 13/485,702, filed on May 31, 2012, now Pat. No. 8,609,094, which is a division of application No. 12/751,907, filed on Mar. 31, 2010, now Pat. No. 8,221,753, which is a continuation of application No. 12/570,918, filed on Sep. 30, 2009, now abandoned.
(60) Provisional application No. 61/247,290, filed on Sep. 30, 2009.

(51) Int. Cl.
| | |
|---|---|
| *A61K 39/395* | (2006.01) |
| *C07K 16/28* | (2006.01) |
| *A61K 31/282* | (2006.01) |
| *A61K 31/337* | (2006.01) |
| *A61K 31/4045* | (2006.01) |
| *A61K 31/44* | (2006.01) |
| *A61K 31/69* | (2006.01) |
| *A61K 31/704* | (2006.01) |
| *A61K 47/48* | (2006.01) |
| *G01N 33/574* | (2006.01) |
| *A61K 45/06* | (2006.01) |
| *C07K 16/30* | (2006.01) |
| *G01N 33/68* | (2006.01) |
| *A61K 39/00* | (2006.01) |

(52) U.S. Cl.
CPC ......... *C07K 16/2896* (2013.01); *A61K 31/282* (2013.01); *A61K 31/337* (2013.01); *A61K 31/4045* (2013.01); *A61K 31/44* (2013.01); *A61K 31/69* (2013.01); *A61K 31/704* (2013.01); *A61K 39/3955* (2013.01); *A61K 45/06* (2013.01); *A61K 47/48561* (2013.01); *C07K 16/2863* (2013.01); *C07K 16/30* (2013.01); *G01N 33/57492* (2013.01); *G01N 33/57496* (2013.01); *G01N 33/6872* (2013.01); *A61K 2039/505* (2013.01); *C07K 2317/24* (2013.01); *C07K 2317/34* (2013.01); *C07K 2317/56* (2013.01); *C07K 2317/565* (2013.01); *C07K 2317/73* (2013.01); *C07K 2317/732* (2013.01); *C07K 2317/92* (2013.01); *G01N 2333/70596* (2013.01); *G01N 2800/16* (2013.01); *G01N 2800/164* (2013.01)

(58) Field of Classification Search
None
See application file for complete search history.

(56) References Cited

U.S. PATENT DOCUMENTS

| | | |
|---|---|---|
| 928,641 A | 7/1909 | Levi |
| 4,472,509 A | 9/1984 | Gansow et al. |
| 4,683,202 A | 7/1987 | Mullis |
| 4,816,567 A | 3/1989 | Cabilly et al. |
| 4,868,103 A | 9/1989 | Stavrianopoulos et al. |
| 4,938,948 A | 7/1990 | Ring et al. |
| 5,021,236 A | 6/1991 | Gries et al. |
| 5,391,377 A | 2/1995 | Barnwell |
| 5,530,101 A | 6/1996 | Queen et al. |
| 5,591,828 A | 1/1997 | Bosslet et al. |

(Continued)

FOREIGN PATENT DOCUMENTS

| | | |
|---|---|---|
| CN | 101084015 A | 12/2007 |
| CN | 104788562 A | 7/2015 |

(Continued)

OTHER PUBLICATIONS

International Search Report mailed Oct. 14, 2013 for PCT/US2013/058265.
Liu et al., Effects of the combination of TRC105 and bevacizumab on endothelial cell biology. Invest New Drugs, DOI 10.1007/s10637-014-0129-y.
Liu et al., ENDOGLIN is dispensable for Vasculogenesis, but required for vascular endothelial growth factor-induced angiogenesis. PLOS/One, 9(1):e86273 (2014).
Lowe et al., Aggregation, stability and formulation of human antibody therapeutics, Advances I Protein Chemistry and Structural Biology, 84:41-61, 2011.
Tracon Pharmaceuticals. Tracon pharmaceuticals announces dosing of initial three cancer patients in a Phase 1 clinical trial with TRC105, a human chimeric antibody. Company News. Jan. 8, 2008. www.traconpharma.com/content/pr_01_9_08.html.
Written Opinion mailed Oct. 14, 2013 for PCT/US2013/058265.
Altman et al., "The American College of Rheumatology criteria for the classification and reporting of osteoarthritis of the hip," Arthritis Rheum. 34:505-514 (1991).
Altschul et al., "Basic Local Alignment Search Tool," J. Mol. Biol. 215:403-410 (1990).
Altschul et al., "Gapped BLAST and PSI-BLAST: a new generation of protein database search programs," Nucl. Acids. Res. 25(17):3389-3402 (1997).
Antitope, "Meeting Report" 5th Annual Monoclonal Antibodies Conference, Aug. 2000, pp. 308-317.

(Continued)

*Primary Examiner* — Laura B Goddard
*Assistant Examiner* — Meera Natarajan
(74) *Attorney, Agent, or Firm* — Wilson Sonsini Goodrich & Rosati

(57) ABSTRACT

The present application relates to compositions of humanized and humanized/deimmunized anti-endoglin antibodies and antigen-binding fragments thereof. One aspect relates to antibodies having one or more modifications in at least one amino acid residue of at least one of the framework regions of the variable heavy chain, the variable light chain or both. Another aspect relates to antibodies which bind endoglin and inhibit angiogenesis. Another aspect relates to the deimmunization of humanized antibodies to reduce immunogenicity. Another aspect relates to the use of humanized and humanized/deimmunized antibodies which bind endoglin for the detection, diagnosis or treatment of a disease or condition associated with endoglin, angiogenesis or a combination thereof.

24 Claims, 29 Drawing Sheets

(56) References Cited

U.S. PATENT DOCUMENTS

| | | | |
|---|---|---|---|
| 5,631,169 | A | 5/1997 | Lakowicz et al. |
| 5,756,097 | A | 5/1998 | Landucci et al. |
| 5,796,097 | A | 8/1998 | Lawrence |
| 5,928,641 | A | 7/1999 | Seon |
| 6,096,289 | A | 8/2000 | Goldenberg |
| 6,190,660 | B1 | 2/2001 | Seon |
| 6,200,566 | B1 | 3/2001 | Seon |
| 6,350,861 | B1 | 2/2002 | Co et al. |
| 6,407,213 | B1 | 6/2002 | Carter et al. |
| 6,610,293 | B1 | 8/2003 | Fischer et al. |
| 6,737,056 | B1 | 5/2004 | Presta |
| 7,091,321 | B2 | 8/2006 | Gillies et al. |
| 7,097,836 | B1 | 8/2006 | Seon |
| 7,112,412 | B1 | 9/2006 | Bander |
| 7,115,716 | B2 | 10/2006 | Watkins |
| 7,217,798 | B2 | 5/2007 | Hinton et al. |
| 8,221,753 | B2 | 7/2012 | Theuer et al. |
| 8,609,094 | B2 | 12/2013 | Theuer et al. |
| 9,150,652 | B2 | 10/2015 | Theuer et al. |
| 2002/0136725 | A1 | 9/2002 | Blackburn et al. |
| 2003/0003048 | A1 | 1/2003 | Li et al. |
| 2003/0129193 | A1 | 7/2003 | Thorpe et al. |
| 2004/0023313 | A1 | 2/2004 | Boyle et al. |
| 2004/0033228 | A1 | 2/2004 | Krause et al. |
| 2004/0175756 | A1 | 9/2004 | Kolkman et al. |
| 2005/0037421 | A1 | 2/2005 | Honda et al. |
| 2005/0048512 | A1 | 3/2005 | Kolkman et al. |
| 2005/0053973 | A1 | 3/2005 | Kolkman et al. |
| 2005/0089932 | A1 | 4/2005 | Kolkman et al. |
| 2005/0164301 | A1 | 7/2005 | Kolkman et al. |
| 2005/0221384 | A1 | 10/2005 | Kolkman et al. |
| 2005/0238646 | A1 | 10/2005 | Ledbetter et al. |
| 2006/0147379 | A1 | 7/2006 | Bornhop et al. |
| 2006/0223096 | A1 | 10/2006 | Umana et al. |
| 2006/0292643 | A1 | 12/2006 | Goletz et al. |
| 2007/0008238 | A1 | 1/2007 | Liu et al. |
| 2007/0071761 | A1 | 3/2007 | Seon |
| 2007/0072797 | A1 | 3/2007 | Robinson et al. |
| 2007/0082380 | A1 | 4/2007 | Pardridge et al. |
| 2008/0199464 | A1 | 8/2008 | Plowman et al. |
| 2009/0142343 | A1 | 6/2009 | Fuh et al. |
| 2010/0015157 | A1 | 1/2010 | Andya et al. |
| 2010/0098692 | A1 | 4/2010 | Theuer et al. |
| 2011/0076263 | A1 | 3/2011 | Theuer et al. |
| 2012/0244147 | A1 | 9/2012 | Theuer et al. |
| 2012/0294864 | A1 | 11/2012 | Theuer et al. |
| 2015/0209430 | A1 | 7/2015 | Benedict et al. |

FOREIGN PATENT DOCUMENTS

| | | | |
|---|---|---|---|
| EP | 0404097 | A2 | 12/1990 |
| EP | 0404097 | A3 | 10/1991 |
| EP | 2892559 | A1 | 7/2015 |
| JP | 2000511425 | A | 9/2000 |
| WO | WO-9311161 | A1 | 6/1993 |
| WO | WO-9745450 | A1 | 12/1997 |
| WO | WO-02069232 | A2 | 9/2002 |
| WO | WO-02069232 | A3 | 2/2003 |
| WO | WO-2008038127 | A2 | 4/2008 |
| WO | WO-2008154351 | A1 | 12/2008 |
| WO | WO-2009033581 | A1 | 3/2009 |
| WO | WO-2009091810 | A1 | 7/2009 |
| WO | WO-2010032059 | A2 | 3/2010 |
| WO | WO-2010039873 | A2 | 4/2010 |
| WO | WO-2011022339 | A1 | 2/2011 |
| WO | WO-2011041441 | A1 | 4/2011 |
| WO | WO-2012003470 | A2 | 1/2012 |

OTHER PUBLICATIONS

Argarana et al., "Molecular cloning and nucleotide sequences of the streptavidin gene," Nucl. Acids Res. 14(4):1871-1882 (1986).
Baker, et al. "Identification and Removal of Immunogenicity in Therapeutic Proteins." Current Opinion in Drug Discovery and Development, vol. 10, No. 2, Jan. 1, 2007, pp. 219-227.
Bernebeu et al., "Novel biochemical pathways of endoglin in vascular cell physiology," J. Cell Biochem. 102(6):1375-1388 (2007).
Bird, et al. Single-chain antigen-binding proteins. Science. Oct. 21, 1988;242(4877):423-6.
Blood et al., "Tumor interactions with the vasculature: angiogenesis and tumore metastasis," Biochim. Biophys. Acta 1032:89-118 (1990).
Bockhorn, et al. "Differential Vascular and Transcriptional Responses to Anti-Vascular Endothelial Growth Factor Antibody in Orthotopic Human Pancreatic Cancer Xenografts." Clinical Cancer Research: An Official Journal of the American Association for Cancer Research, vol. 9, No. 11, Sep. 15, 2003, pp. 4221-4226.
Bonnet & Walsh, "Osteoarthritis, angiogenesis and inflammation," Rheumotol. 44:7-16 (2005).
Brooks, et al. Insulin-like growth factor receptor cooperates with integrin alpha v beta 5 to promote tumor cell dissemination in vivo. J Clin Invest. Mar. 15, 1997; 99(6):1390-8.
Burrows, et al. Up-regulation of endoglin on vascular endothelial cells in human solid tumors: Implications for diagnosis and therapy. Clin Cancer Res. Dec. 1995;1(12):1623-34.
Carillo and Lipman, "The Multiple Sequence Alignment Problem in Biology," SIAM J. Appl. Math 48(5):907-1082 (1988).
Chad and Chamow, "Therapeutic antibody expression technology," Curr Opin Biotechnol. Apr. 2001;12(2):188-94.
Chidlow, et al. Pathogenic angiogenesis in IBD and experimental colitis: new ideas and therapeutic avenues. Am J Physiol Gastrointest Liver Physiol. Jul. 2007;293(1):G5-G18. Epub Apr. 26, 2007.
Chothia, et al. Canonical structures for the hypervariable regions of immunoglobulins. J Mol Biol. Aug. 20, 1987;196(4):901-17.
Clackson, et al. Making antibody fragments using phage display libraries. Nature. Aug. 15, 1991;352(6336):624-8.
D'Amato, et al. Thalidomide is an inhibitor of angiogenesis. Proc Natl Acad Sci U S A. Apr. 26, 1994;91(9):4082-5.
Davis, et al. "Regional effects of an antivascular endothelial growth factor receptor monoclonal antibody on receptor phosphorylation and apoptosis in human 253J B-V bladder cancer xenografts." Cancer Research, vol. 64, No. 13, Jul. 1, 2004, pp. 4601-4610.
Derbalian et al., "Fluorescein labeling of fab while preserving single thiol," Anal. Biochem. 173:59-63 (1988).
Devereux et al., "A comprehensive set of sequence analysis programs for the VAX," Nucl. Acids Res. 12(1):387-395 (1984).
Dobeli et al., "Recombinant Fusion Proteins for the Industrial Production of Disulfide Bridge Containin Peptides: Purification, Oxidation without Concatamer Formation, and Selective Cleavage," Protein Expression and Purification 12(3):404-414 (1998).
Duff et al., "CD105 is important for angiogenesis evidence and potential applications," FASEB J. 17:984-992 (2003).
Edge, et al. Total synthesis of a human leukocyte interferon gene. Nature. Aug. 20, 1981;292(5825):756-62.
European Patent Application No. EP10810448.0 Search Report dated Mar. 1, 2013.
European Patent Application No. EP10821188.9 Search Report dated Mar. 14, 2013.
European Patent Application No. EP10810448.0 Communication dated Aug. 25, 2015.
European Patent Application No. EP14151471.1 Communication dated Aug. 17, 2015.
Fix et al., "Oral controlled release technology for peptides: status and future prospects," Pharm Res. 13:1760-1764 (1996).
Furstenberger, et al. Insulin-like growth factors and cancer. Lancet Oncol. May 2002;3(5):298-302.
Gao, et al. Anal Chem 2004, 76(24), 7179-7186.
Ghetie, et al. Immunotoxins in the therapy of cancer: from bench to clinic. Pharmacol Ther. Sep. 1994;63(3):209-34.
Gigli, et al. The stoichiometric measurement of the serum inhibition of the first component of complement by the inhibition of immune hemolysis. J Immunol. Jun. 1968;100(6):1154-64.
Gilles et al., "Stability of water-soluble carbodiimides in aqueous solution," Anal. Biochem. 184(2):244-248 (1990).
Glazer et al., "Emerging Techniques: Phycofluor probes," Trends Biochem. Sci. 9:423-427 (1984).

(56) References Cited

OTHER PUBLICATIONS

Gougos, et al. Identification of a human endothelial cell antigen with monoclonal antibody 44G4 produced against a pre-B leukemic cell line. J Immunol. Sep. 15, 1988;141(6):1925-33.

Gougos, et al. Primary structure of endoglin, an RGD-containing glycoprotein of human endothelial cells. J Biol Chem. May 25, 1990;265(15):8361-4.

Green, "A spectrophotometric assay for avidin and biotin based on binding of dyes by avidin," Biochem J. 94:23c-24c (1965).

Green, "Avidin" in Advances in Protein Chemistry, Academic Press, New York 39:85-133 (1975).

Green, "The use of bifunctional biotinyl compoounds to determine the arrangement of subunits in avidin," Biochem J. 125:781-791 (1971).

Greenberg et al., "Characteristics of the Effector Cells Mediating Cytotoxicity Against Antibody-Coated Target Cells," Immunol. 21:719 (1975).

Hardy et al., "Demonstration of B-cell maturation in X-linked immunodeficient mice by simultaneous three-colour immunofluorescence," Nature 306:270-272 (1983).

Hardy et al., "Murine B Cell Differentiation Lineages," J. Exp. Med. 159:1169-1188 (1984).

Haruta, et al. Distinct human leukemia-associated cell surface glycoprotein GP160 defined by monoclonal antibody SN6. Proc Natl Acad Sci U S A. Oct. 1986;83(20):7898-902.

Haywood, et al. Inflammation and angiogenesis in osteoarthritis. Arthritis & Rheumatism. 2003; 48(8): 2173-2177.

Heeley, et al. Mutations flanking the polyglutamine repeat in the modulatory domain of rat glucocorticoid receptor lead to an increase in affinity for hormone. Endocr Res. Aug. 2002;28(3):217-29.

Henikoff et al., "Amino acid substitution matrices from protein blocks," PNAS USA 89:10915-10919 (1992).

Holliger, et al. "Diabodies": small bivalent and bispecific antibody fragments. Proc Natl Acad Sci U S A. Jul. 15, 1993;90(14):6444-8.

Huston, et al. Protein engineering of antibody binding sites: recovery of specific activity in an anti-digoxin single-chain Fv analogue produced in *Escherichia coli*. Proc Natl Acad Sci U S A. Aug. 1988;85(16):5879-83.

International preliminary report on patentability mailed Apr. 14, 2011 for PCT/US2009/059086.

International preliminary report on patentability mailed Apr. 3, 2012 for PCT/US2010/050759.

International preliminary report on patentability mailed Mar. 19, 2015 for PCT/US2013/058265.

International search report and written opinion dated Nov. 23, 2010 for PCT/US2010/045651.

International search report and written opinion dated Aug. 18, 2010 for PCT/US2009/059086.

International search report and written opinion mailed Feb. 23, 2011 for PCT/US2010/050759.

Jay, et al. Chemical synthesis of a biologically active gene for human immune interferon-gamma. Prospect for site-specific mutagenesis and structure-function studies. J Biol Chem. May 25, 1984;259(10):6311-7.

Jones and Segal, "Antibody-Dependent Cell Mediated Cytolysis (ADCC) with Antibody-Coated Effectors: New Methods for Enhancing Antibody Binding and Cytolysis," J. Immunol. 125:926-933 (1980).

Jones et al., Adv. Drug Delivery Rev. 10: 29-90 (1993).

Jones, et al. Replacing the complementarity-determining regions in a human antibody with those from a mouse. Nature. May 29-Jun. 4, 1986; 321(6069):522-5.

Journal of Clinical Oncology,2009 ASCO Annual Meeting Proceedings(Post-Meeting Edition).,May 20, 2009, vol. 27, No. 15S, 3518.

Kabat et al., Sequences of Proteins in Immunological Interest, 5th ed., Public Health Service, National Institutes of Health, Bethesda MD 1991, pp. 647-669.

Kim et al., "Three-dimensional in vitro tissue culture models of breast cancer—a review," Breast Cancer Research Treatment 85(3):281-291 (2004).

Koch and Distler, "Vaculopathy and disordered angiogenesis in selected rheumatic diseases: rheumatoid arthritis and systemic sclerosis," Arthritis Res. And Ther. 9(Supp.2):1-9 (2007).

Kohler, et al. Continuous cultures of fused cells secreting antibody of predefined specificity. Nature. Aug. 7, 1975;256(5517):495-7.

Kroll et al., "A Multifunctional Prokaryotic Protein Expression System: Overproduction, Affinity Purification, and Selective Detection," DNA Cell Biol. 12:441-453 (1993).

Kronick et al., "Immunoassay Techniques with Fluorescent Phycobiliprotein Conjugates," Clin. Chem. 29:1582-1586 (1983).

Kronick et al., "The use of phycobiliproteins as fluorescent labels in immunoassay," J. Immunol Meth. 92:1-13 (1986).

Lahn, et al. Aerosolized anti-T-cell-receptor antibodies are effective against airway inflammation and hyperreactivity. Int Arch Allergy Immunol. May 2004;134(1):49-55. Epub Mar. 25, 2004.

Lanier et al, "Human Lymphocyte Subpopulations Identified by Using Three-Color Immunofluorescence and Flow Cytometry Analysis: Correlation of Leu-2, Leu-3, Leu¬7, Leu-8, and Leu-11 Cell Surface Antigen Expression," J. Immunol 132:151-156 (1984).

Leatherbarrow, et al. Effector functions of a monoclonal aglycosylated mouse IgG2a: binding and activation of complement component C1 and interaction with human monocyte Fc receptor. Mol Immunol. Apr. 1985;22(4):407-15.

Liljeblad, et al. Analysis of agalacto-IgG in rheumatoid arthritis using surface plasmon resonance. Glycoconj J. May 2000;17(5):323-9.

Mack, et al. Electrophoresis 2009, 30 (23), 4049-4058.

MacKay et al., "Effect on Natural Killer and Antibody-Dependent Cellular Cytotoxicity of Adjuvant Cytotoxic .Chemotherapy Including Melphalan in Breast Cancer," Cancer Immunol. Immunother. 16:98-100 (1983).

MacLennan. Competition for receptors for immunoglobulin on cytotoxic lymphocytes. Clin Exp Immunol. Feb. 1972;10(2):275-83.

Maio et al., "Is it the primetime for endoglin (CD105) in the clinical setting?" Cardiovascular Research 69(4):781-783 (2006).

Marks, et al. By-passing immunization. Human antibodies from V-gene libraries displayed on phage. J Mol Biol. Dec. 5, 1991;222(3):581-97.

Matsuno, et al. "Induction of Lasting Complete Regression of Preformed Distinct Solid Tumors by Targeting the Tumor Vasculature Using Two New Anti-Endoglin Monoclonal Antibodies." Clinical Cancer Research, vol. 5, No. 2, Feb. 1, 1999m pp. 371-382.

Montesano, et al. In vitro rapid organization of endothelial cells into capillary-like networks is promoted by collagen matrices. J Cell Biol. Nov. 1983;97(5 Pt 1):1648-52.

Muraoka, et al. Structural requirements for IgM assembly and cytolytic activity. Effects of mutations in the oligosaccharide acceptor site at Asn402. J Immunol. Jan. 15, 1989;142(2):695-701.

Muyldermans et al., "Sequence and structure of Vh domain from naturally occurring camel heavy chain immunoglobulins lacking light chains," Protein Engineering 7(9):1129-1135 (1994).

Nakajima et al., "Mechanism of amide formation by carbodiimide for bioconjugation in aqueous media," Bioconjugate Chem. 6(1):123-130 (1995).

Nambiar, et al. Total synthesis and cloning of a gene coding for the ribonuclease S protein. Science. Mar. 23, 1984;223(4642):1299-301.

Nilsson et al., "p-Tolueneslfonyl chloride as an activating agent of agarose for the preparation of immonobilized affinity ligands and proteins," Eur. J. Biochem. 112:397-402 (1980).

Nolan-Stevaux et al., Endoglin requirement for BMP9 signaling in endothelial cells reveals new mechanism of action for selective anti-endoglin antibodies. PLOS One, 7(12): e50920. doi:10.1371/journal.pone.0050920.

Noren et al., "A general method for site-specific incorporation of unnatural amino acids into proteins," Science 244:182-188 (1989).

(56) References Cited

OTHER PUBLICATIONS

Osbourn, et al. Directed selection of MIP-1 alpha neutralizing CCR5 antibodies from a phage display human antibody library. Nat Biotechnol. Aug. 1998;16(8):778-81.

Pahler et al., "Characterization and Crystallization of Core Streptavidin," J. Biol. Chem. 262:13933-13937 (1987).

Parks et al., "Three-Color Immunofluorescence Analysis of Mouse B-Lymphocyte Subpopulations," Cytometry 5:159-168 (1984).

Perry, et al. "New Approaches to Prediction of Immune Responses to Therapeutic Proteins during Preclinical Development." Drugs in R & D, vol. 9, No. 6, Jan. 1, 2008, pp. 386-396.

Pinals, et al. Preliminary criteria for clinical remission in rheumatoid arthritis. Arthritis Rheum. Oct. 1981;24(10):1308-15.

Pluckthun, "Antibodies from *Escherichia coli*," in Handbook of Experimental Pharmacology; The Pharmacology of Monoclonal Antibodies; vol. 113, pp. 269-315 (1994), Rosenburg and Moore eds., Springer-Verlag, New York.

Pluckthun. Antibody engineering: advances from the use of *Escherichia coli* expression systems. Biotechnology (N Y). Jun. 1991;9(6):545-51.

Presta, "Antibody engineering," Curr. Op. Struct. Biol. 2:593-596 (1992).

Reff, "High-level production of recombinant immunoglobulins in mammalian cells," Curr. Op. Biotech. 4:573-576 (1993).

Reichmann et al., "Reshaping human antibodies for therapy," Nature 332:323-329 (1988).

Reiter, et al. Engineering antibody Fv fragments for cancer detection and therapy: disulfide-stabilized Fv fragments. Nat Biotechnol. Oct. 1996;14(10):1239-45.

Rosen. Early evidence of tolerability and clinical activity from a phase 1 study oftrc105 (ant-cd105 antibody) in patients with advanced refractory cancer. 2009 ASCO Annual Meeting. Jun. 2, 2009. Retrieved from the internet: www.traconpharma.com/pdfs/105ST101_TRC105_EORTC_MCI_AACR_Poster.pdf.

Roy-Chaudhury et al., "Endoglin, a transforming growth factor-beta-binding protein, is upregulated in chronic progressive renal disease," Exp. Nephrol. 5:55-60 (1997).

Rudikoff, et al. Single amino acid substitution altering antigen-binding specificity. Proc Natl Acad Sci U S A. Mar. 1982;79(6):1979-83.

Salesi, et al. Clinical experience with bevacizumab in colorectal cancer. Anticancer Research, 2005; 25: 3619-3623.

Schnaper, et al. Type IV collagenase(s) and TIMPs modulate endothelial cell morphogenesis in vitro. J Cell Physiol. Aug. 1993;156(2):235-46.

Sehgal et al., "A Method for the High Efficiency of Water-Soluble Carbodiimide-Mediated Amidation," Anal. Biochem. 218(1):87-91 (1994).

She, et al. Synergy between anti-endoglin (CD105) monoclonal antibodies and TGF-beta in suppression of growth of human endothelial cells. Int J Cancer. Jan. 10, 2004;108(2):251-7.

Shiozaki et al., "Antiangiogenic chimeric anti-endoglin(CD105) antibody: pharmacokinetics and immunogenicity in nonhuman primates and effects of doxor ubicin," Cancer Immunology, Immunotherapy 55(2):140-150 (2005).

Silverman et al., "Corrigendum: Multivalent avimer proteins evolved by exon shuffling of a family of human receptor domains," Nat. Biotech. 24(2):220 (2006).

Silverman et al., "Multivalent avimer proteins evolved by exon shuffling of a family of human receptor domains," Nat. Biotech. 23:1556-1561 (2005).

Sjolander and Urbaniczky, "Integrated Fluid Handling System for Biomolecular Interaction Analysis," Anal. Chem. 63:2338-2345 (1991).

Sox and Hood, "Attachment of Carbohydrate to the Variable Region of Myeloma Immunoglobulin Light Chains," PNAS 66(3):975-982 (1970).

Stahle, et al. Prog. Med. Chem. 1988, 25: 291-338.

Stefansson, et al. Inhibition of angiogenesis in vivo by plasminogen activator inhibitor-1. J Biol Chem. Mar. 16, 2001;276(11):8135-41. Epub Nov. 16, 2000.

Su et al., "PTEN and Phosphatidylinositol 3'-Kinase Inhibitors Up-Regulate p53 and Block Tumor-induced Angiogenesis: Evidence for an Effect on the Tumor and Endothelial Compartment," Cancer Res. 63:3585-3592 (2003).

Szabo et al., "Surface plasmon resonance and its use in biomolecular interaction analysis (BIA)," Curr. Op. Struct. Biol. 5:699-705 (1995).

Szajani et al, "Effects of carbodiimide structure on the immobilization of enzymes," Appl. Biochem. Biotech. 30(2):225-231 (1991).

Tao, et al. Studies of aglycosylated chimeric mouse-human IgG. Role of carbohydrate in the structure and effector functions mediated by the human IgG constant region. J Immunol. Oct. 15, 1989;143(8):2595-601.

Taylor, et al. Selective removal of alpha heavy-chain glycosylation sites causes immunoglobulin A degradation and reduced secretion. Mol Cell Biol. Oct. 1988;8(10):4197-203.

Trill, et al. Production of monoclonal antibodies in COS and CHO cells. Curr Opin Biotechnol. Oct. 1995;6(5):553-60.

Tsujie et al., "Effective anti-angiogenic therapy of established tumors in mice by naked anti-human endoglin (CD105) antibody: Differences in growth rate and therapeutic response between tumors growing at different sites," Int. J. Oncology 29:1087-1094 (2006).

Uneda et al., "Anti-endoglin monoclonal antibodies are effective for suppressing metastasis and the primary tumors by targeting tumor vasculature," Intl. J. Cancer 125:1446-1453 (2009).

U.S. Appl. No. 12/570,918 Office action mailed Mar. 28, 2012.

U.S. Appl. No. 12/570,918 Office action mailed Oct. 17, 2012.

U.S. Appl. No. 12/751,907 Office action mailed Sep. 30, 2011.

U.S. Appl. No. 13/485,702 Notice of Allowance mailed Sep. 3, 2013.

U.S. Appl. No. 14/054,446 Restriction Requirement mailed Mar. 12, 2015.

U.S. Appl. No. 14/054,446 Office Action mailed Jun. 12, 2015.

U.S. Appl. No. 13/390,896 Office Action mailed Jun. 16, 2015.

U.S. Appl. No. 13/390,896 Office action mailed Nov. 21, 2014.

Varner et al., "Review: The Integrin au133: Angiogenesis and Apoptosis," Cell Adh. Commun. 3:367-374 (1995).

Volpert, et al. Id1 regulates angiogenesis through transcriptional repression of thrombospondin-1. Cancer Cell. Dec. 2002;2(6):473-83.

Ward et al., "Binding activities of a repertoire of single immunoglobulin variable domains secreted from *Escherichia coli*," Nature 341:544-546 (1989).

Weidner et al., "Tumor Angiogenesis: A New Significant and Independent Prognostic Indicator in Early-Stage Breast Carcinoma," J. Natl. Cancer Inst. 84:1875-1887 (1992).

Williams, "Dissection of the extracellular human interferon gamma receptor into two immunoglobulin-like domains," Biochem. 34:1787-1797 (1995).

Wold, et al. Chemom. Intell. Lab Syst. 2001, 58: 109-130.

Yan et al., "Human/Severe Combined Immunodeficient Mouse Chimeras," J. Clin. Invest. 91:986-996 (1993).

Zent et al., "Angiogenesis in Diabetic Nephropathy," Seminars in Nephrology 27(2):161-171 (2007).

FIG. 1

O2-Vκ1-39 variable (V_L) light chain with TRC105 V_L grafted CDRs underlined [SEQ ID NO: 4]

| 1 | | 3 | 4 | 5 | | | | | | | | | | | | | | | | | |
|---|---|---|---|---|---|---|---|---|---|---|---|---|---|---|---|---|---|---|---|---|---|
| D | I | Q | M | T | Q | S | P | S | S | L | S | A | S | V | G | D | R | V | T | I | T | C | R | A | S | S | S |
| *Q* | | *V* | *L* | *S* | | | | | | | | | | | | | | | | | | | *R* | *A* | *S* | *S* | *S* |

| | | | | | | | 36 | | | | | | | | 46 | 47 | | | | | | |
|---|---|---|---|---|---|---|---|---|---|---|---|---|---|---|---|---|---|---|---|---|---|---|
| V | S | Y | M | H | W | Y | Q | Q | K | P | G | K | A | P | K | P | W | I | Y | A | T | S |
| | | | | | | | *F* | | | | | | | | | *L* | *L* | | | | | |

| | 60 | | | | | | | 70 | 71 | | | | | | | | | | | | |
|---|---|---|---|---|---|---|---|---|---|---|---|---|---|---|---|---|---|---|---|---|---|
| V | P | S | R | F | S | G | S | G | S | G | T | D | Y | T | L | T | I | S | S | L | Q | P | E | D | F | A | T |
| | | *V* | | | | | | | | | | *S* | *F* | | | | | | | | | | | | | | |

| | | | | | | | | | 100 | | | | | | 106 | | |
|---|---|---|---|---|---|---|---|---|---|---|---|---|---|---|---|---|---|
| Y | Y | C | Q | Q | W | S | S | N | P | L | T | F | G | G | G | T | K | V | E | I | K |
| | | | | | | | | | | | | *A* | | | | | | | | *L* |

FIG. 2

VH3-15 variable (V$_H$) heavy chain with TRC105 V$_H$ grafted CDRs underlined [SEQ ID NO: 42]

| | | | | | | | | | | | | | | | | | | | | | | | | | | | |
|---|---|---|---|---|---|---|---|---|---|---|---|---|---|---|---|---|---|---|---|---|---|---|---|---|---|---|---|
| E | V | Q | L | V | E | S | G | G | G | L | V | K | P | G | G | S | L | R | L | S | C | A | A | S | G | F | T |

| | | | | | | | | | | | | | | | | | | | | | | | | | | | |
|---|---|---|---|---|---|---|---|---|---|---|---|---|---|---|---|---|---|---|---|---|---|---|---|---|---|---|---|
|  |  |  |  |  |  |  |  |  |  |  |  |  |  |  |  |  |  |  |  | 49 |  |  |  |  |  |  |  |
| F | S | D | A | W | M | D | W | V | R | Q | A | P | G | K | G | L | E | W | V | G | E | I | R | S | K | A | S |
|  |  |  |  |  |  |  |  |  |  |  |  |  |  |  |  |  |  |  |  | A |  |  |  |  |  |  |  |

| | | | | | | | | | | | | | | | | | | | | | | | | | | | |
|---|---|---|---|---|---|---|---|---|---|---|---|---|---|---|---|---|---|---|---|---|---|---|---|---|---|---|---|
|  |  |  |  |  |  |  |  |  |  |  |  |  |  |  |  |  |  |  |  |  |  | 76 | 77 | 78 |  |  |  |
| N | H | A | T | Y | Y | A | E | S | V | K | G | R | F | T | I | S | R | D | D | S | K | N | T | L | Y | L | Q |
|  | I |  |  |  |  |  |  |  |  |  |  |  |  |  |  |  |  |  |  |  | S | R | V |  |  |  |  |

| | | | | | | | | | | | | | | | | | | | | | | | | | | | |
|---|---|---|---|---|---|---|---|---|---|---|---|---|---|---|---|---|---|---|---|---|---|---|---|---|---|---|---|
| 82a |  |  |  |  |  |  |  | 89 |  |  |  |  | 94 |  |  |  |  |  |  |  |  |  |  |  |  |  |  |
| M | N | S | L | K | T | E | D | T | A | V | Y | Y | C | T | R | W | R | R | E | F | D | S | W | G | Q | G | T |
|  | I |  |  |  |  |  |  |  |  | I |  |  |  | T |  |  |  |  |  |  |  |  |  |  |  |  |  |
|  |  |  |  |  |  |  |  |  |  | L |  |  |  | G |  |  |  |  |  |  |  |  |  |  |  |  |  |

| 108 | 109 |  |  | 113 |
|---|---|---|---|---|
| L | V | T | V | S | S |
| T | L |  |  | A |

Model of Regulation of Angiogenesis by CD105 (Endoglin)

The TGF-β/ALK5 signaling pathway (A) leads to inhibition of cell proliferation and migration. TGF-β/ALK1 pathway (B) induces endothelial cell proliferation and migration and requires CD105 (endoglin) for ALK1 signaling.

FIG. 4A

| Position | Mouse_VK | V1-39-O2/O12+JK4 | HuVK_v0 | HuVK_v1 | HuVK_v2 |
|---|---|---|---|---|---|
| 1 | Q | D | D | D | D |
| 2 | I | I | I | I | I |
| 3 | V | Q | Q | Q | Q |
| 4 | L | M | M | M | L |
| 5 | S | T | T | T | T |
| 6 | Q | Q | Q | Q | Q |
| 7 | S | S | S | S | S |
| 8 | P | P | P | P | P |
| 9 | A | S | S | S | S |
| 10 | I | S | S | S | S |
| 11 | L | L | L | L | L |
| 12 | S | S | S | S | S |
| 13 | A | A | A | A | A |
| 14 | S | S | S | S | S |
| 15 | P | V | V | V | V |
| 16 | G | G | G | G | G |
| 17 | E | D | D | D | D |
| 18 | K | R | R | R | R |
| 19 | V | V | V | V | V |
| 20 | T | T | T | T | T |
| 21 | M | I | I | I | I |
| 22 | T | T | T | T | T |
| 23 | C | C | C | C | C |
| 24 | R | R | R | R | R |
| 25 | A | A | A | A | A |
| 26 | S | S | S | S | S |
| 27 | S | S | S | S | S |
| 28 | S | Q | Q | S | S |
| 29 | V | S | S | V | V |
| 30 | S | I | I | S | S |
| 31 | - | S | S | - | - |
| 31A | - | - | - | - | - |
| 31B | - | - | - | - | - |
| 31C | - | - | - | - | - |
| 31D | - | - | - | - | - |
| 31E | - | - | - | - | - |
| 31F | - | - | - | - | - |
| 32 | Y | Y | Y | Y | Y |
| 33 | M | L | M | M | M |
| 34 | H | N | H | H | H |
| 35 | W | W | W | W | W |
| 36 | Y | Y | Y | Y | Y |
| 37 | Q | Q | Q | Q | Q |
| 38 | Q | Q | Q | Q | Q |
| 39 | K | K | K | K | K |
| 40 | P | P | P | P | P |
| 41 | G | G | G | G | G |
| 42 | S | K | K | K | K |
| 43 | S | A | A | A | A |
| 44 | P | P | P | P | P |
| 45 | K | K | K | K | K |
| 46 | P | L | L | L | P |
| 47 | W | L | L | L | W |
| 48 | I | I | I | I | I |

| Position | Mouse_VK | V1-39-O2/O12+JK4 | HuVK_v0 | HuVK_v1 | HuVK_v2 |
|---|---|---|---|---|---|
| 49 | Y | Y | Y | Y | Y |
| 50 | A | A | A | A | A |
| 51 | T | A | T | T | T |
| 52 | S | S | S | S | S |
| 53 | N | S | N | N | N |
| 54 | L | L | L | L | L |
| 55 | A | Q | A | A | A |
| 56 | S | S | S | S | S |
| 57 | G | G | G | G | G |
| 58 | V | V | V | V | V |
| 59 | P | P | P | P | P |
| 60 | V | S | S | S | S |
| 61 | R | R | R | R | R |
| 62 | F | F | F | F | F |
| 63 | S | S | S | S | S |
| 64 | G | G | G | G | G |
| 65 | S | S | S | S | S |
| 66 | G | G | G | G | G |
| 67 | S | S | S | S | S |
| 68 | G | G | G | G | G |
| 69 | T | T | T | T | T |
| 70 | S | D | D | D | D |
| 71 | Y | F | F | Y | Y |
| 72 | S | T | T | T | T |
| 73 | L | L | L | L | L |
| 74 | T | T | T | T | T |
| 75 | I | I | I | I | I |
| 76 | S | S | S | S | S |
| 77 | R | S | S | S | S |
| 78 | V | L | L | L | L |
| 79 | E | Q | Q | Q | Q |
| 80 | A | P | P | P | P |
| 81 | E | E | E | E | E |
| 82 | D | D | D | D | D |
| 83 | A | F | F | F | F |
| 84 | A | A | A | A | A |
| 85 | T | T | T | T | T |
| 86 | Y | Y | Y | Y | Y |
| 87 | Y | Y | Y | Y | Y |
| 88 | C | C | C | C | C |
| 89 | Q | Q | Q | Q | Q |
| 90 | Q | Q | Q | Q | Q |
| 91 | W | W | S | W | W |
| 92 | S | S | Y | S | S |
| 93 | S | S | S | S | S |
| 94 | N | N | T | N | N |
| 95 | P | P | P | P | P |
| 96 | L | L | L | L | L |
| 97 | T | T | T | T | T |
| 98 | F | F | F | F | F |
| 99 | G | G | G | G | G |
| 100 | A | G | G | G | G |
| 101 | G | G | G | G | G |
| 102 | T | T | T | T | T |

| Position | Mouse_VK | V1-39-O2/O12+JK4 | HuVK_v0 | HuVK_v1 | HuVK_v2 |
|---|---|---|---|---|---|
| 103 | K | K | K | K | K |
| 104 | L | V | V | V | V |
| 105 | E | E | E | E | E |
| 106 | L | I | I | I | I |
| 107 | K | K | K | K | K |

FIG. 4B

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 31A | 31B | 32 | 33 | 34 | 35 | 36 | 37 | 38 | 39 | 40 | 41 | 42 | 43 | 44 | 45 | 46 | 47 | 48 | 49 | 50 | 51 | 52 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Mouse_VH | E | V | K | L | E | E | S | G | G | G | L | V | Q | P | G | G | S | M | K | L | S | C | A | A | S | G | F | T | F | S | D | - | - | A | W | M | D | W | V | R | Q | S | P | E | K | G | L | E | W | V | A | E | I | R |
| VH3-15+JH4 | E | V | Q | L | V | E | S | G | G | G | L | V | K | P | G | G | S | L | R | L | S | C | A | A | S | G | F | T | F | S | N | - | - | A | W | M | S | W | V | R | Q | A | P | G | K | G | L | E | W | V | G | R | I | K |
| HuVH_v0 | E | V | Q | L | V | E | S | G | G | G | L | V | K | P | G | G | S | L | R | L | S | C | A | A | S | G | F | T | F | S | D | - | - | A | W | M | D | W | V | R | Q | A | P | G | K | G | L | E | W | V | G | R | I | R |
| HuVH_v1 | E | V | Q | L | V | E | S | G | G | G | L | V | K | P | G | G | S | L | R | L | S | C | A | A | S | G | F | T | F | S | D | - | - | A | W | M | D | W | V | R | Q | A | P | G | K | G | L | E | W | V | G | E | I | R |
| HuVH_v2 | E | V | Q | L | V | E | S | G | G | G | L | V | K | P | G | G | S | L | R | L | S | C | A | A | S | G | F | T | F | S | D | - | - | A | W | M | D | W | V | R | Q | A | P | G | K | G | L | E | W | V | [A] | E | I | R |

| | 52A | 52B | 52C | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 | 95 | 96 | 97 | 98 | 99 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Mouse_VH | S | K | A | S | N | H | A | T | Y | Y | A | E | S | V | K | G | R | F | T | I | S | R | D | D | S | K | S | S | V | Y | L | Q | M | N | S | L | R | A | E | D | T | G | I | Y | Y | C | T | R | W | R | R | F | F |
| VH3-15+JH4 | S | K | T | D | G | G | T | T | D | Y | A | A | P | V | K | G | R | F | T | I | S | R | D | D | S | K | N | T | L | Y | L | Q | M | N | S | L | K | T | E | D | T | A | V | Y | Y | C | T | T | - | - | - | Y | F |
| HuVH_v0 | S | K | A | S | N | H | A | T | Y | Y | A | E | S | V | K | G | R | F | T | I | S | R | D | D | S | K | N | T | L | Y | L | Q | M | N | S | L | K | T | E | D | T | A | V | Y | Y | C | T | [R] | W | R | R | F | F |
| HuVH_v1 | S | K | A | S | N | H | A | T | Y | Y | A | E | S | V | K | G | R | F | T | I | S | R | D | D | S | K | N | T | L | Y | L | Q | M | N | S | L | K | T | E | D | T | A | V | Y | Y | C | T | [R] | W | R | R | F | F |
| HuVH_v2 | S | K | A | S | N | H | A | T | Y | Y | A | E | S | V | K | G | R | F | T | I | S | R | D | D | S | K | N | T | [V] | Y | L | Q | M | N | S | L | K | T | E | D | T | A | V | Y | Y | C | T | R | W | R | R | F | F |

| | 101 | 102 | 103 | 104 | 105 | 106 | 107 | 108 | 109 | 110 | 111 | 112 | 113 |
|---|---|---|---|---|---|---|---|---|---|---|---|---|---|
| Mouse_VH | D | S | W | G | Q | G | T | T | L | T | V | S | S |
| VH3-15+JH4 | D | Y | W | G | Q | G | T | L | V | T | V | S | S |
| HuVH_v0 | D | S | W | G | Q | G | T | L | V | T | V | S | S |
| HuVH_v1 | D | S | W | G | Q | G | T | L | V | T | V | S | S |
| HuVH_v2 | D | S | W | G | Q | G | T | L | V | T | V | S | S |

FIG. 5A

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 31A | 31B | 31C | 31D | 31E | 31F | 32 | 33 | 34 | 35 | 36 | 37 | 38 | 39 | 40 | 41 | 42 | 43 | 44 | 45 | 46 | 47 | 48 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| TRC105-VK | Q | I | V | L | S | Q | S | P | A | I | L | S | A | S | P | G | E | K | V | T | M | T | C | R | A | S | S | S | V | S | - | - | - | - | - | - | - | Y | M | H | W | Y | Q | Q | K | P | G | S | S | P | K | P | W | - |
| V3-11-L6+JK4 | E | I | V | L | T | Q | S | P | A | T | L | S | L | S | P | G | E | R | A | T | L | S | C | R | A | S | Q | S | V | S | - | - | - | - | - | - | - | Y | L | N | W | Y | Q | Q | K | P | G | Q | A | P | R | L | L | - |
| SuperVK_v0 | E | I | V | L | T | Q | S | P | A | T | L | S | L | S | P | G | E | R | A | T | L | S | C | R | A | S | S | S | V | S | - | - | - | - | - | - | - | Y | M | H | W | Y | Q | Q | K | P | G | Q | A | P | R | L | L | - |
| SuperVK_v1 | E | I | V | L | T | Q | S | P | A | T | L | S | L | S | P | G | E | R | A | T | L | S | C | R | A | S | S | S | V | S | - | - | - | - | - | - | - | Y | M | H | W | Y | Q | Q | K | P | G | Q | A | P | R | PW | - |
| SuperVK_v2 | E | I | V | L | T | Q | S | P | A | T | L | S | L | S | P | G | E | R | A | T | L | S | C | R | A | S | S | S | V | S | - | - | - | - | - | - | - | Y | M | H | W | Y | Q | Q | K | P | G | Q | A | P | R | PW | - |

| | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| TRC105-VK | Y | A | T | S | N | L | A | S | G | V | P | V | R | F | S | G | S | G | S | G | T | S | Y | S | L | T | I | S | R | V | E | A | E | D | A | A | T | Y | Y | C | Q | Q | W | S | S | N | P | L | T | F | G | A | G |
| V3-11-L6+JK4 | Y | D | A | S | N | R | A | T | G | I | P | A | R | F | S | G | S | G | S | G | T | D | F | T | L | T | I | S | S | L | E | P | E | D | F | A | V | Y | Y | C | Q | Q | R | S | N | W | P | L | T | F | G | G | G |
| SuperVK_v0 | Y | A | T | S | N | L | A | S | G | I | P | A | R | F | S | G | S | G | S | G | T | D | F | T | L | T | I | S | S | L | E | P | E | D | F | A | V | Y | Y | C | Q | Q | W | S | S | N | P | L | T | F | G | G | G |
| SuperVK_v1 | Y | A | T | S | N | L | A | S | G | I | P | A | R | F | S | G | S | G | S | G | T | D | Y | T | L | T | I | S | S | L | E | P | E | D | F | A | V | Y | Y | C | Q | Q | W | S | S | N | P | L | T | F | G | G | G |
| SuperVK_v2 | Y | A | T | S | N | L | A | S | G | V | P | A | R | F | S | G | S | G | S | G | T | D | Y | T | L | T | I | S | S | L | E | P | E | D | F | A | V | Y | Y | C | Q | Q | W | S | S | N | P | L | T | F | G | G | G |

| | 102 | 103 | 104 | 105 | 106 | 107 |
|---|---|---|---|---|---|---|
| TRC105-VK | T | K | L | E | L | K |
| V3-11-L6+JK4 | T | K | V | E | I | K |
| SuperVK_v0 | T | K | V | E | I | K |
| SuperVK_v1 | T | K | V | E | I | K |
| SuperVK_v2 | T | K | V | E | I | K |

FIG. 5B

Positions 1–52 (including 31A, 31B):

| Pos | TRC105-VH | VH3-3-73+JH4 | SuperVH_v0 | SuperVH_v1 |
|---|---|---|---|---|
| 1 | E | E | E | E |
| 2 | V | V | V | V |
| 3 | K | Q | Q | Q |
| 4 | L | L | L | L |
| 5 | E | V | V | V |
| 6 | E | E | E | E |
| 7 | S | S | S | S |
| 8 | G | G | G | G |
| 9 | G | G | G | G |
| 10 | G | G | G | G |
| 11 | L | L | L | L |
| 12 | V | V | V | V |
| 13 | Q | Q | Q | Q |
| 14 | P | P | P | P |
| 15 | G | G | G | G |
| 16 | G | G | G | G |
| 17 | S | S | S | S |
| 18 | M | L | L | L |
| 19 | K | K | K | K |
| 20 | L | L | L | L |
| 21 | S | S | S | S |
| 22 | C | C | C | C |
| 23 | A | A | A | A |
| 24 | A | A | A | A |
| 25 | S | S | S | S |
| 26 | G | G | G | G |
| 27 | F | F | F | F |
| 28 | T | T | T | T |
| 29 | F | F | F | F |
| 30 | S | S | S | S |
| 31 | D | N | D | D |
| 31A | - | - | - | - |
| 31B | - | - | - | - |
| 32 | A | S | A | A |
| 33 | W | A | W | W |
| 34 | M | M | M | M |
| 35 | D | H | D | D |
| 36 | W | W | W | W |
| 37 | V | V | V | V |
| 38 | R | R | R | R |
| 39 | Q | Q | Q | Q |
| 40 | S | A | A | A |
| 41 | P | S | S | S |
| 42 | E | G | G | G |
| 43 | K | K | K | K |
| 44 | G | G | G | G |
| 45 | L | L | L | L |
| 46 | E | E | E | E |
| 47 | W | W | W | W |
| 48 | V | V | V | V |
| 49 | A | G | G | [A] |
| 50 | E | R | E | E |
| 51 | I | I | I | I |
| 52 | R | K | R | R |

Positions 52A–101:

| Pos | TRC105-VH | VH3-3-73+JH4 | SuperVH_v0 | SuperVH_v1 |
|---|---|---|---|---|
| 52A | S | S | S | S |
| 52B | K | K | K | K |
| 52C | A | A | A | A |
| 53 | S | N | S | S |
| 54 | N | S | N | N |
| 55 | H | Y | H | H |
| 56 | A | A | A | A |
| 57 | T | T | T | T |
| 58 | Y | A | Y | Y |
| 59 | Y | Y | Y | Y |
| 60 | A | A | A | A |
| 61 | E | A | E | E |
| 62 | S | S | S | S |
| 63 | V | V | V | V |
| 64 | K | K | K | K |
| 65 | G | G | G | G |
| 66 | R | R | R | R |
| 67 | F | F | F | F |
| 68 | T | T | T | T |
| 69 | I | I | I | I |
| 70 | S | S | S | S |
| 71 | R | R | R | R |
| 72 | D | D | D | D |
| 73 | D | D | D | D |
| 74 | S | S | S | S |
| 75 | K | K | K | K |
| 76 | S | N | N | N |
| 77 | S | T | T | T |
| 78 | V | A | A | [V] |
| 79 | Y | Y | Y | Y |
| 80 | L | L | L | L |
| 81 | Q | Q | Q | Q |
| 82 | M | M | M | M |
| 82A | N | N | N | N |
| 82B | S | S | S | S |
| 82C | L | L | L | L |
| 83 | R | K | K | K |
| 84 | A | T | T | T |
| 85 | E | E | E | E |
| 86 | D | D | D | D |
| 87 | T | T | T | T |
| 88 | G | A | A | A |
| 89 | I | V | V | V |
| 90 | Y | Y | Y | Y |
| 91 | Y | Y | Y | Y |
| 92 | C | C | C | C |
| 93 | T | T | T | T |
| 94 | R | R | R | R |
| 95 | W | - | W | W |
| 96 | R | - | R | R |
| 97 | R | - | R | R |
| 98 | F | Y | F | F |
| 99 | F | F | F | F |
| 100 | D | D | D | D |

Positions 102–113:

| Pos | TRC105-VH | VH3-3-73+JH4 | SuperVH_v0 | SuperVH_v1 |
|---|---|---|---|---|
| 102 | S | Y | S | S |
| 103 | W | W | W | W |
| 104 | G | G | G | G |
| 105 | Q | Q | Q | Q |
| 106 | G | G | G | G |
| 107 | T | T | T | T |
| 108 | T | L | L | L |
| 109 | L | V | V | V |
| 110 | T | T | T | T |
| 111 | V | V | V | V |
| 112 | S | S | S | S |
| 113 | S | S | S | S |

FIG. 6

```
Mouse_VK    1   Q I V L S Q S P A I L S A S P G E K V T M T C R A S S S V S Y M H W Y Q Q K P G S S P K P W I Y A T S N L A S
HuVK_v0     1   D I Q M T Q S P S S L S A S V G D R V T I T C R A S S S V S Y M H W Y Q Q K P G K A P K L L I Y A T S N L A S
SuperVK_v0  1   E I V L T Q S P A T L S L S P G E R A T L S C R A S S S V S Y M H W Y Q Q K P G Q A P R L L I Y A T S N L A S
                                                                                                                56
```

```
Mouse_VK    57  G V P V R F S G S G S G T S Y S L T I S R V E A E D A A T Y Y C Q Q W S S N P L T F G A G T K L E L K
HuVK_v0     57  G V P S R F S G S G S G T D F T L T I S S L Q P E D F A T Y Y C Q Q W S S N P L T F G G G T K V E I K
SuperVK_v0  57  G I P A R F S G S G S G T D F T L T I S S L E P E D F A V Y Y C Q Q W S S N P L T F G G G T K V E I K
                                                                                                        107
```

```
Mouse_VH    1   E V K L E E S G G G L V Q P G G S M K L S C A A S G F T F S D - - A W M D W V R Q S P E K G L E W V A E I R S
HuVH_v0     1   E V Q L V E S G G G L V K P G G S L R L S C A A S G F T F S D - - A W M D W V R Q A P G K G L E W V G E I R S
SuperVH_v0  1   E V Q L V E S G G G L V Q P G G S L K L S C A A S G F T F S D - - A W M D W V R Q A S G K G L E W V G E I R S
                                                              31A 31B                                          52A
```

```
Mouse_VH    52B K A S N H A T Y Y A E S V K G R F T I S R D D S K S S V Y L Q M N S L R A E D T G I Y Y C T R W R R F
HuVH_v0     52B K A S N H A T Y Y A E S V K G R F T I S R D D S K N T L Y L Q M N S L K T E D T A V Y Y C T T W R R F
SuperVH_v0  52B K A S N H A T Y Y A E S V K G R F T I S R D D S K N T A Y L Q M N S L K T E D T A V Y Y C T R W R R F
                                                                          82A 82B 82C                              98
```

```
Mouse_VH    99  F D S W G Q G T T L T V S S
HuVH_v0     99  F D S W G Q G T L V T V S S
SuperVH_v0  99  F D S W G Q G T L V T V S S
                                      113
```

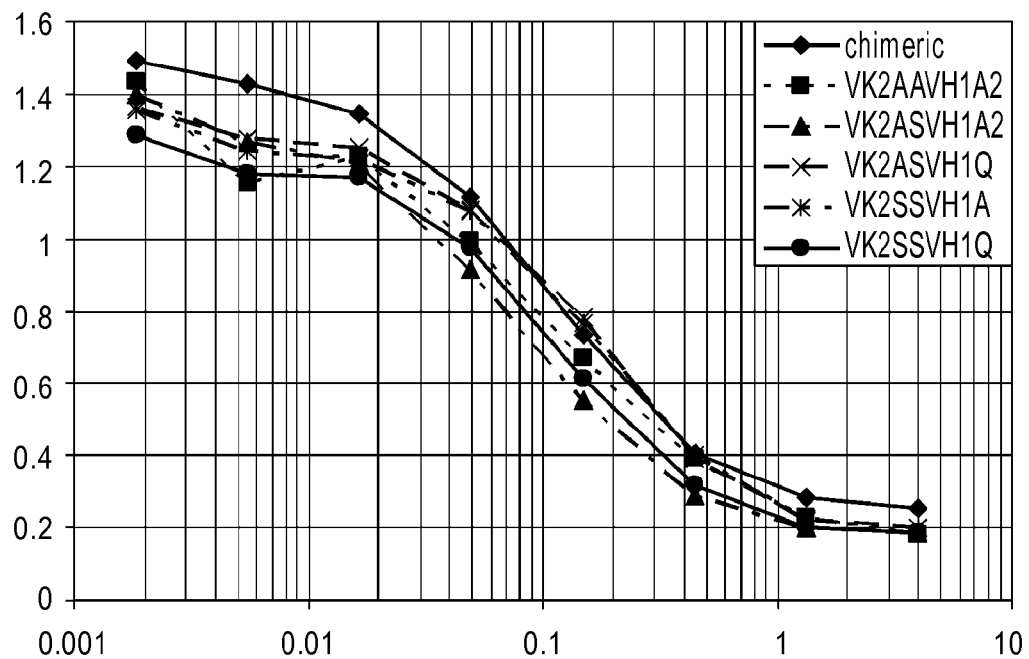
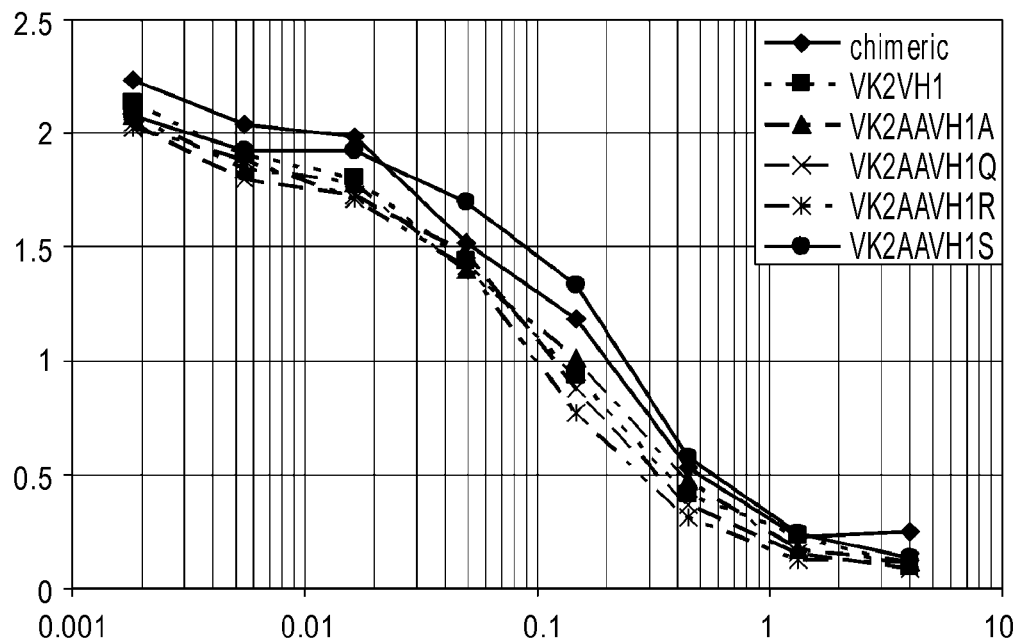

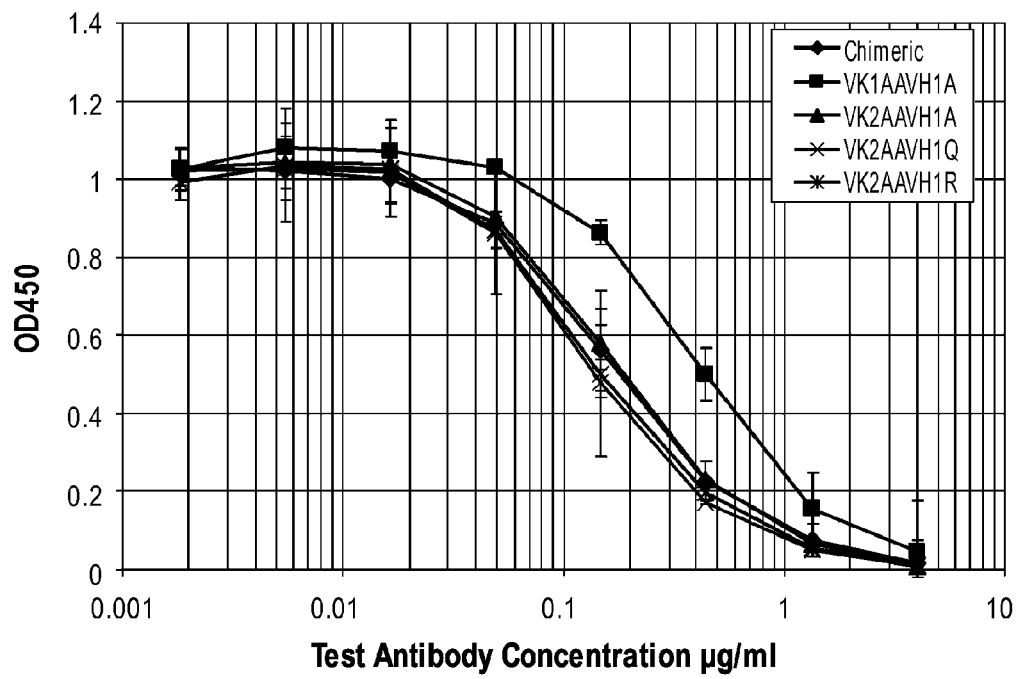
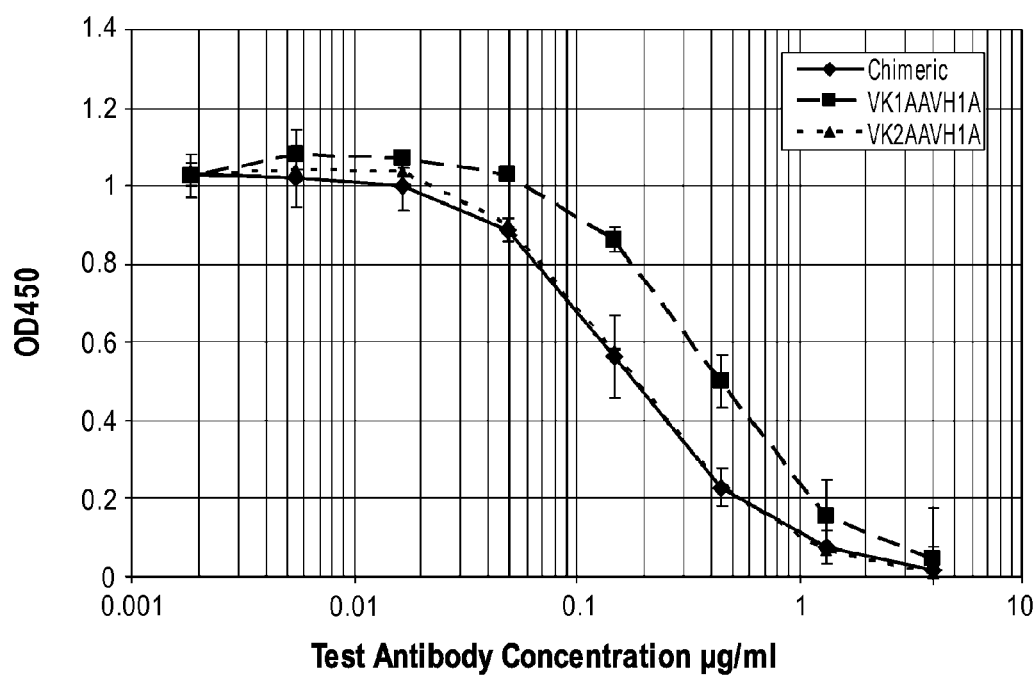

FIG. 17

Humanized Deimmunized VH1A2 [SEQ ID NO: 89] Lead Variant and Modifications Thereof with CDRs underlined

| | | | | | | | | | | | | | | | | | | | | | | |
|---|---|---|---|---|---|---|---|---|---|---|---|---|---|---|---|---|---|---|---|---|---|---|
| E | V | Q | L | V | E | S | G | G | G | L | V | K | P | G | G | S | L | R | L | S | C | A | A | S | G | F | T |
| F | S | D | A | W | M | D | W | V | R | Q | A | P | G | K | G | L | E | W | V | G | E | A | R | S | K | A | S |
| | | | | | | | | | | | | | | | | | | | | 49 | | 51 | | | 52b | | |
| | | | | | | | | | | | | | | | | | | | | | | A | | I | Q | Q | |
| | | | | | | | | | | | | | | | | | | | | | | S | | S | R | | |
| N | H | A | T | Y | Y | A | E | S | V | K | G | R | F | T | I | S | R | D | D | S | K | N | T | L | Y | L | Q |
| | | | | | | | | | | | | | | 94 | | | | | | | | | 78 | | | | |
| | | | | | | | | | | | | | | | | | | | | | | | V | | | | |
| M | N | S | L | K | T | E | D | T | A | V | Y | Y | C | T | R | W | R | R | F | D | S | W | G | Q | G | T |
| L | V | T | V | S | S | | | | | | | | | | | | | | | | | | | | | |

FIG. 18

Humanized Deimmunized VH1AA [SEQ ID NO: 93] Lead Variant and Modifications Thereof with CDRs underlined

| | | | 4 | | | | | | | | | | | | | | | 19 | | 22 | | | | | | |
|---|---|---|---|---|---|---|---|---|---|---|---|---|---|---|---|---|---|---|---|---|---|---|---|---|---|---|
| D | I | Q | M | T | Q | S | P | S | S | L | S | A | S | V | G | D | R | A | T | I | T | C | R | A | S | S | S |
| | | | *L* | | | | | | | | | | | | | | | *V* | | *S* | | | | | | | |

| | | | | | | | | | | | | 48 | | | | | 51 | | | | | | | |
|---|---|---|---|---|---|---|---|---|---|---|---|---|---|---|---|---|---|---|---|---|---|---|---|---|
| V | S | Y | M | H | W | Y | Q | Q | K | P | G | K | A | P | K | P | W | A | T | S | N | L | A | S |
| | | | | | | | | | | | | | *I* | | | | | | *S* | | | | | |

| V | P | S | R | F | S | G | S | G | S | G | T | D | Y | T | L | T | I | S | S | L | Q | P | E | D | F | A | T |

| Y | Y | C | Q | Q | W | S | N | P | L | T | F | G | G | G | T | K | V | E | I | K |

| | |
|---|---|
| High Affinity | |
| Total Alleles Binding | |
| B5'0101 | |
| B1'0817 | |
| B1'0813 | |
| B1'0806 | |
| B1'0804 | |
| B1'0802 | |
| B1'0801 | |
| B1'0701 | |
| B1'1321 | |
| B1'1307 | |
| B1'1304 | |
| B1'1301 | |
| B1'1128 | |
| B1'1120 | |
| B1'1114 | |
| B1'1107 | |
| B1'1104 | |
| B1'1102 | |
| B1'1101 | |
| B1'0421 | |
| B1'0410 | |
| B'0408 | |
| B'0405 | |
| B'0404 | |
| B1'0405 | |
| B1'0401 | |
| B1'0309 | |
| B1'0306 | |
| B1'0305 | |
| B1'0301 | |
| B1'1502 | |
| B1'1501 | |
| B1'0102 | |
| B1'0101 | |
| Sequence | G Q G H L V T V S S |
| iTope | |
| Residue number | 104 105 106 107 108 109 110 111 112 113 |

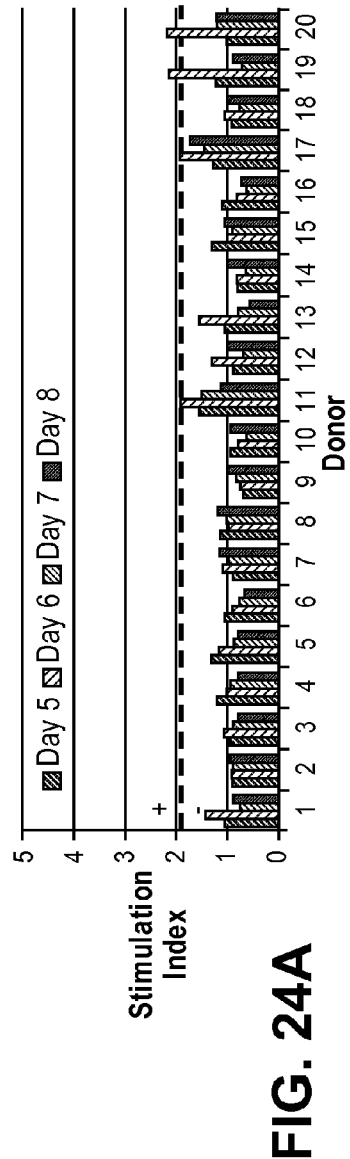
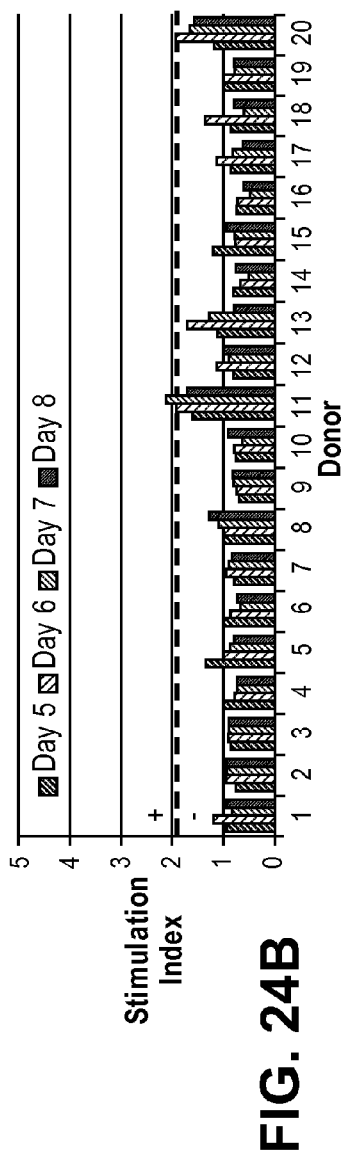
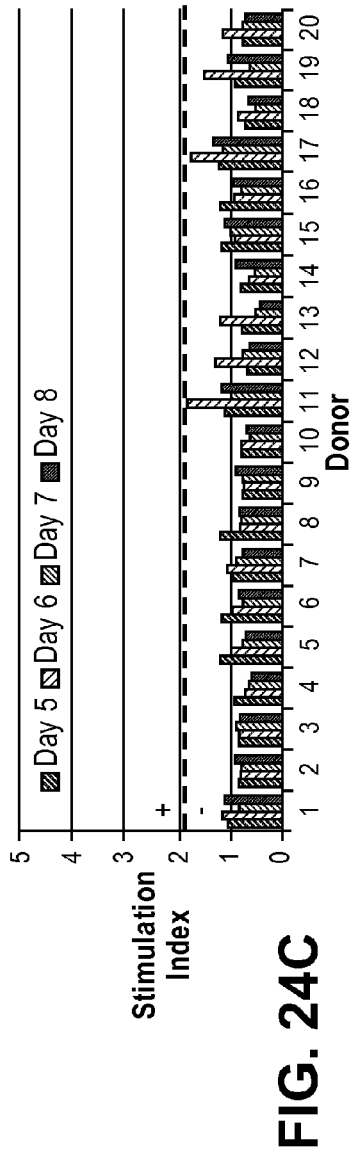
FIG. 24A
FIG. 24B
FIG. 24C

ENDOGLIN ANTIBODIES

CROSS-REFERENCE

This application is a continuation application of U.S. application Ser. No. 14/054,446, filed on Oct. 15, 2013, now U.S. Pat. No. 9,150,652, which is a continuation of U.S. application Ser. No. 13/485,702, filed on May 31, 2012, now U.S. Pat. No. 8,609,094, which is a divisional application of U.S. application Ser. No. 12/751,907, filed Mar. 31, 2010, now U.S. Pat. No. 8,221,753, which claims the benefit of U.S. Provisional Application No. 61/247,290 filed Sep. 30, 2009; and which is a continuation application of U.S. Non-Provisional application Ser. No. 12/570,918 filed Sep. 30, 2009, now abandoned, the disclosures of all of which are hereby incorporated by reference in their entireties.

SEQUENCE LISTING

The instant application contains a Sequence Listing which has been submitted via EFS-Web and is hereby incorporated by reference it its entirety. Said ASCII copy, created on Oct. 16, 2013, is named 35882-706-302-Seqlisting.txt, and is 42 Kilobytes in size.

BACKGROUND OF THE INVENTION

Endoglin, also known as, inter alia, CD105 or edg-1, is a type I homodimeric membrane glycoprotein which is expressed at high levels in proliferating vascular endothelial cells (Burrows et al., 1995, Clin. Cancer Res. 1:1623-1634). Thus, endoglin is primarily a proliferation-associated marker for endothelial cells undergoing active angiogenesis. However, there is some expression of endoglin by the vascular endothelium of normal tissues (Burrows et al., supra; Wang et al., 1993, Int. J. Cancer 54:363-370). Human endoglin is known to specifically bind transforming growth factor-β (TGF-β), and the deduced amino acid sequence of endoglin has strong homology to β-glycan, a type of TGF-β receptor.

Endoglin (EDG) has been targeted in antibody-based methods of reducing tumor vasculature, as EDG is a proliferation-associated antigen on endothelial and leukemia cells. Its expression is up-regulated in tumor-associated vascular endothelium, and EDG is essential for angiogenesis. Angiogenesis includes the formation of new capillary blood vessels leading to neovascularization as well as the maintenance of the existing vasculature. It is a complex process which includes a series of sequential steps including endothelial cell-mediated degradation of vascular basement membrane and interstitial matrices, migration of endothelial cells, proliferation of endothelial cells, and formation of capillary loops by endothelial cells.

Several anti-endoglin antibodies, in particular anti-endoglin monoclonal antibodies ("mAb"), have been described. mAb SN6 is an antibody generated from immunization of mice with glycoprotein mixtures of cell membranes of human leukemia cells (Haruta and Seon, 1986, Proc. Natl. Acad. Sci. 83:7898-7902). SN6 is a murine mAb that recognizes human endoglin. mAb 44G4 is an antibody generated from immunization of mice with whole cell suspensions of human pre-B leukemia cells (Gougos and Letarte, 1988, J. Immunol. 141:1925-1933; 1990, J. Biol. Chem. 265:8361-8364). 44G4 is also a murine mAb that recognizes human endoglin. mAb MJ7/18 is an antibody generated from immunization of rats with inflamed mouse skins (Ge and Butcher, 1994, supra). MJ7/18 is a mAb that recognizes murine endoglin. mAb Tec-11 is an antibody generated from immunization of mice with human umbilical vein endothelial cells (Burrows et al., 1995, Clin. Cancer Res. 1:1623-1634). Tec-11 is a murine mAb with reactivity restricted to human endoglin. Antibodies against endoglin represent an important area for the development of therapies for the treatment of a variety of diseases and conditions which involve, are influenced by, or affected by angiogenesis.

Angiogenesis is the physiological process by which new blood vessels develop from pre-existing vessels (Varner, et al., Cell Adh. Commun. 1995, 3:367-374; Blood, et al., Biochim. Biophys. Acta. 1990, 1032:89-118; Weidner, et al., J. Natl. Cancer Inst. 1992, 84:1875-1887). Angiogenesis has been suggested to play a role in both normal and pathological processes. For example, angiogenic processes are involved in the development of the vascular systems of animal organs and tissues. These processes are also involved in transitory phases of angiogenesis, for example during the menstrual cycle, in pregnancy, and in wound healing. On the other hand, a number of diseases are known to be associated with deregulated angiogenesis.

In certain pathological conditions, angiogenesis is stimulated as a means to provide adequate blood and nutrient supply to the cells within affected tissue. Many of these pathological conditions involve aberrant cell proliferation and/or regulation. Therefore, inhibition of angiogenesis is a potentially useful approach to treating diseases that are characterized by new blood vessel development. For example, angiogenesis is involved in pathologic conditions including: various forms of ocular and non-ocular diseases characterized by angiogenesis/neovascularization (e.g., macular degeneration, diabetic retinopathy), diabetic nephropathy, chronic inflammatory diseases (e.g., IBD), rheumatoid arthritis, osteoarthritis, and various forms of cancer, solid tumors, and metastases and the like.

SUMMARY OF THE INVENTION

Provided herein are humanized antibodies or antigen-binding fragments thereof that bind to endoglin. Such antibodies have in vitro and in vivo purification, detection, diagnostic and therapeutic uses. Also provided herein are humanized antibodies or antigen-binding fragments thereof that bind to one or more species or variants of endoglin and inhibit angiogenesis. Further provided herein are methods of treating angiogenesis-associated diseases with humanized antibodies or antigen-binding fragments thereof that bind to endoglin.

The humanized antibodies and antigen-binding fragments which bind endoglin and are described herein can be used to treat or prevent macular degeneration, CNV, diabetic retinopathy, or proliferative vitreoretinopathy. Described herein are methods of treating or preventing macular degeneration, CNV, diabetic retinopathy, or proliferative vitreoretinopathy via the administration of the antibodies and antigen-binding fragments described herein. The humanized antibodies and antigen-binding fragments which bind endoglin and are described herein can also shrink blood vessels, inhibit endothelial cell proliferation associated with ocular disease, clear symptoms of bleeding, treat cloudy vision, provide stasis of vision loss, and/or prevent leakage of blood vessels. The humanized antibodies and antigen-binding fragments described herein can also be used in medicaments for the treatment of macular degeneration, CNV, diabetic retinopathy or proliferative vitreoretinopathy. The humanized antibodies and antigen-binding fragments described herein can also be used in medicaments for the treatment of cancer.

Provided herein are antibodies, or antigen-binding fragments thereof, having a heavy chain variable region having an amino acid sequence set forth as SEQ ID NO: 41 and a light chain variable region having an amino acid sequence set forth as SEQ ID NO: 3.

Provided herein are antibodies, or antigen-binding fragments thereof that bind endoglin, having comprising a light chain variable region having an amino acid sequence set forth as SEQ ID NO: 3 and a heavy chain variable region having an amino acid sequence set forth as SEQ ID NO: 41, wherein: said heavy chain variable region further comprises one or more modifications selected from the group consisting of a substitution of glycine (G) by alanine (A) at position 49; a substitution of asparagine (N) by serine (S) at position 76; a substitution of threonine (T) by arginine (R) at position 77; a substitution of leucine (L) by valine (V) at position 78; a substitution of asparagine (N) by isoleucine (I) at position 82a; a substitution of valine (V) by isoleucine (I) or leucine (L) at position 89; a substitution of threonine (T) by arginine (R) or glycine (G) at position 94; a substitution of leucine (L) by threonine (T) at position 108; a substitution of valine (V) by leucine (L) at position 109; and a substitution of serine (S) by alanine (A) at position 113 utilizing the Kabat numbering system; and the light chain variable region further comprises one or more modifications selected from the group consisting of a substitution of aspartic acid (D) by glutamine (Q) at position 1; a substitution of glutamine (Q) by valine (V) at position 3; a substitution of methionine (M) by leucine (L) at position 4; a substitution of threonine (T) by serine (S) at position 5; a substitution of tyrosine (Y) by phenylalanine (F) at position 36; a substitution of leucine (L) by proline (P) at position 46; a substitution of leucine (L) by tryptophan (W) at position 47; a substitution of serine (S) by valine (V) or alanine (A) at position 60; a substitution of aspartic acid (D) by serine (S) at position 70; a substitution of phenylalanine (F) by tyrosine (Y) at position 71; a substitution of glutamine (G) by alanine (A) at position 100; and a substitution of isoleucine (I) by leucine (L) at position 106 utilizing the Kabat numbering system Provided herein are antibodies, or antigen-binding fragments thereof that bind endoglin, having a heavy chain variable region and a light chain variable region,
wherein said heavy chain variable region comprises:
  (i) a CDR1 of SEQ ID NO: 66, a CDR2 of SEQ ID NO: 67, and a CDR3 of SEQ ID NO: 68;
  (ii) a heavy chain FR1 having the amino acid sequence of SEQ ID NO: 44 or the amino acid sequence of SEQ ID NO: 44 except for one or more conservative substitutions;
  (iii) a heavy chain FR2 having the amino acid sequence of SEQ ID NO: 45 or the amino acid sequence of SEQ ID NO: 45 except for a substitution of glycine (G) by alanine (A) at position 49 utilizing the Kabat numbering system; and
  (iv) a heavy chain FR3 having the amino acid sequence of SEQ ID NO: 47 or the amino acid sequence of SEQ ID NO: 47 except for one or more substitutions selected from the group consisting of:
    (a) a substitution of asparagine (N) by serine (S) at position 76;
    (b) a substitution of threonine (T) by arginine (R) at position 77;
    (c) a substitution of leucine (L) by valine (V) at position 78;
    (d) a substitution of asparagine (N) by isoleucine (I) at position 82a;
    (e) a substitution of valine (V) by isoleucine (I) or leucine (L) at position 89; and
    (f) a substitution of threonine (T) by arginine (R) or glycine (G) at position 94 utilizing the Kabat numbering system; and
  (v) a heavy chain FR4 having the amino acid sequence of SEQ ID NO: 56 or the amino acid sequence of SEQ ID NO: 56 except for one or more substitutions selected from the group consisting of:
    (a) a substitution of leucine (L) by threonine (T) at position 108;
    (b) a substitution of valine (V) by leucine (L) at position 109; and
    (c) a substitution of serine (S) by alanine (A) at position 113 utilizing the Kabat numbering system;
and said light chain variable region comprises:
  (i) a CDR1 of SEQ ID NO: 63, a CDR2 of SEQ ID NO: 64, and a CDR3 of SEQ ID NO: 65;
  (ii) a light chain FR1 having the amino acid sequence of SEQ ID NO: 6 or the amino acid sequence of SEQ ID NO: 6 except for one or more substitutions selected from the group consisting of:
    (a) a substitution of aspartic acid (D) by glutamine (Q) at position 1;
    (b) a substitution of glutamine (Q) by valine (V) at position 3;
    (c) a substitution of methionine (M) by leucine (L) at position 4; and
    (d) a substitution of threonine (T) by serine (S) at position 5; utilizing the Kabat numbering system; and
  (iii) a light chain FR2 having the amino acid sequence of SEQ ID NO: 20 or the amino acid sequence of SEQ ID NO: 20 except for one or more substitutions selected from the group consisting of:
    (a) a substitution of tyrosine (Y) by phenylalanine (F) at position 36;
    (b) a substitution of leucine (L) by proline (P) at position 46; and
    (c) a substitution of leucine (L) by tryptophan (W) at position 47 utilizing the Kabat numbering system; and
  (iv) a light chain FR3 having the amino acid sequence of SEQ ID NO: 28 or the amino acid sequence of SEQ ID NO: 28 except for one or more substitutions selected from the group consisting of:
    (a) a substitution of serine (S) by valine (V) or alanine (A) at position 60;
    (b) a substitution of aspartic acid (D) by serine (S) at position 70; and
    (b) a substitution of phenylalanine (F) by tyrosine (Y) at position 71 utilizing the Kabat numbering system; and
  (v) a light chain FR4 having the amino acid sequence of SEQ ID NO: 35 or the amino acid sequence of SEQ ID NO: 35 except for one or more substitutions selected from the group consisting of:
    (a) a substitution of glycine (G) by alanine (A) at position 100; and
    (b) a substitution of isoleucine (I) by leucine (L) at position 106 utilizing the Kabat numbering system.

Provided herein is an antibody, or antigen-binding fragment thereof, comprising a heavy chain variable region having an amino acid sequence set forth as SEQ ID NO: 42 and a light chain variable region having an amino acid sequence set forth as SEQ ID NO: 4.

Provided herein is an antibody, or antigen-binding fragment thereof, that binds endoglin, comprising a light chain variable region having an amino acid sequence set forth as SEQ ID NO: 4 and a heavy chain variable region having an amino acid sequence set forth as SEQ ID NO: 42, wherein: said heavy chain variable region further comprises one or more modifications selected from the group consisting of a substitution of glycine (G) by alanine (A) at position 49; a substitution of asparagine (N) by serine (S) at position 76; a substitution of threonine (T) by arginine (R) at position 77; a substitution of leucine (L) by valine (V) at position 78; a substitution of asparagine (N) by isoleucine (I) at position 82a; a substitution of valine (V) by isoleucine (I) or leucine (L) at position 89; a substitution of arginine (R) by threonine (T) or glycine (G) at position 94; a substitution of leucine (L) by threonine (T) at position 108; a substitution of valine (V) by leucine (L) at position 109; and a substitution of serine (S) by alanine (A) at position 113 utilizing the Kabat numbering system; and the light chain variable region further comprises one or more modifications selected from the group consisting of a substitution of aspartic acid (D) by glutamine (Q) at position 1; a substitution of glutamine (Q) by valine (V) at position 3; a substitution of methionine (M) by leucine (L) at position 4; a substitution of threonine (T) by serine (S) at position 5; a substitution of tyrosine (Y) by phenylalanine (F) at position 36; a substitution of proline (P) by leucine (L) at position 46; a substitution of tryptophan (W) by leucine (L) at position 47; a substitution of serine (S) by valine (V) or alanine (A) at position 60; a substitution of aspartic acid (D) by serine (S) at position 70; a substitution of tyrosine (Y) by phenylalanine (F) at position 71; a substitution of glutamine (G) by alanine (A) at position 100; and a substitution of isoleucine (I) by leucine (L) at position 106 utilizing the Kabat numbering system Provided herein is an antibody, or antigen-binding fragment thereof, that binds endoglin, comprising a heavy chain variable region and a light chain variable region, wherein said heavy chain variable region comprises:
(i) a CDR1 of SEQ ID NO: 66, a CDR2 of SEQ ID NO: 67, and a CDR3 of SEQ ID NO: 68;
(ii) a heavy chain FR1 having the amino acid sequence of SEQ ID NO: 44 or the amino acid sequence of SEQ ID NO: 44 except for one or more conservative substitutions;
(iii) a heavy chain FR2 having the amino acid sequence of SEQ ID NO: 45 or the amino acid sequence of SEQ ID NO: 45 except for a substitution of glycine (G) by alanine (A) at position 49 utilizing the Kabat numbering system; and
(iv) a heavy chain FR3 having the amino acid sequence of SEQ ID NO: 47 or the amino acid sequence of SEQ ID NO: 47 except for one or more substitutions selected from the group consisting of:
(a) a substitution of asparagine (N) by serine (S) at position 76;
(b) a substitution of threonine (T) by arginine (R) at position 77;
(c) a substitution of leucine (L) by valine (V) at position 78;
(d) a substitution of asparagine (N) by isoleucine at position 82a;
(e) a substitution of valine (V) by isoleucine (I) or leucine (L) at position 89; and
(f) a substitution of arginine (R) by threonine (T) or glycine (G) at position 94 utilizing the Kabat numbering system; and
(v) a heavy chain FR4 having the amino acid sequence of SEQ ID NO: 56 or the amino acid sequence of SEQ ID NO: 56 except for one or more substitutions selected from the group consisting of:
(a) a substitution of leucine (L) by threonine (T) at position 108;
(b) a substitution of valine (V) by leucine (L) at position 109; and
(c) a substitution of serine (S) by alanine (A) at position 113 utilizing the Kabat numbering system;

and said light chain variable region comprises:
(i) a CDR1 of SEQ ID NO: 63, a CDR2 of SEQ ID NO: 64, and a CDR3 of SEQ ID NO: 65;
(ii) a light chain FR1 having the amino acid sequence of SEQ ID NO: 6 or the amino acid sequence of SEQ ID NO: 6 except for one or more substitutions selected from the group consisting of:
(a) a substitution of aspartic acid (D) by glutamine (Q) at position 1;
(b) a substitution of glutamine (Q) by valine (V) at position 3;
(c) a substitution of methionine (M) by leucine (L) at position 4; and
(d) a substitution of threonine (T) by serine (S) at position 5; utilizing the Kabat numbering system; and
(iii) a light chain FR2 having the amino acid sequence of SEQ ID NO: 21 or the amino acid sequence of SEQ ID NO: 20 except for one or more substitutions selected from the group consisting of:
(a) a substitution of tyrosine (Y) by phenylalanine (F) at position 36;
(b) a substitution of proline (P) by leucine (L) at position 46; and
(c) a substitution of tryptophan (W) by leucine (L) at position 47 utilizing the Kabat numbering system; and
(iv) a light chain FR3 having the amino acid sequence of SEQ ID NO: 29 or the amino acid sequence of SEQ ID NO: 28 except for one or more substitutions selected from the group consisting of:
(a) a substitution of serine (S) by valine (V) or alanine (A) at position 60;
(b) a substitution of aspartic acid (D) by serine (S) at position 70; and
(b) a substitution of tyrosine (Y) by phenylalanine (F) at position 71 utilizing the Kabat numbering system; and
(v) a light chain FR4 having the amino acid sequence of SEQ ID NO: 35 or the amino acid sequence of SEQ ID NO: 35 except for one or more substitutions selected from the group consisting of:
(a) a substitution of glycine (G) by alanine (A) at position 100; and
(b) a substitution of isoleucine (I) by leucine (L) at position 106 utilizing the Kabat numbering system.

Provided herein is an antibody, or antigen-binding fragment thereof, comprising a light chain variable region having an amino acid sequence set forth as SEQ ID NO: 93 (VK1AA) and a heavy chain variable region having an amino acid sequence set forth as SEQ ID NO: 89 (VH1A2).

Provided herein is an antibody, or antigen-binding fragment thereof, that binds endoglin, comprising a heavy chain variable region having an amino acid sequence set forth as SEQ ID NO: 89 and a light chain variable region having an amino acid sequence set forth as SEQ ID NO: 93, wherein:

(i) the heavy chain variable region further comprises one or more modifications selected from the group consisting of a substitution of glycine (G) by alanine (A) or serine (S) at position 49; a substitution of alanine (A) by isoleucine (I) at position 51; a substitution of lysine (K) by arginine (R) or asparagine (Q) at position 52b; a substitution of leucine (L) by valine (V) at position 78 utilizing the Kabat numbering system; and (ii) the light chain variable region further comprises one or more modifications selected from the group consisting of a substitution of methionine (M) by leucine (L) at position 4; a substitution of alanine (A) by valine (V) at position 19; a substitution of threonine (T) by serine (S) at position 22; a substitution of alanine (A) by isoleucine (I) at position 48; and a substitution of threonine (T) by serine (S) at position 51 utilizing the Kabat numbering system.

Provided herein is an antibody, or antigen-binding fragment thereof, of claim 2 comprising a heavy chain variable region having an amino acid sequence set forth as SEQ ID NO: 88, 89, 90, 91 or 92; and a light chain variable region having an amino acid sequence set forth as SEQ ID NO: 93, 94, 95, 96, 97, 100, 102, or 103.

In one aspect, the antibodies and antigen-binding fragments described herein are humanized and can be any isotype. Also encompassed herein are AVIMERs, diabodies, and heavy chain dimers (including camelids and shark heavy chain constructs).

The terms "antigen-binding portion of an antibody," "antigen-binding fragment," "antigen-binding domain," "antibody fragment" or a "functional fragment of an antibody" are used interchangeably herein to refer to one or more fragments of an antibody that retain the ability to specifically bind to an antigen. Non-limiting examples of antibody fragments included within such terms include, but are not limited to, (i) a Fab fragment, a monovalent fragment consisting of the $V_L$, $V_H$, $C_L$ and $C_{H1}$ domains; (ii) a F(ab')$_2$ fragment, a bivalent fragment containing two Fab fragments linked by a disulfide bridge at the hinge region; (iii) a Fd fragment consisting of the $V_H$ and $C_{H1}$ domains; (iv) a Fv fragment containing the $V_L$ and $V_H$ domains of a single arm of an antibody, (v) a dAb fragment (Ward et al., (1989) Nature 341:544 546), which containing a $V_H$ domain; and (vi) an isolated CDR. Additionally included in this definition are "one-half" antibodies comprising a single heavy chain and a single light chain. Other forms of single chain antibodies, such as diabodies are also encompassed herein.

An antigen-binding fragment can be any of those described herein including, but not limited to, a Fab fragment, a Fab', a F(ab')$_2$ fragment, an Fv fragment (including non-covalently and covalently linked Fv fragments), an scFv fragment, a single chain binding polypeptide, an Fd fragment, an Fv fragment or a dAb fragment. In one non-limiting embodiment, the antigen-binding fragment is a scFv which can, optionally, be further fused to a human Fc portion of an antibody.

In one non-limiting embodiment, the antibody, or antigen-binding fragment thereof that binds endoglin comprises a heavy chain variable region having an amino acid sequence set forth as SEQ ID NO: 41, 42, or 43, and a light chain variable region having an amino acid sequence set forth as SEQ ID NO: 3, 4, or 5.

In another non-limiting embodiment, the antibody, or antigen-binding fragment thereof comprises a heavy chain variable region having an amino acid sequence set forth as SEQ ID NO: 41 and a light chain variable region having an amino acid sequence set forth as SEQ ID NO: 3.

In another non-limiting embodiment, the antibody, or antigen-binding fragment thereof comprises a heavy chain variable region having an amino acid sequence set forth as SEQ ID NO: 41 and a light chain variable region having an amino acid sequence set forth as SEQ ID NO: 4.

In another non-limiting embodiment, the antibody, or antigen-binding fragment thereof comprises a comprising a heavy chain variable region having an amino acid sequence set forth as SEQ ID NO: 41 and a light chain variable region having an amino acid sequence set forth as SEQ ID NO: 5.

In another non-limiting embodiment, the antibody, or antigen-binding fragment thereof comprises a heavy chain variable region having an amino acid sequence set forth as SEQ ID NO: 42 and a light chain variable region having an amino acid sequence set forth as SEQ ID NO: 3.

In another non-limiting embodiment, the antibody, or antigen-binding fragment thereof comprises a heavy chain variable region having an amino acid sequence set forth as SEQ ID NO: 42 and a light chain variable region having an amino acid sequence set forth as SEQ ID NO: 4.

In another non-limiting embodiment, the antibody, or antigen-binding fragment thereof comprises a heavy chain variable region having an amino acid sequence set forth as SEQ ID NO: 42 and a light chain variable region having an amino acid sequence set forth as SEQ ID NO: 5.

In another non-limiting embodiment, the antibody, or antigen-binding fragment thereof comprises a heavy chain variable region having an amino acid sequence set forth as SEQ ID NO: 43 and a light chain variable region having an amino acid sequence set forth as SEQ ID NO: 3.

In another non-limiting embodiment, the antibody, or antigen-binding fragment thereof comprises a heavy chain variable region having an amino acid sequence set forth as SEQ ID NO: 43 and a light chain variable region having an amino acid sequence set forth as SEQ ID NO: 4.

In another non-limiting embodiment, the antibody, or antigen-binding fragment thereof comprises a heavy chain variable region having an amino acid sequence set forth as SEQ ID NO: 43 and a light chain variable region having an amino acid sequence set forth as SEQ ID NO: 5.

In yet another non-limiting embodiment, the antibody, or antigen-binding fragment thereof heavy chain variable region further comprises one or more modifications selected from the group consisting of: a substitution of asparagine (N) by serine (S) at position 76; a substitution of threonine (T) by arginine (R) at position 77; a substitution of asparagine (N) by isoleucine (I) at position 82a; a substitution of valine (V) by isoleucine (I) or leucine (L) at position 89; a substitution of threonine (T) by glycine (G) at position 94; a substitution of leucine (L) by threonine (T) at position 108; a substitution of valine (V) by leucine (L) at position 109; and a substitution of serine (S) by alanine (A) a position 113; and said light chain variable region further comprises one or more modifications selected from the group consisting of: a substitution of aspartic acid (D) by glutamine (Q) at position 1; a substitution of glutamine (Q) by valine (V) at position 3; a substitution of threonine (T) by serine (S) at position 5; a substitution of tyrosine (Y) by phenylalanine (F) a position 36; a substitution of serine (S) by valine (V) or alanine (A) at position 60; a substitution of aspartic acid (D) by serine (S) at position 70; a substitution of glycine (G) by alanine (A) at position 100, and a substitution of isoleucine (I) by leucine (L) at position 106 utilizing the Kabat numbering system.

In one aspect, the antibodies and antigen-binding fragments described herein can be modified. For example, in one embodiment, the compound can be modified to alter a pharmacokinetic property of the compound such as, for example, in vivo stability, solubility, bioavailability or half-life. Such modifications include, but are not limited to, PEGylation and/or glycosylation.

The antibodies and antigen-binding fragments described herein can be formulated for rapid or extended delivery using conventional means. In one non-limiting embodiment, rapid delivery is, for example, by intravenous injection. In another non-limiting embodiment, extended delivery is, for example, by subcutaneous deposition. In another non-limiting embodiment, delivery is achieved via administration by aerosol.

Provided herein are compositions of the antibodies and antigen-binding fragments described herein and an acceptable carrier or excipient.

Provided herein are polynucleotides (nucleic acids) comprising a nucleotide sequence encoding antibodies or antigen-binding fragments described herein.

Antibodies and antigen-binding fragments thereof as described herein can be used to treat various diseases and conditions associated with angiogenesis, e.g., various forms of ocular diseases characterized by angiogenesis/neovascularization (e.g., macular degeneration, diabetic retinopathy), diabetic nephropathy, chronic inflammatory diseases (e.g., IBD), rheumatoid arthritis, osteoarthritis, and various forms of cancer, solid tumors, and metastases. Additionally, these antibodies and antigen-binding fragments thereof described herein can be used in the formulation of a medicament for the prophylaxis, treatment, or diagnosis of diseases and conditions associated with angiogenesis, e.g., various forms of ocular and non-ocular diseases characterized by angiogenesis/neovascularization (e.g., macular degeneration, diabetic retinopathy), diabetic nephropathy, chronic inflammatory diseases (e.g., IBD), rheumatoid arthritis, osteoarthritis, and various forms of cancer, solid tumors, and metastases.

Provided herein is a method for inducing a host immune response in a patient against endoglin, by administering to the patient a composition, where the composition comprises a humanized anti-endoglin antibody or antigen-binding fragment thereof that induces an effective host immune response against the epitope specifically recognized by said antibody or fragment thereof.

The host immune response can be a humoral immune response or a cell-mediated immune response. If the immune response is a humoral immune response, it can be a protective antibody response that inhibits angiogenesis, an angiogenesis-dependent disease or an angiogenesis-dependent disorder. Immune responses also include induction or blockage of cell signaling pathways (e.g. Smad signaling). The angiogenesis-dependent disease or disorder can be, for example, various forms of ocular and non-ocular diseases characterized by angiogenesis/neovascularization (e.g., macular degeneration, diabetic retinopathy), diabetic nephropathy, chronic inflammatory diseases (e.g., IBD), rheumatoid arthritis, osteoarthritis, various forms of cancer (primary tumors and metastases) and the like. In one embodiment, the protective antibody response inhibits angiogenesis.

Provided herein is a method of affecting cell signaling pathways associated with endoglin and angiogenesis. Angiogenic cells can be contacted (in vitro, in vivo or ex vivo) with an antibody or antigen-binding fragment thereof described herein in an amount sufficient to alter cell signaling pathways. In one non-limiting example, in response to antibody binding, Smad 1, 5 and/or 8 signaling is inhibited by about 1.5 fold or more in angiogenic cells. In another non-limiting example, Smad 3 levels increase by about 1.5 fold or more, indicating that cells are returning to a quiescent state.

Provided herein is a method of inhibiting angiogenesis or an angiogenesis-dependent disease or disorder in a subject by administering a composition provided herein to a patient. The angiogenesis-dependent disease or disorder can be any of the following: various forms of ocular and non-ocular diseases characterized by angiogenesis/neovascularization (e.g., macular degeneration, diabetic retinopathy), diabetic nephropathy, chronic inflammatory diseases (e.g., IBD), rheumatoid arthritis, osteoarthritis, and various forms of cancer, solid tumors and metastases. In one embodiment, inhibiting angiogenesis or an angiogenesis-dependent disease or disorder alleviates symptoms associated with the disease or disorder. In another embodiment, inhibiting angiogenesis or an angiogenesis-dependent disease or disorder results in decreased tumor size, prevention of tumor progression, decreased cell proliferation, increased apoptosis, or increased survival of a patient Inhibiting in angiogenesis can result in decreased tumor size or prevent tumor progression. The method can further include surgical removal of a cancer, and/or administration of one or more additional anti-cancer agents or treatments to a patient suffering from cancer.

Provided herein is a method of preventing or treating a cancer or metastasis in a subject by administering a composition provided herein. In one embodiment, administration of the pharmaceutical composition prolongs life of the subject being treated. A cancer/tumor to be treated includes a solid tumor; a tumor can be a primary tumor or a metastatic tumor. Exemplary solid tumors are of a tissue or organ selected from among skin, melanoma, lung, pancreas, breast, ovary, colon, rectum, stomach, thyroid, laryngeal, ovarian, prostate, colorectal, head, neck, eye, mouth, throat, esophagus, chest, bone, testicular, lymphoid, marrow, bone, sarcoma, renal, sweat gland, liver, kidney, brain, e.g. glioblastoma multiforme and the like tissues. In one non-limiting example a solid tumor is a colon tumor, a breast tumor, a kidney tumor, a lung tumor, a prostate tumor, an ovarian tumor, or metastasis of any of such tumors.

The method can further include surgical removal of the cancer and/or administration of one or more anti-cancer agents. An anti-cancer agent can be administered prior to, concomitant with, or subsequent to, administration of the pharmaceutical composition. An anti-cancer agent can be administered within a week before the pharmaceutical composition, within a week after the pharmaceutical composition, or the anti-cancer agent can be administered on the same day as the pharmaceutical composition. If an anti-cancer agent is administered on the same day as the pharmaceutical composition, administration can be concomitant.

Provided herein is a method for preventing or treating a cancer or a metastasis by surgical removal of the cancer/tumor and concurrent administration of an anti-cancer agent or treatment and a composition provided herein to a subject.

Provided herein is a method of inhibiting angiogenesis by contacting a cell or tissue with a therapeutically effective amount of an antibody or antigen-binding fragment thereof as described herein sufficient to inhibit angiogenesis.

Provided herein is a method of inhibiting cancer cell growth by contacting a therapeutically effective amount of an antibody or antigen-binding fragment thereof as described herein sufficient to inhibit cancer cell growth or cause apoptosis of the cancer cell.

Provided herein is a method, comprising contacting a tissue with an antibody or antigen-binding fragment thereof as described herein, wherein contacting inhibits angiogenesis. The tissue can be a cultured tissue biopsy sample or can be present in a subject.

Provided herein is a method of preventing or treating a cell proliferative (e.g., angiogenic) disorder by administering to a subject having or at risk of having a cell proliferative disorder an effective amount of a composition provided herein effective to treat the cell proliferative disorder. The cell proliferative disorder can be, for example a benign or malignant solid or non-solid tumor and the tumor can be metastatic or non-metastatic. The treatment can result in improving the subject's condition and can be assessed by determining if one or more of the following factors has occurred: decreased cell proliferation, decreased numbers of cells, increased apoptosis, or decreased survival of at least a portion of the cells comprising the cell proliferative disorder. One or more of these occurrences may, in some cases, result in partial or total elimination of the cancer and prolongation of survival of the patient. Optionally, the method can further include administering an anti-cancer agent or treatment to the subject.

Provided herein is a method for treating diabetic retinopathy, macular degeneration, choroidal neovascularization or neovascular glaucoma in a patient by administering to the patient a therapeutically effective amount of a composition provided herein. The treatment can result in improving the subject's condition and can be assess by determining if one or more of the following factors has occurred: decreased macular edema, decreased areas of CNV, or increased visual acuity.

In the methods provided herein, the subject can be a human or a non-human subject. Compositions and the anti-cancer agent or treatments provided herein can be administered once or multiple times depending on the health of the patient, the progression of the disease or condition, and the efficacy of the treatment. Adjustments to therapy and treatments can be made throughout the course of treatment.

Compositions can be administered locally, regionally or systemically, such as, for example, administration by subcutaneous, subcutaneous, intravitreal, intradermal, intravenous, intra-arterial, intraperitoneal or intramuscular injection.

Additionally, humanized antibodies and antigen-binding fragments described herein can also be used in combination with known therapies and/or compounds for the treatment of macular degeneration, CNV, diabetic retinopathy or proliferative vitreoretinopathy. Examples of such compounds include, but are not limited to, bevacizumab (AVASTIN®), ranibizumab (LUCENTIS®), aflibercept (VEGF-Trap), or Macugen. In addition to the modes of administration described herein, the humanized anti-endoglin antibodies and antigen-binding fragments can be administered via intravitreal routes. Non-limiting examples of intravitreal modes of administration include intravitreal injection and the use of intravitreal implants.

Another aspect is the treatment of a chronic inflammatory disease in a subject by administering a composition of an antibody or antigen-binding fragment described herein. Non-limiting examples of chronic inflammatory diseases include IBD, Crohn's disease, and ulcerative colitis.

Another aspect is the treatment of rheumatoid arthritis in a subject by administering a composition of an antibody or antigen-binding fragment described herein.

Another aspect is the treatment of osteoarthritis in a subject by administering a composition of an antibody or antigen-binding fragment described herein.

Treatment of a subject with rheumatoid arthritis and/or osteoarthritis can be assessed by various means, including improvement in the appropriate categories of ACR scores as measured according to published guidelines.

Provided herein is a method of monitoring the efficacy of one or more of any of the methods provided herein. Increased levels of soluble endoglin have been correlated with decreased survival in cancer patients. Thus, in one aspect, levels of soluble endoglin can be monitored prior to and during therapy. A decrease in the levels of soluble endoglin can, therefore, be one indication that a therapeutic regimen is effective in treating the patient.

One embodiment of the present invention contemplates the use of any of the compositions of the present invention to formulate a medicament for treating a disorder of the present invention. Medicaments can be formulated based on the physical characteristics of the patient/subject needing treatment, and can be formulated in single or multiple formulations based on the stage of the cancerous tissue. Medicaments of the present invention can be packaged in a suitable pharmaceutical package with appropriate labels for the distribution to hospitals and clinics wherein the label is for the indication of treating a disorder as described herein in a subject. Medicaments can be packaged as a single or multiple units. Instructions for the dosage and administration of the pharmaceutical compositions of the present invention can be included with the pharmaceutical packages.

Provided herein is a diagnostic method for providing a sample of cancer cells of a solid tumor or plasma from a patient to be tested, detecting in the sample the expression of at least one gene or gene product chosen from a panel of genes or gene products whose expression has been correlated with sensitivity or resistance to an angiogenesis inhibitor, wherein the at least one gene or gene product is chosen from one or more genes or gene products selected from the group consisting of VEGF, VEGF receptor, HIF-1α, placental growth factor receptor, and CD105, and comparing the level of expression of at least one gene or gene product detected in the patient sample to a level of expression of at least one gene or gene product that has been correlated with sensitivity or resistance to the angiogenesis inhibitor. In one embodiment the angiogenesis inhibitor is chosen from VEGF receptor inhibitors, VEGF inhibitors, and endoglin inhibitors.

Provided herein is a kit for the detection of expression levels of genes that have been correlated with sensitivity or resistance to an angiogenesis inhibitor in a sample of cancer cells or human plasma. In one embodiment, one or more genes are selected from VEGF, VEGF receptor, HIF-1α, placental growth factor receptor, and endoglin.

INCORPORATION BY REFERENCE

All publications and patent applications mentioned in this specification are herein incorporated by reference to the same extent as if each individual publication or patent application was specifically and individually indicated to be incorporated by reference in its entirety unless otherwise specifically noted. This application contains references to amino acid sequences which have been submitted concurrently herewith as the sequence listing text file "35882-706-202-SeqList.txt", file size 67,843 KiloBytes (KB), created

BRIEF DESCRIPTION OF THE DRAWINGS

FIG. 1 provides a humanized O2-Vκ1-39 variable ($V_L$) light chain having the monoclonal murine chimeric TRC105 $V_L$ CDRs (underlined) grafted between the framework regions (FRs) 1-3 of the human sequence O2-Vκ1-39 and a framework region 4 from the human Jκ4 sequence (SEQ ID NO: 4) (all in bold). Variations that can be made to the human FRs are indicated at positions 1, 3, 4, 5, 36, 46, 47, 60, 70, 71, 100, and 106 of the sequence (sequence disclosed at SEQ ID NO: 86) utilizing the Kabat numbering system (shown in italics beneath the humanized sequence).

FIG. 2 provides a humanized VH3-15 variable ($V_H$) heavy chain having the monoclonal murine monoclonal murine chimeric TRC105 $V_H$ CDRs (underlined) grafted between the framework regions (FRs) 1-3 of the human sequence VH3-15 and a framework region 4 from the human JH4 sequence (SEQ ID NO: 42) (all in bold). One or more variations that can be made to the human FRs are indicated at positions 49, 76, 77, 78, 82a, 89, 94, 108, 109, and 113 of the sequence (sequence disclosed at SEQ ID NO: 87) utilizing the Kabat numbering system (shown in italics beneath the humanized sequence).

FIGS. 4A-4B provide an amino acid sequence alignment of exemplary mouse and humanized VK chains (FIG. 4A; SEQ ID NOS 1-5, respectively, in order of appearance) and $V_H$ chains (FIG. 4B; SEQ ID NOS 39-43, respectively, in order of appearance) produced according the invention described herein.

FIGS. 5A-5B provide an amino acid sequence alignment of exemplary mouse and super-humanized VK chains (FIG. 5A; SEQ ID NOS 1 and 69-72, respectively, in order of appearance) and $V_H$ chains (FIG. 5B; SEQ ID NOS 39 and 73-75, respectively, in order of appearance) produced according the invention described herein.

FIG. 6 provides an amino acid sequence alignment and comparison of exemplary mouse and humanized and superhumanized VK chains (SEQ ID NOS 1, 3 and 70, respectively, in order of appearance) and $V_H$ chains (SEQ ID NOS 39, 41 and 74, respectively, in order of appearance) produced according to the invention described herein.

FIGS. 8A-8F. Anti-CD105 competition ELISA with humanized and humanized/deimmunized antibodies. Varying concentrations of each antibody were mixed with a fixed concentration of biotinylated reference anti-CD105 antibody (6.25 ng/ml) and bound to CD105 (100 ng/ml) captured on a Nunc MaxiSorp plate. Binding was detected via streptavidin-HRP and TMB substrate. Absorbance (OD) at 450 nm was measured on a plate reader and this was plotted against the test antibody concentration. FIG. 8A provides the results from the chimeric control compared to VK1VH1, VK1VH2, VK2VH1 and VK2VH2. FIG. 8B provides the results from the chimeric control compared to VK1VH1, VK2AVH1A, VK2SAVH1Q, VK2SAVH1R and VK2SAVH1S. FIG. 8C provides the results from the chimeric control compared to VK2AAVH1A2, VK2ASVH1A2, VK2ASVH1Q, VK2SSVH1A and VK2SSVH1Q. FIG. 8D provides the results from the chimeric control compared to VK2VH1, VK2AAVH1A, VK2AAVH1Q, VK2AAVH1R and VK2AAVH1S. FIG. 8E provides the results from the chimeric control compared to VK2VH1, VK2ASVH1A, VK2ASVH1R, VK2ASVH1S, and VK2SAVH1A2. FIG. 8F provides the results from the chimeric control compared to VK2VH1, VK2SSVH1Q, VK2SSVH1A2, VK2SSVH1R and VK2SSVH1S.

FIG. 9 illustrates binding assay data for variant VK1AAVH1A plus VK2 containing controls.

FIG. 10 illustrates binding assay data for chimeric compared to VK1AAVH1A2 and VK2AAVH1A2.

FIG. 17 illustrates the lead humanized deimmunized heavy chain variable region with CDRs in bold and underlined (sequence disclosed at SEQ ID NO: 89). Variations that can be made are indicated at the identified positions of the sequence utilizing the Kabat numbering system (sequence disclosed at SEQ ID NO: 116) (shown in italics beneath the humanized sequence). Variations may be made as a single mutation or as more than one mutation, and variations can be made with mutations in any combination.

FIG. 18 illustrates the lead humanized deimmunized light chain variable region with CDRs in bold and underlined (sequence disclosed at SEQ ID NO: 93). Variations that can be made are indicated at the identified positions of the sequence utilizing the Kabat numbering system (sequence disclosed at SEQ ID NO: 117) (shown in italics beneath the humanized sequence). Variations may be made as a single mutation or as more than one mutation, and variations can be made with mutations in any combination.

Figure 19A:
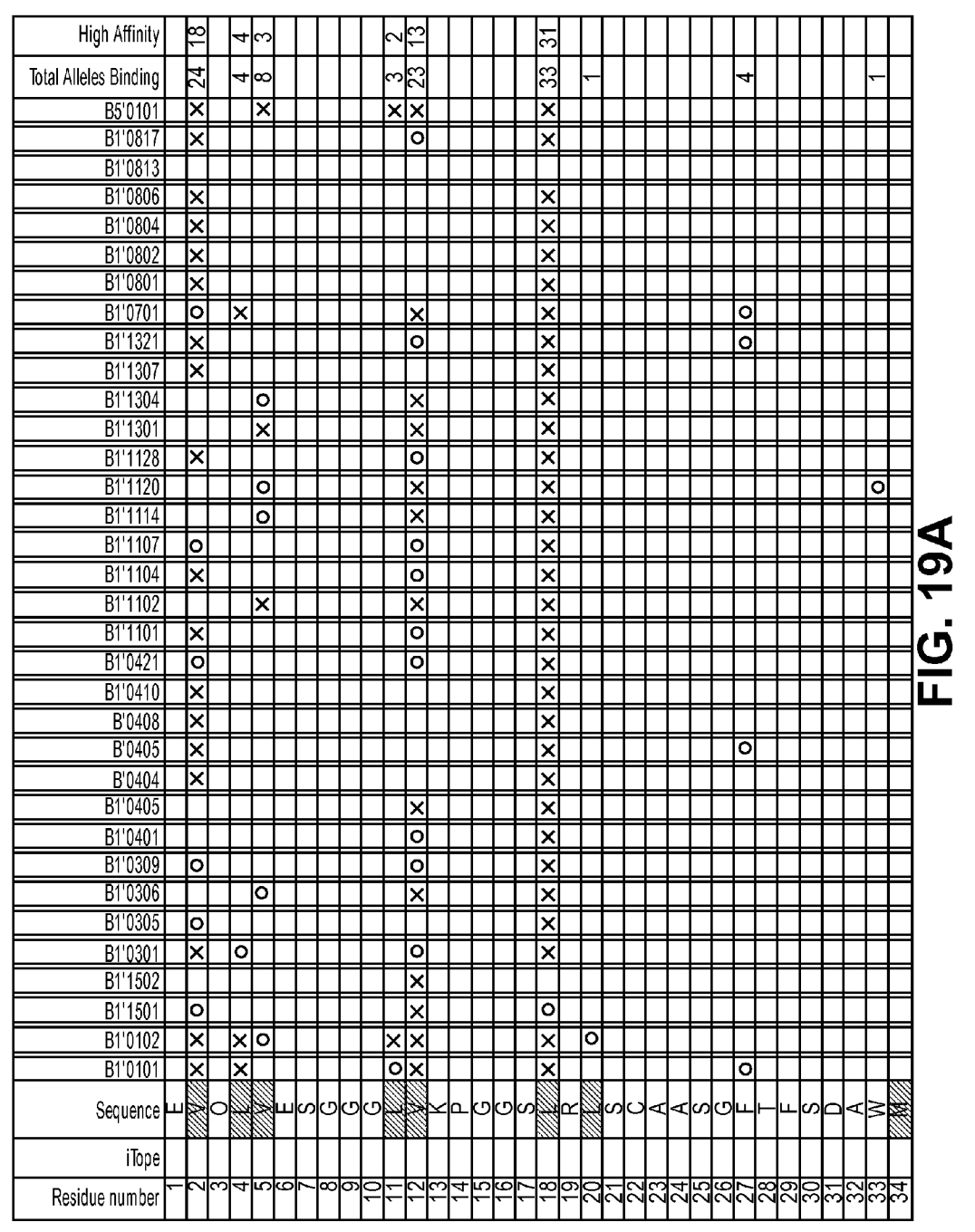
Figure 19B:
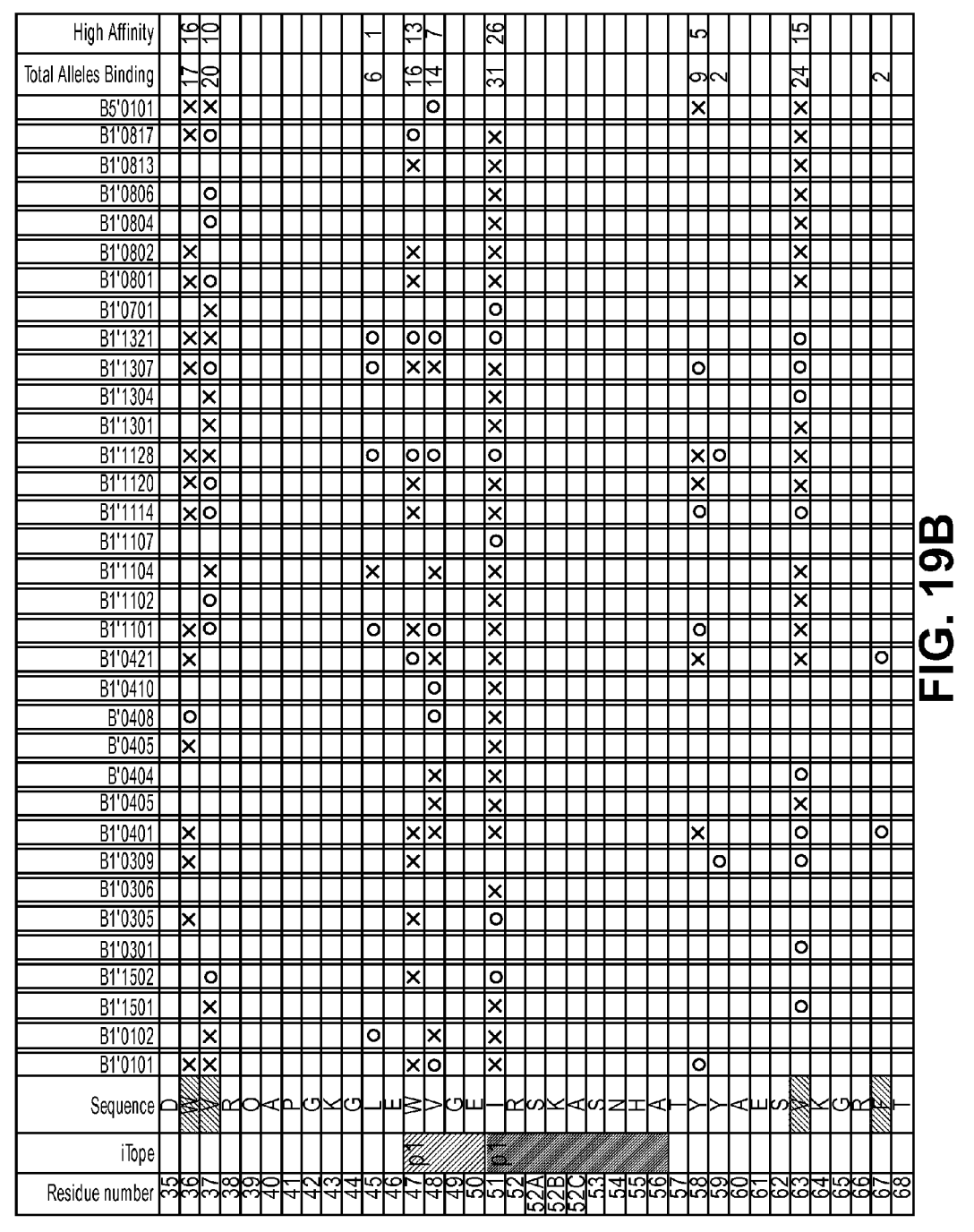
Figure 19C:
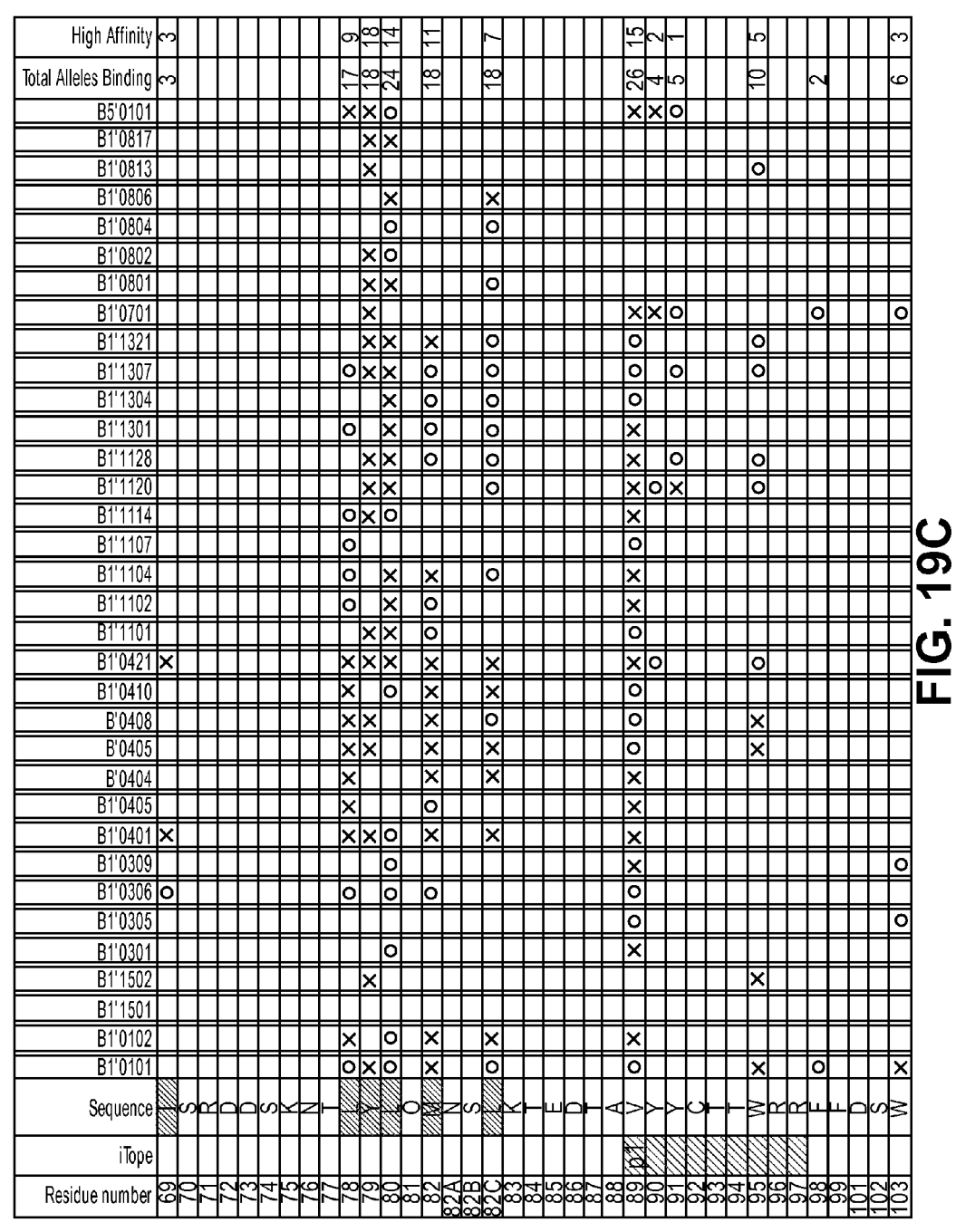

FIGS. 19A-19C illustrate Analysis of the regions of the heavy chain (SEQ ID NO: 41) using iTope™. Peptides spanning the entire sequence were tested as 9 mer peptides in one amino acid increments. The predicted binding of each residue as the p1 anchor of a core 9 mer peptide to MHC class II alleles is indicated by a "O" if the binding score was 0.55-0.6 and by a "X" if the binding score was >0.6. Regions containing potentially immunogenic peptides are indicated in the "iTope" column, dark grey indicates promiscuous high affinity MHC class II binding peptides, light grey indicates promiscuous moderate affinity MHC class II binding peptides. The numbers of MHC class II alleles predicted to bind are shown in the "total" and "high affinity" columns. Potential p1 anchor residues identified as germline sequences are shown in reverse type in the "Sequence" column. FIG. 19A represents the first part of the table of results. FIG. 19B represents the second part of the table of results. FIG. 19C represents the third part of the table of results.

Figure 20:
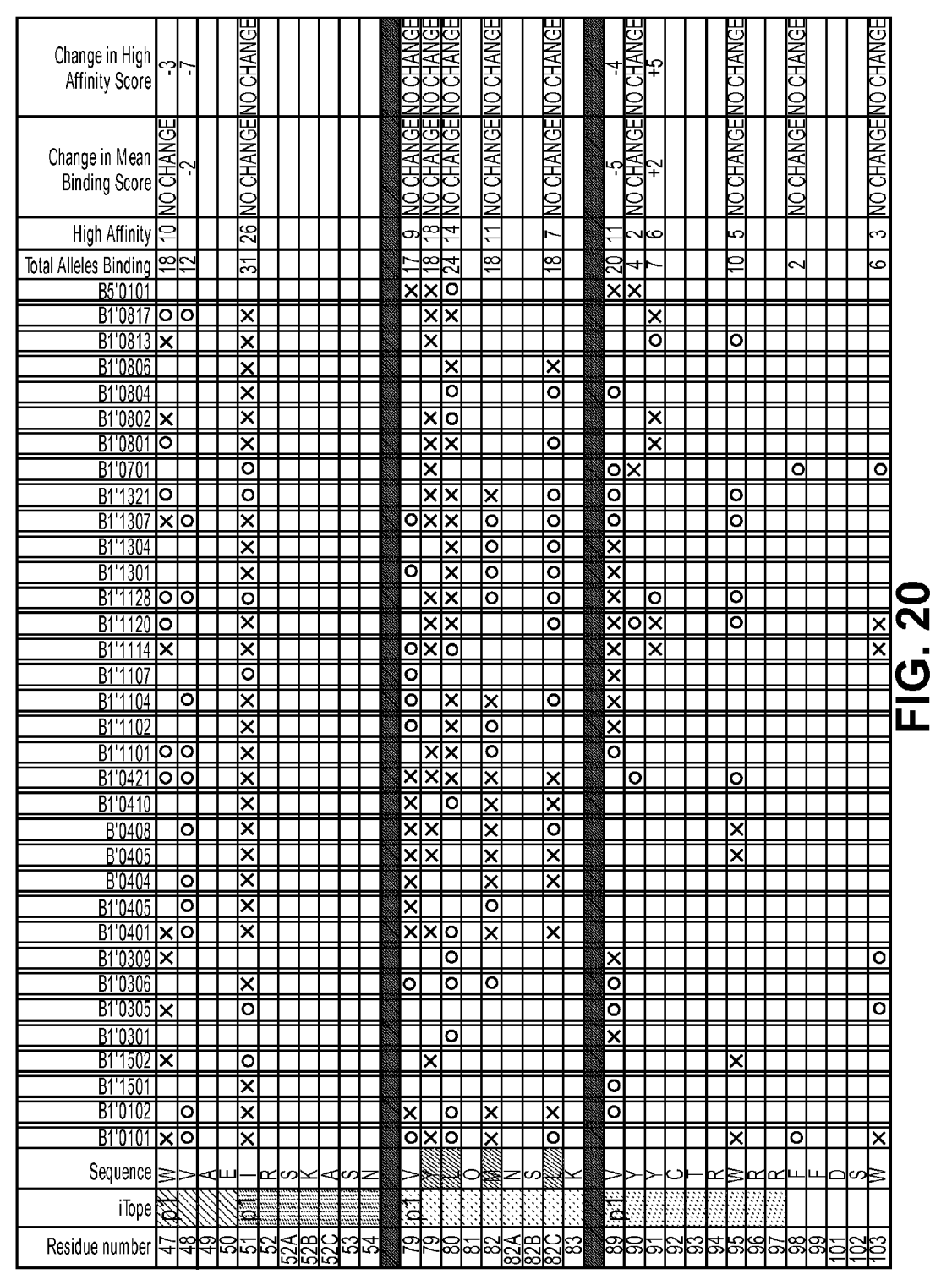

FIG. 20 illustrates analysis of the variant regions of variants of the heavy chain (SEQ ID NO: 118) using iTope™. Peptides spanning the entire sequence were tested as 9 mer peptides in one amino acid increments. The predicted binding of each residue as the p1 anchor of a core 9 mer peptide to MHC class II alleles is indicated by a "O" if the binding score was 0.55-0.6 and by a "X" if the binding score was >0.6. Regions containing potentially immunogenic peptides are indicated in the "iTope" column, dark grey indicates promiscuous high affinity MHC class II binding peptides, light grey indicates promiscuous moderate affinity MHC class II binding peptides. The numbers of MHC class II alleles predicted to bind are shown in the "total" and "high affinity" columns and the difference to binding is shown. Potential p1 anchor residues identified as germline sequences are shown in reverse type in the "Sequence" column and the amino acid differences in the variants are boxed.

Figure 21A:
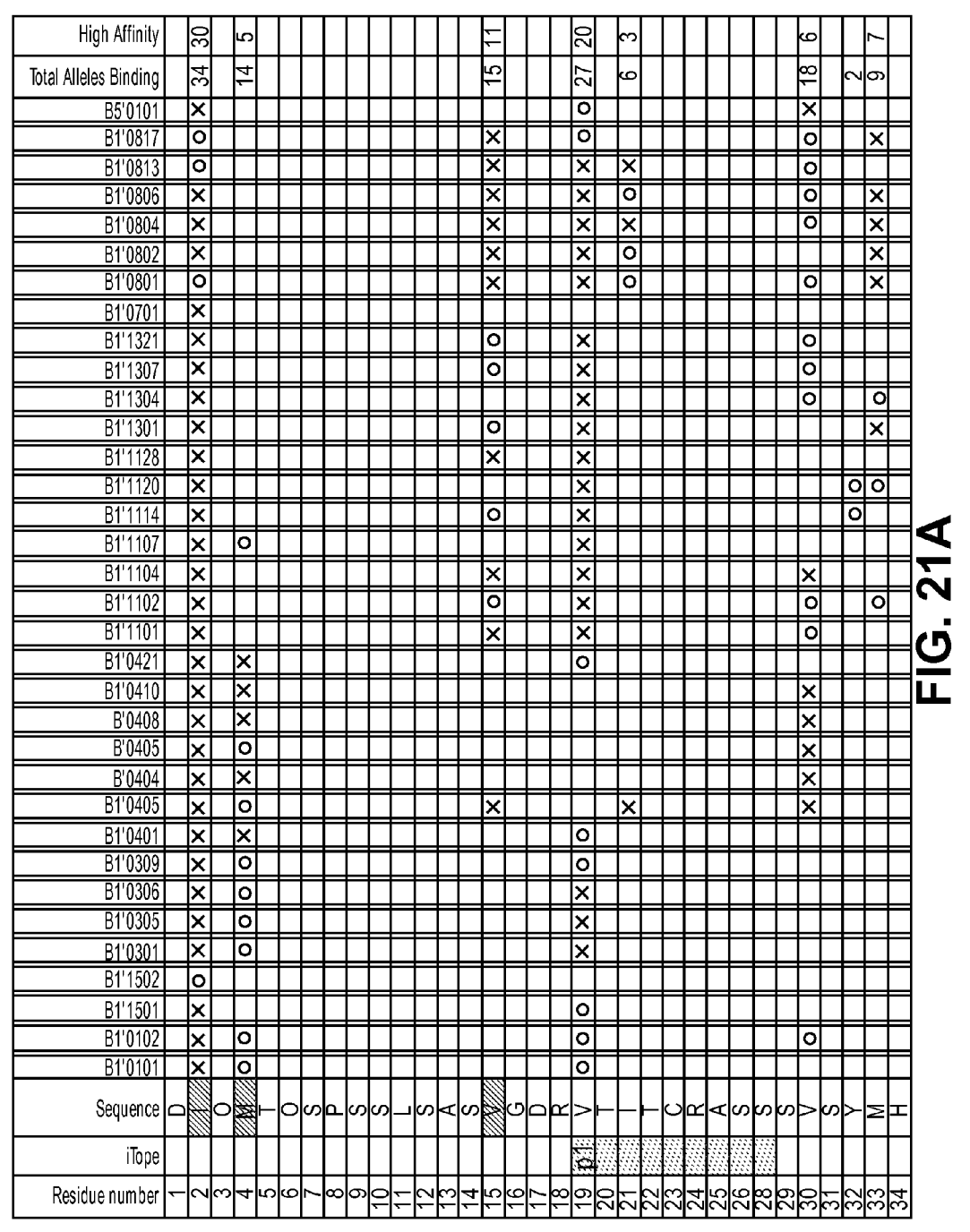
Figure 21B:
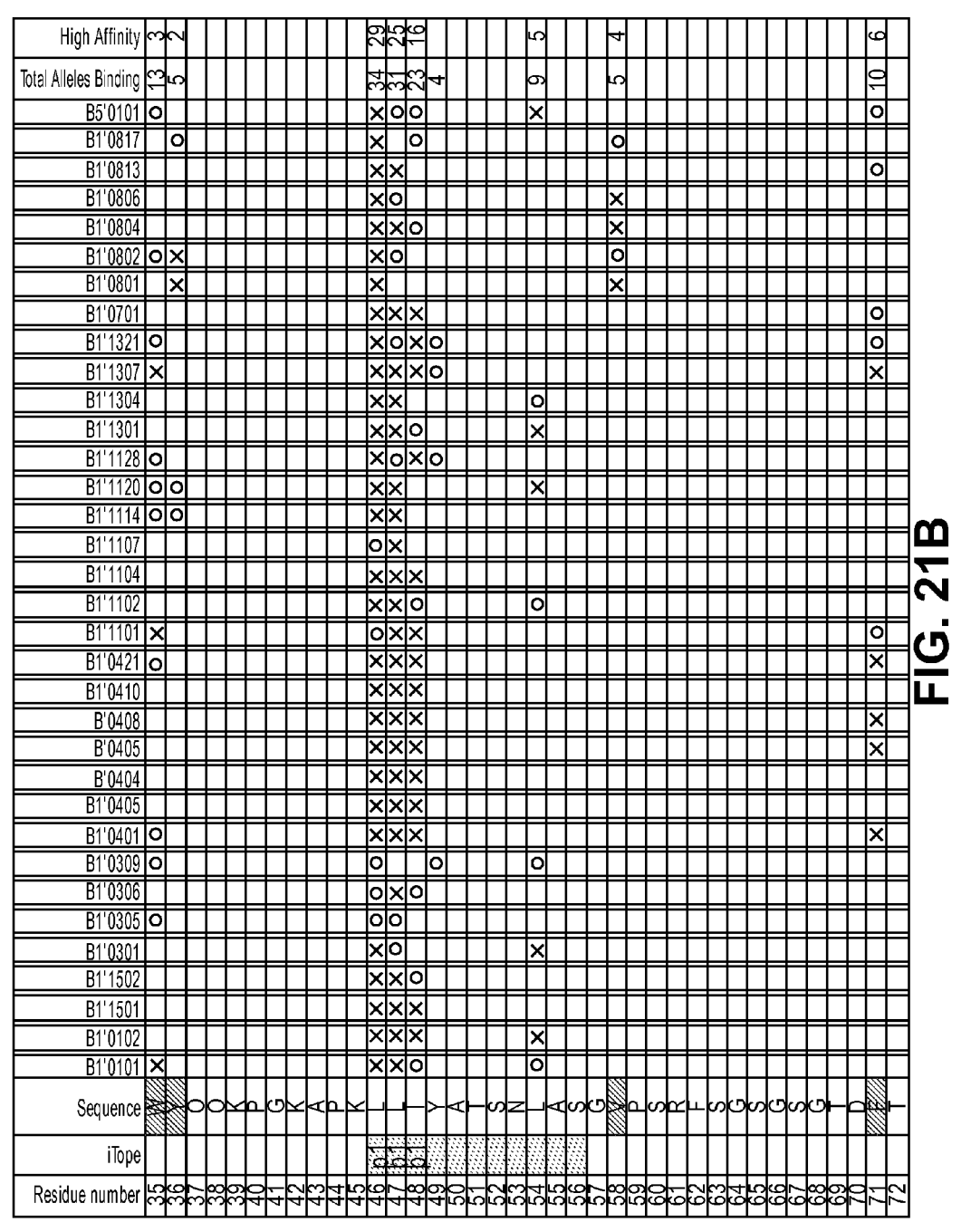
Figure 21C:
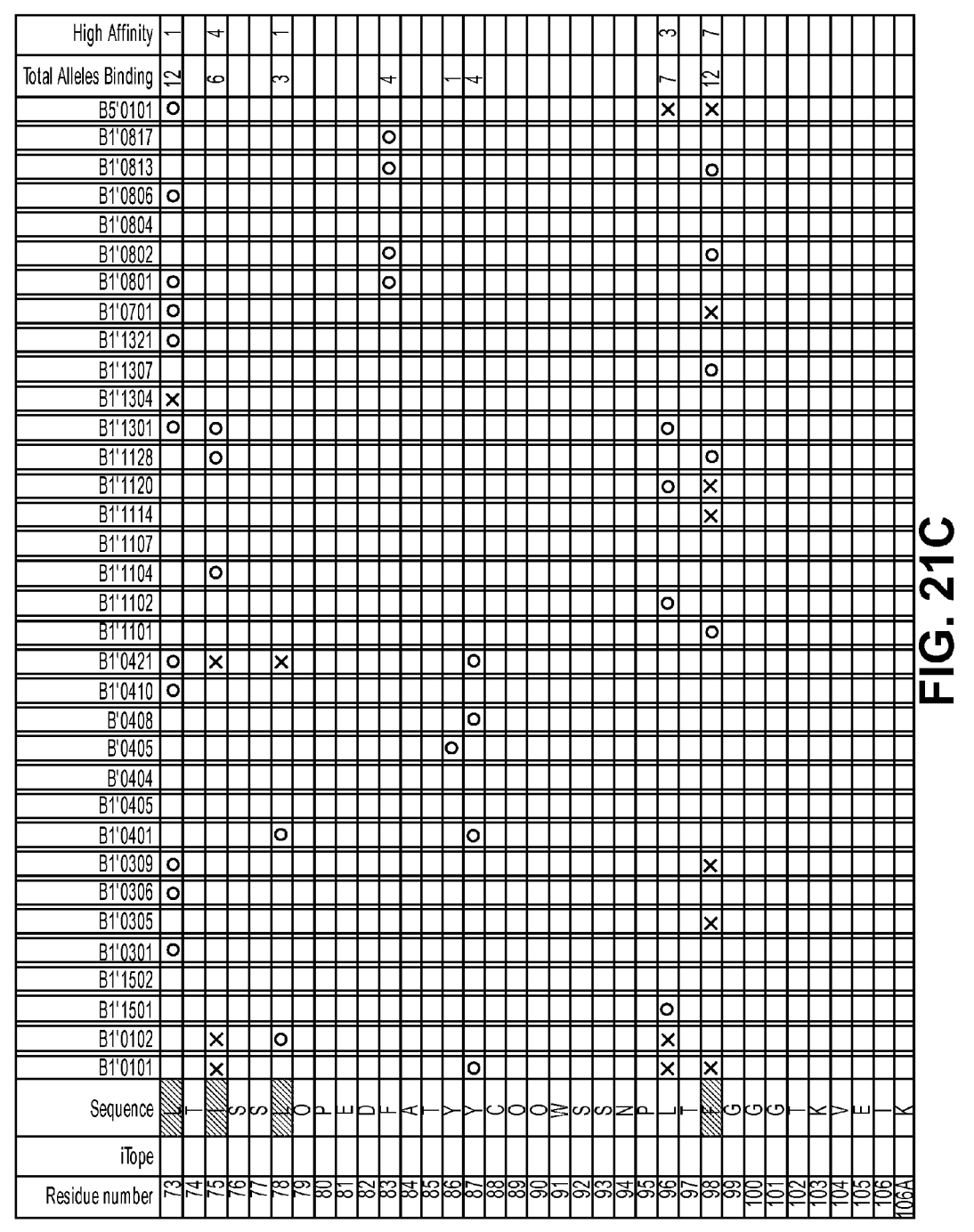

FIGS. 21A-21C illustrate analysis of the regions of the light chain (SEQ ID NO: 3) using iTope™. Peptides spanning the entire sequence were tested as 9 mer peptides in one amino acid increments. The predicted binding of each residue as the p1 anchor of a core 9 mer peptide to MHC class II alleles is indicated by a "O" if the binding score was 0.55-0.6 and by a "X" if the binding score was >0.6. Regions containing potentially immunogenic peptides are indicated in the "iTope" column, dark grey indicates promiscuous high affinity MHC class II binding peptides, light grey indicates promiscuous moderate affinity MHC class II binding peptides. The numbers of MHC class II alleles predicted to bind are shown in the "total" and "high affinity" columns. Potential p1 anchor residues identified as germline sequences are shown in reverse type in the "Sequence" column. FIG. 21A represents the first part of the table of results. FIG. 21B represents the second part of the table of results. FIG. 21C represents the third part of the table of results.

Figure 22:
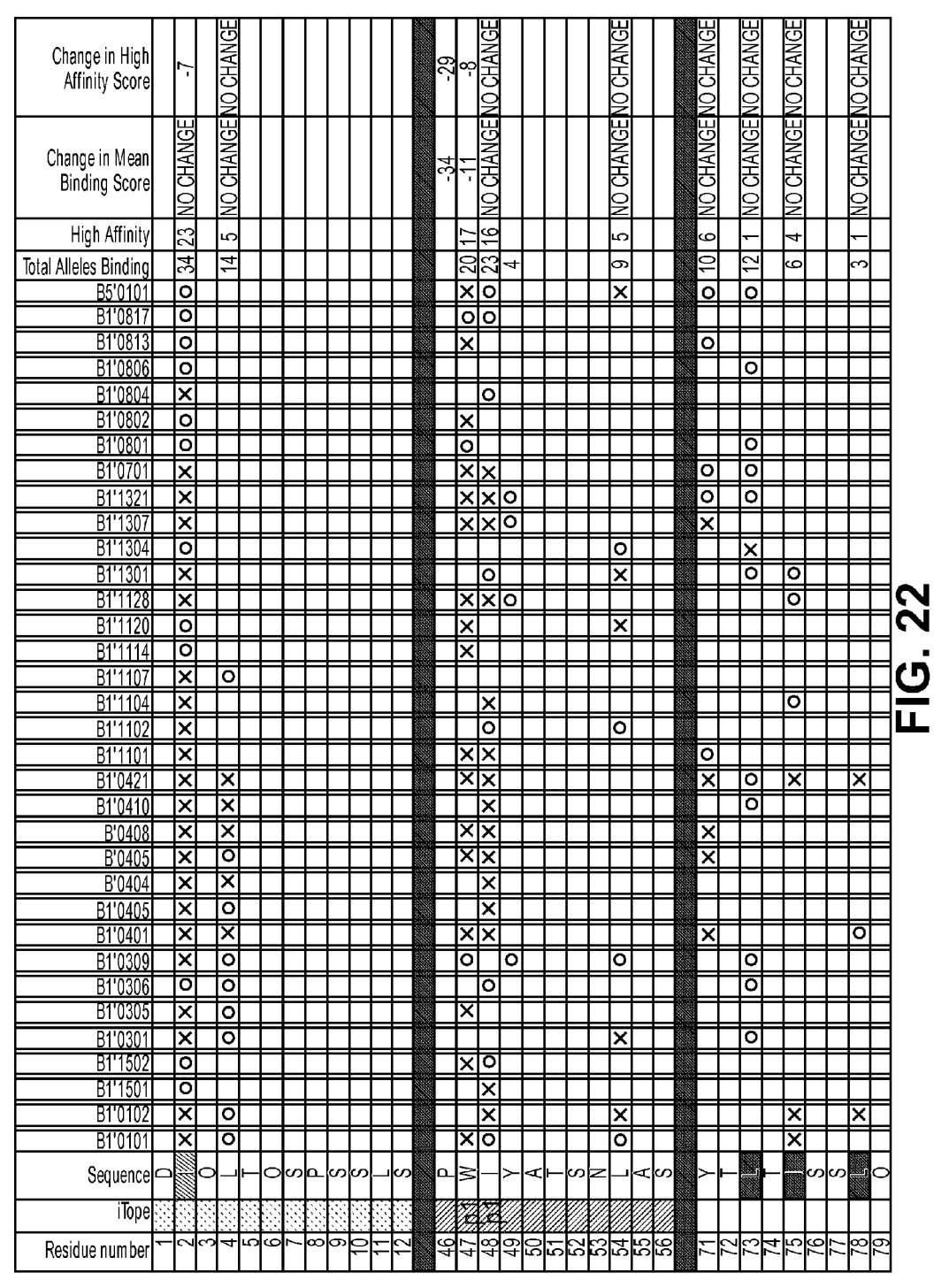

FIG. 22 illustrates analysis of the variant regions of the light chain (SEQ ID NO: 101) using iTope™. Peptides spanning the entire sequence were tested as 9 mer peptides in one amino acid increments. The predicted binding of each residue as the p1 anchor of a core 9 mer peptide to MHC class II alleles is indicated by a "O" if the binding score was 0.55-0.6 and by a "X" if the binding score was >0.6. Regions containing potentially immunogenic peptides are indicated in the "iTope" column, dark grey indicates promiscuous high affinity MHC class II binding peptides, light grey indicates promiscuous moderate affinity MHC class II binding peptides. The numbers of MHC class II alleles predicted to bind are shown in the "total" and "high affinity" columns and the difference to binding is shown. Potential p1 anchor residues identified as germline sequences are shown in reverse type in the "Sequence" column and the amino acid differences in the variants are boxed.

FIGS. 24A-C. Chimeric anti-endoglin antibody, humanized anti-endoglin antibody VK1VH1 and humanized/deimmunized anti-endoglin antibody VK1AAVH1A2 were tested in EpiScreen™ time course T cell assays using PBMC from 20 donors. Bulk cultures of PBMC incubated with test antibodies were sampled on days 5, 6, 7 and 8, and pulsed with $^3$H-Thymidine. Cells were harvested and incorporation of radioactivity measured by scintillation counting. Results for each triplicate sample were averaged and normalized by conversion to Stimulation Index (SI). The SI for each time point with each donor is shown above for the chimeric antibody TRC105 (FIG. 24A), VK1VH1 (FIG. 24B) and VK1AAVH1A2 (FIG. 24C). The cut-off for determining positive responses with an SI≥2 is highlighted by the dotted line and significant responses (p<0.05 in a student's t-test) are indicated (*).

DETAILED DESCRIPTION OF THE INVENTION

Figure 3A:
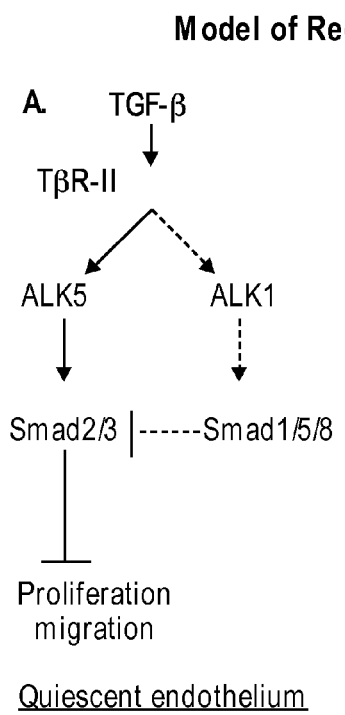
FIGS. 3A-B provide diagrams of the TGF-β/ALK5 signaling pathway. The TGF-β/ALK5 pathway (FIG. 3A) leads to inhibition of cell proliferation and migration. The TGF-β/ALK1 pathway (FIG. 3B) induces endothelial cell proliferation and migration and requires CD105 (endoglin) for ALK1 signaling. The dotted lines indicate inactive or blocked pathways. The bolded arrow indicates stimulation of a signaling pathway.

It is to be understood that this application is not limited to particular formulations or process parameters, as these may, of course, vary. It is also to be understood that the terminology used herein is for the purpose of describing particular embodiments only, and is not intended to be limiting. Further, it is understood that a number of methods and materials similar or equivalent to those described herein can be used in the practice of the present inventions.

In accordance with the present application, there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984), each of which is specifically incorporated herein by reference in its entirety.

Murine monoclonal antibodies (mAbs) have been raised against endoglin which modulate endoglin activity and thereby inhibit angiogenesis and/or inhibit vasodilation of small blood vessels. These murine antibodies are described in U.S. Pat. Nos. 5,928,641, 6,200,566, 6,190,660, and 7,097,836 which are hereby incorporated in their entirety. Additionally, the ex vivo and in vivo efficiency of a number of these antibodies has been demonstrated; these monoclonal antibodies that bind endoglin are of interest as endoglin modulating compounds. Therapeutic use of these murine antibodies is not feasible, however, as their administration has a number of limitations, including immunogenicity in, for example, the form of human anti-mouse antibodies (HAMA). Humanized antibodies are made to address these reactions.

Humanized antibodies that bind endoglin are described herein that exhibit reduced immunogenicity while maintaining and/or improving their specificity. Additionally, to address problems associated with murine antibodies, humanized antibodies that bind endoglin and decrease and/or inhibit angiogenesis are described herein that exhibit reduced immunogenicity while maintaining and/or improving their specificity. These humanized endoglin antibodies are useful for the diagnosis and treatment of various conditions and diseases as well as for purification and detection of endoglin.

I. Anti-Endoglin Antibodies

Provided herein are humanized antibodies, and antigen-binding fragments thereof that bind endoglin. Endoglin can be found on cells that comprise and support existing vasculature as well as cells that are promoting the growth of, and become part of, new vasculature. These antibodies and antigen-binding fragments can bind endoglin and thereby inhibit angiogenesis, inhibit the existing vasculature or the maintenance of the existing vasculature, and/or inhibit small vessel dilation. Hereinafter, a reference to the terms "antibody" or "antibodies" are to be considered inclusive of any of the antigen-binding fragments described herein and the terms are to be interchangeable where applicable. In addition to their use for purification of endoglin, these antibodies are useful for purification, detection and diagnostic purposes as well as therapeutic purposes. The antibodies provided herein can be used for the formulation of medicaments for the treatment a variety of conditions and diseases, methods to treat said conditions and diseases and methods of detection or diagnosis. As used herein, angiogenesis is inclusive of the growth and/or development of new blood vessels (also referred to as neovascularization), dilation of the small vessels, excessive or prolonged vascular growth, and maintenance of the existing vasculature. Angiogenesis conditions and diseases refers to those diseases and conditions related to, caused by, or associated with angiogenesis. Non-limiting examples of such diseases include, for example, various forms of ocular diseases characterized by angiogenesis/neovascularization (e.g., macular degeneration, CNV, diabetic retinopathy), diabetic nephropathy, chronic inflammatory diseases (e.g., IBD), rheumatoid arthritis, osteoarthritis, and various forms of cancer (primary tumors and metastases).

A. Antibody Terminology

As used herein, the term "antibody" refers to an immunoglobulin (Ig) whether natural or partly or wholly synthetically produced. The term also covers any polypeptide or protein having a binding domain which is, or is homologous to, an antigen-binding domain. The term further includes "antigen-binding fragments" and other interchangeable terms for similar binding fragments such as described below. Complementarity determining region (CDR) grafted antibodies and other humanized antibodies (including CDR modifications and framework region modifications) are also contemplated by this term.

Native antibodies and native immunoglobulins are usually heterotetrameric glycoproteins of about 150,000 Daltons, composed of two identical light (L) chains and two identical heavy (H) chains. Each light chain is typically linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ("$V_H$") followed by a number of constant domains ("$C_H$"). Each light chain has a variable domain at one end ("$V_L$") and a constant domain ("$C_L$") at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The terms "synthetic polynucleotide," "synthetic gene" or "synthetic polypeptide," as used herein, mean that the corresponding polynucleotide sequence or portion thereof, or amino acid sequence or portion thereof, is derived, from a sequence that has been designed, or synthesized de novo, or modified, compared to an equivalent naturally-occurring sequence. Synthetic polynucleotides (antibodies or antigen binding fragments) or synthetic genes can be prepared by methods known in the art, including but not limited to, the chemical synthesis of nucleic acid or amino acid sequences. Synthetic genes are typically different from naturally-occurring genes, either at the amino acid, or polynucleotide level, (or both) and are typically located within the context of synthetic expression control sequences. For example, synthetic gene sequences can include amino acid, or polynucleotide, sequences that have been changed, for example, by the replacement, deletion, or addition, of one or more, amino acids, or nucleotides, thereby providing an antibody amino acid sequence, or a polynucleotide coding sequence that is different from the source sequence. Synthetic gene polynucleotide sequences, may not necessarily encode proteins with different amino acids, compared to the natural gene; for example, they can also encompass synthetic polynucleotide sequences that incorporate different codons but which encode the same amino acid (i.e., the nucleotide changes represent silent mutations at the amino acid level).

With respect to antibodies, the term "variable domain" refers to the variable domains of antibodies that are used in the binding and specificity of each particular antibody for its particular antigen. However, the variability is not evenly distributed throughout the variable domains of antibodies. Rather, it is concentrated in three segments called hypervariable regions (also known as CDRs) in both the light chain and the heavy chain variable domains. More highly conserved portions of variable domains are called the "framework regions" or "FRs." The variable domains of unmodified heavy and light chains each contain four FRs (FR1, FR2, FR3 and FR4), largely adopting a β-sheet configuration interspersed with three CDRs which form loops connecting and, in some cases, part of the β-sheet structure. The CDRs in each chain are held together in close proximity by the FRs and, with the CDRs from the other chain, contribute to the formation of the antigen-binding site of antibodies (see Kabat et al., Sequences of Proteins of Immunological Interest, 5th Ed. Public Health Service, National Institutes of Health, Bethesda, Md. (1991), pages 647-669).

The terms "hypervariable region" and "CDR" when used herein, refer to the amino acid residues of an antibody which are responsible for antigen-binding. The CDRs comprise amino acid residues from three sequence regions which bind in a complementary manner to an antigen and are known as CDR1, CDR2, and CDR3 for each of the $V_H$ and $V_L$ chains. In the light chain variable domain, the CDRs typically correspond to approximately residues 24-34 (CDRL1), 50-56 (CDRL2) and 89-97 (CDRL3), and in the heavy chain variable domain the CDRs typically correspond to approximately residues 31-35 (CDRH1), 50-65 (CDRH2) and 95-102 (CDRH3) according to Kabat et al., Sequences of Proteins of Immunological Interest, 5th Ed. Public Health Service, National Institutes of Health, Bethesda, Md. (1991)). It is understood that the CDRs of different antibodies may contain insertions, thus the amino acid numbering may differ. The Kabat numbering system accounts for such insertions with a numbering scheme that utilizes letters attached to specific residues (e.g., 27A, 27B, 27C, 27D, 27E, and 27F of CDRL1 in the light chain) to reflect any insertions in the numberings between different antibodies. Alternatively, in the light chain variable domain, the CDRs typically correspond to approximately residues 26-32 (CDRL1), 50-52 (CDRL2) and 91-96 (CDRL3), and in the heavy chain variable domain, the CDRs typically correspond to approximately residues 26-32 (CDRH1), 53-55 (CDRH2) and 96-101 (CDRH3) according to Chothia and Lesk, J. Mol. Biol., 196: 901-917 (1987)).

As used herein, "framework region" or "FR" refers to framework amino acid residues that form a part of the antigen binding pocket or groove. In some embodiments, the framework residues form a loop that is a part of the antigen binding pocket or groove and the amino acids residues in the loop may or may not contact the antigen. Framework regions generally comprise the regions between the CDRs. In the light chain variable domain, the FRs typically correspond to approximately residues 0-23 (FRL1), 35-49 (FRL2), 57-88 (FRL3), and 98-109 and in the heavy chain variable domain the FRs typically correspond to approximately residues 0-30 (FRH1), 36-49 (FRH2), 66-94 (FRH3), and 103-133 according to Kabat et al., Sequences of Proteins of Immunological Interest, 5th Ed. Public Health Service, National Institutes of Health, Bethesda, Md. (1991)). As discussed above with the Kabat numbering for the light chain, the heavy chain too accounts for insertions in a similar manner (e.g., 35A, 35B of CDRH1 in the heavy chain). Alternatively, in the light chain variable domain, the FRs typically correspond to approximately residues 0-25 (FRL1), 33-49 (FRL2) 53-90 (FRL3), and 97-109 (FRL4), and in the heavy chain variable domain, the FRs typically correspond to approximately residues 0-25 (FRH1), 33-52 (FRH2), 56-95 (FRH3), and 102-113 (FRH4) according to Chothia and Lesk, J. Mol. Biol., 196: 901-917 (1987)).

The loop amino acids of a FR can be assessed and determined by inspection of the three-dimensional structure of an antibody heavy chain and/or antibody light chain. The three-dimensional structure can be analyzed for solvent accessible amino acid positions as such positions are likely to form a loop and/or provide antigen contact in an antibody variable domain. Some of the solvent accessible positions can tolerate amino acid sequence diversity and others (e.g., structural positions) are, generally, less diversified. The three dimensional structure of the antibody variable domain can be derived from a crystal structure or protein modeling.

Constant domains (Fc) of antibodies are not involved directly in binding an antibody to an antigen but, rather, exhibit various effector functions, such as participation of the antibody in antibody-dependent cellular toxicity via interactions with, for example, Fc receptors (FcR). Fc domains can also increase bioavailability of an antibody in circulation following administration to a patient.

Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., IgG1, IgG2, IgG3, IgG4, IgA1, and IgA2. The heavy-chain constant domains (Fc) that correspond to the different classes of immunoglobulins are called α, δ, ε, γ, and μ, respectively. The subunit structures and three-dimensional configurations of different classes of immunoglobulins are well known.

The "light chains" of antibodies (immunoglobulins) from any vertebrate species can be assigned to one of two clearly distinct types, called kappa or ("κ" or "K") and lambda or ("λ"), based on the amino acid sequences of their constant domains.

The terms "antigen-binding portion of an antibody," "antigen-binding fragment," "antigen-binding domain," "antibody fragment" or a "functional fragment of an antibody" are used interchangeably herein to refer to one or more fragments of an antibody that retain the ability to specifically bind to an antigen. Non-limiting examples of antibody fragments included within such terms include, but are not limited to, (i) a Fab fragment, a monovalent fragment consisting of the $V_L$, $V_H$, $C_L$ and $C_{H1}$ domains; (ii) a F(ab')$_2$ fragment, a bivalent fragment containing two Fab fragments linked by a disulfide bridge at the hinge region; (iii) a Fd fragment consisting of the $V_H$ and $C_{H1}$ domains; (iv) a FV fragment containing the $V_L$ and $V_H$ domains of a single arm of an antibody, (v) a dAb fragment (Ward et al., (1989) Nature 341:544 546), which containing a $V_H$ domain; and (vi) an isolated CDR. Additionally included in this definition are "one-half" antibodies comprising a single heavy chain and a single light chain. Other forms of single chain antibodies, such as diabodies are also encompassed herein.

"F(ab')$_2$" and "Fab'" moieties can be produced by treating an Ig with a protease such as pepsin and papain, and include antibody fragments generated by digesting immunoglobulin near the disulfide bonds existing between the hinge regions in each of the two heavy chains. For example, papain cleaves IgG upstream of the disulfide bonds existing between the hinge regions in each of the two heavy chains to generate two homologous antibody fragments in which an light chain composed of $V_L$ and $C_L$ (light chain constant region), and a heavy chain fragment composed of $V_H$ and $C_{H\gamma1}$ (γ1) region in the constant region of the heavy chain) are connected at their C terminal regions through a disulfide bond. Each of these two homologous antibody fragments is called Fab'. Pepsin also cleaves IgG downstream of the disulfide bonds existing between the hinge regions in each of the two heavy chains to generate an antibody fragment slightly larger than the fragment in which the two above-mentioned Fab' are connected at the hinge region. This antibody fragment is called F(ab')$_2$.

The Fab fragment also contains the constant domain of the light chain and the first constant domain ($C_H1$) of the heavy chain. Fab' fragments differ from Fab fragments by the addition of a few residues at the carboxyl terminus of the heavy chain $C_H1$ domain including one or more cysteine(s) from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

"Fv" refers to an antibody fragment which contains a complete antigen-recognition and antigen-binding site. This region consists of a dimer of one heavy chain and one light chain variable domain in tight, non-covalent or covalent association (disulfide linked Fv's have been described in the art, Reiter et al. (1996) Nature Biotechnology 14:1239-1245). It is in this configuration that the three CDRs of each variable domain interact to define an antigen-binding site on the surface of the $V_H$-$V_L$ dimer. Collectively, a combination of one or more of the CDRs from each of the $V_H$ and $V_L$ chains confer antigen-binding specificity to the antibody. For example, it would be understood that, for example, the CDRH3 and CDRL3 could be sufficient to confer antigen-binding specificity to an antibody when transferred to $V_H$ and $V_L$ chains of a recipient antibody or antigen-binding fragment thereof and this combination of CDRs can be tested for binding, affinity, etc. using any of the techniques described herein. Even a single variable domain (or half of an Fv comprising only three CDRs specific for an antigen) has the ability to recognize and bind antigen, although likely at a lower affinity than when combined with a second variable domain. Furthermore, although the two domains of a Fv fragment ($V_L$ and $V_H$), are coded for by separate genes, they can be joined using recombinant methods by a synthetic linker that enables them to be made as a single protein chain in which the $V_L$ and $V_H$ regions pair to form monovalent molecules (known as single chain Fv (scFv); Bird et al. (1988) Science 242:423-426; Huston et al. (1988) Proc. Natl. Acad. Sci. USA 85:5879-5883; and Osbourn et al. (1998) Nat. Biotechnol. 16:778). Such scFvs are also intended to be encompassed within the term "antigen-binding portion" of an antibody. Any $V_H$ and $V_L$ sequences of specific scFv can be linked to an Fc region cDNA or genomic sequences, in order to generate expression vectors encoding complete Ig (e.g., IgG) molecules or other isotypes. $V_H$ and $V_L$ can also be used in the generation of Fab, Fv or other fragments of Igs using either protein chemistry or recombinant DNA technology.

"Single-chain Fv" or "sFv" antibody fragments comprise the $V_H$ and $V_L$ domains of an antibody, wherein these domains are present in a single polypeptide chain. In some embodiments, the Fv polypeptide further comprises a polypeptide linker between the $V_H$ and $V_L$ domains which enables the sFv to form the desired structure for antigen binding. For a review of sFvs see, e.g., Pluckthun in The Pharmacology of Monoclonal Antibodies, Vol. 113, Rosenburg and Moore eds. Springer-Verlag, New York, pp. 269-315 (1994).

The term "AVIMER™" refers to a class of therapeutic proteins of human origin, which are unrelated to antibodies and antibody fragments, and are composed of several modular and reusable binding domains, referred to as A-domains (also referred to as class A module, complement type repeat, or LDL-receptor class A domain). They were developed from human extracellular receptor domains by in vitro exon shuffling and phage display (Silverman et al., 2005, Nat. Biotechnol. 23:1493-1494; Silverman et al., 2006, Nat. Biotechnol. 24:220). The resulting proteins can contain multiple independent binding domains that can exhibit improved affinity (in some cases, sub-nanomolar) and specificity compared with single-epitope binding proteins. See, for example, U.S. Patent Application Publ. Nos. 2005/0221384, 2005/0164301, 2005/0053973 and 2005/0089932, 2005/0048512, and 2004/0175756, each of which is hereby incorporated by reference herein in its entirety.

Each of the known 217 human A-domains comprises ~35 amino acids (~4 kDa); and these domains are separated by linkers that average five amino acids in length. Native A-domains fold quickly and efficiently to a uniform, stable structure mediated primarily by calcium binding and disulfide formation. A conserved scaffold motif of only 12 amino acids is required for this common structure. The end result is a single protein chain containing multiple domains, each of which represents a separate function. Each domain of the proteins binds independently and the energetic contributions of each domain are additive. These proteins were called "AVIMERs™" from avidity multimers.

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA 90:6444 6448 (1993).

Antigen-binding polypeptides also include heavy chain dimers such as, for example, antibodies from camelids and sharks. Camelid and shark antibodies comprise a homodimeric pair of two chains of V-like and C-like domains (neither has a light chain). Since the $V_H$ region of a heavy chain dimer IgG in a camelid does not have to make hydrophobic interactions with a light chain, the region in the heavy chain that normally contacts a light chain is changed to hydrophilic amino acid residues in a camelid. $V_H$ domains of heavy-chain dimer IgGs are called $V_{HH}$ domains. Shark Ig-NARs comprise a homodimer of one variable domain (termed a V-NAR domain) and five C-like constant domains (C-NAR domains). In camelids, the diversity of antibody repertoire is determined by the CDRs 1, 2, and 3 in the $V_H$ or $V_{HH}$ regions. The CDR3 in the camel $V_{HH}$ region is characterized by its relatively long length, averaging 16 amino acids (Muyldermans et al., 1994, Protein Engineering 7(9): 1129). This is in contrast to CDR3 regions of antibodies of many other species. For example, the CDR3 of mouse $V_H$ has an average of 9 amino acids. Libraries of camelid-derived antibody variable regions, which maintain the in vivo diversity of the variable regions of a camelid, can be made by, for example, the methods disclosed in U.S. Patent Application Ser. No. 20050037421.

"Humanized" forms of non-human (e.g., murine) antibodies include chimeric antibodies which contain minimal sequence derived from a non-human Ig. For the most part, humanized antibodies are human Igs (recipient antibody) in which one or more of the CDRs of the recipient are replaced by CDRs from a non-human species antibody (donor antibody) such as mouse, rat, rabbit or non-human primate having the desired specificity, affinity and binding function. In some instances, one or more FR amino acid residues of the human Ig are replaced by corresponding non-human amino acid residues. Furthermore, humanized antibodies can contain residues which are not found in the recipient antibody or in the donor antibody. These modifications can be made to refine antibody performance, if needed. A humanized antibody can comprise substantially all of at least one and, in some cases two, variable domains, in which all or substantially all of the hypervariable regions correspond to those of a non-human immunoglobulin and all, or substantially all, of the FRs are those of a human immunoglobulin sequence. The humanized antibody optionally can also include at least a portion of an immunoglobulin constant region (Fc), typically that of a human immunoglobulin. For details, see Jones et al., Nature 321: 522-525 (1986); Reichmann et al., Nature 332: 323-329 (1988); and Presta, Curr. Op. Struct. Biol. 2: 593-596 (1992).

A humanized antibody also includes antibodies in which part, or all of the CDRs of the heavy and light chain are derived from a non-human monoclonal antibody, substantially all the remaining portions of the variable regions are derived from human variable region (both heavy and light chain), and the constant regions are derived from a human constant region. In one embodiment, the CDR1, CDR2 and CDR3 regions of the heavy and light chains are derived from a non-human antibody. In yet another embodiment, at least one CDR (e.g., a CDR3) of the heavy and light chains is derived from a non-human antibody. Various combinations of CDR1, CDR2, and CDR3 can be derived from a non-human antibody and are contemplated herein. In one non-limiting example, one or more of the CDR1, CDR2 and CDR3 regions of each of the heavy and light chains are derived from a murine chimeric monoclonal antibody clone TRC105.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations, which can include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, monoclonal antibodies can be made by the hybridoma method first described by Kohler et al., Nature 256:495 (1975), or can be made by recombinant DNA methods (see, e.g., U.S. Pat. No. 4,816,567). In certain embodiments, the monoclonal antibodies can be isolated from phage antibody libraries using the techniques described in Clackson et al., Nature 352:624-628 (1991) and Marks et al., J. Mol. Biol. 222:581-597 (1991), for example.

Antibodies can be isolated and purified from the culture supernatant or ascites mentioned above by saturated ammonium sulfate precipitation, euglobulin precipitation method, caproic acid method, caprylic acid method, ion exchange chromatography (DEAE or DE52), or affinity chromatography using anti-Ig column or a protein A, G or L column such as described in more detail below.

Exemplary antibodies for use in the compositions and methods described herein are intact immunoglobulin molecules, such as, for example, a humanized antibody or those portions of a humanized Ig molecule that contain the antigen binding site (i.e., paratope) or a single heavy chain and a single light chain, including those portions known in the art as Fab, Fab', F(ab)', F(ab')$_2$, Fd, scFv, a variable heavy domain, a variable light domain, a variable NAR domain, bi-specific scFv, a bi-specific Fab$_2$, a tri-specific Fab$_3$ and a single chain binding polypeptides and others also referred to as antigen-binding fragments. When constructing an immunoglobulin molecule or fragments thereof, variable regions or portions thereof may be fused to, connected to, or otherwise joined to one or more constant regions or portions thereof to produce any of the antibodies or fragments thereof described herein. This may be accomplished in a variety of ways known in the art, including but not limited to, molecular cloning techniques or direct synthesis of the nucleic acids encoding the molecules. Exemplary non-limiting methods of constructing these molecules can also be found in the examples described herein.

In one exemplary embodiment, the application contemplates a single chain binding polypeptide having a heavy chain variable region, and/or a light chain variable region which binds endoglin and has, optionally, an immunoglobulin Fc region. In one exemplary embodiment, the application contemplates a single chain binding polypeptide having a heavy chain variable region, and/or a light chain variable region which binds endoglin and inhibits angiogenesis and has, optionally, an immunoglobulin Fc region. Such a molecule is a single chain variable fragment optionally having effector function or increased half-life through the presence of the immunoglobulin Fc region. Methods of preparing single chain binding polypeptides are known in the art (e.g., U.S. Patent Application No. 2005/0238646).

The terms "germline gene segments" or "germline sequences" refer to the genes from the germline (the haploid gametes and those diploid cells from which they are formed). The germline DNA contains multiple gene segments that encode a single Ig heavy or light chain. These gene segments are carried in the germ cells but cannot be transcribed and translated into heavy and light chains until they are arranged into functional genes. During B-cell differentiation in the bone marrow, these gene segments are randomly shuffled by a dynamic genetic system capable of generating more than $10^8$ specificities. Most of these gene segments are published and collected by the germline database.

As used herein, "immunoreactive" refers to binding agents, antibodies or fragments thereof that are specific to a sequence of amino acid residues ("binding site" or "epitope"), yet if are cross-reactive to other peptides/proteins, are not toxic at the levels at which they are formulated for administration to human use. The term "binding" refers to a direct association between two molecules, due to, for example, covalent, electrostatic, hydrophobic, and ionic and/or hydrogen-bond interactions under physiological conditions, and including interactions such as salt bridges and water bridges and any other conventional binding means. The term "preferentially binds" means that the binding agent binds to the binding site with greater affinity than it binds unrelated amino acid sequences. Preferably such affinity is at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater than the affinity of the binding agent for unrelated amino acid sequences. The terms "immunoreactive" and "preferentially binds" are used interchangeably herein.

As used herein, the term "affinity" refers to the equilibrium constant for the reversible binding of two agents and is expressed as $K_D$. Affinity of a binding protein to a ligand such as affinity of an antibody for an epitope can be, for example, from about 100 nanomolar (nM) to about 0.1 nM, from about 100 nM to about 1 picomolar (pM), or from about 100 nM to about 1 femtomolar (fM). As used herein, the term "avidity" refers to the resistance of a complex of two or more agents to dissociation after dilution. Apparent affinities can be determined by methods such as an enzyme linked immunosorbent assay (ELISA) or any other technique familiar to one of skill in the art. Avidities can be determined by methods such as a Scatchard analysis or any other technique familiar to one of skill in the art.

"Epitope" refers to that portion of an antigen or other macromolecule capable of forming a binding interaction with the variable region binding pocket of an antibody. Such binding interactions can be manifested as an intermolecular contact with one or more amino acid residues of one or more CDRs. Antigen binding can involve, for example, a CDR3 or a CDR3 pair or, in some cases, interactions of up to all six CDRs of the $V_H$ and $V_L$ chains. An epitope can be a linear peptide sequence (i.e., "continuous") or can be composed of noncontiguous amino acid sequences (i.e., "conformational" or "discontinuous"). An antibody can recognize one or more amino acid sequences; therefore an epitope can define more than one distinct amino acid sequence. Epitopes recognized by antibodies can be determined by peptide mapping and sequence analysis techniques well known to one of skill in the art. Binding interactions are manifested as intermolecular contacts with one or more amino acid residues of a CDR. TRC105 is a chimeric antibody which is the same variable amino acid sequence as the murine antibody described as Y4-2F1 or SN6j in U.S. Pat. Nos. 5,928,641; 6,200,566; 6,190,660; and 7,097,836. Epitopes recognized by Y4-2F1 and SN6j, and thus TRC105, have been previously identified.

The term "specific" refers to a situation in which an antibody will not show any significant binding to molecules other than the antigen containing the epitope recognized by the antibody. The term is also applicable where for example, an antigen binding domain is specific for a particular epitope which is carried by a number of antigens, in which case the antibody or antigen-binding fragment thereof carrying the antigen binding domain will be able to bind to the various antigens carrying the epitope. The terms "preferentially binds" or "specifically binds" mean that the antibodies or fragments thereof bind to an epitope with greater affinity than it binds unrelated amino acid sequences, and, if cross-reactive to other polypeptides containing the epitope, are not toxic at the levels at which they are formulated for administration to human use. In one aspect, such affinity is at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater than the affinity of the antibody or fragment thereof for unrelated amino acid sequences. The terms "immunoreactive," "binds," "preferentially binds" and "specifically binds" are used interchangeably herein. The term "binding" refers to a direct association between two molecules, due to, for example, covalent, electrostatic, hydrophobic, and ionic and/or hydrogen-bond interactions under physiological conditions, and includes interactions such as salt bridges and water bridges, as well as any other conventional means of binding.

The phrase "conservative amino acid substitution" refers to grouping of amino acids on the basis of certain common properties. A functional way to define common properties between individual amino acids is to analyze the normalized frequencies of amino acid changes between corresponding proteins of homologous organisms (Schulz, G. E. and R. H. Schirmer, Principles of Protein Structure, Springer-Verlag). According to such analyses, groups of amino acids may be defined where amino acids within a group exchange preferentially with each other, and therefore resemble each other most in their impact on the overall protein structure (Schulz, G. E. and R. H. Schirmer, Principles of Protein Structure, Springer-Verlag). Examples of amino acid groups defined in this manner include:

(i) a charged group, consisting of Glu and Asp, Lys, Arg and His,
(ii) a positively-charged group, consisting of Lys, Arg and His,
(iii) a negatively-charged group, consisting of Glu and Asp,
(iv) an aromatic group, consisting of Phe, Tyr and Trp,
(v) a nitrogen ring group, consisting of His and Trp,
(vi) a large aliphatic non-polar group, consisting of Val, Leu and Ile,
(vii) a slightly-polar group, consisting of Met and Cys,
(viii) a small-residue group, consisting of Ser, Thr, Asp, Asn, Gly, Ala, Glu, Gln and Pro,
(ix) an aliphatic group consisting of Val, Leu, Ile, Met and Cys, and
(x) a small hydroxyl group consisting of Ser and Thr.

In addition to the groups presented above, each amino acid residue may form its own group, and the group formed by an individual amino acid may be referred to simply by the one and/or three letter abbreviation for that amino acid commonly used in the art as described above.

A "conserved residue" is an amino acid that is relatively invariant across a range of similar proteins. Often conserved residues will vary only by being replaced with a similar amino acid, as described above for "conservative amino acid substitution."

The letter "x" or "xaa" as used in amino acid sequences herein is intended to indicate that any of the twenty standard amino acids may be placed at this position unless specifically noted otherwise. For the purposes of peptidomimetic design, an "x" or a "xaa" in an amino acid sequence may be replaced by a mimic of the amino acid present in the target sequence, or the amino acid may be replaced by a spacer of essentially any form that does not interfere with the activity of the peptidomimetic.

"Homology" or "identity" or "similarity" refers to sequence similarity between two peptides or between two nucleic acid molecules. Homology and identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology/similarity or identity refers to a function of the number of identical or similar amino acids at positions shared by the compared sequences. A sequence which is "unrelated" or "non-homologous" shares less than 40% identity, though preferably less than 25% identity with a sequence of the present invention. In comparing two sequences, the absence of residues (amino acids or nucleic acids) or presence of extra residues also decreases the identity and homology/similarity.

The term "homology" describes a mathematically based comparison of sequence similarities which is used to identify genes or proteins with similar functions or motifs. The nucleic acid (nucleotide, oligonucleotide) and amino acid (protein) sequences of the present invention may be used as a "query sequence" to perform a search against public databases to, for example, identify other family members, related sequences or homologs. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to nucleic acid molecules of the invention. BLAST amino acid searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and BLAST) can be used (see, www.ncbi.nlm.nih.gov).

As used herein, "identity" means the percentage of identical nucleotide or amino acid residues at corresponding positions in two or more sequences when the sequences are aligned to maximize sequence matching, i.e., taking into account gaps and insertions. Identity can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., Nucleic Acids Research 12(1): 387 (1984)), BLASTP, BLASTN, and FASTA (Altschul, S. F. et al., J. Molec. Biol. 215: 403-410 (1990) and Altschul et al. Nuc. Acids Res. 25: 3389-3402 (1997)). The BLAST X program is publicly available from NCBI and other sources (BLAST Manual, Altschul, S., et al., NCBI NLM NIH Bethesda, Md. 20894; Altschul, S., et al., J. Mol. Biol. 215: 403-410 (1990). The well known Smith Waterman algorithm may also be used to determine identity.

"Isolated" (used interchangeably with "substantially pure") when applied to polypeptides means a polypeptide or a portion thereof which, by virtue of its origin or manipulation: (i) is present in a host cell as the expression product of a portion of an expression vector; or (ii) is linked to a protein or other chemical moiety other than that to which it is linked in nature; or (iii) does not occur in nature, for example, a protein that is chemically manipulated by appending, or adding at least one hydrophobic moiety to the protein so that the protein is in a form not found in nature. By "isolated" it is further meant a protein that is: (i) synthesized chemically; or (ii) expressed in a host cell and purified away from associated and contaminating proteins. The term generally means a polypeptide that has been separated from other proteins and nucleic acids with which it naturally occurs. Preferably, the polypeptide is also separated from substances such as antibodies or gel matrices (polyacrylamide) which are used to purify it.

As used herein, the terms "angiogenesis inhibitory," "angiogenesis inhibiting" or "anti-angiogenic" include vasculogenesis, and are intended to mean effecting a decrease in the extent, amount, or rate of neovascularization. Effecting a decrease in the extent, amount, or rate of endothelial cell proliferation or migration in the tissue is a specific example of inhibiting angiogenesis.

The term "angiogenesis inhibitory composition" refers to a composition which inhibits angiogenesis-mediated processes such as endothelial cell migration, proliferation, tube formation and subsequently leading to the inhibition of the generation of new blood vessels from existing ones, and consequently affects angiogenesis-dependent conditions.

As used herein, the term "angiogenesis-dependent condition" is intended to mean a condition where the process of angiogenesis or vasculogenesis sustains or augments a pathological condition or beneficially influences normal physiological processes. Therefore, treatment of an angiogenesis-dependent condition in which angiogenesis sustains a pathological condition could result in mitigation of disease, while treatment of an angiogenesis-dependent condition in which angiogenesis beneficially influences normal physiological processes could result in, e.g., enhancement of a normal process.

Angiogenesis is the formation of new blood vessels from pre-existing capillaries or post-capillary venules. Vasculogenesis results from the formation of new blood vessels arising from angioblasts which are endothelial cell precursors. Both processes result in new blood vessel formation and are included in the meaning of the term angiogenesis-dependent conditions. The term "angiogenesis" as used herein is intended to include de novo formation of vessels such as that arising from vasculogenesis as well as those arising from branching and sprouting of existing vessels, capillaries and venules. Angiogenesis can also be inclusive of induction of ALK1 signaling and related Smad 1/5/8 phosphorylation and/or signaling. CD105 is also known to be involved in the ALK1 signaling pathway and is thus also included within the meaning of angiogenesis.

"Inducing a host immune response" means that a patient experiences alleviation or reduction of signs or symptoms of illness, and specifically includes, without limitation, prolongation of survival. In certain preferred embodiments of the methods according to the invention, a CD8+IFN-γ producing T cell is activated to induce a cytotoxic T lymphocyte (CTL) immune response in the patient administered the antagonist. In certain embodiments of the methods according to the invention, a CD4+IFN-γ producing T cell is activated to induce a helper T cell immune response in the patient administered with the composition. These activated CD4+IFN-γ producing T cells (i.e., helper T cells) provide necessary immunological help (e.g., by release of cytokines) to induce and maintain not only CTL, but also a humoral immune response mediated by B cells. Thus, in certain embodiments of the methods according to the invention, a humoral response to the antigen is activated in the patient administered with the composition. In one aspect, an adjuvant may be added to the composition to increase an immune response. Adjuvants are well-known in the art.

Activation of a CD8+ and/or CD4+ T cells means causing T cells that have the ability to produce cytokines (e.g., IFN-γ) to actually produce one or more cytokine(s), or to increase their production of one or more cytokine(s). "Induction of CTL response" means causing potentially cytotoxic T lymphocytes to exhibit antigen specific cytotoxicity. "Antigen specific cytotoxicity" means cytotoxicity against a cell presenting an antigen that is associated with the antigen associated with the cancer that is greater than an antigen that is not associated with a cancer. "Cytotoxicity" refers to the ability of the cytotoxic T lymphocyte to kill a target cell. Such antigen-specific cytotoxicity can be at least about 3-fold, at least about 10-fold greater, at least about 100-fold greater or more than cytotoxicity against a cell not presenting the antigen not associated with the cancer. Antibody dependent cell-mediated cytotoxicity (ADCC) also includes activation of natural killer cells ("NK cells") which mediate cell killing via antibody binding. The antibodies and antigen-binding fragments described herein can mediate ADCC via NK cells through the binding of endoglin.

As used herein, the terms "proliferative disorder" and "proliferative condition" mean any pathological or non-pathological physiological condition characterized by aberrant or undesirable proliferation. The terms "cell proliferative disorder" and "cell proliferative condition" mean any pathological or non-pathological physiological condition characterized by aberrant or undesirable cell proliferation, as well as including conditions characterized by undesirable or unwanted cell proliferation or cell survival (e.g., due to deficient apoptosis), conditions characterized by deficient or aberrant or deficient apoptosis, as well as conditions characterized by aberrant or undesirable or unwanted cell survival. The term "differentiative disorder" means any pathological or non-pathological physiological condition characterized by aberrant or deficient differentiation.

Proliferative or differentiative disorders amenable to treatment include diseases and non-pathological physiological conditions, benign and neoplastic, characterized by abnormal or undesirable cell numbers, cell growth or cell survival. Such disorders or conditions may therefore constitute a disease state and include all types of cancerous growths or oncogenic processes, metastatic tissues or malignantly transformed cells, tissues, or organs, or may be non-pathologic, i.e., a deviation from normal but which is not typically associated with disease. A specific example of a non-pathologic condition that may be treated in accordance with the invention is tissue re-growth from wound repair that results in scarring.

Cells comprising the proliferative or differentiative disorder may be aggregated in a cell mass or be dispersed. The term "solid tumor" refers to neoplasias or metastases that typically aggregate together and form a mass. Particular examples include visceral tumors such as gastric or colon cancer, hepatomas, venal carcinomas, lung and brain tumors/cancers. A "non-solid tumor" refers to neoplasias of the hematopoietic system, such as lymphomas, myelomas and leukemias, or neoplasias that are diffuse in nature, as they do not typically form a solid mass. Particular examples of leukemias include for example, acute and chronic lymphoblastic, myeloblastic and multiple myeloma.

Such disorders include neoplasms or cancers, which can affect virtually any cell or tissue type, e.g., carcinoma, sarcoma, melanoma, metastatic disorders or hematopoietic neoplastic disorders. A metastatic tumor can arise from a multitude of primary tumor types, including but not limited to breast, lung, thyroid, head and neck, brain, lymphoid, gastrointestinal (mouth, esophagus, stomach, small intestine, colon, rectum), genito-urinary tract (uterus, ovary, cervix, bladder, testicle, penis, prostate), kidney, pancreas, liver, bone, muscle, skin, etc.

Carcinomas refer to malignancies of epithelial or endocrine tissue, and include respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from the cervix, lung, prostate, breast, head and neck, colon, liver and ovary. The term also includes carcinosarcomas, e.g., which include malignant tumors composed of carcinomatous and sarcomatous tissues. Adenocarcinoma includes a carcinoma of a glandular tissue, or in which the tumor forms a gland like structure.

An ocular tissue to be treated is, for example, a retinal tissue of a patient with diabetic retinopathy, macular degeneration or neovascular glaucoma and the angiogenesis to be inhibited is retinal tissue angiogenesis where there is neovascularization of retinal tissue.

A cancerous tissue to be treated is, for example, an endothelial tissue expressing an abnormal level of endoglin. As used herein, the term "transformed cells" refers to cells that have spontaneously converted to a state of unrestrained growth, i.e., they have acquired the ability to grow through an indefinite number of divisions in culture. Transformed cells may be characterized by such terms as neoplastic, anaplastic and/or hyperplastic, with respect to their loss of growth control. For purposes of this invention, the terms "transformed phenotype of malignant mammalian cells" and "transformed phenotype" are intended to encompass, but not be limited to, any of the following phenotypic traits associated with cellular transformation of mammalian cells: immortalization, morphological or growth transformation, and tumorigenicity, as detected by prolonged growth in cell culture, growth in semi-solid media, or tumorigenic growth in immuno-incompetent or syngeneic animals.

The term "tumor cell antigen" is defined herein as an antigen that is present in higher quantities on a tumor cell or in body fluids than unrelated tumor cells, normal cells, or in normal body fluid. The antigen presence may be tested by any number of assays known to those skilled in the art and include without limitation negative and/or positive selection with antibodies, such as an ELISA assay, a radioimmunoassay, or by Western Blot.

The terms "apoptosis" or "programmed cell death," refers to the physiological process by which unwanted or useless cells are eliminated during development and other normal biological processes. Apoptosis is a mode of cell death that occurs under normal physiological conditions and the cell is an active participant in its own demise ("cellular suicide"). It is most often found during normal cell turnover and tissue homeostasis, embryogenesis, induction and maintenance of immune tolerance, development of the nervous system and endocrine-dependent tissue atrophy. Cells undergoing apoptosis show characteristic morphological and biochemical features. These features include chromatin aggregation, nuclear and cytoplasmic condensation, partition of cytoplasm and nucleus into membrane bound vesicles (apoptotic bodies), which contain ribosomes, morphologically intact mitochondria and nuclear material. In vivo, these apoptotic bodies are rapidly recognized and phagocytized by macrophages, dendritic cells or adjacent epithelial cells. Due to this efficient mechanism for the removal of apoptotic cells in vivo no inflammatory response is elicited. In vitro, the apoptotic bodies as well as the remaining cell fragments ultimately swell and finally lyse. This terminal phase of in vitro cell death has been termed "secondary necrosis." Apoptosis can be measured by methods known to those skilled in the art like DNA fragmentation, exposure of Annexin V, activation of caspases, release of cytochrome c, etc. A cell that has been induced to die is termed herein as an "apoptotic cell."

"Apoptosis inducing agent" is defined herein to induce apoptosis/programmed cell death, and include, for example, irradiation, chemotherapeutic agents or receptor ligation agents, wherein cells, for example, tumor cells are induced to undergo programmed cell death. Exemplary apoptosis inducing agents are described in more detail below.

Apoptosis can be tested using a standard Annexin V Apoptosis Assay: NIH:OVCAR-3 cells are grown in 6-well plates (NUNC) and irradiated or treated with an antagonist (or in combination with another anti-cancer drug) for 4-48 hours, washed and stained with Annexin V-FITC (BD-Pharmingen) for 1 hour. Cells are analyzed by flow cytometry (Becton-Dickinson, CellQuest), counterstained with Propidium Iodide and analyzed again in the flow cytometer.

B. Methods of Making and Expressing Humanized Anti-Endoglin Antibodies

A chimeric monoclonal antibody has been developed that binds endoglin. This antibody is designated TR105 (also known as c-SN6j).

In one aspect, the antibodies and antigen-binding fragments thereof described herein were created by humanization of the $V_L$ and $V_H$ sequences of the chimeric monoclonal TRC105 antibody (SEQ ID NOS. 1 and 39, respectively).

Humanized immunoglobulins, including humanized antibodies, have been constructed by means of genetic engineering. Most humanized immunoglobulins that have been previously described have comprised a framework that is identical to the framework of a particular human immunoglobulin chain (i.e., an acceptor or recipient), and three CDRs from a non-human (i.e., donor) immunoglobulin chain. As described herein, humanization can also include criteria by which a limited number of amino acids in the framework of a humanized immunoglobulin chain are identified and chosen to be the same as the amino acids at those positions in the donor rather than in the acceptor, in order to increase or maintain the affinity of an antibody comprising the humanized immunoglobulin chain.

The present invention is based in part on the model that two contributing causes of the loss of affinity in prior means of producing humanized antibodies (using as examples mouse antibodies as the source of CDRs) are: (1) when the mouse CDRs are combined with a human framework, the amino acids in the frameworks close to the CDRs become human instead of mouse. Without intending to be bound by theory, these changed amino acids may slightly distort the CDRs (e.g., they may create different electrostatic or hydrophobic forces than in the donor mouse antibody, and the distorted-CDRs may not make as effective contacts with the antigen as the CDRs did in the donor antibody); (2) also, amino acids in the original mouse antibody that are close to, but not part of, the CDRs (i.e., still part of the framework), may make contacts with the antigen that contribute to affinity. These amino acids are lost when the antibody is humanized because, generally, all framework amino acids are made human. To circumvent these issues, and to produce humanized antibodies that have a very strong affinity for a desired antigen, humanized antibodies and antigen-binging fragments thereof can be constructed using one or more of the following principles.

One non-limiting principle is that, for example, as acceptor, a framework is used from a particular human immunoglobulin that is unusually homologous to the donor immunoglobulin to be humanized, or use a consensus framework from many human antibodies is used as an acceptor. For example, comparison of the sequence of a mouse heavy (or light) chain variable region against human heavy (or light) variable regions in a data bank (for example, the National Biomedical Research Foundation Protein Identification Resource or the protein sequence database of the National Center for Biotechnology Information—NCBI) shows that the extent of homology to different human regions can vary greatly, for example from about 40% to about 60%, about 70%, about 80% or higher. By choosing as the acceptor immunoglobulin one of the human heavy chain variable regions that is most homologous to the heavy chain variable region of the donor immunoglobulin, fewer amino acids will be changed in going from the donor immunoglobulin to the humanized immunoglobulin. By choosing as the acceptor immunoglobulin one of the human light chain variable regions that is most homologous to the light chain variable region of the donor immunoglobulin, fewer amino acids will be changed in going from the donor immunoglobulin to the humanized immunoglobulin. Generally, using such techniques, there is a reduced chance of changing an amino acid near one or more of the CDRs that distorts their conformation. Moreover, the precise overall shape of a humanized antibody comprising the humanized immunoglobulin chain may more closely resemble the shape of the donor antibody, thereby also reducing the chance of distorting the CDRs.

One can also use light and heavy chains from the same human antibody as acceptor sequences, to improve the likelihood that the humanized light and heavy chains will make favorable contacts with each other. Alternatively, one can also use light and heavy chains from different human antibody germline sequences as acceptor sequences; when such combinations are used, one can readily determine whether the $V_H$ and $V_L$ bind an epitope of interest using conventional assays (e.g., an ELISA). In one example, the human antibody will be chosen in which the light and heavy chain variable regions sequences, taken together, are overall most homologous to the donor light and heavy chain variable region sequences. Sometimes greater weight will be given to the heavy chain sequence. Regardless of how the acceptor immunoglobulin is chosen, higher affinity can, in some cases, be achieved by selecting a small number of amino acids in the framework of the humanized immunoglobulin chain to be the same as the amino acids at those positions in the donor rather than in the acceptor. Methods of affinity maturation are known in the art.

Humanized antibodies generally have at least three potential advantages over mouse or chimeric antibodies for use in human therapy. Because the effector portion of an antibody is human, it is believed to interact better with the other parts of the human immune system (e.g., destroy the target cells more efficiently by complement-dependent cytotoxicity (CDC) or antibody-dependent cellular cytotoxicity (ADCC)). Additionally, the human immune system should not recognize the framework or constant region of the humanized antibody as foreign, and therefore the antibody response against such an injected antibody should be less than against a totally foreign mouse antibody or a partially foreign chimeric antibody. Finally, mouse antibodies are known to have a half-life in the human circulation that is much shorter than the half-life of human antibodies. Humanized antibodies can, presumably, have a half-life more similar to naturally-occurring human antibodies, allowing smaller and less frequent doses to be given.

Humanization of antibodies and antigen-binding fragments thereof, can be accomplished via a variety of methods known in the art and described herein. Similarly, production of humanized antibodies can also be accomplished via methods known in the art and described herein.

Methods for modifications of framework regions are known in the art and are contemplated herein. Selection of one or more relevant framework amino acid positions to altered depends on a variety of criteria. One criterion for selecting relevant framework amino acids to change can be the relative differences in amino acid framework residues between the donor and acceptor molecules. Selection of relevant framework positions to alter using this approach has the advantage of avoiding any subjective bias in residue determination or any bias in CDR binding affinity contribution by the residue.

Another criterion that can be used for determining the relevant amino acid positions to change can be, for example, selection of framework residues that are known to be important or to contribute to CDR conformation. For example, canonical framework residues are important for CDR conformation and/or structure. Targeting of a canonical framework residue as a relevant position to change can be used to identify a more compatible amino acid residue in context with its associated donor CDR sequence.

The frequency of an amino acid residue at a particular framework position is another criterion which can be used for selecting relevant framework amino acid positions to change. For example, comparison of the selected framework with other framework sequences within its subfamily can reveal residues that occur at minor frequencies at a particular position or positions. Positions harboring less abundant residues are similarly applicable for selection as a position to alter in the acceptor variable region framework.

The relevant amino acid positions to change also can be selected, for example, based on proximity to a CDR. In certain contexts, FR residues can participate in CDR conformation and/or antigen binding. Moreover, this criterion can similarly be used to prioritize relevant positions selected by other criteria described herein. Therefore, differentiating between residues proximal and distal to one or more CDRs represents one way to reduce the number of relevant positions to change.

Other criteria for selecting relevant amino acid framework positions to alter include, for example, residues that are known or predicted to reside in a three dimensional space near the antigen-CDR interface or predicted to modulate CDR activity. Similarly, framework residues that are known to, or predicted to, form contacts between the heavy ($V_H$) and light ($V_L$) chain variable region interface can be selected. Such framework positions can affect the conformation and/or affinity of a CDR by modulating the CDR binding pocket, antigen (epitope) interaction or the $V_H$ and $V_L$ interaction. Therefore, selection of these amino acid positions for constructing a diverse population for screening of binding activity can be used to identify framework changes which replace residues having detrimental effects on CDR conformation or compensate for detrimental effects of residues occurring elsewhere in the framework.

Other framework residues that can be selected for alteration include amino acid positions that are inaccessible to solvent. Such residues are generally buried in the variable region and are, therefore, capable of influencing the conformation of the CDR or $V_H$ and $V_L$ interactions. Solvent accessibility can be predicted, for example, from the relative hydrophobicity of the environment created by the amino acid side chains of the polypeptide and/or by known three-dimensional structural data.

Following selection of relevant amino acid positions in the donor CDRs, as well as any relevant amino acid positions in the framework regions desired to be varied, amino acid changes at some or all of the selected positions can be incorporated into encoding nucleic acids for the acceptor variable region framework and donor CDRs. Altered framework or CDR sequences can be individually made and tested, or can be sequentially or simultaneously combined and tested.

The variability at any or all of the altered positions can range from a few to a plurality of different amino acid residues, including all twenty naturally occurring amino acids or functional equivalents and analogues thereof. In some cases, non-naturally occurring amino acids may also be considered and are known in the art.

Selection of the number and location of the amino acid positions to vary is flexible and can depend on the intended use and desired efficiency for identification of the altered variable region having a desirable activity such as substantially the same or greater binding affinity compared to the donor variable region. In this regard, the greater the number of changes that are incorporated into an altered variable region population, the more efficient it is to identify at least one species that exhibits a desirable activity, for example, substantially the same or greater binding affinity as the donor. Alternatively, where the user has empirical or actual data to the affect that certain amino acid residues or positions contribute disproportionally to binding affinity, then it can be desirable to produce a limited population of altered variable regions which focuses on changes within or around those identified residues or positions.

For example, if CDR grafted variable regions are desired, a large, diverse population of altered variable regions can include all the non-identical framework region positions between the donor and acceptor framework and all single CDR amino acid position changes. Alternatively, a population of intermediate diversity can include subsets, for example, of only the proximal non-identical framework positions to be incorporated together with all single CDR amino acid position changes to, for example, increase affinity of the humanized antibodies or antigen binding fragments. The diversity of the above populations can be further increased by, for example, additionally including all pairwise CDR amino acid position changes. In contrast, populations focusing on predetermined residues or positions which incorporate variant residues at as few as one framework and/or one CDR amino acid position can similarly be constructed for screening and identification of an altered antibody variable region. As with the above populations, the diversity of such focused populations can be further increased by additionally expanding the positions selected for change to include other relevant positions in either or both of the framework and CDR regions. There are numerous other combinations ranging from few changes to many changes in either or both of the framework regions and CDRs that can additionally be employed, all of which will result in a population of altered variable regions that can be screened for the identification of at least one CDR grafted altered variable region having desired activity, for example, binding activity to endoglin. Those skilled in the art will know, or can determine, which selected residue positions in the framework or donor CDRs, or subsets thereof, can be varied to produce a population for screening and identification of an altered antibody of the invention given the teachings and guidance provided herein. Codons encoding amino acids are known in the art.

Another method of humanizing antibodies includes a method termed "superhumanization." Superhumanization involves the steps of obtaining a peptide sequence for a subject variable region encoded by a non-human mature antibody gene and identifying a first set of canonical CDR structure types for at least two CDRs within the non-human antibody variable region. Canonical CDR structure types are the structure types designated by Chothia (CITE). Chothia and coworkers found that critical portions of the CDRs of many antibodies adopt nearly identical peptide backbone conformations, despite great diversity at the level of amino acid sequence. Accordingly, Chothia defined for each CDR in each chain one or a few "canonical structures." Each canonical structure specifies primarily a set of peptide backbone torsion angles for a contiguous segment of amino acid residues forming a loop.

After the identification of the canonical CDR structure type, a library of peptide sequences for human antibody variable regions for human antibodies is also obtained. This library contains sequences for human germline variable regions as encoded by germline nucleic acid segments, and may include mature human antibody sequences. In either case, the method includes identifying canonical CDR structure types (i.e., a second set of canonical CDR structure types) for at least two CDRs for each sequence within the library of human variable region sequences. From this library there is selected a subset of candidate sequences by comparing the first set of canonical CDR structure types to the second set of canonical CDR structure types (i.e., comparing the mouse canonical CDR structure types to the human canonical CDR structure types at corresponding locations within the variable region) and selecting those human sequences where the second set of canonical CDR structure is the same as the first set of canonical CDR structure types for the CDR sequences at corresponding locations within the non-human and human variable regions, respectively. The method uses these candidate human variable region sequences as a basis for constructing a chimeric molecule that includes at least two of the CDR sequences from the non-human variable region (e.g., of the mouse CDRs) combined with the framework regions from candidate human variable region sequences. The result of the construction is that the chimeric antibody contains each of the non-human CDR sequences substituted for each of the human CDR sequences at corresponding locations in the variable regions so that the framework sequences in the chimeric antibody differs from the candidate human framework sequences.

The similarity to the subject CDRs of candidate human antibody sequences is assessed for each domain at two levels. Primarily, identical three-dimensional conformations of CDR peptide backbones are sought. Experimentally determined atomic coordinates of the subject CDRs are seldom available, hence three-dimensional similarity is approximated by determining Chothia canonical structure types of the subject CDRs and excluding from further consideration candidates possessing different canonical structures. Secondarily, residue-to-residue homology between subject CDRs and the remaining human candidate CDRs is considered, and the candidate with the highest homology is chosen.

Choosing highest homology is based on various criterion used to rank candidate human variable regions having the same canonical structure as the subject the non-human variable regions. The criterion for ranking members of the selected set may be by amino acid sequence identity or amino acid homology or both. Amino acid identity is simple a score of position by position matches of amino acid residues. Similarity by amino acid homology is position by position similarity in residue structure of character. Homology may be scored, for example, according to the tables and procedures described by Henikoff and Henikoff, (1992) Amino acid substitution matrices from protein blocks, Proc. Natl. Acad. Sci 89: 10915-10919, or by the BLOSUM series described by Henikoff and Henikoff, (1996). The steps are as follows:

a) Determine the peptide sequences of the heavy and light chain variable domains of the subject antibody. These can be determined by any of several methods, such as DNA sequencing of the respective genes after conventional cDNA cloning; DNA sequencing of cloning products that have been amplified by the polymerase chain reaction from reverse transcripts or DNA of the subject hybridoma line; or peptide sequencing of a purified antibody protein.

b) Apply the Kabat numbering system (Kabat et al, Id. 1991) to the heavy and light chain sequences of the subject non-human antibody. Determine canonical structure types for each of the CDRs of the subject non-human antibody. This determination is made from examination of the peptide sequence in light of the guidelines discussed in Chothia and Lesk (1987), Chothia et al (1992), Tomlinson et al (1995), Martin and Thornton (1996), and Al-Lazikani et al (1997).

The salient features of canonical structure determination for each of the CDRs are as follows. For heavy chain CDR1, three canonical structure types are currently known. Assignment of a new sequence is straightforward because each canonical structure type has a different number of residues. As described in Al-Lazikani et. al (1997), when Kabat numbering is assigned to the sequence, the numbering for residues 31-35 will be as follows for the respective canonical structures.

Canonical structure type 1: 31, 32, 33, 34, 35.
Canonical structure type 2: 31, 32, 33, 34, 35, 35a.
Canonical structure type 3: 31, 32, 33, 34, 35, 35a, 35b.

For heavy chain CDR2, four canonical structure types are currently known. Several have unique numbers of residues, and are easily distinguished from their unique Kabat numbering of positions 52-56, viz.:

Canonical structure type 1: 52, 53, 54, 55, 56.
Canonical structure type 4: 52, 52a, 52b, 52c, 53, 54, 55, 56.

Canonical structure types 2 and 3 for heavy chain CDR2 have equal numbers of residues, hence must be distinguished by clues within their sequence, as discussed by Chothia et al (1992). The Kabat numbering of the segment containing these clues is: 52, 52a, 53, 54, 55. Canonical structure type 2 has Pro or Ser at position 52a and Gly or Ser at position 55, with no restriction at the other positions. Canonical structure type 3 has Gly, Ser, Asn, or Asp at position 54, with no restriction at the other positions. These criteria are sufficient to resolve the correct assignment in most cases. Additionally, framework residue 71 is commonly Ala, Val, Leu, Ile, or Thr for canonical structure type 2 and commonly Arg for canonical structure type 3.

Heavy chain CDR3 is the most diverse of all the CDRs. It is generated by genetic processes, some of a random nature, unique to lymphocytes. Consequently, canonical structures for CDR3 have been difficult to predict. In any case, human germline V gene segments do not encode any part of CDR3; because the V gene segments end at Kabat position 94, whereas positions 95 to 102 encode CDR3. For these reasons, canonical structures of CDR3 are generally not considered for choosing candidate human sequences.

For light chain CDR1, six canonical structure types are currently known for CDR1 in kappa chains. Each canonical structure type has a different number of residues, hence assignment of a canonical structure type to a new sequence is apparent from the Kabat numbering of residue positions 27-31.

Canonical structure type 1: 27, 29, 30, 31.
Canonical structure type 2: 27, 28, 29, 30, 31.
Canonical structure type 3: 27, 27a, 27b, 27c, 27d, 27e, 27f, 28, 29, 30, 31.
Canonical structure type 4: 27, 27a, 27b, 27c, 27d, 27e, 28, 29, 30, 31.
Canonical structure type 5: 27, 27a, 27b, 27c, 27d, 28, 29, 30, 31.
Canonical structure type 6: 27, 27a, 28, 29, 30, 31.

For light chain CDR2, only a single canonical structure type is known for CDR2 in kappa chains, hence, barring exceptional subject antibody sequences, assignment is automatic. For light chain CDR3, up to six canonical structure types have been described for CDR3 in kappa chains, but three of these are rare. The three common ones can be distinguished by their length, reflected in Kabat numbering of residue positions 91-97:

Canonical structure type 1: 91, 92, 93, 94, 95, 96, 97 (also with an obligatory Pro at position 95 and Gln, Asn, or His at position 90).
Canonical structure type 3: 91, 92, 93, 94, 95, 97.
Canonical structure type 5: 91, 92, 93, 94, 95, 96, 96a, 97.

After identifying the canonical CDR structure types of the subject non-human antibody, human genes of the same chain type (heavy or light) that have the same combination of canonical structure types as the subject antibody are identified to form a candidate set of human sequences. Most of these gene fragments have been discovered and have already been assigned to a canonical structure type (Chothia et al, 1992, Tomlinson et al, 1995).

For the heavy chain, conformity of CDR1 and CDR2 to the mouse canonical structure types is assessed, and genes that do not conform are excluded. For the light chain, conformity of CDR1 and CDR2 of each human sequence to the canonical structure types of the subject antibody is first assessed. The potential of residues 89-95 of a candidate Vk gene to form a CDR3 of the same canonical structure type as the subject antibody is assessed, by positing a fusion of the gene with a J region and applying criteria for CDR3 canonical CDR structure type determination to the fused sequence, and non conforming sequences are excluded.

Alternatively, when a variable domain of the subject antibody is of a canonical structure type not available in the human genome, human germline V genes that have three-dimensionally similar, but not identical, canonical structure types are considered for comparison. Such a circumstance often occurs with kappa chain CDR1 in murine antibodies, including two of the examples described below. All 6 possible canonical structure types have been observed at this CDR in murine antibodies, whereas the human genome encodes only canonical types 2, 3, 4 and 6. In these circumstances, a canonical CDR structure type having length of amino acid residues within two of the length of the amino acid residues of the subject non-human sequence may selected for the comparison. For example, where a type 1 canonical structure is found in the subject antibody, human Vk sequences with canonical structure type 2 are used for comparison. Where a type 5 canonical structure is found in the murine antibody, human Vk sequences with either canonical structure type 3 or 4 are be used for comparison.

Mature, rearranged human antibody sequences can be considered for the sequence comparison. Such consideration might be warranted under a variety of circumstances, including but not limited to instances where the mature human sequence (1) is very close to germline; (2) is known not to be immunogenic in humans; or (3) contains a canonical structure type identical to that of the subject antibody, but not found in the human germline.

For each of the candidate V genes with matching canonical structure types, residue to residue sequence identity and/or homology with the subject sequence is also evaluated to rank the candidate human sequences. For example, the residues evaluated are as follows: (1) Kappa (κ) light chain CDR amino acid residue positions are CDR1 (26-32), CDR2 (50-52), CDR3 (91-96); and (2) heavy chain CDR amino acid residue positions are CDR1 (31-35) and CDR2 (50-60). Additionally, heavy chain CDR3 amino acid residue positions 95 to 102 can also be considered.

Residue-to-residue homology is first scored by the number of identical amino acid residues between the subject and the candidate human sequences. The human sequence used for subsequent construction of a converted antibody is chosen from among the 25 percent of candidates with the highest score. When appropriate, such as when several candidate sequences have similar identity scores, similarity between non-identical amino acid residues may be additionally considered as needed. Aliphatic-with-aliphatic, aromatic-with-aromatic, or polar-with-polar matches between subject and object residues are added to the scores. In another example, quantitative evaluation of sequence homology may be performed using amino acid substitution matrices such as the BLOSUM62 matrix of Henikoff and Henikoff.

An object sequence for the framework region C-terminal to CDR3 sequence can be selected from the set of known human germline J segments. A J peptide sequence is selected by evaluating residue to residue homology for each J segment for sequence positions for which CDR3 and J overlap, using the scoring criteria specified for the evaluation of candidate V genes as mentioned above. The J gene segment peptide sequence used for subsequent construction of a converted antibody is chosen from among the 25 percent of candidates with the highest score.

As an example, the chimeric variable chain contains at least two CDRs from a subject non-human sequence, and framework sequences from a candidate human sequence. In another example, chimeric light chain contains three CDRs from a subject non-human sequence and framework sequences from a candidate human sequence. In additional examples, a chimeric heavy chain contains at least two CDRs of a subject heavy chain, and framework sequence of a candidate human heavy chain, or a chimeric heavy chin contains each of the CDRs from the subject heavy chain and framework sequences of a candidate human heavy chain. In still another example, a chimeric antibody heavy chain contains CDRs 1 and 2 from a subject non-human sequence and residues 50-60 for CDR3 and residues 61-65 of a CDR from the candidate human heavy chain, along with the framework sequences of the candidate human sequence. In another example, a chimeric heavy chain sequence contains each CDR from the subject non-human sequence; frameworks sequences 27-30 form the subject sequence, and the framework sequences from the candidate sequences. In all cases however, the chimeric antibody molecule contains no more than 10 amino acid residues in the framework sequence that differ from those in the framework sequence of the candidate human variable ration.

When increased affinity of a humanized antibody is desired, residues within the CDRs of a converted antibody may be additionally substituted with other amino acids. Typically, no more than four amino acid residues in a CDR are changed, and most typically no more than two residues in the CDR will be changed, except for heavy chain CDR2, where as many as 10 residues may be changed. Changes in affinity can be measured by conventional methods such as those described herein (e.g., Biacore).

The methods of superhumanizing antibodies are described in more detail in U.S. Pat. No. 6,881,557 which is hereby incorporated by reference in its entirety.

Humanized antibodies and antigen-binding fragments can be constructed and produced using conventional techniques known in the art. In addition, recombinantly prepared antibodies can often be produced in large quantities, particularly when utilizing high level expression vectors.

Antibodies can be sequenced using conventional techniques known in the art. In one aspect, the amino acid sequences of one or more of the CDRs is inserted into a synthetic sequence of, for example, a human antibody (or antigen-binding fragment thereof) framework to create a human antibody that could limit adverse side reactions of treating a human patient with a non-human antibody. The amino acid sequences of one or more of the CDRs can also be inserted into a synthetic sequence of, for example, into a binding protein such as an AVIMER™ to create a construct for administration to a human patient. Such techniques can be modified depending on the species of animal to be treated. For example, for veterinary uses, an antibody, antigen-binding fragment or binding protein can be synthesized for administration of a non-human (e.g., a primate, a cow, a horse, etc.).

In another aspect, using art-recognized techniques such as those provided and incorporated herein, nucleotides encoding amino acid sequences of one or more of the CDRs can inserted, for example, by recombinant techniques in restriction endonuclease sites of an existing polynucleotide that encodes an antibody, antigen-binding fragment or binding protein.

For expression, an expression system is one which utilizes the GS system (Lonza) using a glutamine synthetase gene as the selectable marker. Briefly, a transfection is performed in CHO cells by electroporation (250V) using the GS system (Lonza) using the glutamine synthetase gene as the selectable marker. Wild type CHO cells are grown in DMEM (Sigma) containing 10% dialyzed Fetal Calf Serum (FCS) with 2 mM glutamine. $6 \times 10^7$ CHO cells are transfected with 300 μg of linearized DNA by electroporation. After electroporation the cells are resuspended in DMEM with glutamine and plated out into 36×96-well plates (50 μl/well), and incubated at 37° C. in 5% $CO_2$. The following day, 150 μl/well of selective medium (DMEM without glutamine) is added. After approximately 3 weeks the colonies are screened by ELISA (see below) using an irrelevant antibody as a negative control. All colonies producing >20 μg/ml are expanded into 24-well plates and then into duplicate T25 flasks.

For high level production, the most widely used mammalian expression system is one which utilizes the gene amplification procedure offered by dihydrofolate reductase deficient ("dhfr-") Chinese hamster ovary cells. The system is well known to the skilled artisan. The system is based upon the dehydrofolate reductase "dhfr" gene, which encodes the DHFR enzyme, which catalyzes conversion of dehydrofolate to tetrahydrofolate. In order to achieve high production, dhfr-CHO cells are transfected with an expression vector containing a functional DHFR gene, together with a gene that encodes a desired protein. In this case, the desired protein is recombinant antibody heavy chain and/or light chain.

By increasing the amount of the competitive DHFR inhibitor methotrexate (MTX), the recombinant cells develop resistance by amplifying the dhfr gene. In standard cases, the amplification unit employed is much larger than the size of the dhfr gene, and as a result the antibody heavy chain is co-amplified.

When large scale production of the protein, such as the antibody chain, is desired, both the expression level and the stability of the cells being employed are taken into account. In long term culture, recombinant CHO cell populations lose homogeneity with respect to their specific antibody productivity during amplification, even though they derive from a single, parental clone.

The present application provides an isolated polynucleotide (nucleic acid) encoding an antibody or antigen-binding fragment as described herein, vectors containing such polynucleotides, and host cells and expression systems for transcribing and translating such polynucleotides into polypeptides.

The present application also provides constructs in the form of plasmids, vectors, transcription or expression cassettes which comprise at least one polynucleotide as above.

The present application also provides a recombinant host cell which comprises one or more constructs as above. A nucleic acid encoding any antibody or antigen-binding fragments thereof described herein as provided itself forms an aspect of the present application, as does a method of production of the antibody or antigen-binding fragments thereof described herein which method comprises expression from encoding nucleic acid therefrom. Expression can conveniently be achieved by culturing under appropriate conditions recombinant host cells containing the nucleic acid. Following production by expression, an antibody or antigen-binding fragment can be isolated and/or purified using any suitable technique, then used as appropriate.

Specific antibodies, antigen-binding fragments, and encoding nucleic acid molecules and vectors described herein can be provided isolated and/or purified, e.g., from their natural environment, in substantially pure or homogeneous form. In the case of nucleic acid, free or substantially free of nucleic acid or genes origin other than the sequence encoding a polypeptide with the required function. Nucleic acid can comprise DNA or RNA and can be wholly or partially synthetic. Methods of purification are well known in the art.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NS0 mouse myeloma cells and many others. A common bacterial host is *E. coli*.

The expression of antibodies and antibody fragments in prokaryotic cells such as *E. coli* is well established in the art. For a review, see for example Plückthun, A. Bio/Technology 9: 545-551 (1991). Expression in eukaryotic cells in culture is also available to those skilled in the art as an option for production of the antibodies and antigen-binding fragments described herein, see for recent reviews, for example Raff, M. E. (1993) Curr. Opinion Biotech. 4: 573-576; Trill J. J. et al. (1995) Curr. Opinion Biotech 6: 553-560, each of which is which is incorporated herein by reference in its entirety.

Suitable vectors can be chosen or constructed, containing appropriate regulatory sequences, including promoter sequences, terminator sequences, polyadenylation sequences, enhancer sequences, marker genes and other sequences as appropriate. Vectors can be plasmids, viral e.g. 'phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Short Protocols in Molecular Biology, Second Edition, Ausubel et al. eds., John Wiley & Sons, 1992. The methods disclosures of Sambrook et al. and Ausubel et al. are incorporated herein by reference in their entirety and are well known in the art.

Thus, a further aspect provides a host cell containing nucleic acid as disclosed herein. A still further aspect provides a method comprising introducing such nucleic acid into a host cell. The introduction can employ any available technique. For eukaryotic cells, suitable techniques can include, for example, calcium phosphate transfection, DEAE Dextran, electroporation, liposome-mediated transfection and transduction using retrovirus or other virus, e.g., vaccinia or, for insect cells, baculovirus. For bacterial cells, suitable techniques can include, for example, calcium chloride transformation, electroporation and transfection using bacteriophage.

The introduction can be followed by causing or allowing expression from the nucleic acid, e.g. by culturing host cells under conditions for expression of the gene.

In one embodiment, the nucleic acid is integrated into the genome (e.g. chromosome) of the host cell. Integration can be promoted by inclusion of sequences which promote recombination with the genome, in accordance with standard techniques. Ig enhances can be initialized as needed to maximize expression.

The present application also provides a method which comprises using a construct as stated above in an expression system in order to express the antibodies or antigen-binding fragments thereof as above.

The present application also relates to isolated nucleic acids, such as recombinant DNA molecules or cloned genes, or degenerate variants thereof, mutants, analogs, or fragments thereof, which encode an antibody or antigen-binding sequence described herein that binds endoglin.

In one aspect, the present application provides a nucleic acid which codes for an antibody or antigen-binding fragment thereof as described herein which binds endoglin.

In a further embodiment, the full DNA sequence of the recombinant DNA molecule or cloned gene of an antibody or antigen-binding fragment described herein can be operatively linked to an expression control sequence which can be introduced into an appropriate host. The application accordingly extends to unicellular hosts transformed with the cloned gene or recombinant DNA molecule comprising a DNA sequence encoding the $V_H$ and/or $V_L$, or portions thereof, of the antibody.

Another feature is the expression of the DNA sequences disclosed herein. As is well known in the art, DNA sequences can be expressed by operatively linking them to an expression control sequence in an appropriate expression vector and employing that expression vector to transform an appropriate unicellular host.

Such operative linking of a DNA sequence to an expression control sequence, of course, includes, if not already part of the DNA sequence, the provision of an initiation codon, ATG, in the correct reading frame upstream of the DNA sequence.

Polynucleotides and vectors can be provided in an isolated and/or a purified form (e.g., free or substantially free of polynucleotides of origin other than the polynucleotide encoding a polypeptide with the required function). As used herein, "substantially pure," and "substantially free" refer to a solution or suspension containing less than, for example, about 20% or less extraneous material, about 10% or less extraneous material, about 5% or less extraneous material, about 4% or less extraneous material, about 3% or less extraneous material, about 2% or less extraneous material, or about 1% or less extraneous material.

A wide variety of host/expression vector combinations can be employed in expressing the DNA sequences of this invention. Useful expression vectors, for example, can consist of segments of chromosomal, non-chromosomal and synthetic DNA sequences. Suitable vectors include, but are not limited to, derivatives of SV40 and known bacterial plasmids, e.g., E. coli plasmids col El, Pcr1, Pbr322, Pmb9 and their derivatives, plasmids such as RP4; phage DNAs, e.g., the numerous derivatives of phage λ, e.g., NM989, and other phage DNA, e.g., M13 and filamentous single stranded phage DNA; yeast plasmids such as the 2u plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Also provided herein is a recombinant host cell which comprises one or more polynucleotide constructs. A polynucleotide encoding an antibody or antigen-binding fragment as provided herein forms an aspect of the present application, as does a method of production of the antibody or antigen-binding fragment which method comprises expression from the polynucleotide. Expression can be achieved, for example, by culturing under appropriate conditions recombinant host cells containing the polynucleotide. An antibody or antigen-binding fragment can then be isolated and/or purified using any suitable technique, and used as appropriate.

Any of a wide variety of expression control sequences—sequences that control the expression of a DNA sequence operatively linked to it—can be used in these vectors to express the DNA sequences. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast α-mating factors, and other sequences known to control the expression of genes of prokaryotic or eukaryotic cells or their viruses, and various combinations thereof.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary (CHO) cells, HeLa cells, baby hamster kidney cells, NS0 mouse myeloma cells and many others. A common, bacterial host can be, for example, E. coli.

The expression of antibodies or antigen-binding fragments in prokaryotic cells, such as E. coli, is well established in the art. For a review, see for example Plückthun, A. Bio/Technology 9: 545-551 (1991). Expression in eukaryotic cells in culture is also available to those skilled in the art (Raff, M. E. (1993) Curr. Opinion Biotech. 4: 573-576; Trill J. J. et al. (1995) Curr. Opinion Biotech 6: 553-560).

A wide variety of unicellular host cells are also useful in expressing the DNA sequences. These hosts include well-known eukaryotic and prokaryotic hosts, such as strains of E. coli, Pseudomonas, Bacillus, Streptomyces, fungi such as yeasts, and animal cells, such as CHO, YB/20, NS0, SP2/0, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences. Neither will all hosts function equally well with the same expression system. However, one skilled in the art will be able to select the proper vectors, expression control sequences, and hosts without undue experimentation to accomplish the desired expression without departing from the scope of this application. For example, in selecting a vector, the host must be considered because the vector must function in it. The vector's copy number, the ability to control that copy number, and the expression of any other proteins encoded by the vector, such as antibiotic markers, will also be considered. One of ordinary skill in the art can select the proper vectors, expression control sequences, and hosts to accomplish the desired expression without departing from the scope of this application. For example, in selecting a vector, the host is considered because the vector functions in it. The vector's copy number, the ability to control that copy number, and the expression of any other proteins encoded by the vector, such as antibiotic markers, can also be considered.

The present application also provides constructs in the form of plasmids, vectors, transcription or expression cassettes as described elsewhere herein which comprise at least one polynucleotide as above. Suitable vectors can be chosen or constructed, containing appropriate regulatory sequences, including promoter sequences, terminator sequences, polyadenylation sequences, enhancer sequences, selectable markers and other sequences as appropriate. Vectors can be plasmids, viral e.g., phage, phagemid, etc., as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Short Protocols in Molecular Biology, Second Edition, Ausubel et al. eds., John Wiley & Sons, 1992. The methods and disclosures of Sambrook et al. and Ausubel et al. are incorporated herein by reference.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

A further aspect provides a host cell containing one or more polynucleotides as disclosed herein. Yet a further aspect provides a method of introducing such one or more polynucleotides into a host cell, any available technique. For eukaryotic cells, suitable techniques can include, for example, calcium phosphate transfection, DEAEDextran, electroporation, liposome-mediated transfection and transduction using retrovirus or other virus (e.g. vaccinia) or, for insect cells, baculovirus. For bacterial cells, suitable techniques can include, for example calcium chloride transformation, electroporation and transfection using bacteriophages.

The introduction can be followed by causing or allowing expression from the one or more polynucleotides, e.g. by culturing host cells under conditions for expression of one or more polypeptides from one or more polynucleotides. Inducible systems can be used and expression induced by addition of an activator.

In one embodiment, the polynucleotides can be integrated into the genome (e.g., chromosome) of the host cell. Integration can be promoted by inclusion of sequences which promote recombination with the genome, in accordance with standard techniques. In another embodiment, the nucleic acid is maintained on an episomal vector in the host cell.

Methods are provided herein which include using a construct as stated above in an expression system in order to express a specific polypeptide.

Considering these and other factors, a person skilled in the art will be able to construct a variety of vector/expression control sequence/host combinations that will express the DNA sequences on fermentation or in large scale animal culture.

A polynucleotide encoding an antibody, antigen-binding fragment, or a binding protein can be prepared recombinantly/synthetically in addition to, or rather than, cloned. The polynucleotide can be designed with the appropriate codons for the antibody, antigen-binding fragment, or a binding protein. In general, one will select preferred codons for an intended host if the sequence will be used for expression. The complete polynucleotide can be assembled from overlapping oligonucleotides prepared by standard methods and assembled into a complete coding sequence. See, e.g., Edge, Nature, 292:756 (1981); Nambair et al., Science, 223:1299 (1984); Jay et al., J. Biol. Chem., 259: 6311 (1984).

A general method for site-specific incorporation of unnatural amino acids into proteins is described in Christopher J. Noren, Spencer J. Anthony-Cahill, Michael C. Griffith, Peter G. Schultz, Science, 244:182-188 (April 1989). This method can be used to create analogs with unnatural amino acids.

As mentioned above, a DNA sequence encoding an antibody or antigen-binding fragment thereof can be prepared synthetically rather than cloned. The DNA sequence can be designed with the appropriate codons for the antibody or antigen-binding fragment amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, Nature, 292:756 (1981); Nambair et al., Science, 223:1299 (1984); Jay et al., J. Biol. Chem., 259:6311 (1984), each of which is which is incorporated herein by reference in its entirety.

C. In Silico Analysis of Immunogenicity

If needed, an antibody or an antigen binding fragment thereof described herein can be assessed for immunogenicity and, as needed, be deimmunized (i.e. the antibody is made less immuno reactive by altering one or more T cell epitopes). Analysis of immunogenicity and T-cell epitopes present in the humanized anti-endoglin antibodies and antigen-binding fragments described herein can be carried out via the use of software and specific databases. Exemplary software and databases include iTope™ developed by Antitope of Cambridge, England. iTope™ is an in silico technology for analysis of peptide binding to human MHC class II alleles.

The iTope™ software predicts peptide binding to human MHC class II alleles and thereby provides an initial screen for the location of such "potential T cell epitopes." iTope™ software predicts favorable interactions between amino acid side chains of a peptide and specific binding pockets within the binding grooves of 34 human MHC class II allelles. The location of key binding residues is achieved by the in silico generation of 9 mer peptides that overlap by one amino acid spanning the test antibody variable region sequence. Each 9 mer peptide can be tested against each of the 34 MHC class II allotypes and scored based on their potential "fit" and interactions with the MHC class II binding groove. Peptides that produce a high mean binding score (>0.55 in the iTope™ scoring function) against >50% of the MHC class II alleles are considered as potential T cell epitopes. In such regions, the core 9 amino acid sequence for peptide binding within the MHC class II groove is analyzed to determine the MHC class II pocket residues (P1, P4, P6, P7 and P9) and the possible T cell receptor (TCR) contact residues (P-1, P2, P3, P5, P8).

After identification of any T-cell epitopes, amino acid residue changes, substitutions, additions, and/or deletions can be introduced to remove the identified T-cell epitope. Such changes can be made so as to preserve antibody structure and function while still removing the identified epitope. Exemplary changes can include, but are not limited to, conservative amino acid changes.

Techniques exploiting soluble complexes of recombinant MHC molecules in combination with synthetic peptides have come into use. These reagents and procedures may be used to identify the presence of T-cell clones from peripheral blood samples from human or experimental animal subjects that are able to bind particular MHC-peptide complexes and are not adapted for the screening multiple potential epitopes to a wide diversity of MHC allotypes.

Biological assays of T-cell activation remain the best practical option to providing a reading of the ability of a test peptide/protein sequence to evoke an immune response. Examples of this kind of approach include the use of T-cell proliferation assays to the bacterial protein staphylokinase, followed by epitope mapping using synthetic peptides to stimulate T-cell lines. Similarly, T-cell proliferation assays using synthetic peptides of the tetanus toxin protein have resulted in definition of immunodominant epitope regions of the toxin. In one embodiment, T-cell epitopes in a test protein may be determined using isolated sub-sets of human immune cells, promoting their differentiation in vitro and culture of the cells in the presence of synthetic peptides of interest and measurement of any induced proliferation in the cultured T-cells. Other techniques may also be used. Such a technique involves careful application of cell isolation techniques and cell culture with multiple cytokine supplements to obtain the desired immune cell sub-sets (dendritic cells, CD4+ and or CD8+ T-cells). In another embodiment, the presence of T cell epitopes in an antibody may be determined by adding the antibody to isolated sub-sets of human immune cells, and assessing their differentiation in vitro and measuring any induced proliferation in the cultured T cells.

In silico techniques to define MHC class II ligands for multiple proteins of therapeutic interest may also be utilized. However, for reasons such as the requirement for proteolytic processing and other physiologic steps leading to the presentation of immunogenic peptides in vivo, a sub-set of the entire repertoire of peptides definable by computer-based schemes may have ultimate biological relevance. Thus, ex vivo human T-cell activation assays may be used to identify the regions within the protein sequence of a polypeptide that are able to support T-cell activation and are thereby most biologically relevant to the problem of immunogenicity in this protein. As used herein, "T-cell epitope" refers to an amino acid sequence which is able to bind MHC class II, able to stimulate T-cells and/or also to bind (without necessarily measurably activating) T-cells in complex with MHC class II.

According to a method disclosed herein, synthetic peptides or whole antibodies are tested for their ability to evoke a proliferative response in human T-cells cultured in vitro. The T-cells are present within a peripheral blood mononuclear cell (PBMC) layer readily obtainable by well known means from whole blood samples. Moreover, the PBMC preparation contains physiological ratios of T-cells and antigen presenting cells and is, therefore, a good source of materials with which to conduct a surrogate immune reaction in vitro. In the operation of such an assay, a stimulation index approaching or exceeding 2.0 is a useful measure of induced proliferation. However, the stimulation index may be different depending upon the antibody, or antigen-binding fragment thereof, and may be established with reference to a baseline for each antibody, or antigen-binding fragment thereof, and corresponding peptide library. In one example of such testing, the stimulation index (SI) may be conventionally derived by division of the proliferation score (e.g. counts per minute of radioactivity if using for example $^3$H-thymidine incorporation) measured to the test peptide by the score measured in cells not contacted with a test peptide. Peptides which evoke no response may give a SI=1.0 although SI values in the range 0.8-1.2 may also be unremarkable. A number of technical procedures can be built into the operation of such assays in order to ensure confidence in the recorded scores. Typically all determinations are made at least in triplicate and the mean score may be computed. Where a computed SI=>2.0, individual scores of the triplicate can be examined for evidence of outlying data. Test peptides are contacted with cells in at least two different concentrations and the concentrations would typically span a minimum two-fold concentration difference. Such a concentration range provides an off-set to the kinetic dimension to the assay and may be useful where a single time point determination, for example at day plus 7, is being conducted. In some assays, multiple time course determinations may be conducted and these too may be made using peptide immunogen provided at a minimum of two different concentrations. Similarly the inclusion of control peptides for which there is expectation that the majority of PBMC donor samples will be responsive may be included in each assay plate. The influenza haemagglutinin peptide 307-309, sequence PKYVKQNTLKLA (SEQ ID NO: 104); and the *Chlamydia* HSP 60 peptide sequence KVVDQIKKISKPVQH (SEQ ID NO: 105) are examples of control peptides to be used in such an assay. Alternatively, or in addition, assays could also use a potent whole protein antigen, such as hemocyanin from Keyhole Limpet, to which all PBMC samples would be expected to exhibit an SI significantly greater than 2.0. Other control antigens for such use will be well-known in the art.

The methods disclosed herein can provide an epitope map of antibodies, or antigen-binding fragments thereof, where the map has relevance to a wide spectrum of possible MHC allotypes. The map may be sufficiently representative to allow the design or selection of a modified protein for which the ability of the protein to evoke a T-cell driven immune response may be eliminated or at least ameliorated for the majority of patients to whom the protein is likely to be administered. Amelioration can refer to a reduction in an immune response (i.e., reduced immunogenicity) compared to an unmodified protein (e.g. about 1.5 fold less, about 2 fold less, about 5 fold less, about 10 fold less, about 20 fold less, about 50 fold less, about 100 fold less, about 200 fold less, about 500 fold less or more, or any range therein). Alternatively, antibodies, or antigen-binding fragments thereof, with reduced immunogenicity can refer to a percent reduction in its ability to elicit an immune response compared to an unmodified protein (e.g. about 1% less, about 2% less, about 3% less, about 4% less, about 5% less, about 10% less, about 20% less, about 50% less, about 100% less, and any range therein). Accordingly in the practice of the screening process, PBMC derived T-cells from naive donors are collected from a pool of donors of sufficient immunological diversity to provide a sample of at least greater than 90% of the MHC class II repertoire (HLA-DR) extant in the human population. Where a naive T-cell response is to be detected to a given synthetic peptide (or antibody), the peptide (or antibody) in practice is contacted with PBMC preparations derived from multiple donors in isolation; the numbers of donors (or "donor pool" size), is for practical purposes not likely to be less than 20 unrelated individuals and all samples in the donor pool may be pre-selected according to their MHC class II haplotype.

As used herein, the term "naive donor" refers to a subject that has not been previously exposed to antibodies, or antigen-binding fragments thereof, described herein either environmentally, by vaccination, or by other means such as, for example, blood transfusions.

When screening for T-cell epitopes, T-cells can be provided from a peripheral blood sample from a multiplicity of different healthy donors but who have not been in receipt of the protein therapeutically. If needed, patient blood samples can be tested for the presence of a particular polypeptide using conventional assays such as an ELISA which uses antibodies to identify the presence or absence of one or more polypeptides. The assay is conducted using PBMC cultured in vitro using conventional procedures known in the art and involves contacting the PBMC with synthetic peptide species representative of the protein of interest (i.e. a library), or a whole protein, such as an antibody and following a suitable period of incubation, measurement of induced T cell activation such as cellular proliferation. Measurement can be by any suitable means and may, for example, be conducted using $H^3$-thymidine incorporation whereby the accumulation of $H^3$ into cellular material is readily measured using laboratory instruments. The degree of cellular proliferation for each combination of PBMC sample and synthetic peptide or whole protein can be examined relative to that seen in an untreated PBMC sample. Reference may also be made to the proliferative response seen following treatment with a peptide or peptides or whole proteins for which there is an expected proliferative effect. In this regard, it is advantageous to use a peptide or whole protein with known broad MHC restriction and especially peptide epitopes with MHC restriction to the DP or DQ isotypes, although the invention is not limited to the use of such restricted peptides or proteins. Such peptides have been described above, for example, with respect to influenza haemagglutinin and *chlamydia* HSP60.

In one non-limiting example, T-cell epitopes are mapped and subsequently modified using the methods described herein. To facilitate assembly of an epitope map, a library of synthetic peptides is produced. Each of the peptides is 15 amino acid residues in length and each overlapped the next peptide in the series by 12 amino acid residues; i.e. each successive peptide in the series incrementally added a further 3 amino acids to the analysis. In this way, any given adjacent pair of peptides mapped 18 amino acids of contiguous sequence. One method for defining a T-cell map using naive T-cell assays is illustrated in the Examples below. Each of the peptides identified via the method to define a T-cell map are suggested to be able to bind MHC class II and engage at least one cognate TCR with sufficient affinity to evoke a proliferative burst detectable in the assay system.

In another non-limiting example, the potential of an antibody to be processed to generate T-cell epitopes that bind MHC class II and engage at least one cognate TCR with sufficient affinity to evoke a proliferative burst detectable in the assay system is assessed.

The molecules described herein can be prepared in any of several ways including the use of recombinant methods. The protein sequences and information provided herein can be used to deduce a polynucleotide (DNA) encoding an amino acid sequence. This can be achieved for example using computer software tools such as the DNAstar software suite [DNAstar Inc, Madison, Wis., USA] or similar. Any such polynucleotide encoding the polypeptides or significant homologues, variants, truncations, elongations, or further modifications thereof, are contemplated herein.

Provided herein are methods of mapping (identifying) T-cell epitopes and modifying the epitopes such that the modified sequence reduces (partially or completely) induction of a T-helper response. Modification includes amino acid substitutions, deletions, or insertion made in codons of a polynucleotide encoding modified polypeptides to affect similar changes. Codons encoding amino acid residues are well known in the art. It is possible to use recombinant DNA methods to achieve directed mutagenesis of the target sequences and many such techniques are available, described herein, and known in the art such as described above. In general, the technique of site-specific mutagenesis is well known. Briefly, a bacteriophage vector that produces a single stranded template for oligonucleotide directed PCR mutagenesis is employed. Phage vectors (e.g. M13) are commercially available and their use is generally well known in the art. Similarly, double stranded plasmids are also routinely employed in site directed mutagenesis, which eliminates the step of transferring the polynucleotide of interest from a phage to a plasmid. Synthetic oligonucleotide primers bearing the desired mutated sequence can be used to direct the in vitro synthesis of modified (desired mutant) DNA from this template and the heteroduplex DNA is used to transform competent *E. coli* for the growth selection and identification of desired clones. Alternatively, a pair of primers can be annealed to two separate strands of a double stranded vector to simultaneously synthesize both corresponding complementary strands with the desired mutation(s) in a PCR reaction.

In one embodiment, the Quick Change site-directed mutagenesis method using plasmid DNA templates may be employed. PCR amplification of the plasmid template containing the insert target gene of insert is achieved using two synthetic oligonucleotide primers containing the desired mutation. The oligonucleotide primers, each complementary to opposite strands of the vector, are extended during temperature cycling by mutagenesis-grade PfuTurbo DNA polymerase. On incorporation of the oligonucleotide primers, a mutated plasmid containing staggered nicks is generated. Amplified un-methylated products are treated with Dpn I to digest methylated parental DNA template and select for the newly synthesized DNA containing mutations. Since DNA isolated from most *E. coli* strains is dam methylated, it is susceptible to Dpn I digestion, which is specific for methylated and hemimethylated DNA. The reaction products are transformed into high efficiency strains of *E. coli* to obtain plasmids containing the desired modifications. Additional methods for introducing amino acid modifications into a polypeptide are well known in the art and can also be used herein.

Suitable modifications to a protein may include amino acid substitution of particular residues or combinations of residues. For the elimination of T-cell epitopes, amino acid substitutions are made at appropriate points or amino acid residues within an amino acid sequence predicted to achieve reduction or elimination of the activity of the T-cell epitope. In practice, an appropriate point or amino acid residue will preferably equate to an amino acid residue binding within one of the pockets provided within the MHC class II binding groove. Such modifications may alter binding within the first pocket of the cleft at the so-called "P1" or "P1 anchor" position of the peptide. The quality of binding interaction between the P1 anchor residue of the peptide and the first pocket of the MHC class II binding groove is recognized as being a major determinant of overall binding affinity for the whole peptide. An appropriate substitution at this position of the amino acid sequence will generally incorporate an amino acid residue less readily accommodated within the pocket (e.g., substitution to a more hydrophilic residue). Amino acid residues in the peptide at positions equating to binding within other pocket regions within the MHC binding cleft are also considered and fall under the scope of the present.

It is understood that single amino acid modifications within a given potential T-cell epitope represent one route by which one or more T-cell epitopes may be eliminated. Combinations of modifications within a single epitope may be contemplated and can be appropriate where individually defined epitopes are in overlap with each other. Moreover, amino acid modifications (either singly within a given epitope or in combination within a single epitope) may be made at positions not equating to the "pocket residues" with respect to the MHC class II binding groove, but at any point within the amino acid sequence. Modifications may be made with reference to a homologous structure or structural method produced using in silico techniques known in the art and described herein may be based on known structural features of the polypeptide. A change (modification) may be contemplated to restore structure or biological activity of the variant molecule. Such compensatory changes and changes may also include deletion or addition (insertion) of particular amino acid residues from a polypeptide. Additionally, modifications can be made that alter the structure and/or reduce the biological activity of the molecule and also eliminate a T-cell epitope, thus reducing the immunogenicity of the molecule. All types of modifications are contemplated herein.

An additional means of removing epitopes from protein molecules is the concerted use of a naive T-cell activation assay scheme as outlined herein together with an in silico tool developed according to the scheme described in WO 02/069232 which is also incorporated fully herein by reference. The software simulates the process of antigen presentation at the level of the polypeptide-MHC class II binding interaction to provide a binding score for any given polypeptide sequence. Such a score is determined for many of the predominant MHC class II allotypes extant in the population. As this scheme is able to test any polypeptide sequence, the consequences of amino acid substitutions additions or deletions with respect to the ability of a polypeptide to interact with a MHC class II binding groove can be predicted. Consequently new sequence compositions can be designed which contain reduced numbers of amino acids able to interact with a MHC class II and thereby function as immunogenic T-cell epitopes. Where the biological assay using any one given donor sample can assess binding to a maximum of four DR allotypes, the in silico process can test a same polypeptide sequence using >40 allotypes simultaneously. In practice this approach is able to direct the design of new sequence variants which are altered in their ability to interact with multiple MHC allotypes. As will be clear to one in the art, multiple alternative sets of substitutions could be arrived at which achieve the objective of removing undesired epitopes. The resulting sequences would however be recognized to be closely homologous with the specific compositions disclosed herein and therefore fall within the scope of the present application.

A combined approach of using an in silico tool for the identification of MHC class II ligands and design of sequence analogues lacking MHC class II ligands, in concert with epitope mapping and re-testing optionally using biologically based assays of T-cell activation is an additional method and embodiment of the present application. The general method according to this embodiment comprises the following steps:

i) use of naive T-cell activation assays and synthetic peptides collectively encompassing the protein sequence of interest to identify epitope regions capable of activating T-cells;

ii) use of a computational scheme simulating the binding of the peptide ligand with one or more MHC allotypes to analyze the epitope regions identified in step (i) and thereby identify MHC class II ligands within the epitope region;

iii) use of a computational scheme simulating the binding of the peptide ligand with one or more MHC allotypes to identify sequence analogues of the MHC ligands encompassed within the epitope region(s) which no longer bind MHC class II or bind with lowered affinity to a lesser number of MHC allotypes and optionally, iv) use of naive T-cell activation assays and synthetic peptides encompassing entirely or in collection encompassing the epitope regions identified within the protein of interest and testing the sequence analogues in naive T-cell activation assay in parallel with the wild-type (parental) sequences.

In one embodiment, a method of making a modified antibody, or antigen-binding fragment thereof, exhibiting reduced immunogenicity compared to an unmodified antibody, or antigen-binding fragment thereof, comprises identifying at least one T-cell epitope within the amino acid sequence of an antibody, or antigen-binding fragment thereof, and modifying at least one amino acid residue within at least one identified T-cell epitope.

In another embodiment, a modified antibody, or antigen-binding fragment thereof, exhibiting reduced immunogenicity compared to an unmodified antibody, or antigen-binding fragment thereof, is produced by a process of identifying at least one T-cell epitope within the amino acid sequence of a antibody, or antigen-binding fragment thereof, and modifying at least one amino acid residue within at least one identified T-cell epitope.

In yet another embodiment, a method of selecting a modified antibody, or antigen-binding fragment thereof, that exhibits reduced immunogenicity compared to an unmodified antibody, or antigen-binding fragment thereof, comprises identifying at least one T-cell epitope within the amino acid sequence of a antibody, or antigen-binding fragment thereof, modifying at least one amino acid residue within at least one identified T-cell epitope, and selecting a modified antibody, or antigen-binding fragment thereof, that exhibits reduced immunogenicity compared to an unmodified antibody, or antigen-binding fragment thereof.

T-cell epitopes described herein can be further characterized by the regions of the epitope. Such regions include the epitope core, the N-terminus and the C-terminus. As used herein "epitope core" refers to the core 9-mer amino acid sequences of the T-cell epitopes. The epitope core can further include 0, 1, 2, or 3 amino acid residues adjacent to the core 9-mer amino acid sequence on the N-terminus and/or the C-terminus. Thus the epitope core, in certain embodiments, can range in length from about 9 amino acids up to about 15 amino acids.

As used herein, "N-terminus" refers to the amino acids adjacent to the N-terminus of the epitope core and includes at least 1, 2, 3, 4, 5, 6, 7, 8 or 9 amino acids adjacent to and upstream of the N-terminus of the epitope core.

As used herein, "C-terminus" refers to the amino acids adjacent to the C-terminus of the epitope core and includes at least 1, 2, 3, 4, 5, 6, 7, 8, or 9 amino acids adjacent to and downstream of the C-terminus of the epitope core.

In one embodiment, a modified antibody, or antigen-binding fragment thereof, contains one or more modifications.

In one embodiment, a modified antibody, or antigen-binding fragment thereof, contains two modifications.

In one embodiment, a modified antibody, or antigen-binding fragment thereof, contains three modifications.

In one embodiment, a modified antibody, or antigen-binding fragment thereof, contains four modifications.

In one embodiment, a modified antibody, or antigen-binding fragment thereof, contains five modifications.

In one embodiment, a modified antibody, or antigen-binding fragment thereof, contains six modifications.

In one embodiment, a modified antibody, or antigen-binding fragment thereof, contains seven modifications.

In one embodiment, a modified antibody, or antigen-binding fragment thereof, contains eight modifications.

In one embodiment, a modified antibody, or antigen-binding fragment thereof, contains nine modifications.

In one embodiment, a modified antibody, or antigen-binding fragment thereof, contains ten modifications.

In one embodiment, a modified antibody, or antigen-binding fragment thereof, contains up to twenty modifications.

Provided herein is an antibody, or antigen-binding fragment thereof, comprising a light chain variable region having an amino acid sequence set forth as SEQ ID NO: 93—(VK1AA) and a heavy chain variable region having an amino acid sequence set forth as SEQ ID NO: 89 (VH1A2).

Provided herein is an antibody, or antigen-binding fragment thereof, comprising a heavy chain variable region having an amino acid sequence set forth as any one of SEQ ID NOS: 88, 89, 90, 91 and 92.

Provided herein is an antibody, or antigen-binding fragment thereof, comprising a light chain variable region having an amino acid sequence set forth as any one of SEQ ID NOS: 93, 94, 95, 96, 97, 100, 102, and 103.

Provided herein is an antibody, or antigen-binding fragment thereof, that binds endoglin, comprising a heavy chain variable region having an amino acid sequence set forth as SEQ ID NO: 89 and a light chain variable region having an amino acid sequence set forth as SEQ ID NO: 93, wherein:

(i) the heavy chain variable region further comprises one or more modifications selected from the group consisting of a substitution of glycine (G) by alanine (A) or serine (S) at position 49; a substitution of alanine (A) by isoleucine (I) at position 51; a substitution of lysine (K) by arginine (R) or asparagine (Q) at position 52b; a substitution of leucine (L) by valine (V) at position 78 utilizing the Kabat numbering system; and (ii) the light chain variable region further comprises one or more modifications selected from the group consisting of a substitution of methionine (M) by leucine (L) at position 4; a substitution of alanine (A) by valine (V) at position 19; a substitution of threonine (T) by serine (S) at position 22; a substitution of alanine (A) by isoleucine (I) at position 48; and a substitution of threonine (T) by serine (S) at position 51 utilizing the Kabat numbering system Provided herein is an antibody, or antigen-binding fragment thereof comprising a heavy chain variable region having an amino acid sequence set forth as SEQ ID NO: 88, 89, 90, 91 and 92; and a light chain variable region having an amino acid sequence set forth as SEQ ID NO: 93, 95, 96, 97, 100, 102, or 103.

In addition to the aforementioned examples and embodiments, a modified antibody, or antigen-binding fragment thereof, with one or more amino acid modifications in one or more T-cell epitopes are contemplated herein. In one non-limiting example, provided herein are antibodies, or antigen-binding fragments thereof, having at least one modification in at least one T-cell epitope. In another non-limiting example, provided herein are antibodies, or antigen-binding fragments thereof, having at least one amino acid modification in 1, 2, 3, 4, 5, 6, or 7 of the T-cell epitopes described herein. Additional non-limiting examples include antibodies, or antigen-binding fragments thereof, having more than one amino acid modification in more than one T-cell epitope. Any combination of the amino acid modifications in any number of the antibodies, or antigen-binding fragments thereof, T-cell epitopes described above are contemplated herein.

T-Cell Epitopes and Allotype Frequency

Individual epitopes found within antigens can be preferentially presented by specific MHC class II allotypes, and similarly other specific epitopes within the same antigen may not be presented on MHC class II molecules at all. Such associations of particular epitopes with specific MCH class II molecules have been shown to depend upon the MHC class II allotype of the individual. The association of a specific epitope with a specific allotype can also be considered when modifying antibodies, or antigen-binding fragments thereof, for the removal of T-cell epitopes. Such considerations can allow for the highly specific modification of an antibody, or antigen-binding fragment thereof, for specific allotypes (e.g. for specific populations of subjects having certain MHC class II allotypes). The MHC class II allotype of a subject or subjects can be easily determined by genotyping methods known in the art, and the association of T-cell epitopes with the given allotype thus easily identified, for consideration in modification of antibodies, or antigen-binding fragments thereof, tailored to that allotype. Identification of associations between T-cell epitopes and MHC class II allotypes are described in more detail in the examples below. Contemplated herein are modified antibodies, or antigen-binding fragments thereof, that have T-cell epitope modifications tailored to the MHC class II associations identified for the given epitopes.

D. Anti-Endoglin Antibodies

Simultaneous incorporation of all of the FR and/or CDR encoding nucleic acids and all of the selected amino acid position changes can be accomplished by a variety of methods known to those skilled in the art, including for example, recombinant and chemical synthesis. For example, simultaneous incorporation can be accomplished by, for example, chemically synthesizing the nucleotide sequence for the acceptor variable region, fused together with the donor CDR encoding nucleic acids, and incorporating at the positions selected for harboring variable amino acid residues a plurality of corresponding amino acid codons.

Provided herein are antibodies and antigen-binding fragments thereof that bind to endoglin. Also provided are antibodies and antigen-binding fragments thereof that bind endoglin and inhibit (partially or fully) or manage/treat (partially or fully) angiogenesis/neovascularization, dilation of small vessels, and/or diseases associated with excessive angiogenesis. Similarly, inhibition of endoglin function (e.g. signaling, binding, activation, and the like) is also included within the meaning of inhibiting or binding endoglin. In yet another embodiment, an antibody or antigen-binding fragment inhibits angiogenesis by binding to endoglin. The application also provides cell lines which can be used to produce the antibodies, methods for producing the cell lines, methods for expressing antibodies or antigen-binding fragments and purifying the same.

One can recognize that the antibodies and antigen-binding fragments thereof that specifically bind endoglin generated using the methods described herein can be tested using the assays provided herein or known in the art for the ability to bind to endoglin using conventional methods including, but not limited to, ELISA. Affinity of antibodies described herein can also be determined using conventional methods including, but not limited to, Biacore or surface plasmon resonance.

The antibodies and antigen binding fragments thereof described herein were constructed by humanization of the $V_H$ and $V_L$ sequences of the TRC105 antibody. To accomplish this humanization, a 3-dimensional model of the $V_H$ and $V_L$ chains of TRC105 was created and analyzed. The $V_H$ and $V_L$ sequences were then compared individually to a database of human germline sequences, from which human $V_H$ and $V_L$ sequences were chosen based on their homology to the $V_H$ and $V_L$ sequences of TRC105. The human $V_L$ sequence chosen for humanization was O2/O12 (VK1-39) (SEQ ID NO. 2). O2/O12 has a sequence identity with TRC105 of 65% and the gene is highly expressed in the human germline repertoire. The human $V_H$ sequence chosen for humanization was VH3-15 (SEQ ID NO. 40). VH3-15 has sequence identity with TRC105 of 70% and is expressed with reasonable frequency in the human germline repertoire. The amino acid positions which were different between TRC105 and the human sequences were examined in the 3D model of TRC105 to determine which substitutions would be considered for modification. Amino acid selection criteria based on the 3D model analysis included, but was not limited to, for example, steric effects related to the amino acid, relative charge of the amino acid, and the location of the amino acid within the variable heavy and/or light chains. The identified and proposed substitutions for the human framework regions are incorporated into the O2 and VH3-15 human framework regions, and the CDRs of TRC105 are grafted into the corresponding O2 and VH3-15 human framework regions resulting in a multitude of humanized antibodies or antigen-binding fragments. Additionally, the FR-4 of the light chain is derived from human J germline sequence Jk4. Similarly, the FR-4 of the heavy chain is derived from human J germline sequence JH4.

Described herein are humanized antibodies and antigen-binding fragments that bind endoglin. Also described herein are humanized antibodies and antigen-binding fragments that bind endoglin and inhibit angiogenesis. The antibodies and antigen-binding fragments described herein were generated as described above.

Antibodies and antigen-binding fragments thereof can have a variable heavy ($V_H$) chain, a variable light ($V_L$) chain, both, or binding portions thereof. In one embodiment, the $V_H$ chain has an amino acid sequence set forth as any of SEQ ID NOS: 41-43, or a binding portion thereof. Such $V_H$ chains can have framework regions sequences set forth as any of SEQ ID NOS: 44-62. In another embodiment, the $V_L$ chain has an amino acid sequence set forth as any of SEQ ID NOS: 3-5, or a binding portion thereof. Such $V_L$ chains can have framework regions sequences set forth as any of SEQ ID NOS: 6-38.

Provided herein is an antibody, or antigen-binding fragment thereof, comprising a light chain variable region having an amino acid sequence set forth as SEQ ID NO: 3 and a heavy chain variable region having an amino acid sequence set forth as SEQ ID NO: 41.

Provided herein is an antibody, or antigen-binding fragment thereof, comprising a light chain variable region having an amino acid sequence set forth as SEQ ID NO: 3 and a heavy chain variable region having an amino acid sequence set forth as SEQ ID NO: 41, wherein: the heavy chain variable region further comprises one or more modifications selected from the group consisting of a substitution of glycine (G) by alanine (A) at position 49; a substitution of asparagine (N) by serine (S) at position 76; a substitution of threonine (T) by arginine (R) at position 77; a substitution of leucine (L) by valine (V) at position 78; a substitution of asparagine (N) by isoleucine (I) at position 82a; a substitution of valine (V) by isoleucine (I) or leucine (L) at position 89; a substitution of threonine (T) by arginine (R) or glycine (G) at position 94; a substitution of leucine (L) by threonine (T) at position 108; a substitution of valine (V) by leucine (L) at position 109; and a substitution of serine (S) by alanine (A) at position 113 utilizing the Kabat numbering system; and the light chain variable region further comprises one or more modifications selected from the group consisting of a substitution of aspartic acid (D) by glutamine (Q) at position 1; a substitution of glutamine (Q) by valine (V) at position 3; a substitution of methionine (M) by leucine (L) at position 4; a substitution of threonine (T) by serine (S) at position 5; a substitution of tyrosine (Y) by phenylalanine (F) at position 36; a substitution of leucine (L) by proline (P) at position 46; a substitution of leucine (L) by tryptophan (W) at position 47; a substitution of serine (S) by valine (V) or alanine (A) at position 60; a substitution of aspartic acid (D) by serine (S) at position 70; a substitution of phenylalanine (F) by tyrosine (Y) at position 71; a substitution of glutamine (G) by alanine (A) at position 100; and a substitution of isoleucine (I) by leucine (L) at position 106 utilizing the Kabat numbering system.

Provided herein is an antibody, or antigen-binding fragment thereof, that binds endoglin comprising a heavy chain variable region having an amino acid sequence set forth as SEQ ID NO: 41, 42, or 43; and a light chain variable region having an amino acid sequence set forth as SEQ ID NO: 3, 4, or 5. An antibody, or antigen-binding fragment thereof, can comprise a heavy chain variable region having an amino acid sequence set forth as SEQ ID NO: 41 and a light chain variable region having an amino acid sequence set forth as SEQ ID NO: 3. An antibody, or antigen-binding fragment thereof, can comprise a heavy chain variable region having an amino acid sequence set forth as SEQ ID NO: 41 and a light chain variable region having an amino acid sequence set forth as SEQ ID NO: 4. An antibody, or antigen-binding fragment thereof, can comprise a heavy chain variable region having an amino acid sequence set forth as SEQ ID NO: 41 and a light chain variable region having an amino acid sequence set forth as SEQ ID NO: 5. An antibody, or antigen-binding fragment thereof, can comprise a heavy chain variable region having an amino acid sequence set forth as SEQ ID NO: 42 and a light chain variable region having an amino acid sequence set forth as SEQ ID NO: 3. An antibody, or antigen-binding fragment thereof, can comprise a heavy chain variable region having an amino acid sequence set forth as SEQ ID NO: 42 and a light chain variable region having an amino acid sequence set forth as SEQ ID NO: 4. An antibody, or antigen-binding fragment thereof, can comprise a heavy chain variable region having an amino acid sequence set forth as SEQ ID NO: 42 and a light chain variable region having an amino acid sequence set forth as SEQ ID NO: 5. An antibody, or antigen-binding fragment thereof, can comprise a heavy chain variable region having an amino acid sequence set forth as SEQ ID NO: 43 and a light chain variable region having an amino acid sequence set forth as SEQ ID NO: 3. An antibody, or antigen-binding fragment thereof, can comprise a heavy chain variable region having an amino acid sequence set forth as SEQ ID NO: 43 and a light chain variable region having an amino acid sequence set forth as SEQ ID NO: 4. An antibody, or antigen-binding fragment thereof, can comprise a heavy chain variable region having an amino acid sequence set forth as SEQ ID NO: 43 and a light chain variable region having an amino acid sequence set forth as SEQ ID NO: 5. Such antibodies can bind to endoglin and inhibit angiogenesis.

In any of such embodiments, a heavy chain variable region can further comprise one or more modifications selected from the group consisting of: a substitution of asparagine (N) by serine (S) at position 76; a substitution of threonine (T) by arginine (R) at position 77; a substitution of asparagine (N) by isoleucine (I) at position 82a; a substitution of valine (V) by isoleucine (I) or leucine (L) at position 89; a substitution of threonine (T) by glycine (G) at position 94; a substitution of leucine (L) by threonine (T) at position 108; a substitution of valine (V) by leucine (L) at position 109; and a substitution of serine (S) by alanine (A) a position 113; and the light chain variable region can further comprise one or more modifications selected from the group consisting of: a substitution of aspartic acid (D) by glutamine (Q) at position 1; a substitution of glutamine (Q) by valine (V) at position 3; a substitution of threonine (T) by serine (S) at position 5; a substitution of tyrosine (Y) by phenylalanine (F) a position 36; a substitution of serine (S) by valine (V) or alanine (A) at position 60; a substitution of aspartic acid (D) by serine (S) at position 70; a substitution of glycine (G) by alanine (A) at position 100, and a substitution of isoleucine (I) by leucine (L) at position 106 utilizing the Kabat numbering system.

Provided herein is an antibody, or antigen-binding fragment thereof, that binds endoglin, comprising a heavy chain variable region and a light chain variable region, wherein said heavy chain variable region comprises:
  (i) a CDR1 of SEQ ID NO: 66, a CDR2 of SEQ ID NO: 67, and a CDR3 of SEQ ID NO: 68;
  (ii) a heavy chain FR1 having the amino acid sequence of SEQ ID NO: 44 or the amino acid sequence of SEQ ID NO: 44 except for one or more conservative substitutions;
  (iii) a heavy chain FR2 having the amino acid sequence of SEQ ID NO: 45 or the amino acid sequence of SEQ ID NO: 45 except for a substitution of glycine (G) by alanine (A) at position 49 utilizing the Kabat numbering system; and
  (iv) a heavy chain FR3 having the amino acid sequence of SEQ ID NO: 47 or the amino acid sequence of SEQ ID NO: 47 except for one or more substitutions selected from the group consisting of:
    (a) a substitution of asparagine (N) by serine (S) at position 76;
    (b) a substitution of threonine (T) by arginine (R) at position 77;
    (c) a substitution of leucine (L) by valine (V) at position 78;
    (d) a substitution of asparagine (N) by isoleucine (I) at position 82a;
    (e) a substitution of valine (V) by isoleucine (I) or leucine (L) at position 89; and
    (f) a substitution of threonine (T) by arginine (R) or glycine (G) at position 94 utilizing the Kabat numbering system; and
  (v) a heavy chain FR4 having the amino acid sequence of SEQ ID NO: 56 or the amino acid sequence of SEQ ID NO: 56 except for one or more substitutions selected from the group consisting of:
    (a) a substitution of leucine (L) by threonine (T) at position 108;
    (b) a substitution of valine (V) by leucine (L) at position 109; and
    (c) a substitution of serine (S) by alanine (A) at position 113 utilizing the Kabat numbering system;
and said light chain variable region comprises:
  (i) a CDR1 of SEQ ID NO: 63, a CDR2 of SEQ ID NO: 64, and a CDR3 of SEQ ID NO: 65;
  (ii) a light chain FR1 having the amino acid sequence of SEQ ID NO: 6 or the amino acid sequence of SEQ ID NO: 6 except for one or more substitutions selected from the group consisting of:
    (a) a substitution of aspartic acid (D) by glutamine (Q) at position 1;
    (b) a substitution of glutamine (Q) by valine (V) at position 3;
    (c) a substitution of methionine (M) by leucine (L) at position 4; and
    (d) a substitution of threonine (T) by serine (S) at position 5; utilizing the Kabat numbering system; and
  (iii) a light chain FR2 having the amino acid sequence of SEQ ID NO: 20 or the amino acid sequence of SEQ ID NO: 20 except for one or more substitutions selected from the group consisting of:
    (a) a substitution of tyrosine (Y) by phenylalanine (F) at position 36;
    (b) a substitution of leucine (L) by proline (P) at position 46; and
    (c) a substitution of leucine (L) by tryptophan (W) at position 47 utilizing the Kabat numbering system; and
  (iv) a light chain FR3 having the amino acid sequence of SEQ ID NO: 28 or the amino acid sequence of SEQ ID NO: 28 except for one or more substitutions selected from the group consisting of:
    (a) a substitution of serine (S) by valine (V) or alanine (A) at position 60;
    (b) a substitution of aspartic acid (D) by serine (S) at position 70; and
    (b) a substitution of phenylalanine (F) by tyrosine (Y) at position 71 utilizing the Kabat numbering system; and
  (v) a light chain FR4 having the amino acid sequence of SEQ ID NO: 35 or the amino acid sequence of SEQ ID NO: 35 except for one or more substitutions selected from the group consisting of:
    (a) a substitution of glycine (G) by alanine (A) at position 100; and
    (b) a substitution of isoleucine (I) by leucine (L) at position 106 utilizing the Kabat numbering system.

An antibody, or antigen-binding fragment thereof, provided herein can comprise a heavy chain variable region CDR1 having an amino acid sequence as set forth in SEQ ID NO: 66, a heavy chain variable region CDR2 having an amino acid sequence as set forth in SEQ ID NO: 67, a heavy chain variable region CDR3 having an amino acid sequence as set forth in SEQ ID NO: 68, a light chain variable region CDR1 having an amino acid sequence as set forth in SEQ ID NO: 63, a light chain variable region CDR2 having an amino acid sequence as set forth in SEQ ID NO: 64, and a light chain variable region CDR3 having an amino acid sequence as set forth in SEQ ID NO: 65.

In one embodiment, the antibody, or antigen-binding fragment thereof binds endoglin and comprises a heavy chain variable region FR1 having an amino acid sequence as set forth in SEQ ID NO: 44; a heavy chain variable region FR2 having an amino acid sequence as set forth in SEQ ID NO: 45; a heavy chain variable region FR3 having an amino acid sequence as set forth in SEQ ID NO: 47; a heavy chain variable region FR4 having an amino acid sequence as set forth in SEQ ID NO: 56.

In another embodiment, the antibody, or antigen-binding fragment thereof binds endoglin and comprises a heavy chain variable region FR1 having an amino acid sequence as set forth in SEQ ID NO: 44; a heavy chain variable region FR2 having an amino acid sequence as set forth in SEQ ID NO: 46; a heavy chain variable region FR3 having an amino acid sequence as set forth in SEQ ID NO: 48; a heavy chain variable region FR4 having an amino acid sequence as set forth in SEQ ID NO: 56.

In another embodiment, the antibody, or antigen-binding fragment thereof, comprises a light chain variable region FR1 having an amino acid sequence as set forth in SEQ ID NO: 6; a light chain variable region FR2 having an amino acid sequence as set forth in SEQ ID NO: 20; a light chain variable region FR3 having an amino acid sequence as set forth in SEQ ID NO: 28; and a light chain variable region FR4 having an amino acid sequence as set forth in SEQ ID NO: 35.

In another embodiment, the antibody, or antigen-binding fragment thereof binds endoglin and comprises a light chain variable region FR1 having an amino acid sequence as set forth in SEQ ID NO: 6; a light chain variable region FR2 having an amino acid sequence as set forth in SEQ ID NO: 21; a light chain variable region FR3 having an amino acid sequence as set forth in SEQ ID NO: 29; and a light chain variable region FR4 having an amino acid sequence as set forth in SEQ ID NO: 35.

In another embodiment, the antibody, or antigen-binding fragment thereof binds endoglin and comprises a light chain variable region FR1 having an amino acid sequence as set forth in SEQ ID NO: 7; a light chain variable region FR2 having an amino acid sequence as set forth in SEQ ID NO: 21; a light chain variable region FR3 having an amino acid sequence as set forth in SEQ ID NO: 29; and a light chain variable region FR4 having an amino acid sequence as set forth in SEQ ID NO: 35.

Provided herein is an antibody, or antigen-binding fragment thereof, comprising a heavy chain variable region having an amino acid sequence set forth as SEQ ID NO: 42 and a light chain variable region having an amino acid sequence set forth as SEQ ID NO: 4.

Provided herein is an antibody, or antigen-binding fragment thereof, that binds endoglin, comprising a light chain variable region having an amino acid sequence set forth as SEQ ID NO: 4 and a heavy chain variable region having an amino acid sequence set forth as SEQ ID NO: 42, wherein: said heavy chain variable region further comprises one or more modifications selected from the group consisting of a substitution of glycine (G) by alanine (A) at position 49; a substitution of asparagine (N) by serine (S) at position 76; a substitution of threonine (T) by arginine (R) at position 77; a substitution of leucine (L) by valine (V) at position 78; a substitution of asparagine (N) by isoleucine (I) at position 82a; a substitution of valine (V) by isoleucine (I) or leucine (L) at position 89; a substitution of arginine (R) by threonine (T) or glycine (G) at position 94; a substitution of leucine (L) by threonine (T) at position 108; a substitution of valine (V) by leucine (L) at position 109; and a substitution of serine (S) by alanine (A) at position 113 utilizing the Kabat numbering system; and the light chain variable region further comprises one or more modifications selected from the group consisting of a substitution of aspartic acid (D) by glutamine (Q) at position 1; a substitution of glutamine (Q) by valine (V) at position 3; a substitution of methionine (M) by leucine (L) at position 4; a substitution of threonine (T) by serine (S) at position 5; a substitution of tyrosine (Y) by phenylalanine (F) at position 36; a substitution of proline (P) by leucine (L) at position 46; a substitution of tryptophan (W) by leucine (L) at position 47; a substitution of serine (S) by valine (V) or alanine (A) at position 60; a substitution of aspartic acid (D) by serine (S) at position 70; a substitution of tyrosine (Y) by phenylalanine (F) at position 71; a substitution of glutamine (G) by alanine (A) at position 100; and a substitution of isoleucine (I) by leucine (L) at position 106 utilizing the Kabat numbering system Provided herein is an antibody, or antigen-binding fragment thereof, that binds endoglin, comprising a heavy chain variable region and a light chain variable region, wherein said heavy chain variable region comprises:
(i) a CDR1 of SEQ ID NO: 66, a CDR2 of SEQ ID NO: 67, and a CDR3 of SEQ ID NO: 68;
(ii) a heavy chain FR1 having the amino acid sequence of SEQ ID NO: 44 or the amino acid sequence of SEQ ID NO: 44 except for one or more conservative substitutions;
(iii) a heavy chain FR2 having the amino acid sequence of SEQ ID NO: 45 or the amino acid sequence of SEQ ID NO: 45 except for a substitution of glycine (G) by alanine (A) at position 49 utilizing the Kabat numbering system; and
(iv) a heavy chain FR3 having the amino acid sequence of SEQ ID NO: 47 or the amino acid sequence of SEQ ID NO: 47 except for one or more substitutions selected from the group consisting of:
  (a) a substitution of asparagine (N) by serine (S) at position 76;
  (b) a substitution of threonine (T) by arginine (R) at position 77;
  (c) a substitution of leucine (L) by valine (V) at position 78;
  (d) a substitution of asparagine (N) by isoleucine (I) at position 82a;
  (e) a substitution of valine (V) by isoleucine (I) or leucine (L) at position 89; and
  (f) a substitution of arginine (R) by threonine (T) or glycine (G) at position 94 utilizing the Kabat numbering system; and
(v) a heavy chain FR4 having the amino acid sequence of SEQ ID NO: 56 or the amino acid sequence of SEQ ID NO: 56 except for one or more substitutions selected from the group consisting of:
  (a) a substitution of leucine (L) by threonine (T) at position 108;
  (b) a substitution of valine (V) by leucine (L) at position 109; and
  (c) a substitution of serine (S) by alanine (A) at position 113 utilizing the Kabat numbering system;
and said light chain variable region comprises:
(i) a CDR1 of SEQ ID NO: 63, a CDR2 of SEQ ID NO: 64, and a CDR3 of SEQ ID NO: 65;
(ii) a light chain FR1 having the amino acid sequence of SEQ ID NO: 6 or the amino acid sequence of SEQ ID NO: 6 except for one or more substitutions selected from the group consisting of:
  (a) a substitution of aspartic acid (D) by glutamine (Q) at position 1;
  (b) a substitution of glutamine (Q) by valine (V) at position 3;
  (c) a substitution of methionine (M) by leucine (L) at position 4; and
  (d) a substitution of threonine (T) by serine (S) at position 5; utilizing the Kabat numbering system; and
(iii) a light chain FR2 having the amino acid sequence of SEQ ID NO: 21 or the amino acid sequence of SEQ ID NO: 20 except for one or more substitutions selected from the group consisting of:
  (a) a substitution of tyrosine (Y) by phenylalanine (F) at position 36;
  (b) a substitution of proline (P) by leucine (L) at position 46; and
  (c) a substitution of tryptophan (W) by leucine (L) at position 47 utilizing the Kabat numbering system; and
(iv) a light chain FR3 having the amino acid sequence of SEQ ID NO: 29 or the amino acid sequence of SEQ ID NO: 28 except for one or more substitutions selected from the group consisting of:
  (a) a substitution of serine (S) by valine (V) or alanine (A) at position 60;
  (b) a substitution of aspartic acid (D) by serine (S) at position 70; and
  (b) a substitution of tyrosine (Y) by phenylalanine (F) at position 71 utilizing the Kabat numbering system; and
(v) a light chain FR4 having the amino acid sequence of SEQ ID NO: 35 or the amino acid sequence of SEQ ID NO: 35 except for one or more substitutions selected from the group consisting of:
  (a) a substitution of glycine (G) by alanine (A) at position 100; and
  (b) a substitution of isoleucine (I) by leucine (L) at position 106 utilizing the Kabat numbering system.

A substantial portion of a variable domain will include three CDR regions, together with their intervening framework regions. The portion can also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally-occurring variable domain regions. For example, construction of humanized endoglin antibodies and antigen-binding fragments described herein made by recombinant DNA techniques can result in the introduction of N- or C-terminal residues encoded by linkers introduced to facilitate cloning or other manipulation steps. Other manipulation steps include the introduction of linkers to join variable domains to further protein sequences including immunoglobulin heavy chains, other variable domains (for example in the production of diabodies) or protein labels as discussed in more detail below.

Humanized endoglin CDR3 regions having amino acid sequences substantially as set out as the CDR3 regions of the antibodies described herein will be carried in a structure which allows for binding of the CDR3 regions to endoglin. The structure for carrying the CDR3s can be of an antibody heavy or light chain sequence or substantial portion thereof in which the CDR3 regions are located at locations corresponding to the CDR3 region of naturally-occurring $V_H$ and $V_L$ antibody variable domains encoded by rearranged immunoglobulin genes.

In one non-limiting example, provided herein are antibodies or antigen binding fragments thereof containing a variable heavy chain having a CDR3 which has an amino acid sequence set forth as SEQ ID NO: 68 and/or a variable light chain having a CDR3 which has an amino acid sequence set forth as SEQ ID NO: 65. In one embodiment, the variable heavy chain has an amino acid sequence set forth as SEQ ID NO: 40 except for a substitution of the CDR3 by the CDR3 amino sequence set forth as SEQ ID NO: 68. In another embodiment, the variable light chain has an amino acid sequence set forth as SEQ ID NO: 2 except for a substitution of the CDR3 by the CDR3 amino acid sequence set forth as SEQ ID NO: 65. Additionally, such CDR3 containing variable regions/chains can comprise one or more FR amino acid sequences set forth as, for example, described above (or such FRs containing one or more additional modifications), where the antibodies or antigen binding fragments have 3 CDRs and 4 FRs in each of the VH and VL regions, have specific binding activity for endoglin and which are able to inhibit angiogenesis. Additionally, various antibody J segments can also be substituted within these variable regions for further variation within the variable region chains.

In one aspect, variable heavy and light chains described herein can also be created by further replacing FR4 sequences. In one embodiment, heavy chain FR4 sequences can be substituted for one of the following:

| SEQ ID NO: | Kabat-Number | 103 | 104 | 105 | 106 | 107 | 108 | 109 | 110 | 111 | 112 | 113 |
|---|---|---|---|---|---|---|---|---|---|---|---|---|
| 76 | FRM4 from JH1, JH4 or JH5 | W | G | Q | G | T | L | V | T | V | S | S |
| 77 | FRM4 from JH2 | W | G | R | G | T | L | V | T | V | S | S |
| 78 | FRM4 from JH3 | W | G | Q | G | T | M | V | T | V | S | S |
| 79 | FRM4 from JH6 | W | G | Q | G | T | T | V | T | V | S | S |

In one embodiment, light chain FR4 sequences can be substituted for one of the following:

| SEQ ID NO | Kabat Number | 98 | 99 | 100 | 101 | 102 | 103 | 104 | 105 | 106 | 107 |
|---|---|---|---|---|---|---|---|---|---|---|---|
| 80 | JK1 | F | G | Q | G | T | K | V | E | I | K |
| 81 | JK2 | F | G | Q | G | T | K | L | E | I | K |
| 82 | JK3 | F | G | P | G | T | K | V | D | I | K |
| 83 | JK4 | F | G | G | G | T | K | V | E | I | K |
| 84 | JK5 | F | G | Q | G | T | R | L | E | I | K |

Further provided herein are humanized versions of anti-endoglin antibodies alternatively named "superhumanized" anti-endoglin antibodies or antigen-binding fragments thereof. Such superhumanized antibodies, or antigen-binding fragments thereof, can comprise a light chain variable region having an amino acid sequence set forth as SEQ ID NOS: 71 or 72 and a heavy chain variable region having an amino acid sequence set forth as SEQ ID NO: 75.

In another aspect, the present application provides a humanized antibody capable of competing with a humanized anti-endoglin antibody or antigen-binding described herein under conditions in which at least 5% of an antibody having the $V_H$ and $V_L$ sequences of the antibody is blocked from binding to endoglin by competition with such an antibody in an ELISA assay.

Provided herein are neutralizing antibodies or antigen-binding fragments that bind to endoglin and modulate the activity of endoglin. The neutralizing antibody can for example, inhibit angiogenesis by binding to endoglin.

Percentage of (%) inhibition of angiogenesis by an humanized anti-endoglin antibody or antigen-binding fragment thereof of at least 2-fold, at least 3-fold, at least 4-fold, at least 5-fold, at least 6-fold, at least 7-fold, at least 8-fold, at least 9-fold, at least 10-fold, at least 20-fold, at least 30-fold, at least 40-fold, at least 50-fold, at least 60-fold, or greater than negative controls is indicative of a antibody or antigen-binding fragment thereof inhibits angiogenesis. Percentage (%) of inhibition of angiogenesis by a humanized anti-endoglin antibody or antigen-binding fragment thereof of less than 2-fold greater than negative controls is indicative of an antibody or antigen-binding fragment thereof that does not inhibit angiogenesis.

Binding of an antibody or antigen-binding fragment to endoglin can partially (e.g., 5%, 10%, 20%, 30%, 40%, 50%, 60%, 70%, 80%, 90%, 95%, 98%, 99% or any number therein) or completely inhibit angiogenesis. The neutralizing or inhibiting activity of an antibody or antigen-binding fragment can be determined using an in vitro assay and/or in vivo using art-recognized assays such as those described herein or otherwise known in the art.

In one aspect, the antigen-binding fragment of any one of the humanized antibodies described above is a Fab, a Fab', a Fd, a F(ab')$_2$, a Fv, a scFv, a single chain binding polypeptide (e.g., a scFv with Fc portion) or any other functional fragment thereof as described herein.

Antibodies or antigen-binding fragments described herein are useful in detection or diagnostic applications as described in more detail below. Antibodies or antigen-binding fragments described herein are useful for binding to endoglin, which, in turn, can inhibit angiogenesis as described herein.

Antibodies, or antigen-binding fragments thereof, described herein can be further modified to alter the specific properties of the antibody while retaining the desired functionality, if needed. For example, in one embodiment, the compound can be modified to alter a pharmacokinetic property of the compound, such as in vivo stability, solubility, bioavailability or half-life. Antibodies, or antigen-binding fragments thereof, described herein can further comprise a therapeutic moiety, a detectable moiety, or both, for use in diagnostic and/or therapeutic applications.

Antibodies, or antigen-binding fragments thereof, described herein can also be used as immunoconjugates. As used herein, for purposes of the specification and claims, immunoconjugates refer to conjugates comprised of the humanized anti-endoglin antibodies or fragments thereof according to the present invention and at least one therapeutic label. Therapeutic labels include antitumor agents and angiogenesis-inhibitors. Such antitumor agents are known in the art and include, but not limited to, toxins, drugs, enzymes, cytokines, radionuclides, photodynamic agents, and angiogenesis inhibitors. Toxins include, but are not limited to, ricin A chain, mutant *Pseudomonas* exotoxins, diphtheria toxoid, streptonigrin, boamycin, saporin, gelonin, and pokeweed antiviral protein. Drugs include daunorubicin, methotrexate, and calicheamicins. Radionuclides include radiometals. Cytokines include, but are not limited to, transforming growth factor (TGF)-β, interleukins, interferons, and tumor necrosis factors. Photodynamic agents include, but are not limited to, porphyrins and their derivatives. Additional therapeutic labels will be known in the art and are also contemplated herein. The methods for complexing the anti-endoglin mAbs or a fragment thereof with at least one antitumor agent are well known to those skilled in the art (i.e., antibody conjugates as reviewed by Ghetie et al., 1994, Pharmacol. Ther. 63:209-34). Such methods may utilize one of several available heterobifunctional reagents used for coupling or linking molecules. Additional radionuclides are further described herein along with additional methods for linking molecules, such as therapeutic and diagnostic labels.

Antibodies, or antigen-binding fragments thereof, can be modified using techniques known in the art for various purposes such as, for example, by addition of polyethylene glycol (PEG). PEG modification (PEGylation) can lead to one or more of improved circulation time, improved solubility, improved resistance to proteolysis, reduced antigenicity and immunogenicity, improved bioavailability, reduced toxicity, improved stability, and easier formulation (for a review see, Francis et al., International Journal of Hematology 68:1-18, 1998).

In the case of an antigen-binding fragment which does not contain an Fc portion, an Fc portion can be added to (e.g., recombinantly) the fragment, for example, to increase half-life of the antigen-binding fragment in circulation in blood when administered to a patient. Choice of an appropriate Fc region and methods of to incorporate such fragments are known in the art. Incorporating a Fc region of an IgG into a polypeptide of interest so as to increase its circulatory half-life, but so as not to lose its biological activity can be accomplished using conventional techniques known in the art such as, for example, described in U.S. Pat. No. 6,096, 871, which is hereby incorporated by reference in its entirety. Fc portions of antibodies can be further modified to increase half-life of the antigen-binding fragment in circulation in blood when administered to a patient. Modifications can be determined using conventional means in the art such as, for example, described in U.S. Pat. No. 7,217,798, which is hereby incorporated by reference in its entirety.

Other methods of improving the half-life of antibody-based fusion proteins in circulation are also known such as, for example, described in U.S. Pat. Nos. 7,091,321 and 6,737,056, each of which is hereby incorporated by reference. Additionally, antibodies and antigen-binding fragments thereof may be produced or expressed so that they do not contain fucose on their complex N-glycoside-linked sugar chains. The removal of the fucose from the complex N-glycoside-linked sugar chains is known to increase effector functions of the antibodies and antigen-binding fragments, including but not limited to, antibody dependent cell-mediated cytotoxicity (ADCC) and complement dependent cytotoxicity (CDC). Similarly, antibodies or antigen-binding fragments thereof that can bind endoglin can be attached at their C-terminal end to all or part of an immunoglobulin heavy chain derived from any antibody isotype, e.g., IgG, IgA, IgE, IgD and IgM and any of the isotype sub-classes, particularly IgG1, IgG2b, IgG2a, IgG3 and IgG4.

Additionally, the antibodies or antigen-binding fragments described herein can also be modified so that they are able to cross the blood-brain barrier. Such modification of the antibodies or antigen-binding fragments described herein allows for the treatment of brain diseases such as glioblastoma multiforme (GBM). Exemplary modifications to allow proteins such as antibodies or antigen-binding fragments to cross the blood-brain barrier are described in US Patent Application Publication 2007/0082380 which is hereby incorporated by reference in its entirety.

Glycosylation of immunoglobulins has been shown to have significant effects on their effector functions, structural stability, and rate of secretion from antibody-producing cells (Leatherbarrow et al., Mol. Immunol. 22:407 (1985)). The carbohydrate groups responsible for these properties are generally attached to the constant (C) regions of the antibodies. For example, glycosylation of IgG at asparagine 297 in the $C_H2$ domain is required for full capacity of IgG to activate the classical pathway of complement-dependent cytolysis (Tao and Morrison, J. Immunol. 143:2595 (1989)). Glycosylation of IgM at asparagine 402 in the $C_H3$ domain is necessary for proper assembly and cytolytic activity of the antibody (Muraoka and Shulman, J. Immunol. 142:695 (1989)). Removal of glycosylation sites as positions 162 and 419 in the $C_H1$ and $C_H3$ domains of an IgA antibody led to intracellular degradation and at least 90% inhibition of secretion (Taylor and Wall, Mol. Cell. Biol. 8:4197 (1988)). Additionally, antibodies and antigen-binding fragments thereof may be produced or expressed so that they do not contain fucose on their complex N-glycoside-linked sugar chains. The removal of the fucose from the complex N-glycoside-linked sugar chains is known to increase effector functions of the antibodies and antigen-binding fragments, including but not limited to, antibody dependent cell-mediated cytotoxicity (ADCC) and complement dependent cytotoxicity (CDC). These "defucosylated" antibodies and antigen-binding fragments may be produced through a variety of systems utilizing molecular cloning techniques known in the art, including but not limited to, transgenic animals, transgenic plants, or cell-lines that have been genetically engineered so that they no longer contain the enzymes and biochemical pathways necessary for the inclusion of a fucose in the complex N-glycoside-linked sugar chains (also known as fucosyltransferase knock-out animals, plants, or cells). Non-limiting examples of cells that can be engineered to be fucosyltransferase knock-out cells include CHO cells, SP2/0 cells, NS0 cells, and YB2/0 cells.

Glycosylation of immunoglobulins in the variable (V) region has also been observed. Sox and Hood reported that about 20% of human antibodies are glycosylated in the V region (Proc. Natl. Acad. Sci. USA 66:975 (1970)). Glycosylation of the V domain is believed to arise from fortuitous occurrences of the N-linked glycosylation signal Asn-Xaa-Ser/Thr in the V region sequence and has not been recognized in the art as playing a role in immunoglobulin function.

Glycosylation at a variable domain framework residue can alter the binding interaction of the antibody with antigen. The present invention includes criteria by which a limited number of amino acids in the framework or CDRs of a humanized immunoglobulin chain are chosen to be mutated (e.g., by substitution, deletion, or addition of residues) in order to increase the affinity of an antibody.

Affinity for binding a pre-determined polypeptide antigen can, generally, be modulated by introducing one or more mutations into the V region framework, typically in areas adjacent to one or more CDRs and/or in one or more framework regions. Typically, such mutations involve the introduction of conservative amino acid substitutions that either destroy or create the glycosylation site sequences but do not substantially affect the hydropathic structural properties of the polypeptide. Typically, mutations that introduce a proline residue are avoided. Glycosylation of antibodies and antigen-binding fragments thereof is further described in U.S. Pat. No. 6,350,861, which is incorporated by reference herein with respect to glycosylation.

Antibodies, or antigen-binding fragments thereof, can be formulated for short-term delivery or extended (long term) delivery.

Antibodies, or antigen-binding fragments thereof, that bind to endoglin can also be used for purification of endoglin and/or to detect endoglin levels in a sample or patient to detect or diagnose a disease or disorder associated with endoglin as described in more detail below.

Humanized antibodies, antigen-binding fragments, and binding proteins which bind endoglin generated using such methods can be tested for one or more of their binding affinity, avidity, and neutralizing capabilities. Useful humanized antibodies, antigen-binding fragments, and binding proteins can be used to administer a patient to prevent, inhibit, manage or treat a condition disease or disorder associated with angiogenesis.

Provided herein are methods of identifying humanized antibodies or antigen-binding fragments thereof that bind to endoglin. Antibodies and antigen-binding fragments can be evaluated for one or more of binding affinity, association rates, disassociation rates and avidity. In one aspect, antibodies can be evaluated for their ability to neutralize the activity of endoglin or a polypeptide in which the endoglin binding sequence is present. Measurement binding affinity, association rates, disassociation rates and avidity can be accomplished using art-recognized assays including (Surface Plasmon Resonance), but not limited to, an enzyme-linked-immunosorbent assay (ELISA), Scatchard Analysis, BIACORE analysis, etc., as well as other assays commonly used and known to those of ordinary skill in the art.

Measurement of binding of antibodies to endoglin and/or the ability of the antibodies and antigen-binding fragments thereof, for example, to inhibit angiogenesis, can be determined using, for example, an enzyme-linked-immunosorbent assay (ELISA), a competitive binding assay, an ELISPOT assay, or any other useful assay known in the art. These assays are commonly used and well-known to those of ordinary skill in the art.

In one non-limiting embodiment, an ELISA assay can be used to measure the binding capability of specific antibodies or antigen-binding fragments that bind to endoglin.

Assays, such as an ELISA, also can be used to identify antibodies or antigen-binding fragments thereof which exhibit increased specificity for endoglin in comparison to other antibodies or antigen-binding fragments thereof. Assays, such as an ELISA, also can be used to identify antibodies or antigen-binding fragments thereof with bind to epitopes across one or more polypeptides and across one or more species of endoglin. The specificity assay can be conducted by running parallel ELISAs in which a test antibodies or antigen-binding fragments thereof is screened concurrently in separate assay chambers for the ability to bind one or more epitopes on different species of the polypeptide containing the endoglin epitopes to identify antibodies or antigen-binding fragments thereof that bind to endoglin. Another technique for measuring apparent binding affinity familiar to those of skill in the art is a surface plasmon resonance technique (analyzed on a BIACORE 2000 system) (Liljeblad, et al., Glyco. J. 2000, 17:323-329). Standard measurements and traditional binding assays are described by Heeley, R. P., Endocr. Res. 2002, 28:217-229.

Humanized antibodies to endoglin can also be assayed for their ability to treat various diseases and conditions associated with angiogenesis, e.g., various forms of ocular diseases characterized by angiogenesis/neovascularization (e.g., macular degeneration, diabetic retinopathy), diabetic nephropathy, chronic inflammatory diseases (e.g., IBD), rheumatoid arthritis, osteoarthritis, and various forms of cancer (primary tumors and metastases). Any suitable assay known to one of skill in the art can be used to monitor such effects. Several such techniques are described herein. In one example, the antibodies and antigen-binding fragments described herein are assayed for their ability to bind endoglin. In another example, affinity constants for the antibodies and antigen-binding fragments described herein are determined by surface plasmon resonance (SPR). In yet another example, the antibodies and antigen-binding fragments described herein are assayed for their effect on the inhibition of angiogenesis.

II. Compositions

Each of the compounds described herein can be used as a composition when combined with an acceptable carrier or excipient. Such compositions are useful for in vitro or in vivo analysis or for administration to a subject in vivo or ex vivo for treating a subject with the disclosed compounds.

Thus pharmaceutical compositions can include, in addition to active ingredient, a pharmaceutically acceptable excipient, carrier, buffer, stabilizer or other materials well known to those skilled in the art. Such materials should be non-toxic and should not interfere with the efficacy of the active ingredient. The precise nature of the carrier or other material will depend on the route of administration.

Pharmaceutical formulations comprising a protein of interest, e.g., an antibody or antigen-binding fragment, identified by the methods described herein can be prepared for storage by mixing the protein having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are those that are non-toxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN®, PLURONICS® or polyethylene glycol (PEG).

Acceptable carriers are physiologically acceptable to the administered patient and retain the therapeutic properties of the compounds with/in which it is administered. Acceptable carriers and their formulations are and generally described in, for example, Remington' pharmaceutical Sciences (18th Edition, ed. A. Gennaro, Mack Publishing Co., Easton, Pa. 1990). One exemplary carrier is physiological saline. The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject compounds from the administration site of one organ, or portion of the body, to another organ, or portion of the body, or in an in vitro assay system. Each carrier is acceptable in the sense of being compatible with the other ingredients of the formulation and not injurious to a subject to whom it is administered. Nor should an acceptable carrier alter the specific activity of the subject compounds.

In one aspect, provided herein are pharmaceutically acceptable or physiologically acceptable compositions including solvents (aqueous or non-aqueous), solutions, emulsions, dispersion media, coatings, isotonic and absorption promoting or delaying agents, compatible with pharmaceutical administration. Pharmaceutical compositions or pharmaceutical formulations therefore refer to a composition suitable for pharmaceutical use in a subject. The pharmaceutical compositions and formulations include an amount of a compound described herein and a pharmaceutically or physiologically acceptable carrier.

Compositions can be formulated to be compatible with a particular route of administration (i.e., systemic or local). Thus, compositions include carriers, diluents, or excipients suitable for administration by various routes.

In another embodiment, the compositions can further comprise, if needed, an acceptable additive in order to improve the stability of the compounds in composition and/or to control the release rate of the composition. Acceptable additives do not alter the specific activity of the subject compounds. Exemplary acceptable additives include, but are not limited to, a sugar such as mannitol, sorbitol, glucose, xylitol, trehalose, sorbose, sucrose, galactose, dextran, dextrose, fructose, lactose and mixtures thereof. Acceptable additives can be combined with acceptable carriers and/or excipients such as dextrose. Alternatively, exemplary acceptable additives include, but are not limited to, a surfactant such as polysorbate 20 or polysorbate 80 to increase stability of the peptide and decrease gelling of the solution. The surfactant can be added to the composition in an amount of 0.01% to 5% of the solution. Addition of such acceptable additives increases the stability and half-life of the composition in storage.

The pharmaceutical composition can be administered, for example, by injection, including, but not limited to, subcutaneous, subcutaneous, intravitreal, intradermal, intravenous, intra-arterial, intraperitoneal, or intramuscular injection. Excipients and carriers for use in formulation of compositions for each type of injection are contemplated herein. The following descriptions are by example only and are not meant to limit the scope of the compositions. Compositions for injection include aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (for example, glycerol, propylene glycol, and liquid polyetheylene glycol, and the like), and suitable mixtures thereof. Fluidity can be maintained, for example, by the use of a coating such as lecithin, by the maintenance of the required particle size in the case of dispersion and by the use of surfactants. Antibacterial and antifungal agents include, for example, parabens, chlorobutanol, phenol, ascorbic acid and thimerosal. Isotonic agents, for example, sugars, polyalcohols such as manitol, sorbitol, and sodium chloride may be included in the composition. The resulting solutions can be packaged for use as is, or lyophilized; the lyophilized preparation can later be combined with a sterile solution prior to administration. For intravenous, injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as needed. Sterile injectable solutions can be prepared by incorporating an active ingredient in the required amount in an appropriate solvent with one or a combination of ingredients enumerated above, as required, followed by filtered sterilization. Generally, dispersions are prepared by incorporating the active ingredient into a sterile vehicle which contains a basic dispersion medium and the required other ingredients from those enumerated above. In the case of sterile powders for the preparation of sterile injectable solutions, the preferred methods of preparation are vacuum drying and freeze drying which yields a powder of the active ingredient plus any additional desired ingredient from a previously sterile-filtered solution thereof.

Compositions can be conventionally administered intravitreally, sub-cutaneous, or via intravitreal implant.

Compositions can be conventionally administered intravenously, such as by injection of a unit dose, for example. For injection, an active ingredient can be in the form of a parenterally acceptable aqueous solution which is substantially pyrogen-free and has suitable pH, isotonicity and stability. One can prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required. Additionally, compositions can be administered via aerosolization. (Lahn et al., *Aerosolized Anti-T-cell-Receptor Antibodies Are Effective against Airway Inflammation and Hyperreactivity*, Int. Arch. Allegery Immuno., 134: 49-55 (2004)).

In one embodiment, the composition is lyophilized, for example, to increase shelf-life in storage. When the compositions are considered for use in medicaments or any of the methods provided herein, it is contemplated that the composition can be substantially free of pyrogens such that the composition will not cause an inflammatory reaction or an unsafe allergic reaction when administered to a human patient. Testing compositions for pyrogens and preparing compositions substantially free of pyrogens are well understood to one or ordinary skill of the art and can be accomplished using commercially available kits.

Acceptable carriers can contain a compound that stabilizes, increases or delays absorption or clearance. Such compounds include, for example, carbohydrates, such as glucose, sucrose, or dextrans; low molecular weight proteins; compositions that reduce the clearance or hydrolysis of peptides; or excipients or other stabilizers and/or buffers. Agents that delay absorption include, for example, aluminum monostearate and gelatin. Detergents can also be used to stabilize or to increase or decrease the absorption of the pharmaceutical composition, including liposomal carriers. To protect from digestion the compound can be complexed with a composition to render it resistant to acidic and enzymatic hydrolysis, or the compound can be complexed in an appropriately resistant carrier such as a liposome. Means of protecting compounds from digestion are known in the art (see, e.g., Fix (1996) Pharm Res. 13:1760 1764; Samanen (1996) J. Pharm. Pharmacol. 48:119 135; and U.S. Pat. No. 5,391,377, describing lipid compositions for oral delivery of therapeutic agents).

The phrase "pharmaceutically acceptable" refers to molecular entities and compositions that are physiologically tolerable and do not typically produce an allergic or similar untoward reaction, such as gastric upset, dizziness and the like, when administered to a human.

The term "unit dose" when used in reference to a therapeutic composition refers to physically discrete units suitable as unitary dosage for humans, each unit containing a predetermined quantity of active material calculated to produce the desired therapeutic effect in association with the required diluent; i.e., carrier, or vehicle.

The compositions can be administered in a manner compatible with the dosage formulation, and in a therapeutically effective amount. The quantity to be administered depends on the subject to be treated, capacity of the subject's immune system to utilize the active ingredient, and degree of binding capacity desired. Precise amounts of active ingredient required to be administered depend on the judgment of the practitioner and are peculiar to each individual. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations in the blood are contemplated.

One embodiment contemplates the use of the compositions described herein to make a medicament for treating a condition, disease or disorder described herein. Medicaments can be formulated based on the physical characteristics of the patient/subject needing treatment, and can be formulated in single or multiple formulations based on the stage of the condition, disease or disorder. Medicaments can be packaged in a suitable package with appropriate labels for the distribution to hospitals and clinics wherein the label is for the indication of treating a subject having a disease described herein. Medicaments can be packaged as a single or multiple units. Instructions for the dosage and administration of the compositions can be included with the packages as described below. The invention is further directed to medicaments of a humanized anti-endoglin antibody or antigen binding fragment thereof described hereinabove and a pharmaceutically acceptable carrier.

Provided herein are compositions of humanized antibodies and antigen-binding fragments thereof that bind endoglin and include those such as described elsewhere herein. Humanized antibodies and antigen-binding fragments thereof that bind endoglin as described herein can be used for the treatment of various forms of ocular diseases characterized by angiogenesis/neovascularization (e.g., macular degeneration, diabetic retinopathy), diabetic nephropathy, chronic inflammatory diseases (e.g., IBD), rheumatoid arthritis, osteoarthritis, and various forms of cancer (primary tumors and metastases).

A composition (an antibody or an antigen-binding fragment described herein) can be administered alone or in combination with a second composition either simultaneously or sequentially dependent upon the condition to be treated. In one embodiment, a second therapeutic treatment is an angiogenesis inhibitor (as described herein). When two or more compositions are administered, the compositions can be administered in combination (either sequentially or simultaneously). A composition can be administered in a single dose or multiple doses.

In one embodiment of the present invention, the compositions are formulated to be free of pyrogens such that they are acceptable for administration to human patients. Testing compositions for pyrogens and preparing pharmaceutical compositions free of pyrogens are well understood to one of ordinary skill in the art.

One embodiment of the present invention contemplates the use of any of the compositions of the present invention to make a medicament for treating a disorder of the present invention. Medicaments can be formulated based on the physical characteristics of the patient/subject needing treatment, and can be formulated in single or multiple formulations based on the disorder. Medicaments of the present invention can be packaged in a suitable pharmaceutical package with appropriate labels for the distribution to hospitals and clinics wherein the label is for the indication of treating a disorder as described herein in a subject. Medicaments can be packaged as a single or multiple units. Instructions for the dosage and administration of the pharmaceutical compositions of the present invention can be included with the pharmaceutical packages.

III. Methods of Use

Provided herein is a method of inducing a response in a patient (human or non-human) by administering to the patient a composition of an antibody or antigen-binding fragment thereof that preferentially binds to endoglin. The binding site to which the antibody binds can be a continuous or conformation/dis-continuous epitope.

An effective response of the present invention is achieved when the patient experiences partial or total alleviation or reduction of signs or symptoms of illness, and specifically includes, without limitation, prolongation of survival and/or visual acuity. The expected progression-free survival times may be measured in months to years, depending on prognostic factors including the number of relapses, stage of disease, and other factors. Prolonging survival includes without limitation times of at least 1 month (mo), about at least 2 mos., about at least 3 mos., about at least 4 mos., about at least 6 mos., about at least 1 year, about at least 2 years, about at least 3 years, etc. Overall survival can be also measured in months to years. Alternatively, an effective response may be that a patient's symptoms remain static. Further indications of treatment of indications are described in more detail below.

Compositions of antibodies and antigen-binding fragments described herein can be used as non-therapeutic agents (e.g., as affinity purification agents). Generally, in one such embodiment, a protein of interest is immobilized on a solid phase such a Sephadex resin or filter paper, using conventional methods known in the art. The immobilized protein is contacted with a sample containing the target of interest (or fragment thereof) to be purified, and thereafter the support is washed with a suitable solvent that will remove substantially all the material in the sample except the target protein, which is bound to the immobilized antibody. Finally, the support is washed with another suitable solvent, such as glycine buffer, pH 5.0, which will release the target protein. In addition to purification, compositions can be used for detection, diagnosis and therapy of diseases and disorders associated with endoglin and angiogenesis.

The term "contacting" as used herein refers to adding together a solution or composition of a compound with a liquid medium bathing the polypeptides, cells, tissue or organ from an organism. Alternately, "contacting" refers to mixing together a solution or composition of a compound, with a liquid such as blood, serum, or plasma derived from an organism. For in vitro applications, a composition can also comprise another component, such as dimethyl sulfoxide (DMSO). DMSO facilitates the uptake of the compounds or solubility of the compounds. The solution comprising the test compound may be added to the medium bathing the cells, tissues, or organs, or mixed with another liquid such as blood, by utilizing a delivery apparatus, such as a pipette-based device or syringe-based device. For in vivo applications, contacting can occur, for example, via administration of a composition to a patient by any suitable means; compositions with pharmaceutically acceptable excipients and carriers have been described in more detail above.

A "patient" (e.g., a mammal such as a human or a non-human animal such as a primate, rodent, cow, horse, pig, sheep, etc.) according to one embodiment of the present application, is a mammal who exhibits one or more clinical manifestations and/or symptoms of a disease or disorder described herein. In certain situations, the patient may be asymptomatic and yet still have clinical manifestations of the disease or disorder. An antibody or antigen-binding fragment thereof can be conjugated to a therapeutic moiety or be a fusion protein containing a therapeutic moiety. An antibody or antigen-binding fragment thereof can be conjugated to a detectable moiety or be a fusion protein containing a detectable moiety. In one embodiment, the antibody or antigen-binding fragment thereof can be conjugated to both a therapeutic moiety and a detectable moiety. An antibody or antigen-binding fragment thereof can be conjugated to, or recombinantly engineered with, an affinity tag (e.g., a purification tag). Affinity tags such as, for example, His6 tags (SEQ ID NO: 85) are conventional in the art.

Antibodies or antigen-binding fragments thereof provided herein are such that they can be conjugated or linked to a therapeutic moiety and/or an imaging or a detectable moiety and/or an affinity tag. Methods for conjugating or linking polypeptides are well known in the art. Associations (binding) between compounds and labels include any means known in the art including, but not limited to, covalent and non-covalent interactions, chemical conjugation as well as recombinant techniques.

A. Binding of Endoglin and Angiogenesis

Endoglin (CD105) is expressed on the cell surface as a 180 kDa homodimeric transmembrane protein. The external domain binds TGF-β1 and -3 isoforms with high affinity (50 nM), and the transmembrane and the intracellular domains of CD105 share a 71% sequence similarity with betaglycan. The human CD105 gene is located on chromosome 9q34, identified using fluorescence in situ hybridization, and the coding region contains 14 exons, and two different isoforms (L and S) of CD105 with capacity to bind TGF-β have been characterized. The L-CD105 consists of 633 amino acid residues with 47 amino acid residues in the cytoplasmic tail as opposed to the S-CD105, which consists of 600 amino acid residues with a 14 amino acid cytoplasmic tail. However, L-CD105 is the predominant form. CD105 is constitutively phosphorylated in endothelial cells, mainly on serine and threonine residues, and this phosphorylation is due to the constitutively active TGF-β RII within the cell. TGF-β binding to CD105 results in down-regulation of phosphorylation, similar to effects seen with protein kinase C inhibitors. The human CD105 amino acid sequence contains the tripeptide arginine-glycine-aspartic acid (RGD) located in an exposed region of the extracellular domain. The RGD peptide is a key recognition structure found on ECM proteins such as fibronectin, vitronectin, von Willebrand factor (vWF), type I collagen, and fibrinogen and is recognized by cell surface integrins. Integrin adhesion has been implicated in hemostasis, thrombosis, angiogenesis and inflammation, processes in which the endothelium plays a critical role. (Duff et al., FASEB J., 17:984-992 (2003)).

CD105 is a member of the TGF-β receptor family that is expressed by proliferating endothelial cells. Normal levels of CD105 are needed for endothelial cell proliferation. CD105 expression is increased by cellular hypoxia through the production of hypoxia-inducible factor-1-α (HIF-1-α) and protects hypoxic cells from apoptosis. Several functions of CD105 are associated with TGF-β signaling. TGF-β signals through heterodimeric receptors consisting of serine kinases, receptor I (RI), and receptor II (RII). Binding of TGF-β to the external domains of the receptor unmasks the cytoplasmic RII kinase activity that phosphorylates the TGF-β RI, which can then interact with downstream signalers such as the Smad proteins. CD105 forms part of the TGF-β receptor complex but it can exist independently on the cell surface. In many cells in vitro, CD105 suppresses TGF-β signaling.

CD105 also binds other growth factors such as activin A and bone morphogenic proteins (BMP)-10, -9, -7 and -2. Binding of TGF-β or other growth factor ligands to CD105 requires the presence of at least the receptor RII, and it cannot bind ligands by itself. CD105 association with receptors does not alter their affinity for the ligand itself. Upon association, the cytoplasmic domain of CD105 is phosphorylated by TGF-β RI and TGF-β RII; then TGF-β RI, but not TGF-β RII, kinase dissociates from the receptor complex.

CD105 expression inhibits phosphorylation levels of TGF-β RII but increases that of TGF-β RI, resulting in increased phosphorylation of Smad 2 but not Smad 3. Since Smad 2 can interact with a variety of transcription factors, co-activators, and suppressors, phosphorylated Smad 2 may act as an integrator of multiple signals to modulate gene transcription. Thus, CD105 modulates TGF-β functions via interaction with TGF-β RI and TGF-β RII and modifies the phosphorylation of downstream Smad proteins.

Figure 3B:
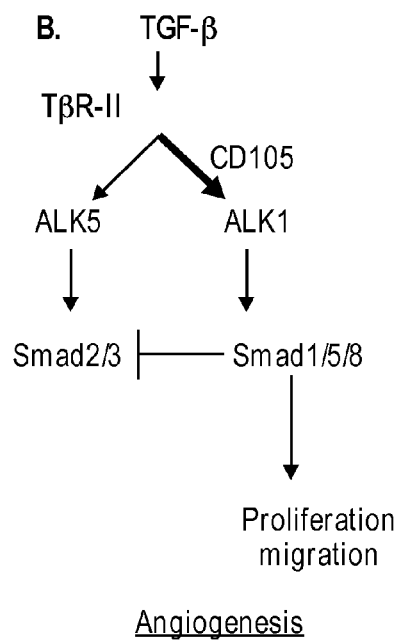

CD105 acts to modulate signaling of multiple kinase receptor complexes of the TGF-β superfamily, including TGF-β receptors (TGF-βR), activin receptor-like kinases (ALK) and activin receptors. In the absence of CD105, activation of TGF-β receptors results in phosphorylation of SMAD proteins (SMAD 2 and 3) that inhibit endothelial cell growth. However, activation of CD105 by TGF-β modulates SMAD protein phosphorylation (including the phosphorylation of SMAD 1, 5 and 8). The end result is release of the growth inhibitory effects of TGF-β receptor activation on endothelial cells (see FIG. 3). Not surprisingly, prevention of CD105 activation by anti-CD105 antibody or antisense oligonucleotide acts synergistically with TGF-β to suppress endothelial cell growth.

The CD105 promoter is 2.6 kb in length but does not contain TATA or CAAT transcription initiation boxes. However, it has two GC-rich regions, consensus motifs for Sp1, ets, GATA, AP-2, NGF-β, and Mad, as well as TGF-β response elements. Nonetheless, CD105 has a relatively restricted cellular distribution. The basal level of transcription appears to require an ets site at position −68 and the Sp1 sites, but the relative restriction of expression, for example, to endothelial cells, appears to involve multiple regulatory regions, in particular, one at −1294 to −932 and another very close to the transcription initiation site. CD105 is up-regulated by TGF-β, and this has been shown to require a Sp1 site at −37 to −29, also involving one or more juxtaposed upstream SBE sites binding Smads 3 and/or 4 (which are activated by TGF-β signaling). Hypoxia is a common feature of ischemic tissues and tumors, and is a potent stimulator for CD105 gene expression in vascular endothelial cells (ECs). Such an effect is potentiated in combination with TGF-β 1. The up-regulated CD105 can exert a self-protective role in ECs under hypoxic stress.

Vascular EC are the major source of CD105. Other cell types including vascular smooth muscle cells, fibroblasts, macrophages, leukemic cells of pre-B and myelomonocytic origin, and erythroid precursors express CD105 to a lesser extent.

CD105 is involved in angiogenesis. Antisense experiments have demonstrated that suppression of CD105 expression in HUVEC results in marked inhibition of in vitro angiogenesis in combination with TGF-β1, indicating that CD105 is a proangiogenic component in the endothelial cells. Further evidence of the important role of CD105 in angiogenesis comes from CD105 knockout mice. The CD105 null mice exhibit multiple vascular and cardiac defects leading to death at an early embryonic stage. Severe vascular impairments observed in CD105 null mice indicate that CD105 is required for the formation of mature blood vessels in the extraembryonic vasculature, further confirming the direct role of endoglin in angiogenesis.

Endoglin, also known as, inter alia, CD105 or edg-1, is a type I homodimeric membrane glycoprotein which is expressed at high levels in proliferating vascular endothelial cells. Thus, endoglin is primarily a proliferation-associated marker for endothelial cells undergoing active angiogenesis. However, there may be limited expression of endoglin by the vascular endothelium of normal tissues. Human endoglin is known to specifically bind transforming growth factor-β (TGF-β), and the deduced amino acid sequence of endoglin has strong homology to β-glycan, a type of TGF-β receptor.

Endoglin (EDG) has been targeted in antibody-based methods of reducing tumor vasculature, as EDG is a proliferation-associated antigen on endothelial and leukemia cells. Its expression is up-regulated in tumor-associated vascular endothelium, and EDG is essential for angiogenesis. Angiogenesis includes the formation of new capillary blood vessels leading to neovascularization as well as the maintenance of the existing vasculature. It is a complex process which includes a series of sequential steps including endothelial cell-mediated degradation of vascular basement membrane and interstitial matrices, migration of endothelial cells, proliferation of endothelial cells, and formation of capillary loops by endothelial cells.

Provided herein are humanized antibodies that bind endoglin. Endoglin can be found on cells that comprise and support existing vasculature as well as cells that are promoting the growth of, and become part of, new vasculature. The antibodies can bind endoglin and thereby inhibit angiogenesis, inhibit the existing vasculature or the maintenance of the existing vasculature, and/or inhibit small vessel dilation. In addition to their use for purification of endoglin, these antibodies are useful for purification, detection and diagnostic purposes as well as therapeutic purposes. The antibodies provided herein can be used for the formulation of medicaments for the treatment a variety of conditions and diseases, methods to treat said conditions and diseases and methods of detection or diagnosis.

Murine monoclonal antibodies (mAbs) have been raised against endoglin which modulate endoglin activity and thereby inhibit angiogenesis and/or inhibit vasodilation of small blood vessels. These murine antibodies are described in U.S. Pat. Nos. 5,928,641, 6,200,566, 6,190,660, and 7,097,836, each of which is hereby incorporated in their entirety. Additionally, the ex vivo and in vivo efficiency of a number of these antibodies has been demonstrated; monoclonal antibodies that bind endoglin are of interest as endoglin modulating compounds. Therapeutic use of murine antibodies is not feasible, however, as administration of the murine antibodies has a number of limitations, including immunogenicity in, for example, the form of human anti-mouse antibodies (HAMA).

"Angiogenesis" is used herein to include all aspects of blood vessel maintenance and development. Thus, angiogenesis includes the formation of new capillary blood vessels leading to neovascularization as well as the maintenance and control of the existing vasculature and small blood vessels. Angiogenesis is a complex process which includes a series of sequential steps including endothelial cell-mediated degradation of vascular basement membrane and interstitial matrices, migration of endothelial cells, proliferation of endothelial cells, and formation of capillary loops by endothelial cells. Angiogenesis is inclusive of the growth and/or development of new blood vessels (also referred to as neovascularization), dilation of the small vessels, excessive or prolonged vascular growth, and maintenance of the existing vasculature. Endoglin is known to be involved in the regulation of angiogenesis and is believed to be involved in multiple biochemical pathways related to the induction of angiogenesis. (Duff et al., FASEB J., 17:984-992 (2003); Bernabeu et al., J. Cell. Biochem., 102(6):1375-1388 (2007)).

As used herein, the terms "angiogenesis inhibitory," "angiogenesis inhibiting" or "anti-angiogenic" include inhibition of vasculogenesis, and are intended to mean affecting a decrease in the extent, amount, or rate of neovascularization. Effecting a decrease in the extent, amount, or rate of endothelial cell proliferation or migration in the tissue is a specific example of inhibiting angiogenesis.

The term "angiogenesis inhibitory composition" refers to a composition which inhibits angiogenesis-mediated processes such as endothelial cell migration, proliferation, tube formation and subsequently leading to the inhibition of the generation of new blood vessels from existing ones, and consequently affects angiogenesis-dependent conditions.

The term "angiogenesis-associated disease" is used herein, for purposes of the specification and claims, to mean certain pathological processes in humans where angiogenesis is abnormally prolonged. This further includes angiogenesis conditions and diseases, such as those diseases and conditions related to, caused by, or associated with angiogenesis. Non-limiting examples of such diseases include various forms of ocular diseases characterized by angiogenesis/neovascularization (e.g., macular degeneration, diabetic retinopathy), diabetic nephropathy, chronic inflammatory diseases (e.g., IBD), rheumatoid arthritis, osteoarthritis, and various forms of cancers and metastasis. The antibodies and antigen-binding fragments thereof described herein can be used to treat an angiogenesis-associated disease by binding endoglin and inhibiting angiogenesis.

The term "anti-angiogenic therapy" is used herein, for purposes of the specification and claims, to mean therapy targeted to cells and/or vasculature expressing endoglin (expressed at higher levels on proliferating vasculature as compared to quiescent vasculature); this further includes therapy that is directed against angiogenesis (i.e., the formation of new capillary blood vessels leading to neovascularization), therapy that is directed against existing vasculature and/or excessive vascularization or blood vessel growth, therapy directed towards the dilation of small vessels, and therapy directed to a disease or condition (e.g., vascular targeting therapy). Exemplary diseases or conditions contemplated within the invention include, but are not limited to, various forms of ocular diseases characterized by angiogenesis/neovascularization (e.g., macular degeneration, diabetic retinopathy), diabetic nephropathy, chronic inflammatory diseases (e.g., IBD), rheumatoid arthritis, osteoarthritis, and various forms of cancer, solid tumors, and metastases.

"Ocular disease characterized by neovascularization" is used herein, for purposes of the specification and claims, to mean any ocular disease caused by, or resulting in, increased angiogenesis within any portion of the eye, including the retina, cornea, pupil, iris, vitreous humor or aqueous humor. Such diseases include for example, age-related macular degeneration, diabetic retinopathy, non-diabetic retinopathy, choroidal neovascularization (CNV) and subretinal neovascularization (SRN or SRNV) and neoplasms of the eye.

B. Diagnostic Applications

Humanized anti-endoglin antibodies and fragments thereof can be used for in vivo and in vitro detection, diagnostic and/or monitoring purposes. Endoglin is believed to be involved in multiple diseases and disorders as described further below. Treatment of endoglin related diseases and conditions depends, in part, upon their diagnosis, and the antibodies and antigen-binding fragments thereof described herein are useful for the diagnosis of excess endoglin or for diagnosis for diseases and conditions associated with endoglin activity.

Provided herein is method of detecting levels of endoglin in a sample or a subject comprising (i) contacting an antibody or antigen binding fragment described herein with the sample or subject, and (ii) detecting a complex of the antibody or antigen-binding fragment thereof and endoglin.

Provided herein is a method of imaging or diagnosing angiogenesis or an angiogenic-dependent disease or disorder, comprising contacting a composition of an antibody or antigen-binding fragment thereof as described herein with a sample. The sample can be, for example, blood, serum, plasma, platelets, biopsy fluid, spinal tap fluid, meninges and urine. Imaging or diagnosis method can occur in an in vitro assay. Alternatively, when contacting is by administration of the composition to a patient, the angiogenesis or angiogenic-dependent disease or disorder is imaged or diagnosed in vivo.

In one embodiment, the antibody or antigen-binding fragment further comprises a detectable moiety. Detection can occur in vitro, in vivo or ex vivo. In vitro assays for the detection and/or determination (quantification, qualification, etc.) of endoglin with the antibodies or antigen-binding fragments thereof include but are not limited to, for example, ELISAs, RIAs and western blots. In vitro detection, diagnosis or monitoring of endoglin can occur by obtaining a sample (e.g., a blood sample) from a patient and testing the sample in, for example, a standard ELISA assay. For example, a 96-well microtiter plate can be coated with an antibody or antigen-binding fragment thereof described herein, washed and coating with PBS-Tween/BSA to inhibit non-specific binding. The blood sample can be serially diluted and placed in duplicate wells compared to a serially-diluted standard curve of endoglin. After incubating and washing the wells, an anti-endoglin antibody labeled with biotin can be added, followed by addition of streptavidin-alkaline phosphatase. The wells can be washed and a substrate (horseradish peroxidase) added to develop the plate. The plate can be read using a conventional plate reader and software.

When detection occurs in vivo, contacting occurs via administration of the antibody or antigen binding fragment using any conventional means such as those described elsewhere herein. In such methods, detection of endoglin in a sample or a subject can be used to diagnose a disease or disorder associated with, or correlated with the activity of endoglin such as those diseases and disorders described herein.

In the in vivo detection, diagnosis or monitoring of endoglin, a patient is administered an antibody or antigen-binding fragment that binds to endoglin, which antibody or antigen-binding fragment is bound to a detectable moiety. The detectable moiety can be visualized using art-recognized methods such as, but not limited to, magnetic resonance imaging (MRI), fluorescence, radioimaging, light sources supplied by endoscopes, laparoscopes, or intravascular catheter (i.e., via detection of photoactive agents), photoscanning, positron emission tomography (PET) scanning, whole body nuclear magnetic resonance (NMR), radioscintography, single photon emission computed tomography (SPECT), targeted near infrared region (NIR) scanning, X-ray, ultrasound, etc. such as described, for example, in U.S. Pat. No. 6,096,289, U.S. Pat. No. 7,115,716, U.S. Pat. No. 7,112,412, U.S. Patent Application No. 20030003048 and U.S. Patent Application No. 20060147379, each of which is incorporated herein in its entirety by reference. Labels for detecting compounds using such methods are also known in the art and described in such patents and applications and are incorporated herein by reference. Visualization of the detectable moiety can allow for detection, diagnosis, and/or monitoring of a condition or disease associated with endoglin and/or angiogenesis.

Additional diagnostic assays that utilize antibodies specific to the desired target protein, i.e., endoglin, are known in the art and are also contemplated herein.

Non-limiting conditions, diseases and disorders to be considered for these methods include, but are not limited to, those associated with angiogenesis such as, for example, various forms of ocular diseases characterized by angiogenesis/neovascularization (e.g., macular degeneration, diabetic retinopathy), diabetic nephropathy, chronic inflammatory diseases (e.g., IBD), rheumatoid arthritis, osteoarthritis, and various forms of cancer (primary tumors and metastases). In the detection, diagnosis or monitoring of such diseases, the subject patient is administered a composition of an antibody or antigen-binding fragment thereof described herein, which antibody or antigen-binding fragment thereof is conjugated to a detectable moiety. The moiety can be visualized using art-recognized methods such as those described above. Visualization of the detectable moiety can allow for detection, diagnosis, and/or monitoring of such conditions and diseases.

For in vitro detection methods, samples to be obtained from a patient include, but are not limited to, blood, tissue biopsy samples and fluid therefrom.

Thus, the present invention provides humanized antibodies and antigen-binding fragments thereof against endoglin which are useful for detecting or diagnosing levels of endoglin associated with a disease or disorder, potentially indicating need for therapeutic treatment. In certain embodiments, the antibodies comprise a humanized anti-endoglin antibody described herein. In other embodiments the antibody further comprises a second agent. Such an agent can be a molecule or moiety such as, for example, a reporter molecule or a detectable label. Detectable labels/moieties for such detection methods are known in the art and are described in more detail below. Reporter molecules are any moiety which can be detected using an assay. Non-limiting examples of reporter molecules which have been conjugated to polypeptides include enzymes, radiolabels, haptens, fluorescent labels, phosphorescent molecules, chemiluminescent molecules, chromophores, luminescent molecules, photoaffinity molecules, colored particles or ligands, such as biotin. Detectable labels include compounds and/or elements that can be detected due to their specific functional properties, and/or chemical characteristics, the use of which allows the polypeptide to which they are attached to be detected, and/or further quantified if desired. Many appropriate detectable (imaging) agents are known in the art, as are methods for their attachment to polypeptides (see, for e.g., U.S. Pat. Nos. 5,021,236; 4,938,948; and 4,472,509, each of which is hereby incorporated by reference).

Methods of joining polypeptides such as antibodies with detectable moieties are known in the art and include, for example, recombinant DNA technology to form fusion proteins and conjugation (e.g., chemical conjugation). Methods for preparing fusion proteins by chemical conjugation or recombinant engineering are well-known in the art. Methods of covalently and non-covalently linking components are also known in the art. See, e.g., Williams (1995) Biochemistry 34:1787 1797; Dobeli (1998) Protein Expr. Purif. 12:404-414; and Kroll (1993) DNA Cell. Biol. 12: 441-453.

It may be necessary, in some instances, to introduce an unstructured polypeptide linker region between a label or a moiety and one or more portion of the antibodies, antigen-binding fragments or binding proteins described herein. A linker can facilitate enhanced flexibility, and/or reduce steric hindrance between any two fragments. The linker can also facilitate the appropriate folding of each fragment to occur. The linker can be of natural origin, such as a sequence determined to exist in random coil between two domains of a protein. One linker sequence is the linker found between the C-terminal and N-terminal domains of the RNA polymerase α subunit. Other examples of naturally occurring linkers include linkers found in the 1CI and LexA proteins.

Within a linker, an amino acid sequence can be varied based on the characteristics of the linker as determined empirically or as revealed by modeling. Considerations in choosing a linker include flexibility of the linker, charge of the linker, and presence of some amino acids of the linker in the naturally-occurring subunits. The linker can also be designed such that residues in the linker contact deoxyribose nucleic acid (DNA), thereby influencing binding affinity or specificity, or to interact with other proteins. In some cases, such as when it is necessary to span a longer distance between subunits or when the domains must be held in a particular configuration, the linker can, optionally, contain an additional folded domain. In some embodiments, the design of a linker can involve an arrangement of domains which requires the linker to span a relatively short distance, e.g., less than about 10 Angstroms (Å). However, in certain embodiments, linkers span a distance of up to about 50 Angstroms.

Within the linker, the amino acid sequence can be varied based on the characteristics of the linker as determined empirically or as revealed by modeling. Considerations in choosing a linker include flexibility of the linker, charge of the linker, and presence of some amino acids of the linker in the naturally-occurring subunits. The linker can also be designed such that residues in the linker contact DNA, thereby influencing binding affinity or specificity, or to interact with other proteins. In some cases, when it is necessary to span a longer distance between subunits or when the domains must be held in a particular configuration, the linker can optionally contain an additional folded domain.

Methods for coupling polypeptides (free or cell-bound) to beads are known in the art. Methods for selecting coupled polypeptides or cells displaying a polypeptide are also known in the art. Briefly, paramagnetic polystyrene microparticles are commercially available (Spherotech, Inc., Libertyville, Ill.; Invitrogen, Carlsbad, Calif.) that couple peptides to microparticle surfaces that have been modified with functional groups or coated with various antibodies or ligands such as, for example, avidin, streptavidin or biotin. The paramagnetic property of microparticles allows them to be separated from solution using a magnet. The microparticles can be easily re-suspended when removed from the magnet. Polypeptides can be coupled to paramagnetic polystyrene microparticles coated with a polyurethane layer in a tube. The hydroxy groups on the microparticle surface are activated by reaction with p-toluensulphonyl chloride (Nilsson K and Mosbach K. "p-Toluenesulfonyl chloride as an activating agent of agarose for the preparation of immobilized affinity ligands and proteins." Eur. J. Biochem. 1980: 112: 397-402). Alternatively, paramagnetic polystyrene microparticles containing surface carboxylic acid can be activated with a carbodiimide followed by coupling to a polypeptide, resulting in a stable amide bond between a primary amino group of the polypeptide and the carboxylic acid groups on the surface of the microparticles (Nakajima N and Ikade Y, Mechanism of amide formation by carbodiimide for bioconjugation in aqueous media, Bioconjugate Chem. 1995, 6(1): 123-130; Gilles M A, Hudson A Q and Borders C L Jr, Stability of water-soluble carbodiimides in aqueous solution, Anal Biochem. 1990 Feb. 1; 184(2):244-248; Sehgal D and Vijay I K, a method for the high efficiency of water-soluble carbodiimide-mediated amidation, Anal Biochem. 1994 April; 218(1):87-91; Szajani B et al, Effects of carbodiimide structure on the immobilization of enzymes, Appl Biochem Biotechnol. 1991 August; 30(2): 225-231). Another option is to couple biotinylated polypeptides to paramagnetic polystyrene microparticles whose surfaces have been covalently linked with a monolayer of streptavidin. (Argarana C E, Kuntz I D, Birken S, Axel R, Cantor C R. Molecular cloning and nucleotide sequence of the streptavidin gene. Nucleic Acids Res. 1986; 14(4):1871-82; Pahler A, Hendrickson W A, Gawinowicz Kolks M A, Aragana C E, Cantor C R. Characterization and crystallization of core streptavidin. J Biol Chem 1987:262(29):13933-13937).

Polypeptides can be conjugated to a wide variety of fluorescent dyes, quenchers and haptens such as fluorescein, R-phycoerythrin, and biotin. Conjugation can occur either during polypeptide synthesis or after the polypeptide has been synthesized and purified. Biotin is a small (244 kilodaltons) vitamin that binds with high affinity to avidin and streptavidin proteins and can be conjugated to most peptides without altering their biological activities. Biotin-labeled polypeptides are easily purified from unlabeled polypeptides using immobilized streptavidin and avidin affinity gels, and streptavidin or avidin-conjugated probes can be used to detect biotinylated polypeptides in, for example, ELISA, dot blot or Western blot applications. N-hydroxysuccinimide esters of biotin are the most commonly used type of biotinylation agent. N-hydroxysuccinimide-activated biotins react efficiently with primary amino groups in physiological buffers to form stable amide bonds. Polypeptides have primary amines at the N-terminus and can also have several primary amines in the side chain of lysine residues that are available as targets for labeling with N-hydroxysuccinimide-activated biotin reagents. Several different N-hydroxysuccinimide esters of biotin are available, with varying properties and spacer arm length (Pierce, Rockford, Ill.). The sulfo-N-hydroxysuccinimide ester reagents are water soluble, enabling reactions to be performed in the absence of organic solvents.

The mole-to-mole ratio of biotin to polypeptide can be estimated using a 2-(4'-Hydroxyazobenzene-2-carboxylic acid) assay using art-recognized techniques (Green, N M, (1975) "Avidin. In Advances in Protein Chemistry." Academic Press, New York. 29, 85-133; Green, N M, (1971) "The use of bifunctional biotinyl compounds to determine the arrangement of subunits in avidin." Biochem J. 125, 781-791; Green, N M., (1965) "A spectrophotometric assay for avidin and biotin based on binding of dyes by avidin." Biochem. J. 94: 23c-24c). Several biotin molecules can be conjugated to a polypeptide and each biotin molecule can bind one molecule of avidin. The biotin-avidin bond formation is very rapid and stable in organic solvents, extreme pH and denaturing reagents. To quantitate biotinylation, a solution containing the biotinylated polypeptide is added to a mixture of 2-(4'-Hydroxyazobenzene-2-carboxylic acid) and avidin. Because biotin has a higher affinity for avidin, it displaces the 2-(4'-Hydroxyazobenzene-2-carboxylic acid) and the absorbance at 500 nanometers decreases proportionately. The amount of biotin in a solution can be quantitated in a single cuvette by measuring the absorbance of the 2-(4'-Hydroxyazobenzene-2-carboxylic acid)-avidin solution before and after addition of the biotin-containing peptide. The change in absorbance relates to the amount of biotin in the sample by the extinction coefficient of the 2-(4'-Hydroxyazobenzene-2-carboxylic acid)-avidin complex.

Alternatively, an antibody, antigen-binding fragment or binding protein can be conjugated with a fluorescent moiety Conjugating polypeptides with fluorescent moieties (e.g., R-Phycoerythrin, fluorescein isothiocyanate (FITC), etc.) can be accomplished using art-recognized techniques described in, for example, Glazer, A N and Stryer L. (1984). Trends Biochem. Sci. 9:423-7; Kronick, M N and Grossman, P D (1983) Clin. Chem. 29:1582-6; Lanier, L L and Loken, M R (1984) J. Immunol., 132:151-156; Parks, D R et al. (1984) Cytometry 5:159-68; Hardy, R R et al. (1983) Nature 306:270-2; Hardy R R et al. (1984) J. Exp. Med. 159:1169-88; Kronick, M N (1986) J. Immuno. Meth. 92:1-13; Der-Balian G, Kameda, N and Rowley, G. (1988) Anal. Biochem. 173:59-63.

In one non-limiting embodiment, an antibody antigen-binding fragment can be associated with (conjugated to) a detectable label, such as a radionuclide, iron-related compound, a dye, an imaging agent or a fluorescent agent for immunodetection of endoglin which can be used to visualize binding of the antibodies to endoglin in vitro and/or in vivo.

Non-limiting examples of radiolabels include, for example, $^{32}P$, $^{33}P$, $^{43}K$, $^{52}Fe$, $^{57}Co$, $^{64}Cu$, $^{67}Ga$, $^{67}Cu$, $^{68}Ga$, $^{71}Ge$, $^{75}Br$, $^{76}Br$, $^{77}Br$, $^{77}As$, $^{77}Br$, $^{81}Rb/^{81}MKr$, $87MSr$, $^{90}Y$, $^{97}Ru$, $^{99}Te$, $^{100}Pd$, $^{101}Rh$, $^{103}Pb$, $^{105}Rh$, $^{109}Pd$, $^{111}Ag$, $^{111}In$, $^{113}In$, $^{119}Sb$, $^{121}Sn$, $^{123}I$, $^{125}I$, $^{127}Cs$, $^{128}Ba$, $^{129}Cs$, $^{131}I$, $^{131}Cs$, $^{143}Pr$, $^{153}Sm$, $^{161}Tb$, $^{166}Ho$, $^{169}Eu$, $^{171}Lu$, $^{186}Re$, $^{188}Re$, $^{189}Re$, $^{191}Os$, $^{193}Pt$, $^{194}Ir$, $^{197}Hg$, $^{199}Au$, $^{203}Pb$, $^{211}At$, $^{212}Pb$, $^{212}Bi$ and $^{213}Bi$. Radiolabels can be attached to compounds using conventional chemistry known in the art of antibody imaging. Radiolabeled compounds are useful in in vitro diagnostics techniques and in in vivo radioimaging techniques and in radioimmunotherapy. For example, in the instance of in vivo imaging, the antibodies and antigen-binding fragments thereof can be conjugated to an imaging agent rather than a radioisotope(s), including but not limited to a magnetic resonance image enhancing agent, wherein for instance an antibody molecule is loaded with a large number of paramagnetic ions through chelating groups. Examples of chelating groups include EDTA, porphyrins, polyamines crown ethers and polyoximes. Examples of paramagnetic ions include gadolinium, iron, manganese, rhenium, europium, lanthanum, holmium and ferbium. Such detectable moieties also include: metals; metal chelators; lanthanides; lanthanide chelators; radiometals; radiometal chelators; positron-emitting nuclei; microbubbles (for ultrasound); liposomes; molecules microencapsulated in liposomes or nanosphere; monocrystalline iron oxide nanocompounds; magnetic resonance imaging contrast agents; light absorbing, reflecting and/or scattering agents; colloidal particles; fluorophores, such as near-infrared fluorophores. In many embodiments, such secondary functionality/moiety will be relatively large, e.g., at least 25 amu in size, and in many instances can be at least 50, 100 or 250 amu in size. In certain embodiments, the secondary functionality is a chelate moiety for chelating a metal, e.g., a chelator for a radiometal or paramagnetic ion. In embodiments, it is a chelator for a radionuclide useful for radiotherapy or imaging procedures.

Antagonists of the invention also can be assayed for their ability to modulate angiogenesis in a tissue. Any suitable assay known to one of skill in the art can be used to monitor such effects. Several such techniques are described herein.

One measures angiogenesis is an in vivo rabbit eye model and is referred to as the rabbit eye assay. The rabbit eye assay has been described in detail by others, and further has been used to measure both angiogenesis and neovascularization in the presence of angiogenic inhibitors such as thalidomide. See D'Amato et al. (1994) Proc. Natl. Acad. Sci. 91:4082-4085.

The rabbit eye assay is a well recognized assay model for in vivo angiogenesis because the neovascularization process, exemplified by rabbit blood vessels growing from the rim of the cornea into the cornea, is easily visualized through the naturally transparent cornea of the eye. Additionally, both the extent and the amount of stimulation or inhibition of neovascularization or regression of neovascularization can easily be monitored over time.

Finally, the rabbit is exposed to any test reagent, and therefore the health of the rabbit is an indication of toxicity of the test reagent.

Another assay measures angiogenesis in the chimeric mouse:human mouse model and is referred to as the chimeric mouse assay. The assay has been described in detail by others, and further has been described herein to measure angiogenesis, neovascularization, and regression of tumor tissues. See Yan, et al. (1993) J. Clin. Invest. 91:986-996.

The chimeric mouse assay is a useful assay model for in vivo angiogenesis because the transplanted skin grafts closely resemble normal human skin histologically and neovascularization of whole tissue is occurring wherein actual human blood vessels are growing from the grafted human skin into the human tumor tissue on the surface of the grafted human skin. The origin of the neovascularization into the human graft can be demonstrated by immunohistochemical staining of the neovasculature with human-specific endothelial cell markers.

The chimeric mouse assay demonstrates regression of neovascularization based on both the amount and extent of regression of new vessel growth. Furthermore, it is easy to monitor effects on the growth of any tissue transplanted upon the grafted skin, such as a tumor tissue. Finally, the assay is useful because there is an internal control for toxicity in the assay system. The chimeric mouse is exposed to any test reagent, and therefore the health of the mouse is an indication of toxicity. Other animal models described herein and known in the art can also be utilized in the methods described herein.

C. Treatment with Humanized Endoglin Antibodies

Provided herein are methods of preventing or treating one or more diseases or disorders associated with angiogenesis/neovascularization, excessive vascularization, or small vessel dilation comprising administering a composition comprising a humanized antibody or antigen-binding fragment described herein that binds to endoglin associated with the disease or disorder and prevents angiogenesis, thereby preventing, treating, ameliorating, or lessening the disease or its severity.

Provided herein are methods of preventing or treating one or more diseases or disorders associated with angiogenesis/neovascularization comprising administering a composition comprising a humanized antibody or antigen-binding fragment described herein that binds to endoglin associated with the disease or disorder, decreases angiogenesis, or prevents excessive angiogenesis.

As used herein, "prevention" refers to prophylaxis, prevention of onset of symptoms, prevention of progression of a disease or disorder associated with angiogenesis or correlated with endoglin activity. As used herein, "inhibition," "treatment" and "treating" are used interchangeably and refer to, for example, stasis of symptoms, prolongation of survival, partial or full amelioration of symptoms, and partial or full eradication of a condition, disease or disorder associated with angiogenesis or correlated with endoglin activity.

Compositions can be administered to a patient in a therapeutically effective amount which are effective for producing some desired therapeutic effect by inhibiting a disease or disorder such as described herein which can be associated with endoglin, at a reasonable benefit/risk ratio applicable to any medical treatment. For the administration of the present compositions to human patients, the compositions can be formulated by methodology known by one of ordinary skill in the art. A therapeutically effective amount is an amount achieves at least partially a desired therapeutic or prophylactic effect in an organ or tissue. The amount of a humanized anti-endoglin antibody or antigen binding fragment thereof necessary to bring about prevention and/or therapeutic treatment of a disease or disorder is not fixed per se. The amount of humanized anti-endoglin antibody or antigen binding fragment thereof administered may vary with the type of disease, extensiveness of the disease, and size of the mammal suffering from the disease or disorder. In one embodiment, two or more humanized anti-endoglin antibodies described herein are administered to a patient in combination. Combination includes concomitant or subsequent administration of the antibodies.

"Administering" is defined herein as a means providing the composition to the patient in a manner that results in the composition being inside the patient's body. Such an administration can be by any route including, without limitation, locally, regionally or systemically by subcutaneous, intravitreal, intradermal, intravenous, intra-arterial, intraperitoneal, or intramuscular administration (e.g., injection). "Concurrent administration" means administration within a relatively short time period from each other; such time period can be less than 2 weeks, less than 7 days, less than 1 day and could even be administered simultaneously.

Actual dosage levels of the active ingredients in the compositions can be varied so as to obtain an amount of the active ingredient that is effective to achieve the desired therapeutic response for a particular patient, composition, and mode of administration, without being toxic to the patient. The selected dosage level will depend upon a variety of factors including the activity of the particular compound employed, the route of administration, the time of administration, the rate of excretion of the particular compound being employed, the duration of the treatment, other drugs, compounds and/or materials used in combination with the particular composition employed, the age, sex, weight, condition, general health and prior medical history of the patient being treated, and like factors well known in the medical arts. The antibodies and antigen-binding fragments described herein can be administered to a subject in various dosing amounts and over various time frames. Non-limiting doses include about 0.01 mg/kg, about 0.05 mg/kg, about 0.1 mg/kg, about 0.5 mg/kg, about 1 mg/kg, about 5 mg/kg, about 10 mg/kg, about 20 mg/kg, about 30 mg/kg, about 40 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg, or any integer in between. Additionally, the dose(s) of an antibody or antigen-binding fragment can be administered twice a week, weekly, every two weeks, every three weeks, every 4 weeks, every 6 weeks, every 8 weeks, every 12 weeks, or any combination of weeks therein. Dosing cycles are also contemplated such as, for example, administering antibodies or antigen-binding fragments thereof once or twice a week for 4 weeks, followed by two weeks without therapy. Additional dosing cycles including, for example, different combinations of the doses and weekly cycles described herein are also contemplated within the invention.

"Contacting" is defined herein as a means of bringing a composition as provided herein in physical proximity with a cell, organ, tissue or fluid as described herein. Contacting encompasses systemic or local administration of any of the compositions provided herein and includes, without limitation, in vitro, in vivo and/or ex vivo procedures and methods. "Combining" and "contacting" are used interchangeably herein and are meant to be defined in the same way.

A response is achieved when the patient experiences partial or total alleviation, or reduction of signs or symptoms of illness, and specifically includes, without limitation, prolongation of survival. The expected progression-free survival times can be measured in months to years, depending on prognostic factors including the number of relapses, stage of disease, and other factors. Prolonging survival includes without limitation times of at least 1 month (mo), about at least 2 months (mos.), about at least 3 mos., about at least 4 mos., about at least 6 mos., about at least 1 year, about at least 2 years, about at least 3 years, or more. Overall survival can also be measured in months to years. The patient's symptoms can remain static or can decrease.

A physician or veterinarian having ordinary skill in the art can readily determine and prescribe the effective amount (ED50) of the composition required. For example, the physician or veterinarian could start doses of the compounds employed in the composition at levels lower than that required in order to achieve the desired therapeutic effect and gradually increase the dosage until the desired effect is achieved. Alternatively, a dose can remain constant.

Compositions can be administered to a patient by any convenient route such as described above. Regardless of the route of administration selected, the compounds of the present invention, which can be used in a suitable hydrated form, and/or the compositions, are formulated into acceptable dosage forms such as described below or by other conventional methods known to those of skill in the art.

Antibodies can be combined with a therapeutic moiety or to a detectable (imaging) moiety using methods known in the art such as, for example, chemical conjugation, covalent or non-covalent bonds or recombinant techniques to create conjugates or fusion proteins such as described in more detail below. Alternatively, antibodies and/or other agents can be combined in separate compositions for simultaneous or sequential administration.

Toxicity and therapeutic efficacy of such ingredient can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. While compounds that exhibit toxic side effects may be used, care should be taken to design a delivery system that targets such compounds to the site of affected tissue in order to minimize potential damage to healthy cells and, thereby, reduce side effects.

Data obtained from cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration arrange that includes the $IC_{50}$ (i.e., the concentration of the test compound which achieves a half-maximal inhibition) as determined in cell culture. Levels in plasma can be measured, for example, by high performance liquid chromatography. Such information can be used to more accurately determine useful doses in humans.

The pro-angiogenic role of endoglin has been established in many models including endothelial cell culture and knock-out mouse models. Endothelial and the associated cells are well known to express endoglin (CD105), and the role of endoglin in angiogenesis, generally, as well as cardiac development has also been confirmed in numerous studies, culture models, and animal models. (Duff et al., FASEB J., 17:984-992 (2003); Bernabeu et al., J. Cell. Biochem., 102(6): 1375-1388 (2007); U.S. Pat. No. 7,097, 836).

Thus, methods which inhibit angiogenesis in a diseased tissue ameliorate symptoms of the disease and, depending upon the disease, can contribute to cure of the disease. In one embodiment, the invention contemplates inhibition of angiogenesis in a tissue. The extent of angiogenesis in a tissue, and therefore the extent of inhibition achieved by the present methods, can be evaluated by a variety of methods, such as are described herein.

The unique specificity of the antibodies which recognize (e.g., bind) an epitope on endoglin and inhibits angiogenesis, provides diagnostic and therapeutic uses for diseases characterized by angiogenesis (neovascularization), small vessel dilation, and/or excessive vascularization such as described herein. Humanized anti-endoglin antibodies and fragments thereof can be administered to a subject such as a mammal (e.g., a human), suffering from a medical disorder, e.g., various forms of ocular diseases characterized by angiogenesis/neovascularization (e.g., macular degeneration, diabetic retinopathy), diabetic nephropathy, chronic inflammatory diseases (e.g., IBD), rheumatoid arthritis, osteoarthritis, and various forms of cancer (primary tumors and metastases). Provided herein is a method for treating a subject having an ocular disease characterized by angiogenesis by administering a humanized antibody or fragment thereof described herein that binds endoglin and inhibits angiogenesis. Also provided herein is a method for treating a subject having a chronic inflammatory disease by administering a humanized antibody or fragment thereof described herein that binds endoglin and inhibits angiogenesis. Examples of such chronic inflammatory diseases include, but are not limited to, Crohn's disease and ulcerative colitis. Further provided herein is a method for treating a subject having diabetic nephropathy by administering a humanized antibody or fragment thereof described herein. Provided herein is a method for treating a subject having rheumatoid arthritis or osteoarthritis by administering a humanized antibody or fragment thereof described herein.

One would understand that the anti-endoglin antibodies can be effective for treating angiogenesis, it is contemplated herein that a subject can also be treated with one or more additional angiogenesis inhibitors.

The term "angiogenesis inhibitor" is used herein, for purposes of the specification and claims, to mean a compound or molecule including, but not limited to, peptides, proteins, enzymes, polysaccharides, oligonucleotides, DNA, RNA, recombinant vectors, and drugs which function to inhibit angiogenesis. Angiogenesis inhibitors are known in the art and all types are contemplated herein. Non-limiting examples of compounds and molecules include natural and synthetic biomolecules such as paclitaxel, O-(chloroacetyl-carbomyl) fumagillol ("TNP-470" or "AGM 1470"), thrombospondin-1, thrombospondin-2, angiostatin, human chondrocyte-derived inhibitor of angiogenesis ("hCHIAMP"), cartilage-derived angiogenic inhibitor, platelet factor-4, gro-beta, human interferon-inducible protein 10 ("IP10"), interleukin 12, Ro 318220, tricyclodecan-9-yl xanthate ("D609"), irsogladine, 8,9-dihydroxy-7-methyl-benzo[b] quinolizinium bromide ("GPA 1734"), medroxyprogesterone, a combination of heparin and cortisone, glucosidase inhibitors, genistein, thalidomide, diamino-antraquinone, herbimycin, ursolic acid, and oleanolic acid. Non-limiting examples of antibodies include those directed towards molecules such as VEGF, VEGF receptor, or different epitopes of endoglin. Additionally, small molecular inhibitors of VEGF receptor are known and contemplated herein. Non-limiting examples of VEGF receptor inhibitors include bevacizumab (AVASTIN®), ranibizumab (Lucentis), aflibercept (VEGF-Trap), sunitinib (Sutent), sorafenib (Nexavar), axitinib, pegaptanib and pazopanib.

The antibodies and antigen-binding fragments described herein can be administered in combination with VEGF receptor inhibitors for combination therapy of any of the angiogenesis-related conditions or diseases described herein. In one non-limiting embodiment, the VEGF receptor inhibitor is bevacizumab. Exemplary dosage for bevacizumab are about 7.5, about 10, or about 15 mg/kg, administered every 2 or 3 weeks.

In one non-limiting embodiment, the VEGF receptor inhibitor is ranibizumab. Exemplary ocular dosages for ranibizumab include about 0.5 mg, administered intravitreally monthly. In one non-limiting embodiment, the VEGF receptor inhibitor is aflibercept (VEGF-Trap). Exemplary dosages for VEGF-Trap include about 0.5-about 10 mg/kg administered every 2 or 3 weeks. Exemplary ocular dosages for VEGF-Trap include about 0.5-about 2.0 mg administered intravitreally monthly or quarterly.

In another non-limiting embodiment, the VEGF receptor inhibitor is sunitinib. Exemplary regimens for sunitinib include about 50 mg administered for 4 weeks, followed by 2 weeks of no drug. Treatment regimens can be repeated in a cyclic or acyclic basis.

In another non-limiting embodiment, the VEGF receptor inhibitor is sorafenib. Exemplary dosages for sorafenib include about 400 mg administered daily.

In another non-limiting embodiment the VEGF receptor inhibitor is axitinib. Exemplary dosages for axitinib include about 3, about 5, or about 10 mg administered twice daily.

In another non-limiting embodiment the VEGF receptor inhibitor is pegaptanib. Exemplary dosages for pegaptanib include about 0.3-about 3 mg administered intravitreally every 6 weeks.

In yet another non-limiting embodiment, the VEGF receptor inhibitor is pazopanib. Exemplary dosages for pazopanib include about 200-about 1000 mg administered daily.

Multiple combinations of these VEGF receptor inhibitors can be administered with the antibodies and antigen-binding fragments described herein. In one embodiment, combinations may result in the use of lower doses for the antibodies or antigen binding fragments described herein, the VEGF receptor inhibitors, or both. Such alterations in dosing may result from synergistic effects of the combinations of the antibodies and antigen-binding fragments described herein with the VEGF receptor inhibitors.

Ocular Conditions Involving Angiogenesis

Macular Degeneration Conditions and Diabetic Retinopathy

In one aspect, the present invention provides a method for treating diabetic retinopathy, macular degeneration, choroidal neovascularization or neovascular glaucoma in a patient by administering to the patient a therapeutically effective amount of any of the compositions provided herein.

Endoglin is a receptor associated with angiogenesis and the extracellular matrix. Macular degeneration (AMD) is the loss of photoreceptors in the portion of the central retina, termed the macula, responsible for high-acuity vision. Degeneration of the macula is associated with abnormal deposition of extracellular matrix components and other debris in the membrane between the retinal pigment epithelium and the vascular choroid. This debris-like material is termed drusen. Drusen is observed with a funduscopic eye examination. Normal eyes may have maculas free of drusen, yet drusen may be abundant in the retinal periphery. The presence of soft drusen in the macula, in the absence of any loss of macular vision, is considered an early stage of AMD. Macular degeneration is characterized by choroidal neovascularization (CNV), the development of abnormal blood vessels beneath the retinal pigment epithelium (RPE) layer of the retina. These vessels break through the Bruch's membrane, disrupting the retinal pigmented epithelium, bleed, and eventually cause macular scarring which results in profound loss of central vision (disciform scarring).

Choroidal neovascularization (CNV) commonly occurs in macular degeneration in addition to other ocular disorders and is associated with proliferation of choroidal endothelial cells, overproduction of extracellular matrix, and formation of a fibrovascular subretinal membrane. Retinal pigment epithelium cell proliferation and production of angiogenic factors appears to effect choroidal neovascularization.

Diabetic retinopathy (DR) is an ocular disorder characterized by excessive angiogenesis that develops in diabetes due to thickening of capillary basement membranes, and lack of contact between pericytes and endothelial cells of the capillaries. Loss of pericytes increases leakage of the capillaries and leads to breakdown of the blood-retina barrier. Diabetic retinopathy is the result of microvascular retinal changes. Hyperglycemia-induced pericyte death and thickening of the basement membrane lead to incompetence of the vascular walls. These damages change the formation of the blood-retinal barrier and also make the retinal blood vessels become more permeable. Small blood vessels—such as those in the eye—are especially vulnerable to poor blood sugar (blood glucose) control. An over-accumulation of glucose and/or fructose damages the tiny blood vessels in the retina. Macular edema can also develop when the damaged blood vessels leak fluid and lipids onto the macula. These fluids make the macula swell, which blurs vision. This damage also results in a lack of oxygen at the retina.

As the disease progresses, the lack of oxygen in the retina stimulates angiogenesis along the retina and in the clear, gel-like vitreous humour that fills the inside of the eye. Without timely treatment, these new blood vessels can bleed, cloud vision, and destroy the retina. Fibrovascular proliferation can also cause tractional retinal detachment. The new blood vessels can also grow into the angle of the anterior chamber of the eye and cause neovascular glaucoma.

Proliferative vitreoretinopathy is associated with cellular proliferation of cellular and fibrotic membranes within the vitreous membranes and on the surfaces of the retina. Retinal pigment epithelium cell proliferation and migration is common with this ocular disorder. The membranes associated with proliferative vitreoretinopathy contain extracellular matrix components such as collagen types I, II, and IV and fibronectin, and become progressively fibrotic.

Age-related macular degeneration (AMD) and diabetic retinopathy are the two leading causes of blindness in the developed world. The recent approval of the macromolecules LUCENTIS®, AVASTIN®, and MACUGEN® have improved the treatment options available for AMD patients. LUCENTIS® is a Fab and AVASTIN® is a monoclonal antibody. They both bind vascular endothelial growth factor (VEGF) and have demonstrated the most impressive results to date treating AMD; however, only a minority of treated patients experience a significant improvement in visual acuity. Anti-angiogenic therapy focused on a target other than VEGF may overcome some of the limitations associated with agents that target the VEGF pathway.

The humanized antibodies and antigen-binding fragments which bind endoglin and are described herein can be used to treat or prevent macular degeneration, CNV, diabetic retinopathy, or proliferative vitreoretinopathy. Described herein are methods of treating or preventing macular degeneration, CNV, diabetic retinopathy, or proliferative vitreoretinopathy via the administration of the antibodies and antigen-binding fragments described herein. The humanized antibodies and antigen-binding fragments which bind endoglin and are described herein can also shrink blood vessels, inhibit endothelial cell proliferation associated with ocular disease, clear symptoms of bleeding, treat cloudy vision, provide stasis of vision loss, and/or prevent leakage of blood vessels. The humanized antibodies and antigen-binding fragments described herein can also be used in medicaments for the treatment of macular degeneration, CNV, diabetic retinopathy or proliferative vitreoretinopathy.

Additionally, humanized antibodies and antigen-binding fragments described herein can also be used in combination with known therapies and/or compounds for the treatment of macular degeneration, CNV, diabetic retinopathy or proliferative vitreoretinopathy. Examples of such compounds include, but are not limited to, bevacizumab (AVASTIN®), ranibizumab (LUCENTIS®), aflibercept (VEGF-Trap), sunitinib (SUTENT®), sorafenib (NEXAVAR®), axitinib, pegaptanib, pazopanib or MACUGEN®. In addition to the modes of administration described herein, the humanized anti-endoglin antibodies and antigen-binding fragments can be administered via intravitreal routes. Non-limiting examples of intravitreal modes of administration include intravitreal injection and the use of intravitreal implants.

Patients can be assessed for improvement and responsiveness to treatment. Treatment includes, but is not limited to, decreasing the macular edema, decreased areas of CNV, and increased visual acuity. Measurements of symptoms are as known in the art and are further described in the examples below.

Chronic Inflammatory Diseases

Any of a variety of tissues or organs comprised of organized tissues, can support angiogenesis in disease conditions including skin, muscle, gut, connective tissue, joints, bones and the like tissue in which blood vessels can invade upon angiogenic stimuli. Thus, in one embodiment, a tissue to be treated is an inflamed tissue and the angiogenesis to be inhibited is inflamed tissue angiogenesis where there is neovascularization of inflamed tissue.

Inflammatory Bowel Diseases

Angiogenesis plays an important role in inflammatory bowel disease (IBD). IBD is an umbrella term for a set of bowel and intestinal diseases or conditions including Crohn's disease and ulcerative colitis. Crohn's disease is typically characterized by inflammation of the small and large bowel, whereas ulcerative colitis is generally localized to the colon. Abnormal or pathological angiogenesis is central to both Crohn's disease and ulcerative colitis. Both diseases involve increased microvascular density and microvascular dysfunction, and this angiogenesis is temporally related with tissue pathology and the inflammatory cycles found in both diseases. Endoglin is known to be expressed in these tissues and to play a role in the dysregulation of angiogenesis during IBD. (Chidlow et al., Am. J. Physiol. Gastrointest. Liver Physiol., 293:5-18 (2007)).

The humanized antibodies and antigen-binding fragments which bind endoglin and are described herein can be used to treat IBD. Additionally, humanized antibodies and antigen-binding fragments which bind endoglin can be used for the treatment of Crohn's disease or ulcerative colitis. The humanized anti-endoglin antibodies and antigen-binding fragments can also be used in combination with surgery and/or known therapies for IBD, Crohn's disease or ulcerative colitis. Examples of such known therapies include, but are not limited to, Aminosalicylates (e.g., Mesalamine), corticosteroids (e.g., budesonide, prednisone, etc.), antibiotics (e.g., metronidizole, etc.), immunosuppresive drugs (e.g., azathioprine, 6-mercaptopurine, methotrexate, Tacrolimus, and cyclosporine, etc.), and biologic drugs such as proteins and antibodies (e.g., infliximab, etc.).

Treatment of IBD can be assessed by decreased vascularization of the inflamed tissue. Treatment can also be assessed by stasis, resolution, and/or healing of the ulcerative lesions which characterize IBD.

Diabetic Nephropathy & Renal Transplantation Ischemia

Diabetic nephropathy is a major cause of morbidity and mortality in both type 1 and type 2 diabetics. It is the leading cause of end-stage renal disease world-wide. Diabetic nephropathy is characterized by glomerular microvascular injury due to the increased synthesis of pro-angiogenic factors. These pro-angiogenic factors cause increased endothelial cell proliferation and subsequent angiogenesis, and endoglin is known to be upregulated in chronic renal disease. This angiogenesis results in destruction of the glomeruli and finally renal failure. (Zent et al., Seminars in Nephrology, 27(2): 161-171 (2007); Roy-Chaudhury et al., Exp. Nephrol., 5:55-60 (1997)).

Similar effects are seen in renal transplantation resulting in ischemia and failure of the transplanted organ. The upregulation of endoglin results in upregulated angiogenesis and inflammation in the kidney. Conversely, studies with endoglin null mice show significantly reduced renal damage after transplantation/ischemia and increased organ survival. (Docherty et al., Nephol. Dial. Transplant., 21:2106-2119 (2006)).

The humanized antibodies and antigen-binding fragments which bind endoglin and are described herein can be used to treat or prevent diabetic nephropathy, renal failure following transplantation, and/or ischemic renal injury following transplantation.

Described herein are methods of treating or preventing diabetic nephropathy, renal failure following transplantation, and/or ischemic renal injury following transplantation via the administration of the antibodies and antigen-binding fragments described herein. The humanized antibodies and antigen-binding fragments described herein can also be used in medicaments for the treatment of diabetic nephropathy, renal failure following transplantation, and/or ischemic renal injury following transplantation. Additionally, humanized antibodies and antigen-binding fragments described herein can also be used in combination with known therapies and/or compounds for the treatment of diabetic nephropathy, renal failure following transplantation, and/or ischemic renal injury following transplantation.

Patients can be assessed with respect to the efficacy of treatment by, for example, improvement in renal function.

Rheumatoid Arthritis & Osteoarthritis

Rheumatoid arthritis is characterized by excessive angiogenesis, and is well understood in this regard. The inflammation and destruction found in the synovial fluids is directly related to the increased angiogenesis found surrounding and in the synovial tissues. Numerous pro-angiogenic factors are present in the affected tissues of rheumatoid arthritis patients. (Koch and Distler, Arthritis Res. & Ther., 9(Suppl. 2): S3, 1-9 (2007).

Osteoarthritis is a group of chronic disabling conditions that affects the synovial joints. Angiogenesis and inflammation are integral processes in the pathophysiology of the disease, and they contribute to joint damage through a variety of mechanisms, including but not limited to, stimulation of MMP production and endochondral ossification. Additionally, angiogenesis in osteoarthritis induces further innervation, which develops into a feedback loop where each continues to stimulate the other. (Bonnet & Walsh, Rheumatology, 44:7-16 (2005)).

The humanized antibodies and antigen-binding fragments which bind endoglin and are described herein can be used to treat or prevent rheumatoid arthritis and osteoarthritis. Described herein are methods of treating or preventing rheumatoid arthritis and osteoarthritis via the administration of the antibodies and antigen-binding fragments described herein. The humanized antibodies and antigen-binding fragments described herein can also be used in medicaments for the treatment of rheumatoid arthritis and osteoarthritis.

Two well accepted composite measures of improvement of RA in trials are: the Paulus Criteria and The American College of Rheumatology Criteria (ACR). Paulus Criteria is defined as improvement in 4 of the following: tender and swollen joint counts, morning stiffness, patient assessment of disease activity, physician assessment of disease activity and erythrocyte sedimentation rate (ESR) rage. The level of improvement is set as a percentage improvement of each of these variables i.e. a Paulus 20 classification indicates a responder who has shown 20% improvement in 4 of the 6 parameters.

Rheumatoid arthritis can also be assessed using American College of Rheumatology (ACR) Scoring. Briefly, ACR Classification Criteria for Determining Clinical Remission in Rheumatoid Arthritis is assessed by the presence of 5 or more of the following factors present at least two consecutive months:

a. Morning stiffness<15 minutes;
b. No fatigue;
c. No joint pain;
d. No joint tenderness or pain on motion;
e. No soft tissue swelling in joints or tendon sheaths; and
f. ESR (Westergren method)<30 mm/hour for a female or 20 mm/hour for a male.

Exclusions may occur and include: clinical manifestations of active vasculitis, pericarditis, pleuritis or myositis, and unexplained recent weight loss or fever attributable to rheumatoid arthritis will prohibit a designation of complete clinical remission (Pinals R S, et. al.: Arthritis Rheum 24:1308, 1981). Additionally, ACR Classification Criteria of Functional Status in Rheumatoid Arthritis includes classification based on the following patient abilities:

Class I: Completely able to perform usual activities of daily living (self-care, vocational, and avocational);
Class II: Able to perform usual self-care and vocational activities, but limited in avocational activities;
Class III: Able to perform usual self-care activities, but limited in vocational and avocational activities; and
Class IV: Limited ability to perform usual self-care, vocational, and avocational activities.

Osteoarthritis can also be assessed using ACR scoring. ACR Clinical Classification Criteria for Osteoarthritis of the hip is assessed utilizing patient history, physical examination and laboratory findings: a patient is assessed for pain in the hip and one of the following:

(1) internal hip rotation of less than 15 degrees and ESR less than or equal to 45 degrees mm/hour or hip flexion less than or equal to 115 degrees if ESR is unavailable; or
(2) Internal hip rotation of less than 15 degrees, pain associated with internal hip, morning stiffness of the hip for less than or equal to 60 minutes and the patient is over 50 years of age.

Using history, physical examination, laboratory and radiographic findings, traditional format is pain in the hip and two of the following indications: ESR less than 20 mm/hour, radiographic femoral and/or acetabular osteophytes, or radiographic joint space narrowing (superior, axial, and/or medial). A classification tree is as follows: pain in the hip in association with (1) radiographic femoral and/or acetabular osteophytes or (2) ESR less than or equal to 20 mm/hour and radiographic axial joint space narrowing (Altman, R, et al.: Arthritis Rheum 34:505, 1991).

ACR Clinical Classification Criteria for Osteoarthritis of the Knee

ACR Clinical Classification Criteria for Osteoarthritis of the knee is assessed using history and physical examination utilizing the following criteria: pain in the knee in connection with three (3) of the following:

(1) a patient is over 50 years of age;
(2) less than 30 minutes of morning stiffness;
(3) Crepitus on active motion;
(4) bony tenderness;
(5) bony enlargement; and
(6) no palpable warmth of synovium.

Using patient history, physical examination and radiographic findings, pain in the knee can be assessed in connection with one of the following patient characteristics: (1) a patient is over 50 years of age; (2) less than 30 minutes of morning stiffness; and (3) Crepitus on active motion and osteophytes. Using history, physical examination and laboratory findings: pain in the knee can be assessed in connection with five (5) of the following characteristics:

(1) a patient is over 50 years of age;
(2) less than 30 minutes of morning stiffness;
(3) Crepitus on active motion;
(4) bony tenderness;
(5) bony enlargement;
(6) No palpable warmth of synovium;
(7) ESF is less than 40 mm/hour;
(8) Rheumatoid factor (RF) of less than 1:40; and
(9) Synovial Fluid (SF) signs of osteoarthritis.

See, e.g., Altman, R, et al.: Arthritis Rheum 29:1039, 1986.

ACR Clinical Classification Criteria for Osteoarthritis of the hand can be assessed as follows: pain, aching or stiffness in the hand in connection with three (3) of the following: (1) hard tissue enlargement of two or more of the following joints (second and third distal interphalangeal, the second and third proximal interphalangeal, and the first carpometacarpal joints of both hands; (2) hard tissue enlargement of two or more distal interphalangeal joints; (3) less than three swollen MCP joints and (4) deformity of at least one of the joints listed above in (1).

Cancer

CD105 is associated with tumor angiogenesis and is strongly up-regulated in the endothelium of various tumor tissues compared with that in normal tissues. CD105 is up-regulated in a wide range of tumor endothelia including, for example, colon, breast, brain, lung, prostate, endometrial, kidney, liver, gastric, head & neck and cervical cancer. Additionally, it is known that there is stronger expression of CD105 in tumor endothelium than corresponding normal tissues. (Duff et al., FASEB J., 17:984-992 (2003); Bernabeu et al., J. Cell. Biochem., 102(6): 1375-1388 (2007); U.S. Pat. No. 7,097,836). Thus, the inhibition of angiogenesis with anti-endoglin humanized antibodies represents a treatment option for cancerous tumors. The humanized antibodies and antigen-binding fragments which bind endoglin and are described herein can be used to treat cancerous tumors. The humanized antibodies and antigen-binding fragments described herein can also be used in medicaments for the treatment cancerous tumors.

The term "tumor" is used herein to refer to a cancerous tissue expressing endoglin (as compared to expression by normal tissue of the same type). Tumors can include solid tumors and semi-solid tumors. Non-limiting examples of tumors include human leukemias, including non-T-cell-type (non-T) acute lymphoblastic leukemia (ALL), myelo-monocytic leukemia; and human solid and semi-solid tumors, with its surrounding vasculature expressing endoglin at moderate to high levels (as compared to expression by normal tissue of the same type) including angiosarcoma, breast carcinoma, stomach cancer, colon carcinoma, Hodgkins lymphoma, lymphoma, glioblastoma multiforme (GBM), lung carcinoma, melanoma, myeloma, lymphoma, osteosarcoma, ovarian carcinoma, parotid tumor, pharyngeal carcinoma, prostate carcinoma, hepatocellular carcinoma, renal carcinoma, and rectosigmoid carcinoma.

A cancerous tissue to be treated is, for example, an endothelial tissue expressing an abnormal level of endoglin.

In the absence of neovascularization of tumor tissue, the tumor tissue does not obtain the required nutrients, slows in growth, ceases additional growth, regresses and ultimately becomes necrotic resulting in killing of the tumor. The present invention provides for a method of inhibiting tumor neovascularization by inhibiting tumor angiogenesis according to the present methods. Similarly, the invention provides a method of inhibiting tumor growth by practicing the angiogenesis-inhibiting methods.

The methods are also particularly effective against the formation of metastases because their formation requires vascularization of a primary tumor so that the metastatic cancer cells can exit the primary tumor and their establishment in a secondary site requires neovascularization to support growth of the metastases.

It will be appreciated that a "patient suffering from a cancer/metastasis" of the invention may express a mutant protein (tumor associated antigen) or a mutant gene and not yet be symptomatic for the disease. In one non-limiting example, where the cancer is colon cancer (which is associated with the mutant K-ras protein), a patient with a mutant K-ras protein in some cells of the colon is a patient according to the invention even though that patient may not yet be symptomatic for colon cancer. "Signs or symptoms of illness" are clinically recognized manifestations or indications of disease.

By "treating" a patient suffering from cancer it is meant that the patient's symptoms are partially or totally alleviated, or remain static following treatment according to the invention. A patient that has been treated can exhibit a partial or total alleviation of symptoms and/or tumor load. This is intended to encompass prophylaxis, therapy and cure. In one non-limiting example, a patient suffering from a highly metastatic cancer (e.g., breast cancer) is treated where additional metastasis either do not occur, or are reduced in number as compared to a patient who does not receive treatment. In another non-limiting example, a patient is treated where the patient's solid cancer either becomes reduced in size or does not increase in size as compared to a patient who does not receive treatment. In yet another non-limiting example, the number of cancer cells in a treated patient either does not increase or is reduced as compared to the number of cancer cells in a patient who does not receive treatment. Improvement can also be defined, for example, as decreased cell proliferation, decreased numbers of cells, increased apoptosis, and/or increased survival of the patient being treated.

As further used herein, treatment of cancer includes stasis, partial or total elimination of a cancerous growth or tumor. Treatment or partial elimination includes, for example, a fold reduction in growth or tumor size and/or volume such as about 2-fold, about 3-fold, about 4-fold, about 5-fold, about 10-fold, about 20-fold, about 50-fold, or any fold reduction in between. Similarly, treatment or partial elimination can include a percent reduction in growth or tumor size and/or volume of about 1%, 2%, 3%, 4%, 5%, 10%, 20%, 30%, 40%, 50%, 60%, 70%, 80%, 90%, 95% or any percentage reduction in between.

A tumor or cancer to be treated in the methods described herein includes, but is not limited to, a lung cancer, a gynecologic malignancy, a melanoma, a breast cancer, a brain cancer (e.g., glioblastoma multiforme, "GBM") a pancreatic cancer, an ovarian cancer, a uterine cancer, a colorectal cancer, a prostate cancer, a kidney cancer, a head cancer, a liver cancer (hepatocellular cancer), a uterine cancer, a neck cancer, a kidney cancer (renal cell cancer), a sarcoma, a myeloma, and lymphoma. In one embodiment, a tumor to be treated is a solid or semi-solid tumor. In another embodiment, a tumor to be treated is a primary tumor. In another embodiment, a tumor to be treated is a metastatic tumor. In one embodiment, a tumor or cancer to be treated is of epithelial origin. In another embodiment, the cancer to be treated is myeloma. In another embodiment, the cancer to be treated is ovarian cancer. In another embodiment, the cancer to be treated is kidney/renal cancer. In yet another embodiment, the cancer to be treated is hepatocellular/liver cancer.

Lung Cancer

In one aspect, provided herein is a method to treat lung cancer. The most common type of lung cancer is non-small cell lung cancer (NSCLC), which accounts for approximately 80-85% of lung cancers and is divided into squamous cell carcinomas, adenocarcinomas, and large cell undifferentiated carcinomas. Small cell lung cancer accounts for 15-20% of lung cancers.

Lung cancer staging is an assessment of the degree of spread of the cancer from its original source. It is an important factor affecting the prognosis and potential treatment of lung cancer. Non-small cell lung carcinoma is staged from IA ("one A"; best prognosis) to IV ("four"; worst prognosis). Small cell lung carcinoma is classified as limited stage if it is confined to one half of the chest and within the scope of a single radiotherapy field; otherwise, it is extensive stage.

Non-small cell lung cancer may be staged using EUS (endoscopic ultrasound) or CT or MRI scan or at surgery to classify the extent of disease according to the TNM system. These subjects undergo staging as part of the process of considering prognosis and treatment. The AJCC recommends TNM staging followed by further grouping.

Primary tumor (T): TX: The primary tumor cannot be assessed, or there are malignant cells in the sputum or bronchoalveolar lavage but not seen on imaging or bronchoscopy; Tis: Carcinoma in situ. T0: No evidence of primary tumor. T1: Tumor less than 3 cm in its greatest dimension, surrounded by lung or visceral pleura and without bronchoscopic invasion into the main bronchus. T2: A tumor with any of: more than 3 cm in greatest dimension; extending into the main bronchus (but more than 2 cm distal to the carina), and obstructive pneumonitis (but not involving the entire lung). T3: A tumor with any of: invasion of the chest wall, diaphragm, mediastinal pleura, or parietal pericardium; extending into the main bronchus, within 2 cm of the carina, but not involving the carina; and obstructive pneumonitis of the entire lung. T4: A tumor with any of: invasion of the mediastinum, heart, great vessels, trachea, esophagus, vertebra, or carina; separate tumor nodules in the same lobe; and malignant pleural effusion. Lymph nodes (N): NX: Lymph nodes cannot be assessed; N0: No lymph nodes involved; N1: Metastasis to ipsilateral peribronchial or ipsilateral hilar lymph nodes; N2: Metastasis to ipsilateral mediastinal or subcarinal lymph nodes; and N3: Metastasis to any of: ipsilateral supraclavicular lymph nodes; ipsilateral scalene lymph nodes; and contralateral lymph nodes. Distant metastasis (M): MX: Distant metastasis cannot be assessed; M0: No distant metastasis; and M1: Distant metastasis is present.

Uterine Cancers/Gynecologic Malignancy

Uterine cancers may refer to any of several different types of cancer which occur in the uterus, namely: uterine sarcomas (e.g., sarcomas of the myometrium, or muscular layer of the uterus, are most commonly leiomyosarcomas); endometrial cancer; and cervical cancer.

In another aspect, provided herein is a method to treat endometrium cancer. Endometrial cancer is a cancer that starts in the endometrium, the inner lining of the uterus. Some of the examples of the cancer of uterus and endometrium include, but are not limited to, adenocarcinomas, adenoacanthomas, adenosquamous carcinomas, papillary serous adenocarcinomas, clear cell adenocarcinomas, uterine sarcomas, stromal sarcomas, malignant mixed mesodermal tumors, and leiomyosarcomas.

In another aspect, the method treats cervical cancer, preferably an adenocarcinoma in the cervix epithelial. Two main types of this cancer exist: squamous cell carcinoma and adenocarcinomas. The former constitutes about 80-90% of all cervical cancers and develops where the ectocervix (portion closest to the vagina) and the endocervix (portion closest to the uterus) join. The latter develop in the mucous-producing gland cells of the endocervix. Some cervical cancers have characteristics of both of these and are called adenosquamous carcinomas or mixed carcinomas.

Ovarian Cancer

In another aspect, provided herein is a method of treating ovarian cancer, including epithelial ovarian tumors.

Ovarian cancer is classified according to the histology of the tumor, obtained in a pathology report. Surface epithelial-stromal tumor, also known as ovarian epithelial carcinoma, is the most typical type of ovarian cancer. It includes serous tumor, endometrioid tumor and mucinous cystadenocarcinoma. Sex cord-stromal tumor, including estrogen-producing granulosa cell tumor and virilizing Sertoli-Leydig cell tumor or arrhenoblastoma, accounts for 8% of ovarian cancers. Germ cell tumor accounts for approximately 30% of ovarian tumors but only 5% of ovarian cancers because most germ cell tumors are teratomas and most teratomas are benign. Germ cell tumor tends to occur in young women and girls. The prognosis depends on the specific histology of germ cell tumor, but overall is favorable. Mixed tumors contain elements of more than one of the above classes of tumor histology.

Ovarian cancer can also be a secondary cancer, the result of metastasis from a primary cancer elsewhere in the body. Common primary cancers are breast cancer and gastrointestinal cancer (in which case the ovarian cancer is a Krukenberg cancer). Surface epithelial-stromal tumor can originate in the peritoneum (the lining of the abdominal cavity), in which case the ovarian cancer is secondary to primary peritoneal cancer, but treatment is basically the same as for primary surface epithelial-stromal tumor involving the peritoneum.

Ovarian cancer staging is by the FIGO staging system and uses information obtained after surgery, which can include a total abdominal hysterectomy, removal of both ovaries and fallopian tubes, the omentum, and pelvic (peritoneal) washings for cytology. The AJCC stage is the same as the FIGO stage.

Stage I refers to ovarian cancer limited to one or both ovaries: IA—involves one ovary; capsule intact; no tumor on ovarian surface; no malignant cells in ascites or peritoneal washings; IB—involves both ovaries; capsule intact; no tumor on ovarian surface; negative washings; and IC—tumor limited to ovaries with any of the following: capsule ruptured, tumor on ovarian surface, positive washings.

Stage II refers to pelvic extension or implants: IIA—extension or implants onto uterus or fallopian tube; negative washings; IIB—extension or implants onto other pelvic structures; negative washings; and IIC—pelvic extension or implants with positive peritoneal washings Stage III refers to microscopic peritoneal implants outside of the pelvis; or limited to the pelvis with extension to the small bowel or omentum: IIIA—microscopic peritoneal metastases beyond pelvis; IIIB—macroscopic peritoneal metastases beyond pelvis less than 2 cm in size; and IIIC—peritoneal metastases beyond pelvis>2 cm or lymph node metastases Stage IV refers to distant metastases to the liver or outside the peritoneal cavity.

Para-aortic lymph node metastases are considered regional lymph nodes (Stage IIIC).

In some embodiments, the methods described herein treat an ovarian cancer selected from the following: an adenocarcinoma in the ovary and an adenocarcinoma that has migrated from the ovary into the abdominal cavity.

Melanoma

A melanoma is a malignant tumor of melanocytes which are found predominantly in skin but also in the bowel and the eye (uveal melanoma). It is one of the rarer types of skin cancer but causes the majority of skin cancer related deaths. Malignant melanoma is a serious type of skin cancer caused by uncontrolled growth of pigment cells, called melanocytes. Melanomas also include, but are not limited to, a choroidea melanoma, malignant melanomas, cutaneous melanomas and intraocular melanomas.

Melanoma may be divided into the following types: Lentigo maligna, Lentigo maligna melanoma, superficially spreading melanoma, acral lentiginous melanoma, mucosal melanoma, nodular melanoma, polypoid melanoma, desmoplastic melanoma, amelanotic melanoma, soft-tissue melanoma, and uveal melanoma. Melanoma stages are as follows:

Stage 0—melanoma in situ (Clark Level I).

Stage I/II—invasive melanoma: T1a: less than 1.00 mm primary, without ulceration, Clark Level II-III; T1b: less than 1.00 mm primary, with ulceration or Clark Level IV-V; and T2a: 1.00-2.00 mm primary, without ulceration.

Stage II—High Risk Melanoma: T2b: 1.00-2.00 mm primary, with ulceration; T3a: 2.00-4.00 mm primary, without ulceration; T3b: 2.00-4.00 mm primary, with ulceration; T4a: 4.00 mm or greater primary without ulceration; and T4b: 4.00 mm or greater primary with ulceration.

Stage III—Regional Metastasis: N1: single positive lymph node; N2: 2-3 positive lymph nodes or regional skin/in-transit metastasis; and N3: 4 positive lymph nodes or lymph node and regional skin/in transit metastases.

Stage IV—Distant Metastasis: M1a: Distant Skin Metastasis, Normal LDH; M1b: Lung Metastasis, Normal LDH; and M1c: Other Distant Metastasis OR Any Distant Metastasis with Elevated LDH.

In one embodiment, the methods described herein treat a melanoma.

Colon Cancer and Colorectal Cancer

Colorectal cancer (also called colon cancer or large bowel cancer) includes cancerous growths in the colon, rectum (anus) and appendix. With 655,000 deaths worldwide per year, it is the third most common form of cancer and the second leading cause of cancer-related death in the Western world. Many colorectal cancers are thought to arise from adenomatous polyps in the colon. These mushroom-like growths are usually benign, but some may develop into cancer over time.

In another embodiment, Dukes classification may be used to classify colorectal cancer based on stages A-D. Stage A refers to colorectal cancer that is limited to mucosa (i.e., has not invaded through the bowel wall). Stage B1 refers to extending into muscularis propria, but not penetrating through it (i.e., lymph nodes have not been invaded); whereas Stage B2 cancer has penetrated through the muscularis propria, but not penetrating through it (i.e., lymph nodes have not been invaded). Stage C1 refers to cancer that extends into the muscularis propria, but not penetrating through it (i.e., lymph nodes are involved); whereas Stage C2 refers to cancer that extends into the muscularis propria and penetrating through it (i.e., lymph nodes are involved). Stage D refers to distant metastatic spread. The TNM system may also be used to stage colorectal cancer according to conventional means known in the art.

Breast Cancer

Several types of breast cancer exist that may be treated by the methods described herein. A lobular carcinoma in situ and a ductal carcinoma in situ are breast cancers that have developed in the lobules and ducts, respectively, but have not spread to the fatty tissue surrounding the breast or to other areas of the body. Infiltrating (or invasive) lobular and ductal carcinoma are cancers that have developed in the lobules and ducts, respectively, and have spread to either the breast's fatty tissue and/or other parts of the body. In one aspect, provided herein is a method of treating breast cancer, such as a ductal carcinoma in duct tissue in a mammary gland, a breast cancer that is Her2- and/or ER- and/or PR-. Other cancers of the breast that would benefit from treatment by the methods are medullary carcinomas, colloid carcinomas, tubular carcinomas, and inflammatory breast cancer.

In one embodiment, breast cancer is staged according to the TNM system. Prognosis is closely linked to results of staging, and staging is also used to allocate patients to treatments both in clinical trials and clinical practice.

Briefly, the information for staging is as follows: TX: Primary tumor cannot be assessed. T0: No evidence of tumor. Tis: Carcinoma in situ, no invasion; T1: Tumor is 2 cm or less; T2: Tumor is more than 2 cm but not more than 5 cm; T3: Tumor is more than 5 cm; T4: Tumor of any size growing into the chest wall or skin, or inflammatory breast cancer. NX: Nearby lymph nodes cannot be assessed N0: cancer has not spread to regional lymph nodes. N1: cancer has spread to 1 to 3 maxillary or one internal mammary lymph node N2: cancer has spread to 4 to 9 maxillary lymph nodes or multiple internal mammary lymph nodes N3: One of the following applies: cancer has spread to 10 or more maxillary lymph nodes, or cancer has spread to the lymph nodes under the clavicle (collar bone), or cancer has spread to the lymph nodes above the clavicle, or cancer involves maxillary lymph nodes and has enlarged the internal mammary lymph nodes, or cancer involves 4 or more maxillary lymph nodes, and tiny amounts of cancer are found in internal mammary lymph nodes on sentinel lymph node biopsy. MX: presence of distant spread (metastasis) cannot be assessed. M0: no distant spread. M1: spread to distant organs (not including the supraclavicular lymph node) has occurred.

Pancreatic Cancer

In another aspect, provided herein is a method of treating pancreatic cancer selected from the following: an epithelial carcinoma in the pancreatic duct tissue and an adenocarcinoma in a pancreatic duct. The most common type of pancreatic cancer is an adenocarcinoma, which occurs in the lining of the pancreatic duct.

In one embodiment, the methods described herein treat a pancreatic cancer.

Prostate Cancer

In one other aspect, provided herein is a method to treat prostate cancer selected from the following: an adenocarcinoma or an adenocarcinoma that has migrated to the bone. Prostate cancer develops in the prostate organ in men, which surrounds the first part of the urethra. The prostate has several cell types but 99% of tumors are adenocarcinomas that develop in the glandular cells responsible for generating seminal fluid.

There are two schemes commonly used to stage prostate cancer. The most common is the TNM system, which evaluates the size of the tumor, the extent of involved lymph nodes, and any metastasis (distant spread). As with many other cancers, these are often grouped into four stages (I-IV). Another scheme, used less commonly, is the Whitmore-Jewett stage.

Briefly, Stage I disease is cancer that is found incidentally in a small part of the sample when prostate tissue was removed for other reasons, such as benign prostatic hypertrophy, and the cells closely resemble normal cells and the gland feels normal to the examining finger. In Stage II more of the prostate is involved and a lump can be felt within the gland. In Stage III, the tumor has spread through the prostatic capsule and the lump can be felt on the surface of the gland. In Stage IV disease, the tumor has invaded nearby structures, or has spread to lymph nodes or other organs. Grading is based on cellular content and tissue architecture from biopsies (Gleason) which provides an estimate of the destructive potential and ultimate prognosis of the disease.

In one embodiment, the methods described herein treat a prostate cancer.

Head and Neck Cancers

Head and neck cancers (e.g., oral, laryngeal, nasopharyngeal, esophageal, etc.), refer to a group of biologically similar cancers originating from the upper aerodigestive tract, including the lip, oral cavity (mouth), nasal cavity, paranasal sinuses, pharynx, and larynx. Most head and neck cancers are squamous cell carcinomas, originating from the mucosal lining (epithelium) of these regions. Head and neck cancers often spread to the lymph nodes of the neck, and this is often the first (and sometimes only) manifestation of the disease at the time of diagnosis. Head and neck cancer is strongly associated with certain environmental and lifestyle risk factors, including tobacco smoking, alcohol consumption, and certain strains of the sexually transmitted human papillomavirus. Management of patients with head and neck cancers remains a formidable task. Cancers such as, hypopharyngeal cancer, laryngeal cancer, nasopharyngeal cancer, oropharyngeal cancer, may be treated using the compounds described herein.

In one embodiment, the methods described herein treat a head or neck cancer.

Kidney Cancer

In another aspect, provided herein is a method to treat kidney cancer. Kidney cancer (also called renal cell cancer, renal cell carcinoma, renal adenocarcinoma, and hypernephroma) is a disease in which malignant cells are found in the lining of tubules in the kidney. Renal cell carcinoma is the most common form of kidney cancer arising from the proximal renal tubule. It is the most common type of kidney cancer in adults, responsible for approximately 80% of cases.

In one embodiment, the methods described herein treat a kidney cancer.

Liver Cancer

In another aspect, provided herein is a method to treat primary liver cancer (cancer that begins in the liver). Primary liver cancer can occur in both adults and children. Liver cancer is characterized by the presence of malignant hepatic tumors—tumors or growths on or in the liver. They may be discovered on medical imaging (even for a different reason than the cancer itself), or may be present in patients as an abdominal mass, abdominal pain, jaundice, or some other liver dysfunction. There are several types of liver cancer.

Hemangiomas: These are the most common type of benign liver tumor. They start in blood vessels. Most of these tumors do not cause symptoms, they do not need treatment. Some may bleed and need to be removed if it is mild to severe.

Hepatic adenomas: These benign epithelial liver tumors develop in the liver. They are, in most cases, located in the right hepatic lobe and are frequently seen as solitary. The size of adenomas range from 1 to 30 cm. Symptoms associated with hepatic adenomas are all associated with large lesions which can cause intense abdominal pain.

Focal nodular hyperplasia: Focal nodular hyperplasia (FNH) is the second most common tumor of the liver. This tumor is the result of a congenital arteriovenous malformation hepatocyte response. This process is one in which all normal constituents of the liver are present, but the pattern by which they are presented is abnormal. Even though those conditions exist the liver still seems to perform in the normal range.

Hepatocellular Cancer: Hepatocellular cancer (HCC) is the most common cancer of the liver. It is associated with alcohol abuse and hepatitis B infection and is particularly prevalent in Asia. The majority of HCC is detected at a time when cure by surgical resection is not possible; systemic treatment of un-resectable HCC is associated with survival of less than one year.

In one embodiment, the methods described herein treat a liver cancer.

Lymphoma

Lymphoma is a type of cancer that originates in lymphocytes of the immune system. They often originate in lymph nodes, presenting as an enlargement of the node (a tumor). Lymphomas are closely related to lymphoid leukemias, which also originate in lymphocytes but typically involve only circulating blood and the bone marrow (where blood cells are generated in a process termed haematopoesis) and do not usually form tumors. There are many types of lymphomas, and in turn, lymphomas are a part of the broad group of diseases called hematological neoplasms. Some forms of lymphoma are indolent (e.g. small lymphocytic lymphoma), compatible with a long life even without treatment, whereas other forms are aggressive (e.g. Burkitt's lymphoma), causing rapid deterioration and death.

The WHO Classification, published in 2001 and updated in 2008; en.wikipedia.org/wiki/Lymphoma-cite_note-isbn92-832-2411-6-2#cite_note-isbn92-832-2411-6-2 is the latest classification of lymphoma and is based upon the foundations laid within the "Revised European-American Lymphoma classification" (REAL). This system groups lymphomas by cell type (i.e., the normal cell type that most resembles the tumor) and defining phenotypic, molecular or cytogenetic characteristics. There are three large groups: the B cell, T cell, and natural killer cell tumors. Other less common groups are also recognized. Hodgkin's lymphoma, although considered separately within the WHO (and preceding) classifications, is now recognized as being a tumor of, albeit markedly abnormal, lymphocytes of mature B cell lineage.

In one embodiment, the methods described herein treat a lymphoma.

Sarcoma

A sarcoma is a cancer of the connective tissue (bone, cartilage, fat) resulting in mesoderm proliferation.

This is in contrast to carcinomas, which are of epithelial origin (breast, colon, pancreas, and others). However, due to an evolving understanding of tissue origin, the term "sarcoma" is sometimes applied to tumors now known to arise from epithelial tissue. The term soft tissue sarcoma is used to describe tumors of soft tissue, which includes elements that are in connective tissue, but not derived from it (such as muscles and blood vessels).

Sarcomas are given a number of different names, based on the type of tissue from which they arise. For example, osteosarcoma arises from bone, chondrosarcoma arises from cartilage, and leiomyosarcoma arises from smooth muscle. Sarcomas strike people in all age ranges, but they are very rare, accounting for only 1% of all cases of cancer. GIST is the most common form of sarcoma, with approximately 3000-3500 cases per year in the United States. This should be compared with breast cancer, with approximately 200,000 cases per year in North America.

Approximately 50% of bone sarcomas and 20% of soft tissue sarcomas are diagnosed in people under the age of 35. Some sarcomas, such as leiomyosarcoma, chondrosarcoma, and gastrointestinal stromal tumor (GIST), are more common in adults than in children. Most high grade bone sarcomas, including Ewing's sarcoma and osteosarcoma, are much more common in children and young adults.

In one embodiment, the methods described herein treat a sarcoma.

Carcinoma

A carcinoma is any malignant cancer that arises from epithelial cells. Carcinomas invade surrounding tissues and organs and may metastasize, or spread, to lymph nodes and other sites.

Carcinoma, like all neoplasia, is classified by its histopathological appearance. Adenocarcinoma and squamous cell carcinoma, two common descriptive terms for tumors, reflect the fact that these cells may have glandular or squamous cell appearances respectively. Severely anaplastic tumors might be so undifferentiated that they do not have a distinct histological appearance (undifferentiated carcinoma).

Sometimes a tumor is referred to by the presumptive organ of the primary (e.g., carcinoma of the prostate) or the putative cell of origin (hepatocellular carcinoma, renal cell carcinoma).

Adenocarcinoma is a malignant tumor originating in the epithelial cells of glandular tissue and forming glandular structures. This is common in the lung (forming 30-40% of all lung carcinomas). It is found peripherally, arising from goblet cells or type II pneumocytes.

Squamous cell carcinoma results from squamous metaplasia. This accounts for 20-30 percent of lung tumors and is usually hilar in origin.

Small cell carcinoma is almost certainly due to smoking. These metastasize early, and may secrete ADH (lowering patient sodium concentration).

Large cell undifferentiated carcinomas account for 10-15 percent of lung neoplasms. These are aggressive and difficult to recognize due to the undifferentiated nature. These are most commonly central in the lung.

Sinonasal undifferentiated carcinoma.

In one embodiment, the methods described herein treat a carcinoma.

Myeloma

Multiple myeloma (also known as MM, myeloma, plasma cell myeloma, or as Kahler's disease after Otto Kahler) is a cancer of plasma cells. These immune cells are formed in bone marrow, are numerous in lymphatics and produce antibodies. Myeloma is regarded as incurable, but remissions may be induced with steroids, chemotherapy, thalidomide and stem cell transplants. Myeloma is part of the broad group of diseases called hematological malignancies.

Multiple myeloma develops in post-germinal center B lymphocytes. A chromosomal translocation between the immunoglobulin heavy chain gene (on the fourteenth chromosome, locus 14q32) and an oncogene (often 11q13, 4p16.3, 6p21, 16q23 and 20q11) is frequently observed in patients with multiple myeloma. This mutation results in dysregulation of the oncogene which is thought to be an important initiating event in the pathogenesis of myeloma. The result is proliferation of a plasma cell clone and genomic instability that leads to further mutations and translocations. The chromosome 14 abnormality is observed in about 50% of all cases of myeloma. Deletion of (parts of) the thirteenth chromosome is also observed in about 50% of cases.

Production of cytokines (especially IL-6) by the plasma cells causes much of their localized damage, such as osteoporosis, and creates a microenvironment in which the malignant cells thrive. Angiogenesis (the attraction of new blood vessels) is increased.

In one embodiment, the methods described herein treat a myeloma.

Stomach Cancer

Stomach or gastric cancer can develop in any part of the stomach and may spread throughout the stomach and to other organs; particularly the esophagus, lungs and the liver. Stomach cancer causes about 800.000 deaths worldwide per year.

Metastasis occurs in 80-90% of individuals with stomach cancer, with a six month survival rate of 65% in those diagnosed in early stages and less than 15% of those diagnosed in late stages.

Stomach cancer is often asymptomatic or causes only nonspecific symptoms in its early stages. By the time symptoms occur, the cancer has generally metastasized to other parts of the body, one of the main reasons for its poor prognosis.

In one embodiment, the methods described herein treat a stomach cancer.

Thyroid Cancer

Thyroid neoplasm or thyroid cancer usually refers to any of four kinds of malignant tumors of the thyroid gland: papillary, follicular, medullary or anaplastic. Papillary and follicular tumors are the most common. They grow slowly and may recur, but are generally not fatal in patients under 45 years of age. Medullary tumors have a good prognosis if restricted to the thyroid gland and a poorer prognosis if metastasis occurs. Anaplastic tumors are fast-growing and respond poorly to therapy.

Thyroid cancer is usually found in a euthyroid patient, but symptoms of hyperthyroidism or hypothyroidism may be associated with a large or metastatic well-differentiated tumor. Nodules are of particular concern when they are found in those under the age of 20. The presentation of benign nodules at this age is less likely, and thus the potential for malignancy is far greater.

Thyroid cancers can be classified according to their pathological characteristics. The following variants can be distinguished (distribution over various subtypes may show regional variation): papillary thyroid cancer (up to 75%); follicular thyroid cancer (up to 15%); medullary thyroid cancer (up to 8%); and anaplastic thyroid cancer (less than 5%). The follicular and papillary types together can be classified as "differentiated thyroid cancer". These types have a more favorable prognosis than the medullary and undifferentiated types. Thyroid adenoma is a benign neoplasm of the thyroid.

In one embodiment, the methods described herein treat a thyroid cancer.

Bladder Cancer

Bladder cancer refers to any of several types of malignant growths of the urinary bladder. It is a disease in which abnormal cells multiply without control in the bladder. The bladder is a hollow, muscular organ that stores urine; it is located in the pelvis. The most common type of bladder cancer begins in cells lining the inside of the bladder and is called transitional cell carcinoma (sometimes urothelial cell carcinoma).

90% of bladder cancers are transitional cell carcinoma. The other 10% are squamous cell carcinoma, adenocarcinoma, sarcoma, small cell carcinoma and secondary deposits from cancers elsewhere in the body.

The following stages are used to classify the location, size, and spread of the cancer, according to the TNM (tumor, lymph node, and metastasis) staging system: Stage 0: Cancer cells are found only on the inner lining of the bladder. Stage I: Cancer cells have proliferated to the layer beyond the inner lining of the urinary bladder but not to the muscles of the urinary bladder. Stage II: Cancer cells have proliferated to the muscles in the bladder wall but not to the fatty tissue that surrounds the urinary bladder. Stage III: Cancer cells have proliferated to the fatty tissue surrounding the urinary bladder and to the prostate gland, vagina, or uterus, but not to the lymph nodes or other organs. Stage IV: Cancer cells have proliferated to the lymph nodes, pelvic or abdominal wall, and/or other organs. Recurrent: Cancer has recurred in the urinary bladder or in another nearby organ after having been treated.

Bladder TCC is staged according to the 1997 TNM system: Ta Non-invasive papillary tumor; T1 Invasive but not as far as the muscular bladder layer; T2 Invasive into the muscular layer; T3 Invasive beyond the muscle into the fat outside the bladder; and T4 Invasive into surrounding structures like the prostate, uterus or pelvic wall.

In one embodiment, the methods described herein treat a bladder cancer.

In accordance with the invention, the humanized endoglin antibodies or fragments thereof can be administered alone or in combination with active or inactive agents. When combinations are used, the invention contemplates simultaneous or sequential administration of the humanized endoglin antibodies or antigen-binding fragments and the active or inactive agents.

Compounds of the present invention can be, as needed, administered in combination with one or more therapeutic treatments including, but not limited to, adriamycin, cyclophosphamide, paclitaxel, pemetrexed, temozolomide, oxaliplatin, bevacizumab, erbitux, vectibix, sorafenib, sunitinib, gefitinib, erlotinib, 5-fluorouracil (5-FU) irinotecan, topotecan, leucovorin, VELCADE®, lenalidomide, thalidomide, xeloda, taxotere and many other conventional cancer therapies described herein. One would understand that the listing of therapeutic regimens listed below represents conventional therapies, but the present invention encompasses other known therapeutic regimens which are not specifically disclosed herein As used herein, "radiation" refers to, for example, microwaves, ultraviolet (UV), infrared (IR), or alpha-, beta- or gamma-radiation. Radiation can be "focused" or locally delivered using conventional techniques to target radiation to the site of one or more tumors without radiating the entire body.

In one embodiment, the cancer is ovarian cancer and the one or more therapeutic treatments is surgery, chemotherapy (e.g., doxorubicin, doxil, gemcitabine, Rubitecan, and platinum-based chemotherapeutics such as cisplatin, carboplatin and oxaliplatin), melphalan, paclitaxel, topoisomerase I inhibitors such as topotecan and irinotecan, taxane-based therapy, hormones, radiation therapy, whole body hypothermia, isoflavone derivatives such as Phenoxodial, cytotoxic macrolides such as Epothilones, angiogenesis inhibitors such as bevacizumab, signal transduction inhibitors such as trastuzumab, gene therapy, RNAi therapy, immunotherapy, monoclonal antibodies, phosphatidylinositol-like kinase inhibitors such as rapamycin, or any combination thereof. In one embodiment the combination is a humanized anti-endoglin antibody or antigen-binding fragment thereof and doxil. In another embodiment, the combination is a humanized anti-endoglin antibody or antigen-binding fragment thereof and topotecan. In yet another embodiment, the combination is a humanized anti-endoglin antibody or antigen-binding fragment thereof and a VEGF receptor inhibitor. Non-limiting examples of VEGF receptor inhibitors include bevacizumab (AVASTIN®), ranibizumab (LUCENTIS®), aflibercept (VEGF-Trap), sunitinib (SUTENT®), sorafenib (NEXAVAR®), axitinib, pegaptanib and pazopanib. The combination therapy of the antibodies and antigen-binding fragments described herein with the ovarian cancer therapies may also provide for lower doses of either therapy, or both, due to a synergistic effect from the co-administration of the therapies.

In one embodiment, the cancer is renal/kidney cancer and the one or more therapeutic treatments is surgery, chemotherapy, sunitinib, sorafenib, pazopanib, AVASTIN®, interferon-alpha, or IL-2. In one embodiment the combination is a humanized anti-endoglin antibody or antigen-binding fragment thereof and sorafenib. In one embodiment the combination is a humanized anti-endoglin antibody or antigen-binding fragment thereof and sunitinib. In one embodiment the combination is a humanized anti-endoglin antibody or antigen-binding fragment thereof and AVASTIN®. In yet another embodiment, the combination is a humanized anti-endoglin antibody or antigen-binding fragment thereof and a VEGF receptor inhibitor. Non-limiting examples of VEGF receptor inhibitors include bevacizumab (AVASTIN®), ranibizumab (LUCENTIS®), aflibercept (VEGF-Trap), sunitinib (SUTENT®), sorafenib (NEXAVAR®), axitinib, pegaptanib and pazopanib. The combination therapy of the antibodies and antigen-binding fragments described herein with the kidney cancer therapies may also provide for lower doses of either therapy, or both, due to a synergistic effect from the co-administration of the therapies.

In one embodiment, the cancer is myeloma and the one or more therapeutic treatments is surgery, radiotherapy, VELCADE®, lenalidomide, or thalidomide. In one embodiment the combination is a humanized anti-endoglin antibody or antigen-binding fragment thereof and VELCADE®. The dosages for any of these therapies are known in the art and can be adjusted with combination therapy accordingly.

In one embodiment, the cancer is prostate cancer and the one or more therapeutic treatments is surgery, radiotherapy (e.g., external beam or brachytherapy), hormonal deprivation (androgen suppression), heat shock protein 90 (HSP90) inhibitors, chemotherapy (e.g., docetaxel, platinum-based chemotherapy such as cisplatin, carboplatin, satraplatin and oxaliplatin, taxane, estramustine), prednisone or prednisolone, cholesterol-lowering drugs such as statins, leutinizing hormone-releasing hormone (LHRH) agonists, RNAi therapy, whole tumor cells genetically modified to secrete granulocyte macrophage-colony stimulating factor (GM-CSF) (also known as GVAX), or any combination thereof. In yet another embodiment, the combination is a humanized anti-endoglin antibody or antigen-binding fragment thereof and a VEGF receptor inhibitor. Non-limiting examples of VEGF receptor inhibitors include bevacizumab (AVASTIN®), ranibizumab (LUCENTIS®), aflibercept (VEGF-Trap), sunitinib (SUTENT®), sorafenib (NEXAVAR®), axitinib, pegaptanib and pazopanib.

In one embodiment, the cancer is lung cancer and the one or more therapeutic treatments is surgery, radiotherapy (e.g., thoracic radiotherapy, radiation therapy with charged particles, Uracil-tegafur and Platinum-based chemotherapy (e.g., cisplatin, carboplatin, oxaliplatin, etc.) and vinorelbine, Erlotinib (TARCEVA®), Gefitinib (IRESSA®), anti-epidermal growth factor receptor antibodies (e.g., Cetuximab), anti-vascular endothelial growth factor antibodies (e.g., Bevacizumab), small molecule inhibitors of tyrosine kinases, direct inhibitors of proteins involved in lung cancer cell proliferation, Aurora kinase inhibitors, laser-induced thermotherapy, RNAi therapy, whole tumor cells genetically modified to secrete granulocyte macrophage-colony stimulating factor (GM-CSF) (also known as GVAX), or any combination thereof. Additional therapeutic treatments include Taxol and pemetrexed. In one embodiment the combination is a humanized anti-endoglin antibody or antigen-binding fragment thereof and erlotinib. In one embodiment the combination is a humanized anti-endoglin antibody or antigen-binding fragment thereof and gefitinib. In one embodiment the combination is a humanized anti-endoglin antibody or antigen-binding fragment thereof and pemetrexed. In yet another embodiment, the combination is a humanized anti-endoglin antibody or antigen-binding fragment thereof and a VEGF receptor inhibitor. Non-limiting examples of VEGF receptor inhibitors include bevacizumab (AVASTIN®), ranibizumab (LUCENTIS®), aflibercept (VEGF-Trap), sunitinib (SUTENT®), sorafenib (NEXAVAR®), axitinib, pegaptanib and pazopanib. The dosages for any of these therapies are known in the art and can be adjusted with combination therapy accordingly.

In one embodiment, the cancer is breast cancer and the one or more therapeutic treatments is surgery, monoclonal antibodies (e.g., Her-2 antibodies, herceptin), adjuvant chemotherapy such as single agent chemotherapy or combination chemotherapy (e.g., anthracycline- and taxane-based polychemotherapies, taxol, or target-specific trastuzumab with or without endocrine manipulation with or without PMRT, vinorelbine), adriamycin, cyclophosphamide, xeloda, taxotere, selective estrogen receptor modulators such as Tamoxifen and Raloxifene, allosteric estrogen receptor modulators such as Trilostane, radiation (e.g., interstitial brachytherapy, Mammosite device, 3-dimensional conformal external radiation and intraoperative radiotherapy), Aromatase inhibitors that suppress total body synthesis (e.g., anastrozole, exemestane and letrozole), RNAi therapy, intravenous analogs of rapamycin that are immunosuppressive and anti-proliferative such as Temsirolimus (CCI779), or any combination thereof. A review of methods for conducting three-dimensional in vitro tissue culture models of breast cancer are described by Kim et al., Breast Cancer Research Treatment 85(3): 281-91 (2004). Other in vivo and in vitro models for testing cancers are known and can be used to test anti-endoglin antibodies described herein. In one embodiment the combination is a humanized anti-endoglin antibody or antigen-binding fragment thereof, taxol, and AVASTIN®. In one embodiment the combination is a humanized anti-endoglin antibody or antigen-binding fragment thereof and adriamycin. In one embodiment the combination is a humanized anti-endoglin antibody or antigen-binding fragment thereof and xeloda. In one embodiment the combination is a humanized anti-endoglin antibody or antigen-binding fragment thereof and taxotere. In yet another embodiment, the combination is a humanized anti-endoglin antibody or antigen-binding fragment thereof and a VEGF receptor inhibitor. Non-limiting examples of VEGF receptor inhibitors include bevacizumab (AVASTIN®), ranibizumab (LUCENTIS®), aflibercept (VEGF-Trap), sunitinib (SUTENT®), sorafenib (NEXAVAR®), axitinib, pegaptanib and pazopanib. The dosages for any of these therapies are known in the art and can be adjusted with combination therapy accordingly.

In one embodiment, the cancer is colon cancer and the one or more therapeutic treatments is surgery, radiation therapy, and chemotherapy (e.g., 5-fluorouracil, levamisole, leucovorin or semustine (methyl CCNU)), N-[2-(dimethylamino) ethyl]acridine-4-carboxamide and other related carboxamide anticancer drugs; non-topoisomerase II inhibitors, irinotecan, liposomal topotecan, taxane class of anticancer agents (e.g., paclitaxel or docetaxel), a compound of the xanthenone acetic acid class (e.g., 5,6-dimethylxanthenone-4-acetic acid PMAA), laminarin, site-selective cyclic AMP Analogs (e.g., 8-chloroadenosine 3',5'-cyclic phosphate), pyranoindole inhibitors of Cox-2, carbazole inhibitors of Cox-2, tetrahydrocarbazole inhibitors of Cox-2, indene inhibitors of Cox-2, localized inhibitors of NSAIDS (e.g., anthranilic acids, aspirin (5-acetylsalicylic acid), azodisal sodium, carboheterocyclic acids, carprofen, chlorambucil, diclophenac, fenbufen, fenclofenac, fenoprofen, flufenamic acid, flurbiprofen, fluprofen, furosemide, gold sodium thiomalate, ibuprofen, indomethacin, indoprofen, ketoprofen, lonazolac, loxoprofen, meclofenamic acid, mefanamic acid, melphalan, naproxen, penicillamine, phenylacetic acids, proprionic acids, salicylic acids, salazosulfapyridine, sulindac, tolmetin, a pyrazolone butazone propazone NSAID, meloxicam, oxicams, piroxicam, feldene, piroxicam beta cyclodextran, tenoxicam, etodolac, and oxaprozin), an inhibitor of HER-2/neu, RNAi therapy, GM-CSF, monoclonal antibodies (e.g., anti-Her-2/neu antibodies, anti-CEA antibodies, A33 (HB 8779), 100-210 (HB 11764) and 100-310 (HB 11028)), erbitux, vectibix, hormonal therapy, pyrimidineamines, camptothecin derivatives (e.g., CPT-11), folinic acid (FA), Gemcitabine, Ara-C, platinum-based chemotherapeutics such as cisplatin, carboplatin and oxaliplatin, a cGMP-specific phosphodiesterase inhibitor, or any combination thereof. In one embodiment the combination is a humanized anti-endoglin antibody or antigen-binding fragment thereof and a combination of 5-FU, leucovorin and oxaliplatin (FOLFOX). In one embodiment the combination is a humanized anti-endoglin antibody or antigen-binding fragment thereof and a combination of 5-FU, irinotecan and leucovorin (IFL). In one embodiment the combination is a humanized anti-endoglin antibody or antigen-binding fragment thereof and erbitux. In one embodiment the combination is a humanized anti-endoglin antibody or antigen-binding fragment thereof and a vectibix. In yet another embodiment, the combination is a humanized anti-endoglin antibody or antigen-binding fragment thereof and a VEGF receptor inhibitor. Non-limiting examples of VEGF receptor inhibitors include bevacizumab (AVASTIN®), ranibizumab (LUCENTIS®), aflibercept (VEGF-Trap), sunitinib (SUTENT®), sorafenib (NEXAVAR®), axitinib, pegaptanib and pazopanib. The dosages for any of these therapies are known in the art and can be adjusted with combination therapy accordingly.

In one embodiment, the cancer is pancreatic cancer and the one or more therapeutic treatments is surgery, radiation therapy (RT), Fluorouracil (5-FU) and RT, systemic therapy, stenting, Gemcitabine (GEMZAR®), Gemcitabine and RT, Cetuximab, erlotinib (TARCEVA®), chemoradiation, bevacizumab (AVASTIN®), or any combination thereof. In yet another embodiment, the combination is a humanized anti-endoglin antibody or antigen-binding fragment thereof and a VEGF receptor inhibitor. Non-limiting examples of VEGF receptor inhibitors include bevacizumab (AVASTIN®), ranibizumab (LUCENTIS®), aflibercept (VEGF-Trap), sunitinib (SUTENT®), sorafenib (NEXAVAR®), axitinib, pegaptanib and pazopanib.

Patients can be assessed with respect to symptoms at one or more multiple time points including prior to, during, and after treatment regimens. Treatment can result in improving the subject's condition and can be assessed by determining if one or more of the following factors has occurred: decreased tumor size, decreased cell proliferation, decreased numbers of cells, decreased neovascularization, increased apoptosis, or decreased survival of at least a portion of the cells comprising the cell proliferative disorder. One or more of these occurrences may, in some cases, result in partial or total elimination of the cancer and prolongation of survival of the patient. Alternatively, for terminal stage cancers, treatment may result in stasis of disease, better quality of life and/or prolongation of survival.

Biomarker Assessment

Certain genes can be expressed at increased or decreased levels in cancers. Changes in expression levels of genes in cancers can be indicative of resistance or sensitivity to a cancer therapy or treatment.

Provided herein is a diagnostic method for detecting the expression of at least one gene chosen from a panel of genes whose expression has been correlated with sensitivity or resistance to an angiogenesis inhibitor, wherein the at least one gene is: VEGF, VEGF receptor, HIF-1α, placental growth factor receptor or endoglin (CD105). The method can further include the step of comparing the level of expression of at least one gene detected in the patient sample to a level of expression of at least one gene that has been correlated with sensitivity or resistance to the angiogenesis inhibitor. In one non-limiting embodiment, the angiogenesis inhibitor is a humanized anti-endoglin antibody. In another embodiment, the angiogenesis inhibitor is a VEGF receptor inhibitor or a VEGF inhibitor.

As used herein, the term "expression," when used in connection with detecting the expression of a gene, can refer to detecting transcription of the gene and/or to detecting translation of the gene. To detect expression of a gene refers to the act of actively determining whether a gene is expressed or not. This can include determining whether the gene expression is upregulated as compared to a control, downregulated as compared to a control, or unchanged as compared to a control. Therefore, the step of detecting expression does not require that expression of the gene actually is upregulated or downregulated, but rather, can also include detecting that the expression of the gene has not changed (i.e., detecting no expression of the gene or no change in expression of the gene).

Biomarkers to be assessed in connection with the present invention include VEGF receptor, placental growth factor, HIF-1α and endoglin (CD105).

For assessment of biomarker expression, patient samples containing endothelial tissue, tumor cells, or proteins or nucleic acids produced by tumor cells, can be used in methods described herein and further known in the art. Briefly, the level of expression of the biomarker can be assessed by assessing the amount (e.g., absolute amount or concentration) of the marker in a sample, e.g., a tumor biopsy obtained from a patient, or other patient sample containing material derived from the tumor (e.g., blood, serum, urine, or other bodily fluids or excretions as described herein above). The cell sample can, of course, be subjected to a variety of well-known post-collection preparative and storage techniques (e.g., nucleic acid and/or protein extraction, fixation, storage, freezing, ultrafiltration, concentration, evaporation, centrifugation, etc.) prior to assessing the amount of the marker in the sample. Likewise, tumor biopsies can also be subjected to post-collection preparative and storage techniques, e.g., fixation.

One can detect expression of biomarker proteins having at least one portion which is displayed on the surface of cells which express it. One can determine whether a marker protein, or a portion thereof, is exposed on the cell surface. For example, immunological methods can be used to detect such proteins on whole cells, or well known computer-based sequence analysis methods can be used to predict the presence of at least one extracellular domain (i.e., including both secreted proteins and proteins having at least one cell-surface domain). Expression of a marker protein having at least one portion which is displayed on the surface of a cell which expresses it can be detected without necessarily lysing the tumor cell (e.g., using a labeled antibody which binds specifically with a cell-surface domain of the protein).

Expression of biomarkers can be assessed by any of a wide variety of well known methods for detecting expression of a transcribed nucleic acid or protein. Non-limiting examples of such methods include, for example, immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods or any other method known in the art.

A mixture of transcribed polynucleotides obtained from the sample can be contacted with a substrate having fixed thereto a polynucleotide complementary to or homologous with at least a portion (e.g., at least 7, 10, 15, 20, 25, 30, 40, 50, 100, 500, or more nucleotide residues) of a biomarker nucleic acid. If polynucleotides complementary to, or homologous with, are differentially detectable on the substrate (e.g., detectable using different chromophores or fluorophores, or fixed to different selected positions), then the levels of expression of a plurality of biomarkers can be assessed simultaneously using a single substrate (e.g., a "gene chip" microarray of polynucleotides fixed at selected positions). When a method of assessing biomarker expression is used which involves hybridization of one nucleic acid with another, hybridization can be performed under stringent hybridization conditions.

When a plurality of biomarkers of the invention are used in the methods of the invention, the level of expression of each biomarker in a patient sample can be compared with the normal level of expression of each of the plurality of biomarkers in non-cancerous samples of the same type, either in a single reaction mixture (i.e., using reagents, such as different fluorescent probes, for each biomarker) or in individual reaction mixtures corresponding to one or more of the biomarkers.

The level of expression of a biomarker in normal (i.e., non-cancerous) human tissue can be assessed in a variety of ways. This normal level of expression can be assessed by assessing the level of expression of the biomarker in a portion of cells which appears to be non-cancerous, and then comparing the normal level of expression with the level of expression in a portion of the tumor cells. As further information becomes available as a result of routine performance of the methods described herein, population-average values for normal expression of the biomarkers can be used. Alternatively, the normal level of expression of a biomarker can be determined by assessing expression of the biomarker in a patient sample obtained from a non-cancer-afflicted patient, from a patient sample obtained from a patient before the suspected onset of cancer in the patient, from archived patient samples, and the like.

An exemplary method for detecting the presence or absence of a biomarker protein or nucleic acid in a biological sample involves obtaining a biological sample from a test subject and contacting the biological sample with a compound or an agent capable of detecting the polypeptide or nucleic acid (e.g., mRNA, genomic DNA, or cDNA). The detection methods can, thus, be used to detect mRNA, protein, cDNA, or genomic DNA, for example, in a biological sample in vitro as well as in vivo. In vitro techniques for detection of mRNA include, for example, reverse transcriptase-polymerase chain reaction (RT-PCR; e.g., the experimental embodiment set forth in Mullis, 1987, U.S. Pat. No. 4,683,202), Northern hybridizations and in situ hybridizations. In vitro techniques for detection of a biomarker protein include, but are not limited to, enzyme linked immunosorbent assays (ELISAs), Western blots, immunoprecipitations and immunofluorescence. In vitro techniques for detection of genomic DNA include, for example, Southern hybridizations. In vivo techniques for detection of mRNA include, for example, polymerase chain reaction (PCR), quantitative PCR, Northern hybridizations and in situ hybridizations. Furthermore, in vivo techniques for detection of a biomarker protein include introducing into a subject a labeled antibody directed against the protein or fragment thereof. For example, the antibody can be labeled with a radioactive marker whose presence and location in a subject can be detected by standard imaging techniques.

A general principle of such diagnostic and prognostic assays involves preparing a sample or reaction mixture that may contain a biomarker, and a probe, under appropriate conditions and for a time sufficient to allow the biomarker and probe to interact and bind, thus forming a complex that can be removed and/or detected in the reaction mixture. These assays can be conducted in a variety of ways using a variety of methods.

It is also possible to directly detect biomarker/probe complex formation without further manipulation or labeling of either component (biomarker or probe), for example by utilizing the technique of fluorescence energy transfer (i.e., FET, see for example, Lakowicz et al., U.S. Pat. No. 5,631,169; and Stavrianopoulos, et al., U.S. Pat. No. 4,868,103).

In another embodiment, determination of the ability of a probe to recognize a biomarker can be accomplished without labeling either assay component (probe or biomarker) by utilizing a technology such as real-time Biomolecular Interaction Analysis (BIA; see, e.g., Sjolander, S. and Urbaniczky, C., 1991, Anal. Chem. 63:2338-2345 and Szabo et al., 1995, Curr. Opin. Struct. Biol. 5:699-705). As used herein, "BIA" or "surface plasmon resonance" refer to a technology for studying biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

As an alternative to making determinations based on the absolute expression level of the biomarker, determinations can be based on the normalized expression level of the biomarker. Expression levels are normalized by correcting the absolute expression level of a biomarker by comparing its expression to the expression of a gene that is not a biomarker, e.g., a housekeeping gene that is constitutively expressed. Suitable genes for normalization include housekeeping genes such as the actin gene, or epithelial cell-specific genes. This normalization allows the comparison of the expression level in one sample, e.g., a patient sample, to another sample, e.g., a non-tumor sample, or between samples from different sources.

Alternatively, the expression level can be provided as a relative expression level. To determine a relative expression level of a biomarker (e.g., VEGF receptor, placental growth factor, Hif-1α and endoglin (CD105)), the level of expression of the biomarker is determined for 10 or more, 20 or more, 30 or more, 40 or more, or 50 or more samples of normal versus cancer cell isolates prior to the determination of the expression level for the sample in question. The mean expression level of each of the genes assayed in the larger number of samples is determined and this is used as a baseline expression level for the biomarker. The expression level of the biomarker determined for the test sample (absolute level of expression) is then divided by the mean expression value obtained for that biomarker. This provides a relative expression level.

In another embodiment of the present invention, a biomarker protein is detected. One type of agent for detecting biomarker protein of the invention is an antibody capable of binding to such a protein or a fragment thereof such as, for example, a detectably labeled antibody. Antibodies can be polyclonal or monoclonal. An intact antibody, or an antigen binding fragment thereof (e.g., Fab, F(ab')2, Fv, scFv, single binding chain polypeptide) can be used. The term "labeled," with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. A variety of formats can be employed to determine whether a sample contains a protein that binds to a given antibody. Examples of such formats include, but are not limited to, enzyme immunoassay (EIA), radioimmunoassay (RIA), Western blot analysis and enzyme linked immunosorbant assay (ELISA). A skilled artisan can readily adapt known protein/antibody detection methods for use in determining whether tumor cells express a biomarker of the present invention. A combination of two or more of the assays for the detection of biomarkers (non-limiting examples include those described above) can also be used to assess one or more biomarkers.

Also provided herein is a method of selecting a cancer patient for treatment with an angiogenesis inhibitor. The method comprises providing a sample of the cancer from the patient, detecting the expression of one or more genes whose expression has been correlated with sensitivity or resistance to an angiogenesis inhibitor, comparing the level of expression of the gene or genes detected in the patient sample to a level of expression of the gene or genes that have been correlated with sensitivity or resistance to the angiogenesis inhibitor. Non-limiting examples of genes that have been correlated with sensitivity or resistance to the angiogenesis inhibitor include VEGF, VEGF receptor, HIF-1α, placental growth factor receptor, and endoglin (CD105). In a further embodiment, a patient is selected as being predicted to benefit from administration of the angiogenesis inhibitor if the expression of the gene or genes is similar to the expression of the gene or genes that have been correlated with sensitivity to the angiogenesis inhibitor. In one non-limiting embodiment, the angiogenesis inhibitor for which the subject or the subject's cancer is tested for sensitivity or resistance is an endoglin (CD105) inhibitor (e.g., humanized anti-endoglin antibodies). In another embodiment, the angiogenesis inhibitor for which the subject or the subject's cancer is tested for sensitivity or resistance is a VEGF receptor inhibitor or a VEGF inhibitor.

IV. Functional Assays

Antibodies and antigen binding fragments thereof can be tested for a variety of functions using a variety of in vitro and in vivo methods including, but not limited to those known in the art and those described herein.

Methods of Assaying CD105 Signaling and Function

CD105 (endoglin) is a member of the TGF-β receptor family that is expressed by proliferating endothelial cells, and normal levels of CD105 are needed for endothelial cell proliferation. CD105 expression is increased by cellular hypoxia through the production of hypoxia-inducible factor-1-α (HIF-1-α) and protects hypoxic cells from apoptosis. CD105 acts to modulate signaling of multiple kinase receptor complexes of the TGF-β superfamily, including TGF-β receptors (TGF-βR), activin receptor-like kinases (ALK) and activin receptors. In the absence of CD105, activation of TGF-β receptors results in phosphorylation of SMAD proteins that inhibit endothelial cell growth. However, activation of CD105 by TGF-β modulates SMAD protein phosphorylation. The end result is release of the growth inhibitory effects of TGF-β receptor activation on endothelial cells. Prevention of CD105 activation by anti-CD105 antibody acts synergistically with TGF-β to suppress endothelial cell growth. TGF-β can stimulate two distinct type I receptor/SMAD signaling pathways with opposite effects in endothelial cells. The TGF-β/ALK5 signaling pathway (A) leads to inhibition of cell proliferation and migration, whereas the TGF-β/ALK1 pathway (B) induces endothelial cell proliferation and migration. CD105, an accessory TGF-β receptor, highly expressed during angiogenesis, is essential for ALK1 signaling. In the absence of CD105, TGF-β/ALK5 signaling is predominant and maintains quiescent endothelium. High CD105 expression stimulates the ALK1 pathway and indirectly inhibits ALK5 signaling, thus promoting the activation state of angiogenesis.

In one non-limiting embodiment, the antibodies and antigen-binding fragments provided herein block angiogenesis by blocking the TGF-β/ALK1 signaling pathway. In another embodiment, the antibodies and antigen-binding fragments provided herein block angiogenesis by preventing Smad1/5/8 phosphorylation and/or signaling. CD105 participates in the promotion of angiogenesis through signaling of the TGF-β/ALK1, which in turn involves the decrease and/or blockage of the phosphorylation of Smad2/3 proteins. In yet another embodiment, the antibodies and antigen-binding fragments provided herein block angiogenesis by enhancing Smad2/3 phosphorylation and/or signaling. Methods and techniques to assay the blocking or inhibitory effect of the antibodies and antigen-binding fragments provided herein on the TGF-β/ALK1 signaling pathway and/or the phosphorylation of Smad1/5 include, but are not limited to, known molecular techniques. By way of example, western blotting with antibodies specific to any of the proteins in the TGF-β/ALK5 or TGF-β/ALK1 pathways can be used to determine the inhibitory and/or stimulatory effect of the antibodies and antigen-binding fragments disclosed herein on the TGF-β/ALK5 or TGF-β/ALK1 pathways. Similarly, detection of mRNA or regulation of the mRNA for the proteins involved in the TGF-β/ALK5 or TGF-β/ALK1 pathways can be used to assay the inhibitory and/or stimulatory effect of the antibodies and antigen-binding fragments disclosed herein. Additional methods for the assaying cell signaling for the TGF-β/ALK5 or TGF-β/ALK1 pathways are known in the art and are contemplated herein.

In one non-limiting embodiment, the antibodies can be assessed with respect to inhibiting angiogenesis and endothelial cell proliferation. Binding of anti-endoglin antibodies to HUVECs does not prevent subsequent binding of TGF-β to HUVECs. Thus, direct suppression of the endothelial cell growth by anti-endoglin antibodies represents one of the underlying mechanisms by which anti-angiogenic and tumor-suppressive effects are observed in vivo. In another embodiment, the antibodies can be assessed with respect to blocking angiogenesis by preventing Smad1/5/8 phosphorylation and/or signaling. CD105 participates in the promotion of angiogenesis through signaling of the TGF-β/ALK1, which in turn involves the decrease and/or blockage of the phosphorylation of Smad2/3 proteins. In yet another embodiment, the antibodies can be assessed with respect to blocking angiogenesis by enhancing Smad2/3 phosphorylation and/or signaling.

Methods and techniques to assay the blocking or inhibitory effect of the antibodies provided herein on the TGF-β/ALK1 signaling pathway and/or the phosphorylation of Smad1/5 include, but are not limited to, known molecular techniques. By way of example, western blotting with antibodies specific to any of the proteins in the TGF-β/ALK5 or TGF-β/ALK1 pathways can be used to determine the inhibitory and/or stimulatory effect of the anti-endoglin antibodies disclosed herein on the TGF-β/ALK5 or TGF-β/ALK1 pathways. Similarly, detection of mRNA or regulation of the mRNA for the proteins involved in the TGF-β/ALK5 or TGF-β/ALK1 pathways can be used to assay the inhibitory and/or stimulatory effect of the antibodies disclosed herein. Additional methods for the assaying cell signaling for the TGF-β/ALK5 or TGF-β/ALK1 pathways are known in the art and are contemplated herein.

Activity of the anti-endoglin antibodies disclosed herein can be assessed using art recognized assays by, for example, binding assays such ELISAs, competitive ELISAs, surface plasmon resonance, and effect on HUVEC cells as described in more detail below.

Methods of Assaying Cell Adhesion

Cell adhesion can be measured by methods known to those of skill in the art. Assays have been described previously, e.g. by Lebrin, et al., J. Clin. Invest 1997, 99:1390-1398. Briefly, cells can be allowed to adhere to substrate (i.e., an ECM component) on coated wells. Non-attached cells are removed by washing, and non-specific binding sites are blocked by incubation with BSA. The attached cells are stained with crystal violet, and cell adhesion is quantified by measuring the optical density of eluted crystal violet from attached cells at a wavelength of 600 nm.

Methods of Assaying Cell Migration

Assays for cell migration have been described in the literature, e.g., by Brooks, et al., J. Clin. Invest 1997, 99:1390-1398 and methods for measuring cell migration are known to those of skill in the art. In one method for measuring cell migration described herein, membranes from transwell migration chambers are coated with substrate, the transwells washed, and non-specific binding sites blocked with BSA. Tumor cells from sub-confluent cultures are harvested, washed, and resuspended in migration buffer in the presence or absence of assay antibodies. After the tumor cells are allowed to migrate to the underside of the coated transwell membranes, the cells remaining on the top-side of the membrane are removed and cells that migrate to the under-side are stained with crystal violet. Cell migration is then quantified by direct cell counts per microscopic field.

SCID/Nude Mice

One method for assaying tumor growth makes use of SCID mouse, as follows: subconfluent human M21 melanoma cells are harvested, washed, and resuspended in sterile PBS ($20 \times 10^6$ per mL). SCID mice are injected subcutaneously with 100 µL of M21 human melanoma cell ($2 \times 10^6$) suspension. Three days after tumor cell injection, mice are either untreated or treated intravenously or intraperitoneally (for example, 100 µg/mouse) with one or more control or test compositions. The mice are treated daily for 24 days. Tumor size is measured with calipers and the volume estimated using the formula $V=(L \times W^2)/2$, where V is equal to the volume, L is equal to the length, and W is equal to the width.

One method for assaying tumor growth makes use of nude mouse, as follows: MDA-MB-435 tumor cells ($0.4 \times 10^6$ cells/mouse) in 50 µl PBS are orthotopically implanted in the mammary fat pad of female nude mice (five to six weeks old). When tumors reached a mean volume of approximately 50-80 mm$^3$, mice are randomized (at least 10/group) and intravenous or intraperitoneal treatment with one or more antibodies at 1 µg (0.05 mg/kg) per dose, 10 µg (0.5 mg/kg), 100 µg (5 mg/kg) or 200 µg (10 mg/kg), or 100 µg control antibody in 100 µl PBS, or vehicle PBS 100 µl twice per week is initiated; in some studies, an untreated group can also be valuated. Tumor size is measured with calipers and the volume estimated using the formula $V=(L \times W^2)/2$, where V is equal to the volume, L is equal to the length, and W is equal to the width.

BALB/c Syngeneic Mouse Models

Alternatively, BALB/c syngeneic mouse models can also be utilized to assess tumor growth and inhibition thereof by the antibodies or described herein as exemplified by, for example, Tsujie et al., Int. J. Oncology, 29: 1087-1094 (2006).

Chimeric Mice

Another assay measures angiogenesis in a chimeric mouse:human mouse model and is referred to as the chimeric mouse assay. The assay has been described in detail by others, and further has been described herein to measure angiogenesis, neovascularization, and regression of tumor tissues. See Yan, et al. (1993) J. Clin. Invest. 91:986-996.

The chimeric mouse assay is a useful assay model for in vivo angiogenesis because the transplanted skin grafts closely resemble normal human skin histologically and neovascularization of whole tissue is occurring wherein actual human blood vessels are growing from the grafted human skin into the human tumor tissue on the surface of the grafted human skin. The origin of the neovascularization into the human graft can be demonstrated by immunohistochemical staining of the neovasculature with human-specific endothelial cell markers.

The chimeric mouse assay demonstrates regression of neovascularization based on both the amount and extent of regression of new vessel growth. Furthermore, it is easy to monitor effects on the growth of any tissue transplanted upon the grafted skin, such as a tumor tissue. Finally, the assay is useful because there is an internal control for toxicity in the assay system. The chimeric mouse is exposed to any test reagent, and therefore the health of the mouse is an indication of toxicity. Other animal models described herein and known in the art can also be utilized in the methods described herein.

Rabbit Eye Assay

Another measure of angiogenesis is an in vivo rabbit eye model and is referred to as the rabbit eye assay. The rabbit eye assay has been described in detail by others, and has been used to measure both angiogenesis and neovascularization in the presence of angiogenic inhibitors as exemplified by D'Amato et al. (1994) Proc. Natl. Acad. Sci. USA, 91(9): 4082-4085.

The rabbit eye assay is a recognized assay model for in vivo angiogenesis because the neovascularization process, exemplified by rabbit blood vessels growing from the rim of the cornea into the cornea, is easily visualized through the naturally transparent cornea of the eye. Additionally, both the extent and the amount of stimulation or inhibition of neovascularization or regression of neovascularization can easily be monitored over time.

Finally, the rabbit is exposed to any test reagent, and therefore the health of the rabbit is an indication of toxicity of the test reagent.

Briefly, chicken chorioallantoic membrane (CAM) assays are performed and the effects on the developing vasculature are recorded at 48 hours after implantation of a 0.5% carboxymethylcellulose pellet containing one or more control or test compounds. Corneal neovascularization is induced by an implanted pellet of poly(hydroxyethyl methacrylate) (Hydron; Interferon Sciences, New Brunswick, N.J.) containing 650 ng of the potent angiogenic protein basic fibroblast growth factor (bFGF) bound to sucralfate (sucrose aluminum sulfate; Bukh Meditec, Copenhagen). The addition of sucralfate to the pellet protects the bFGF from degradation and provides for its slow release, thus producing consistent aggressive angiogenesis that is more pronounced than that induced by bFGF/Hydron alone. Release of bFGF from pellets containing sucralfate/Hydron can be detected in vitro for up to 4 days after the pellets are formed compared to just 1 day for pellets with Hydron alone. Pellets are made by mixing 110 µl of saline containing 12 µg of recombinant bFGF (Takeda, Osaka) with 40 mg of sucralfate; this suspension is added to 80 µl of 12% (wt/vol) Hydron in ethanol. Aliquots (10 µl) of this mixture are then pipetted onto Teflon pegs and allowed to dry producing approximately 17 pellets.

A pellet is implanted into corneal micropockets of each eye of an anesthetized female New Zealand White rabbit, 2 mm from the limbus, followed by a single topical application of erythromycin ointment on the surface of the cornea. Histologic examination on consecutive days demonstrates progressive blood vessel growth into the cornea toward the pellet with only rare inflammatory cells seen. This angiogenic response is not altered by severe immune suppression with total body irradiation, and pellets with sucralfate alone do not induce angiogenesis. New vessels are primarily induced by the bFGF rather than by inflammation. The animals are fed daily from 2 days after implantation by gastric lavage with one or more compounds suspended in 0.5% carboxymethylcellulose or vehicle alone. Immunosuppressed animals receive total body radiation of 6 Gy for 6 minutes immediately prior to implantation of the pellets. This dose of radiation results in a marked leukocytopenia with >80% reduction in the leukocyte count by day 2 and >90% reduction by day 3, results that are consistent with previous reports.

Animals are examined with a slit lamp every other day in a masked manner by the same corneal specialist (M.S.L.). The area of corneal neovascularization is determined by measuring with a reticule the vessel length (L) from the limbus and the number of clock hours (C) of limbus involved. A formula is used to determine the area of a circular band segment: $C/12 \times 3.1416 [r^2-(r-L)^2]$, where r=6 mm, the measured radius of the rabbit cornea. The uniform contiguous band of neovascularization adjacent to the pellet is measured, thus, the total inhibition of neovascularization can be assessed.

Mouse Matrigel Pug Angiogenesis Assays

To confirm the effects of a composition on angiogenesis, a mouse Matrigel plug angiogenesis assay can be used. Various growth factors (e.g., IGF-1, bFGF or VEGF) (250 ng) and Heparin (0.0025 units per/mL) are mixed with growth factor reduced Matrigel as previously described (Montesano, et al., J. Cell Biol. 1983, 97:1648-1652; Stefansson, et al., J. Biol. Chem. 2000, 276:8135-8141). Compositions described herein or control antibodies can be included in the Matrigel preparations utilizing one or more dosage groups of animals. In control experiments, Matrigel is prepared in the absence of growth factors. Mice are injected subcutaneously with 0.5 mL of the Matrigel preparation and allowed to incubate for one week. Following the incubation period, the mice are sacrificed and the polymerized Matrigel plugs surgically removed. Angiogenesis within the Matrigel plugs is quantified by two established methods, including immunohistochemical analysis and hemoglobin content (Furstenberger, et al., Lancet. 2002, 3:298-302; Volpert, et al., Cancer Cell 2002, 2(6):473-83; and Su, et al., Cancer Res. 2003, 63:3585-3592). For immunohistochemical analysis, the Matrigel plugs are embedded in OCT, snap frozen and 4 µm sections prepared. Frozen sections are fixed in methanol/acetone (1:1). Frozen sections are stained with polyclonal antibody directed to CD31. Angiogenesis is quantified by microvascular density counts within 20 high powered (200x) microscopic fields.

Hemoglobin content can be quantified as described previously (Schnaper, et al., J. Cell Physiol. 1993, 256:235-246; Montesano, et al., J. Cell Biol. 1983, 97:1648-1652; Stefansson, et al., J. Biol. Chem. 2000, 276:8135-8141; and Gigli, et al., J. Immunol. 1986, 100:1154-1164). The Matrigel implants are snap frozen on dry ice and lyophilized overnight. The dried implants are resuspended in 0.4 mL of 1.0% saponin (Calbiochem) for one hour, and disrupted by vigorous pipetting. The preparations are centrifuged at 14,000×g for 15 minutes to remove any particulates. The concentration of hemoglobin in the supernatant is then determined directly by measuring the absorbency at 405 nm and compared to a standard concentration of purified hemoglobin.

Methods of Assaying Tumor Growth

Tumor growth can be assayed by methods known to those of skill in the art, e.g., the SCID mouse model, the nude mouse model, and BALB/c mice with syngeneic tumors. SCID mouse models for tumor growth are carried out as follows: subconfluent human M21 melanoma cells (or any desired tumor cell type) are harvested, washed, and resuspended in sterile PBS (20×106 per mL). SCID mice are injected subcutaneously with 100 µL of M21 human melanoma cell ($2\times10^6$) suspension. Three days after tumor cell injection, mice are either untreated or treated intraperitoneally with an antagonist in the desired dose ranges. The mice are treated daily for 24 days. Tumor size is measured with calipers and the volume estimated using the formula $V=(L \times W^2)/2$, where V is equal to the volume, L is equal to the length, and W is equal to the width.

Alternatively, nude mouse models, SCID mouse models and/or BALB/c syngeneic mouse models can also be utilized to assess tumor growth and inhibition thereof by the humanized anti-endoglin antibodies or antigen-binding fragments described herein. (Tsujie et al., Int. J. Oncology, 29: 1087-1094 (2006)).

Methods of Assaying Cell Proliferation

Cell proliferation can be assayed by methods known to those of skill in the art. As described herein, subconfluent human endothelial cells (HUVECs) can be resuspended in proliferation buffer containing low (5.0%) serum in the presence or absence of CM (25 µL) from ECV or ECVL cells, and endothelial cells allowed to proliferate for 24 hours. Proliferation can be quantified by measuring mitochondrial dehydrogenase activity using a commercially available WST-1 assay kit (Chemicon). Also, as described herein, proliferation can be quantified by measuring $^3$H incorporation using standard methods. (She et al., Int. J. Cancer, 108: 251-257 (2004)).

Other methods of assessing cell proliferation are known in the art and are contemplated herein. Further non-limiting examples are described in more detail in the examples.

Methods of Inducing CDC, ADCC and Opsonization

Various therapies have been directed to augmenting the body's natural immune response to transformed cells. Conventional effector methods include complement dependent cytolysis ("CDC"), antibody dependent cellular cytotoxicity ("ADCC") and phagocytosis (clearance by reticuloendothelial system after the target cell is coated with immunoglobulin). It is known that in the presence of antibodies, certain effector cells, such as lymphoid cells having surface bound receptors for the Fc regions of antibodies, mediate an antibody dependent cellular cytoxicity ("ADCC") reaction against target cells. By means of ADCC, these effector cells exert cytolytic activity against such target cells.

Two types of ADCC reactions have been demonstrated in vitro. In classical ADCC reactions, effector cells attach to antibody-coated target cells and subsequently cause cytolysis of the target cells (A. H. Greenberg et al., "Characteristics Of The Effector Cells Mediating Cytotoxicity Against Antibody-Coated Target Cells." I., Immunology, 21, p. 719 (1975)). This attachment between effector and target cell results from the interaction of the Fc region of the antibody coating the target cell and the Fc receptor of the effector cell. One disadvantage of this type of ADCC reaction is that it may be hampered by circulating antigen-antibody complexes, often associated with various diseases, which compete with the target-cell bound antibody for the Fc receptors of the effector cells (I. C. M. MacLennan, "Competition For Receptors For Immunoglobulin On Cytotoxic Lymphocytes," Clin. Exp. Immunol., 10, p. 275 (1972)). Due to this drawback of classical ADCC, a second type of ADCC reaction—antibody-directed ADCC—has been proposed. In antibody-directed ADCC, the target-specific antibody is first attached to the effector cell and the resulting complex is then "directed," via the antibody, to its specific antigen on the target cell surface. Advantageously, antibody-directed ADCC may not be affected by the presence of antigen-antibody complexes circulating in the host system. The interaction between antibodies and effector cells via Fc region/Fc receptor attachment is normally weak. And, in some instances, antibodies do not remain associated with effector cells for a period of time sufficient to permit lysis of target cells. In view of this potential problem, antibodies have been attached to the effector cells using pre-treatment with polyethylene glycol and a mixture of phthalate oils (J. F. Jones and D. M. Segal, "Antibody-Dependent Cell Mediated Cytolysis (ADCC) With Antibody-Coated Effectors: New Methods For Enhancing Antibody Binding And Cytolysis," J. Immunol., 125, pp. 926-33 (1980)). The applicability of this method for in vivo treatments, however, may be diminished by the toxic effects that any polyethylene glycol and phthalate oil residues on the antibody-effector cell complex may have on the body.

Alternatively, a method has been proposed for enhancing antibody-directed ADCC by adjuvant chemotherapy with cytotoxic drugs (I. R. Mackay et al., "Effect On Natural Killer And Antibody-Dependent Cellular Cytotoxicity Of Adjuvant Cytotoxic Chemotherapy Including Melphalan In Breast Cancer," Cancer Immunol. Immunother., 16, pp. 98-100 (1983)). Assays for testing for ADCC are well-known in the art, such as for example, U.S. Pat. No. 5,756,097.

Accordingly, the present invention provides antibodies (e.g., humanized anti-endoglin antibodies) that can bind to cells having a role in neovascularization or angiogenesis of that can enhance phagocytosis and killing of the cells and thereby enhance protection in vivo. Also provided are other antibodies and functional fragments thereof that immunoreact, specifically bind to, or preferentially bind to a binding site or epitope to which such antibodies can bind and which have the same effect.

The antibodies of the invention can also be opsonic, or exhibit opsonic activity, for cells having a role in neovascularization or angiogenesis (e.g., endothelial cells). As those in the art recognize, "opsonic activity" refers to the ability of an opsonin (generally either an antibody or the serum factor C3b) to bind to an antigen or cell receptor to promote attachment of the antigen or cell receptor to a phagocyte and thereby enhance phagocytosis. Certain cells become extremely attractive to phagocytes such as neutrophils and macrophages when coated with an opsonic antibody and their rate of clearance from the bloodstream is strikingly enhanced. Opsonic activity may be measured in any conventional manner as described, for example, in U.S. Pat. No. 6,610,293.

In another non-limiting embodiment, a patient having a neovascular disorder or an angiogenesis dependent disorder sheds antigens/peptides (e.g., endoglin) from the angiogenesis. These antigens/peptides can be "tumor associated antigens." Such patients can be systemically administered an antibody to the antigen/peptide (e.g., endoglin) and can initiate any of the pathways described herein to induce CDC, ADCC, opsonization, or any other form of cell-mediated killing.

V. Packages and Kits

In still further embodiments, the present application concerns kits for use with the compounds described above. Humanized antibodies or antigen-binding fragments that bind endoglin can be provided in a kit. The kits will thus comprise, in suitable container means, a composition comprising an antibody or antigen-binding fragment thereof that binds endoglin. The kit may comprise an antibody or antigen-binding fragment thereof that binds endoglin in suitable container means.

The container means of the kits will generally include at least one vial, test tube, flask, bottle, syringe and/or other container means, into which the at least one polypeptide can be placed, and/or preferably, suitably aliquoted. The kits can include a means for containing at least one fusion protein, detectable moiety, reporter molecule, and/or any other reagent containers in close confinement for commercial sale. Such containers may include injection and/or blow-molded plastic containers into which the desired vials are retained. Kits can also include printed material for use of the materials in the kit.

Packages and kits can additionally include a buffering agent, a preservative and/or a stabilizing agent in a pharmaceutical formulation. Each component of the kit can be enclosed within an individual container and all of the various containers can be within a single package. Invention kits can be designed for cold storage or room temperature storage.

Additionally, the preparations can contain stabilizers to increase the shelf-life of the kits and include, for example, bovine serum albumin (BSA). Where the compositions are lyophilized, the kit can contain further preparations of solutions to reconstitute the lyophilized preparations.

Acceptable reconstitution solutions are well known in the art and include, for example, pharmaceutically acceptable phosphate buffered saline (PBS).

Additionally, the packages or kits provided herein can further include any of the other moieties provided herein such as, for example, one or more reporter molecules and/or one or more detectable moieties/agents.

Packages and kits can further include one or more components for an assay, such as, for example, an ELISA assay. Samples to be tested in this application include, for example, blood, plasma, and tissue sections and secretions, urine, lymph, and products thereof. Packages and kits can further include one or more components for collection of a sample (e.g., a syringe, a cup, a swab, etc.).

Packages and kits can further include a label specifying, for example, a product description, mode of administration and/or indication of treatment. Packages provided herein can include any of the compositions as described herein. The package can further include a label for treating an ocular diseases characterized by angiogenesis/neovascularization (e.g., macular degeneration, CNV, diabetic retinopathy), diabetic nephropathy, a chronic inflammatory disease (e.g., IBD), rheumatoid arthritis, osteoarthritis, a forms of cancer and their metastases.

The term "packaging material" refers to a physical structure housing the components of the kit. The packaging material can maintain the components sterilely and can be made of material commonly used for such purposes (e.g., paper, corrugated fiber, glass, plastic, foil, ampules, etc.). The label or packaging insert can include appropriate written instructions. Kits, therefore, can additionally include labels or instructions for using the kit components in any method of the invention. A kit can include a compound in a pack, or dispenser together with instructions for administering the compound in a method described herein.

The invention further provides kits which utilize the diagnostic methods and assays described herein. In some embodiments, a kit according to the invention comprises reagents for the detection of a gene or genes whose expression levels have been correlated with sensitivity or resistance to an angiogenesis inhibitor in a sample of cancer cells from a patient. In some embodiments, the gene or genes are selected from VEGF, VEGF receptor, HIF-1α, placental growth factor receptor, and CD105. In some embodiments, the kit comprises VEGF. In some embodiments, the kit comprises VEGF receptor. In some embodiments, the kit comprises HIF-1α. In some embodiments, the kit comprises placental growth factor receptor. In some embodiments, the kit comprises CD105. In some embodiments, the kit comprises at least two of VEGF, VEGF receptor, HIF-1α, placental growth factor receptor and CD105. In some embodiments, the kit comprises at least two genes that have been correlated with sensitivity to an angiogenesis inhibitor. In some embodiments, the kit comprises at least two genes that have been correlated with resistance to an angiogenesis inhibitor. In some embodiments, the kit comprises at least one gene that has been correlated with sensitivity to an angiogenesis inhibitor and one gene that has been correlated with resistance to an angiogenesis inhibitor.

In still further embodiments, a kit according to the invention comprises reagents for the detection of VEGF, VEGF receptor, HIF-1α, placental growth factor receptor, and CD105 expression levels in a sample of tumor cells from a patient to be treated; and a dose or doses an inhibitor, including but not limited to humanized anti-endoglin antibodies or antigen-binding fragments described herein, in a variety of dosage forms, such as capsules, caplets, gel caps, powders for suspension, etc. It is further contemplated within the invention that kit comprising reagents for the detection of VEGF, VEGF receptor, HIF-1α, placental growth factor receptor, and CD105 expression levels in a sample of tumor cells from a patient to be treated will further comprise any of the aforementioned embodiments of the kits for co-administration of at least one additional angiogenesis inhibitor.

Instructions can include instructions for practicing any of the methods described herein including treatment methods. Instructions can additionally include indications of a satisfactory clinical endpoint or any adverse symptoms that may occur, or additional information required by regulatory agencies such as the Food and Drug Administration for use on a human subject.

The instructions may be on "printed matter," e.g., on paper or cardboard within or affixed to the kit, or on a label affixed to the kit or packaging material, or attached to a vial or tube containing a component of the kit. Instructions may additionally be included on a computer readable medium, such as a disk (floppy diskette or hard disk), optical CD such as CD- or DVD-ROM/RAM, magnetic tape, electrical storage media such as RAM and ROM, IC tip and hybrids of these such as magnetic/optical storage media.

The embodiments of the compounds and methods of the present application are intended to be illustrative and not limiting. Modifications and variations can be made by persons skilled in the art in light of the above teachings specifically those that may pertain to alterations in the antibodies or antigen-binding fragments which bind endoglin surrounding the described modifications while maintaining near native functionally with respect to binding of endoglin. Therefore, it should be understood that changes may be made in the particular embodiments disclosed which are within the scope of what is described.

EXAMPLES

The application may be better understood by reference to the following non-limiting examples, which are provided as exemplary embodiments of the application. The following examples are presented in order to more fully illustrate embodiments of the invention and should in no way be construed, however, as limiting the broad scope of the application. While certain embodiments of the present application have been shown and described herein, it will be obvious that such embodiments are provided by way of example only. Numerous variations, changes, and substitutions may occur to those skilled in the art without departing from the invention; it should be understood that various alternatives to the embodiments described herein may be employed in practicing the methods described herein.

Example 1

Generation and Binding of Anti-CD105 Humanized and Humanized/Deimmunized Antibodies Construction, Expression and Purification of Antibodies All humanized and humanized/deimmunized VH and VK region genes were synthesized using a series of overlapping oligonucleotides that were annealed, ligated and PCR amplified to give full length synthetic V regions. The assembled variants were then cloned directly into Antitope Ltd.'s pANT expression vector system for IgG1 heavy chains and kappa light chains.

All combinations of humanized heavy and light chains (i.e., a total of 4 pairings) and combinations of humanized/deimmunized heavy and light chains (i.e., a total of 24 pairings) were stably transfected into NS0 cells via electroporation and selected using 200 nM methotrexate (Sigma Cat. No. M8407). Methotrexate-resistant colonies for each construct were tested for IgG expression levels using an IgG1 ELISA. The best expressing lines were selected and frozen under liquid nitrogen. Successful transfection and clone selection was achieved for all variants and expression levels of humanized and humanized/deimmunized antibody variants in saturated static cultures are shown in Table 1.

Twenty-four IgG1 variants were therefore purified from NS0 cell culture supernatants on a Protein A sepharose column (GE Healthcare Cat. No. 110034-93) and quantified by $OD_{280\ nm}$ using an extinction coefficient, $Ec_{(0.1\%)}=1.62$, based on the predicted amino acid sequence. Approximately 500 µg of each antibody variant was purified and lead variants were analyzed by reducing SDS-PAGE. Briefly, Coomassie blue stained reducing SDS-PAGE gel of lead antibody variants. 1 µg of each sample was loaded on a NuPage 4-12% Bis-Tris gel (Invitrogen Cat. No. NP0322BOX) and run at 200 V for 30 minutes. Marker was Bio-Rad Precision Plus (Cat. No. 161-073). Bands corresponding to the predicted sizes of the heavy and light chains were observed with no evidence of any contamination in any lane (data not shown).

ELISA Methodology

An ELISA was used to assay binding of humanized and humanized/deimmunized anti-endoglin antibodies to endoglin. Briefly, an ELISA was performed according to the following steps:

1. Coat a Nunc Maxisorp plate with MAB9811-01 (polyclonal anti-endoglin antibody) at 1500 ng/ml in PBS, 100 µl/well. Cover the plate with a sealer and incubate overnight (16-24 hours) at 4° C.
2. Wash the plate 2× with −200 µl of PBS (without Tween).
3. Add 200 µl/well of BSA blocking solution (1% BSA) and incubate 60 minutes at room temperature.
4. Wash the plate 3× with PBS containing Tween (PBS-T) using the BioTek plate washer.
5. Add 100 µl/well of CD105 (R&D Systems Cat 1097-EN) at 100 ng/ml in PBS-T with 0.1% BSA and incubate 60 minutes at room temperature.
6. Wash the plate 3× with PBS-T using the BioTek plate washer.
7. In test wells: add 100 µl/well of anti-endoglin antibodies at 20, 10, 4, 2, 1, 0.5 and 0.2 ng/ml (diluted in PBS-T with 0.1% BSA) and incubate 60 minutes at room temperature. In negative control wells: add 100 µl/well of isotype matched control antibody.
8. Wash the plate 3× with PBS-T using the BioTek plate washer.
9. Add 100 µl/well of Goat anti-Human IgG conjugated to HRP (Jackson Immunoresearch), diluted 1:10000 in PBS-T with 0.1% BSA to all wells; incubate 30-60 minutes at room temperature.
10. Wash the plate 5× with PBS-T using the BioTek plate washer.
11. Add 100 µl/well of TMB substrate solution and incubate uncovered in the dark for 15 minutes.
12. Stop the reaction by addition of 100 µl/well of TMB Stop Solution.

Samples are run in triplicate and the optical density is read to construct a standard curve and determine the binding constant. Statistical analysis is conducted using the Student's t-test or another standard test.

Competition ELISA

Figure 7:
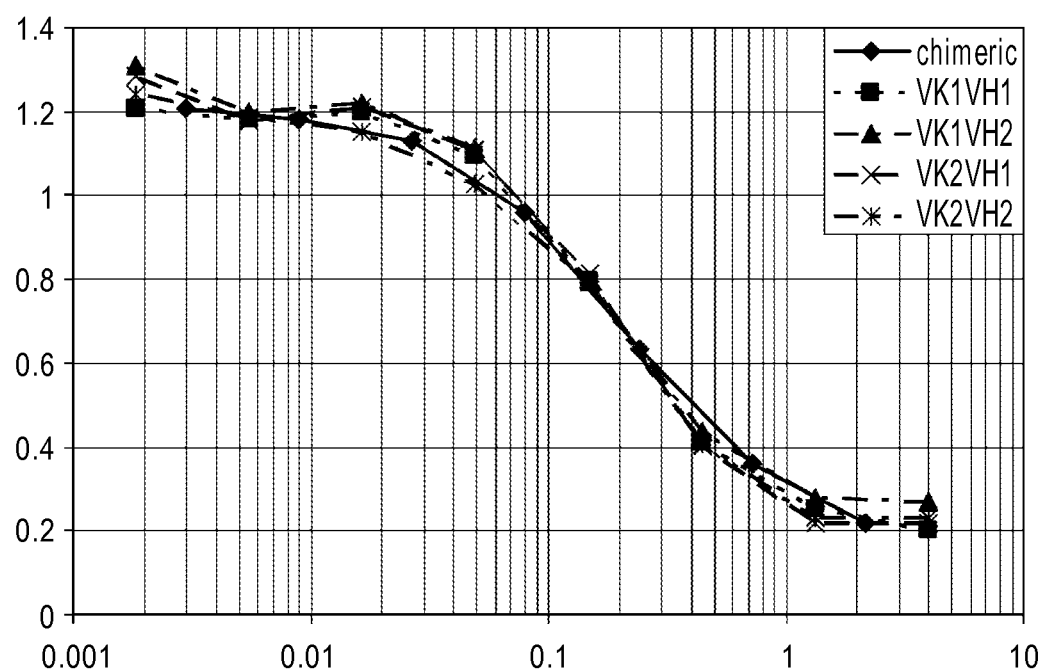
FIG. 7 illustrates binding of humanized variant constructs to endoglin in a competition ELISA assay.
Figure 8A:
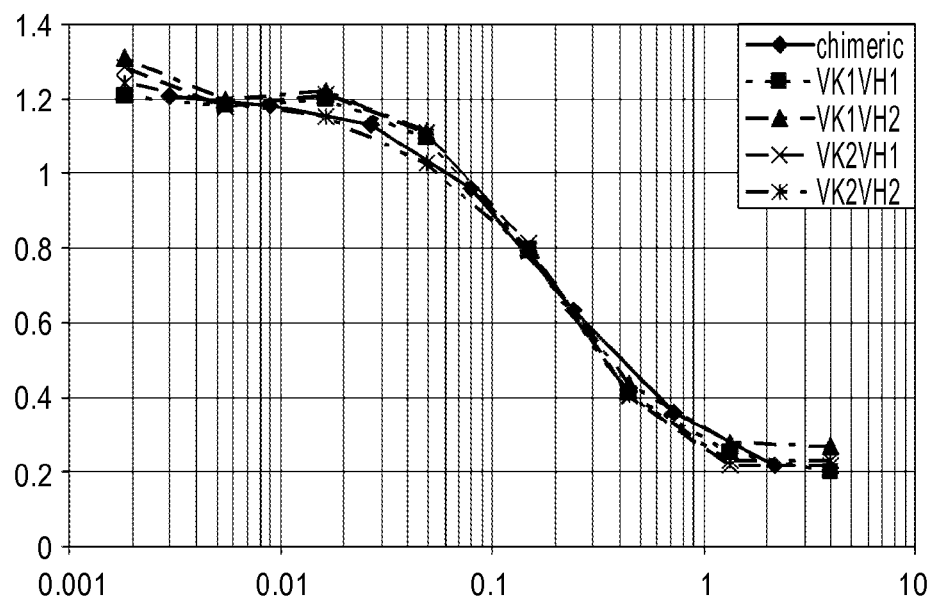
Figure 8B:
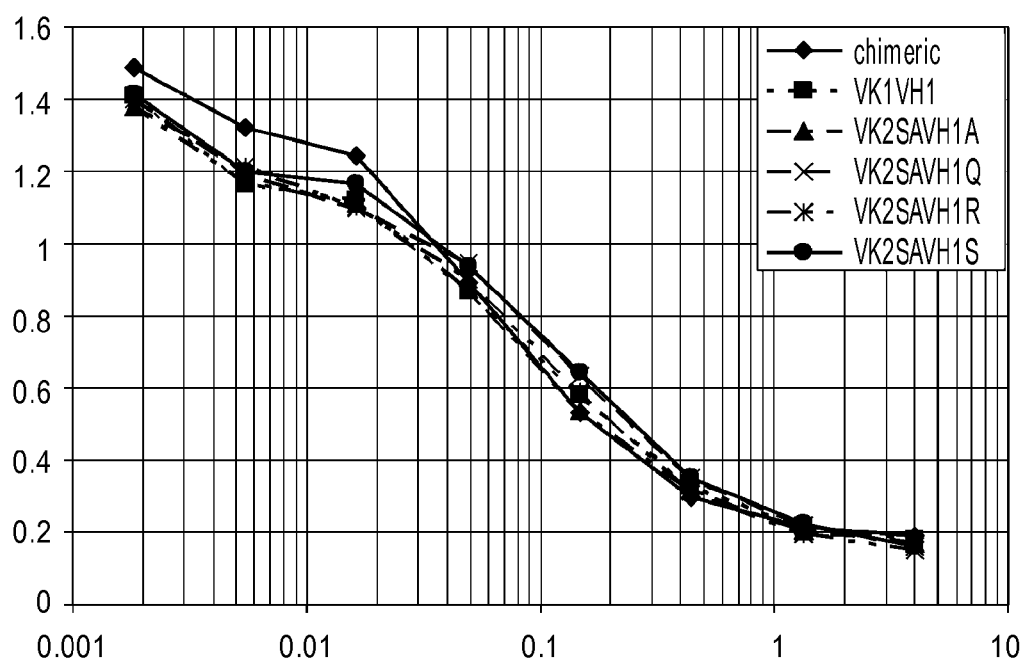
Figure 8E:
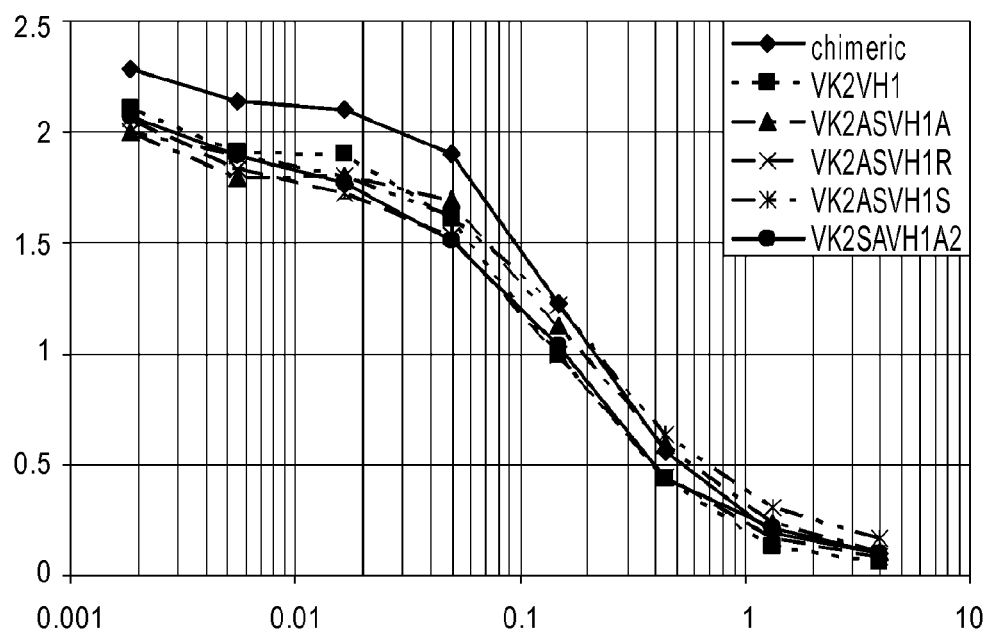
Figure 8F:
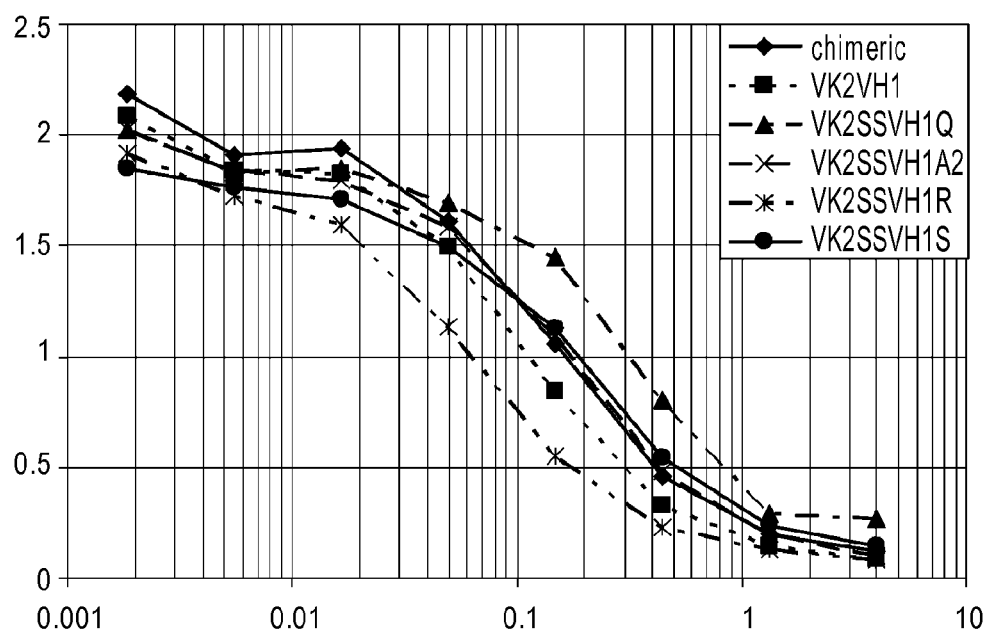
Figure 11:
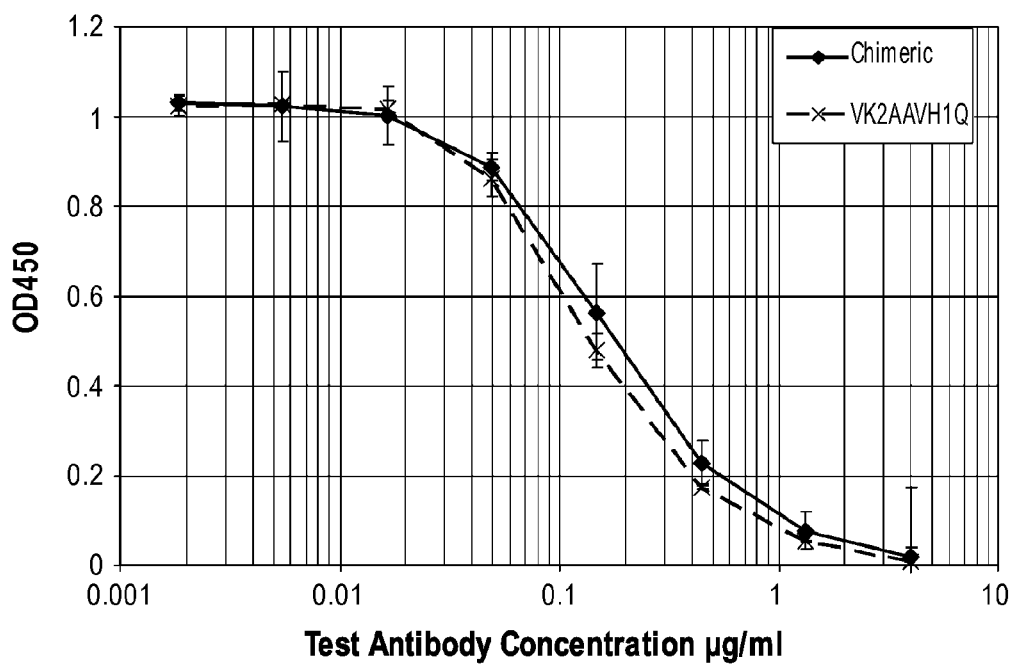
FIG. 11 illustrates binding assay data for chimeric compared to VK2AAVH1Q.
Figure 12:
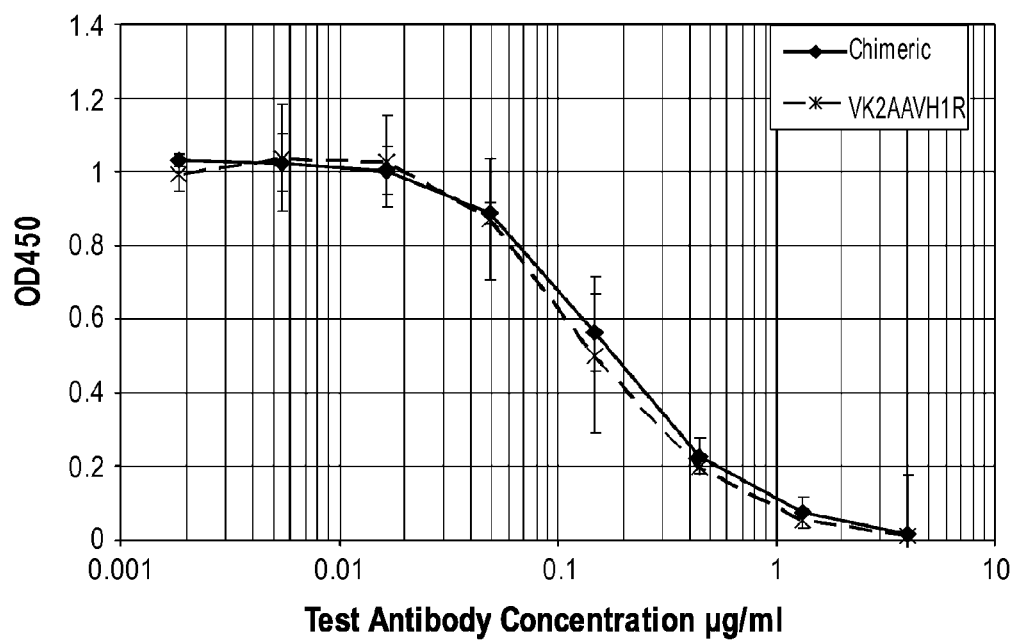
FIG. 12 illustrates binding assay data for chimeric compared to VK2AAVH1R.
Figure 13:
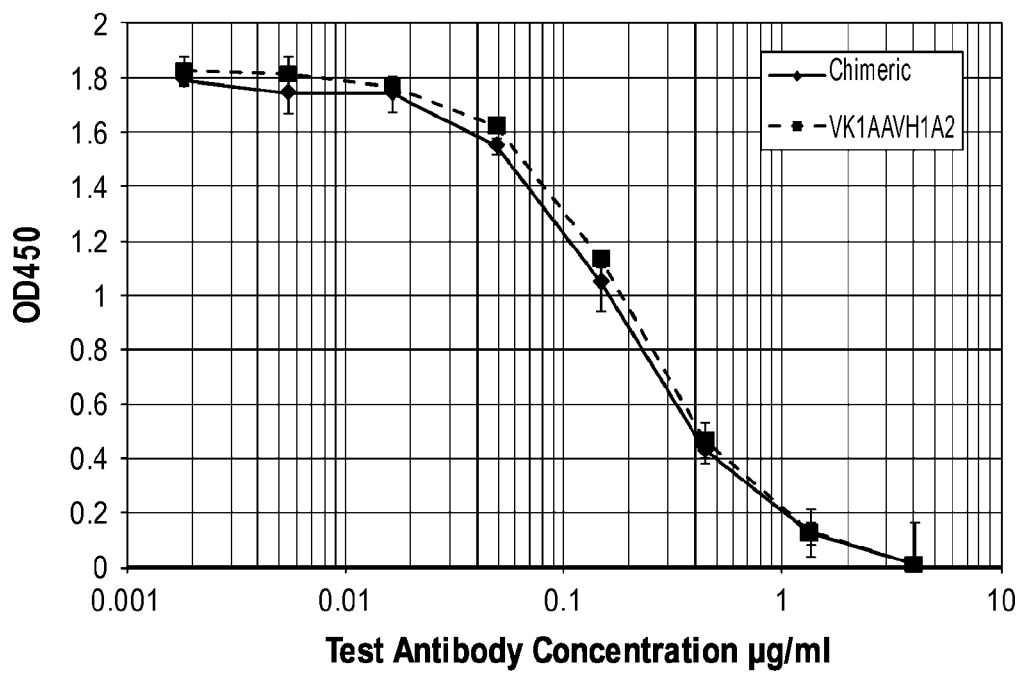
FIG. 13 illustrates binding assay data for chimeric compared to VK1AAVH1A2.
Figure 14:
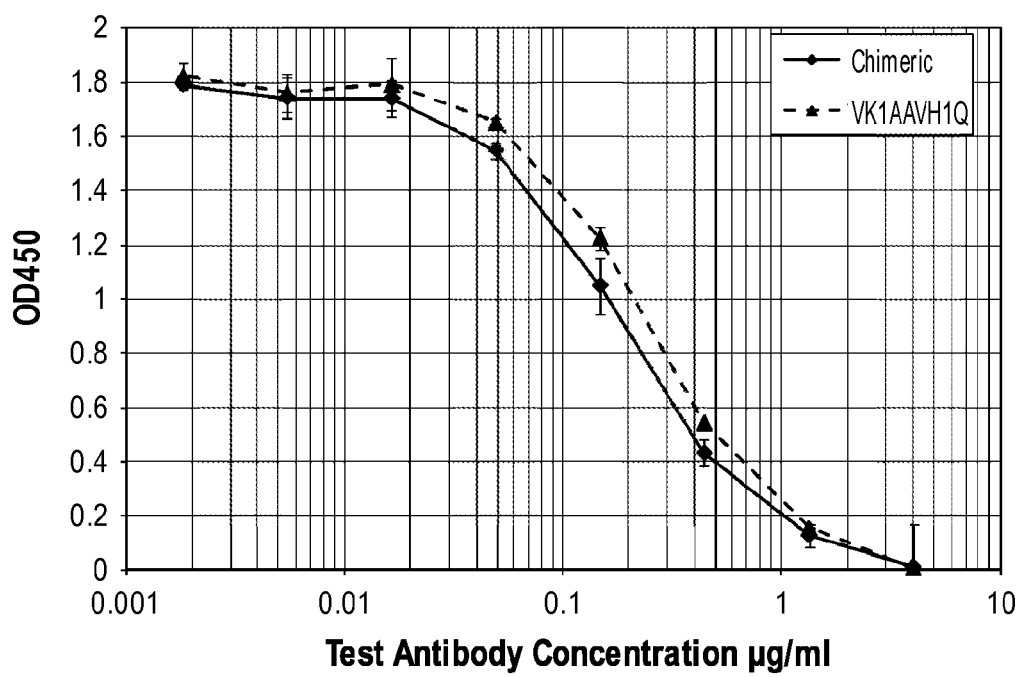
FIG. 14 illustrates binding assay data for chimeric compared to VK1AAVH1Q.
Figure 15:
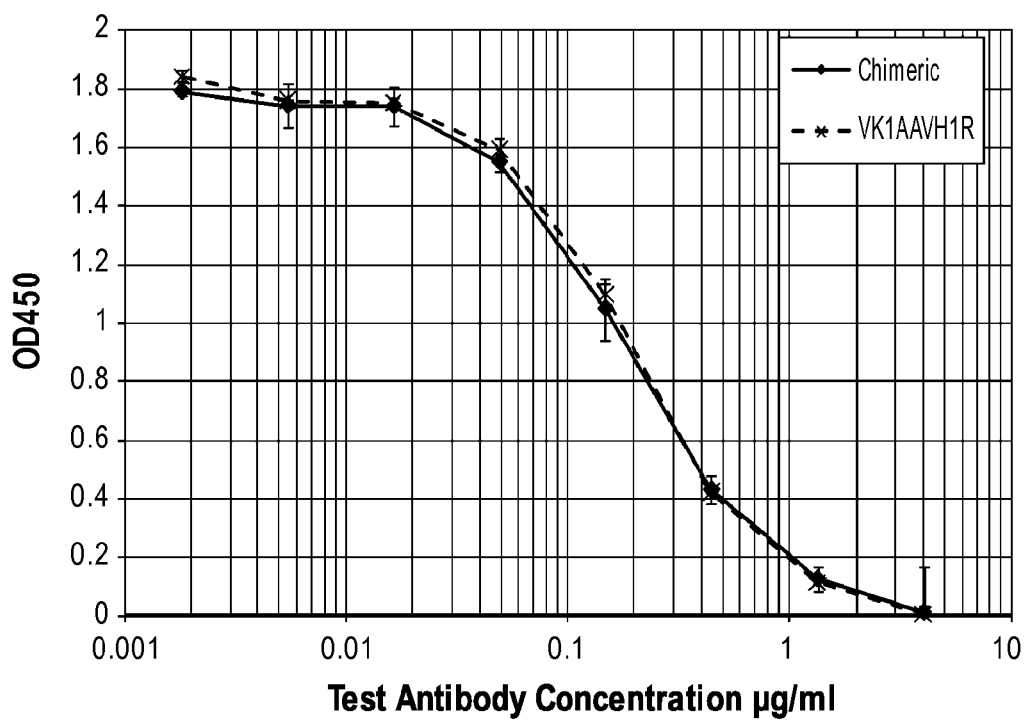
FIG. 15 illustrates binding assay data for chimeric compared to VK1AAVH1R.
Figure 16:
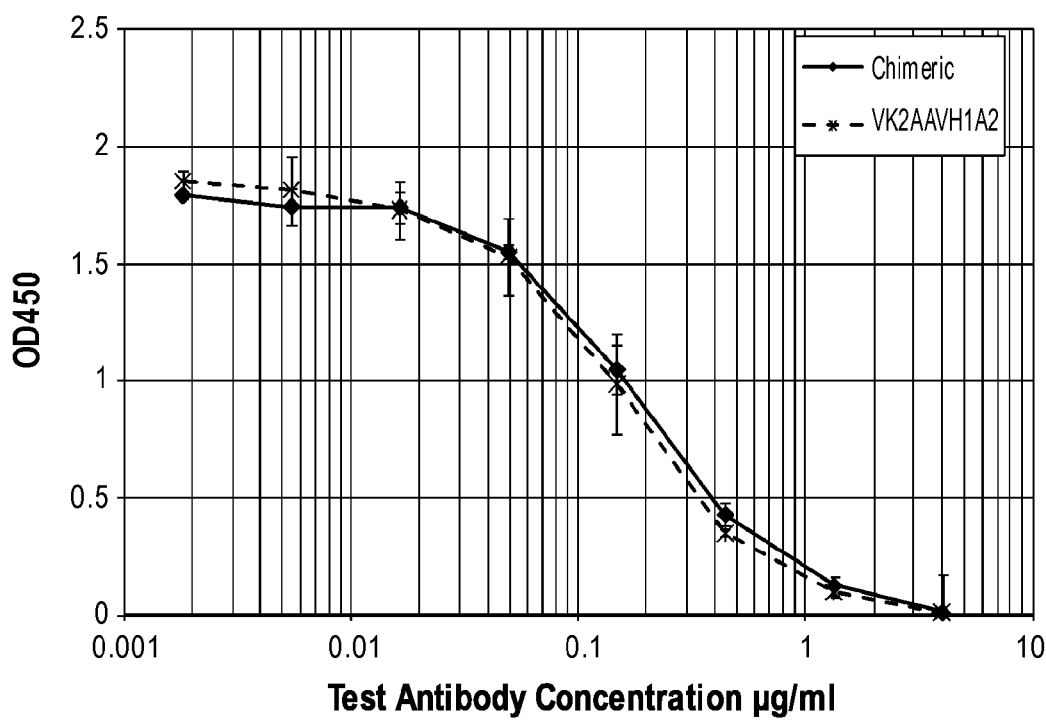
FIG. 16 illustrates binding assay data for chimeric compared to VK2AAVH1A2.
Figure 23:
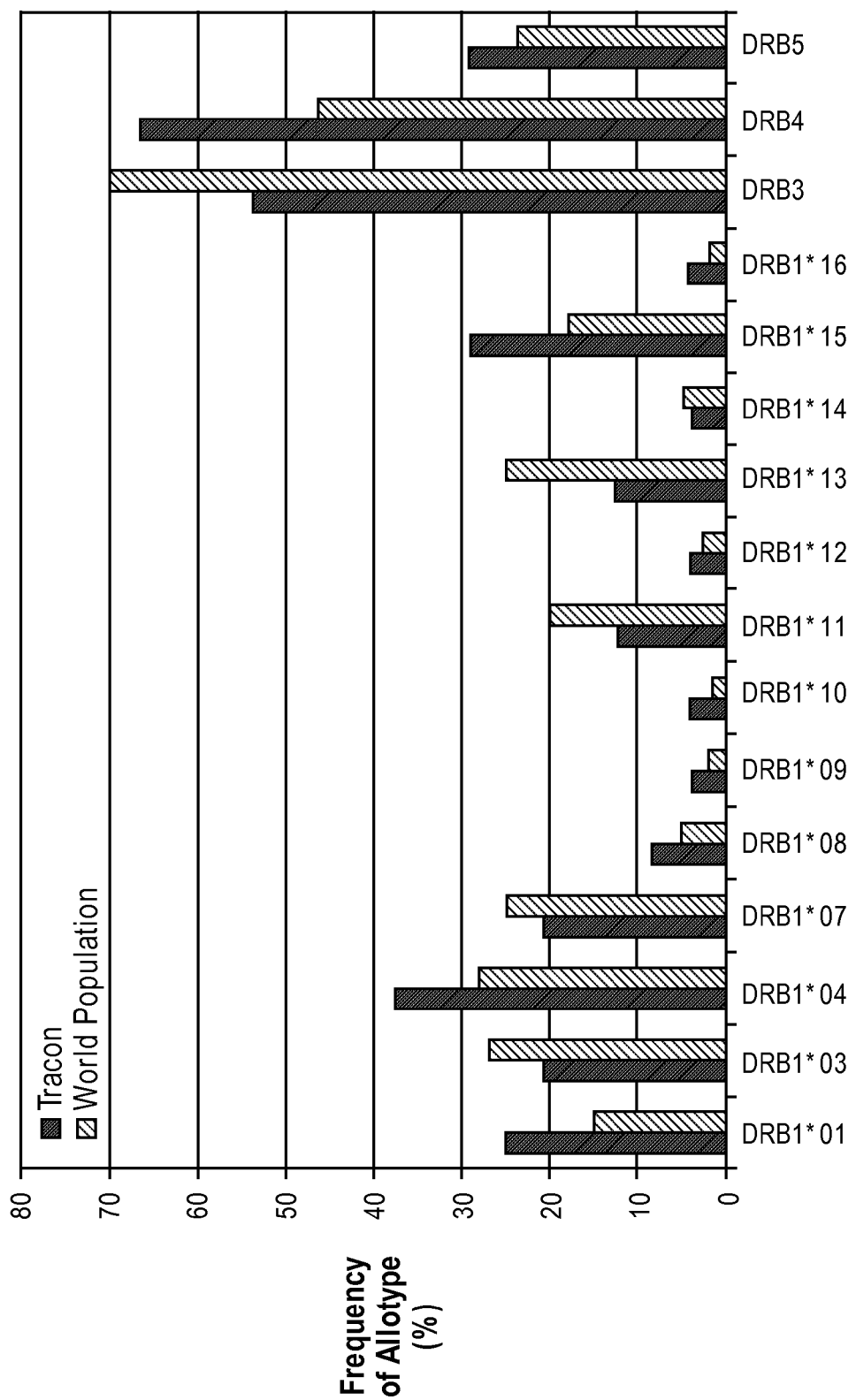
FIG. 23 illustrates the frequency of MHC Class II allotypes in the world population and the study population.

Antibodies were tested in a competition ELISA for binding to CD105 against biotinylated chimeric anti-CD105. Briefly, chimeric anti-CD105 was biotinylated using a micro-biotinylation kit (Sigma, Catalog No. BTAG-1KT) following the manufacturer's instructions. Nunc Immuno MaxiSorp 96-well flat-bottom microtiter plates were coated with mouse anti-human CD105 (Southern Biotechnologies, Catalog No. 9811-01) at 1.5 µg/mL in phosphate buffered saline (PBS) overnight at 4° C. The following day, 100 ng/ml human CD105 (R&D Systems, Catalog No. 1097-EN) in PBS/2% BSA was added to the pre-coated plate and incubated at room temperature for 1 hour. Varying concentrations of either chimeric, humanized or humanized/deimmunized anti-CD105 antibodies (4 µg/mL to 0.0018 µg/mL in three-fold dilutions) were mixed with a fixed concentration of biotinylated chimeric anti-CD105 antibody (6.25 ng/ml) and added to the plate. Binding of the biotinylated chimeric antibody was detected via streptavidin-HRP (Sigma, Catalog No. S5512) and TMB substrate (Sigma, Catalog No. T0440). OD450 nm values were measured on a Dynex MRX TCII plate reader. The results of the competition analysis are illustrated in FIGS. 7 and 8. Curves were fitted through the straight line portion of each of the plots of absorbance against the log sample concentration and the equations of the lines were used to calculate the concentrations of humanized or humanized/deimmunized antibody required to inhibit biotinylated chimeric antibody binding to CD105 by 50% (IC50). To allow for comparisons within and between experiments, IC50 values of humanized or humanized/deimmunized variants were normalized against the reference antibody that was included on each plate to give a value for the fold difference. IC50 values are relative to chimeric anti-CD105 and are representative of three experiments. Summary ELISA data are presented in Table 1 and include antibody expression levels (µg/ml) as assayed in saturated static cultures.

TABLE 1

Characteristics of humanized and humanized/deimmunized antibody variants. IC50 values are relative to chimeric anti-endoglin antibody and are representative of three experiments. Antibody expression levels (µg/ml) were assayed in saturated static cultures. The level of deimmunization is represented by an arbitrary scale based upon the location in the epitopes of the mutations.

| Construct | Relative IC50 | Expression Levels (µg/ml) | Level of Deimmunization |
|---|---|---|---|
| VK1VH1 | 1.51 | 10.2 | n/a |
| VK1VH2 | 1.15 | 12.9 | n/a |
| VK2VH1 | 0.93 | 11.1 | n/a |
| VK2VH2 | 1.19 | 15.8 | n/a |
| VK2AAVH1A | 0.79 | 10.8 | ++++ |
| VK2AAVH1A2 | 0.99 | 6.6 | ++++++ |
| VK2AAVH1Q | 0.76 | 7.5 | +++++ |
| VK2AAVH1R | 0.61 | 10.0 | +++++ |
| VK2AAVH1S | 1.27 | 9.7 | ++++ |
| VK2ASVH1A | 1.41 | 6.6 | +++ |
| VK2ASVH1A2 | 0.85 | 5.9 | +++++ |
| VK2ASVH1Q | 1.04 | 8.7 | ++++ |
| VK2ASVH1R | 1.02 | 7.9 | ++++ |
| VK2ASVH1S | 1.31 | 8.8 | +++ |
| VK2SAVH1A | 0.49 | 7.5 | +++ |
| VK2SAVH1A2 | 0.84 | 10.3 | +++++ |
| VK2SAVH1Q | 0.87 | 11.5 | ++++ |
| VK2SAVH1R | 0.77 | 8.8 | ++++ |
| VK2SAVH1S | 0.96 | 34.6 | +++ |
| VK2SSVH1A | 1.06 | 9.7 | ++ |

TABLE 1-continued

Characteristics of humanized and humanized/deimmunized antibody variants. IC50 values are relative to chimeric anti-endoglin antibody and are representative of three experiments. Antibody expression levels (μg/ml) were assayed in saturated static cultures. The level of deimmunization is represented by an arbitrary scale based upon the location in the epitopes of the mutations.

| Construct | Relative IC50 | Expression Levels (μg/ml) | Level of Deimmunization |
|---|---|---|---|
| VK2SSVH1A2 | 1.03 | 17.4 | ++++ |
| VK2SSVH1Q | 1.21 | 14.7 | +++ |
| VK2SSVH1R | 0.62 | 13.7 | +++ |
| VK2SSVH1S | 1.21 | 16.2 | +++ |
| VK1AAVH1A | 2.52 | 6.9 | ++++ |
| VK1AAVH1A2 | 1.12 | 13.5 | ++++++ |
| VK1AAVH1Q | 1.30 | 7.6 | +++++ |
| VK1AAVH1R | 1.05 | 11.5 | +++++ |

Example 2

BIAcore (Surface Plasmon Resonance: SPR) Analysis of Humanized and Humanized/Deimmunized Anti-Endoglin Antibody Binding Affinity of antibodies can be assessed using, for example, BIAcore analysis using standard protocols. Briefly, protein A is chemically coupled to a BIAcore CM5 chip, with the amount of protein A immobilized corresponding to ~2000 RU. Subsequent steps are performed in a running buffer of 10 mM HEPES, 150 mM NaCl, 3 mM EDTA, 0.05% TWEEN, pH=7.4, at 25 degrees Celsius using a 10 Hz data collection rate. Anti-endoglin antibody (10 nM) is captured at a 10 uL/min flow rate by the immobilized protein A on the BIAcore chip: typically, capture times of 20, 40 and 80 seconds allow the capture of antibody densities corresponding to 130 RU, 330 RU and 570 RU, respectively. Start-up cycles are performed using running buffer at a flow rate of 40 uL/min, a contact time of 90 seconds and a dissociation time of 90 seconds. Sample cycles are performed using recombinant endoglin at concentrations ranging from 0 to 40 nM. Endoglin is passed over the BIAcore chip containing captured antibody at a flow rate of 40 uL/min with a contact time of 525 seconds and dissociation time of 2500 seconds. Eight sample cycles are typically performed at each antibody capture density Regeneration of the chip is accomplished using 10 mM glycine pH=1.7. Data analysis is performed using BIAcore T100 Evaluation Software v1.1 Signals generated using BIAcore chips with different captured antibody densities are compared and data generated in the absence of recombinant endoglin are used to adjust for the intraassay blank signal. For fitting of the data, the $R_{max}$ is allowed to float to account for variation in capture levels of each antibody in each cycle. Data from each capture density is fitted simultaneously during analysis of each antibody. BIAcore data are presented in Table 2 for chimeric, humanized and humanized/deimmunized anti-endoglin antibodies, including $k_a$ (1/Ms), $k_d$ (1/s), $K_D$ (M) and Chi$^2$ (RU$^2$).

TABLE 2

BIAcore binding data for chimeric anti-endoglin antibody, humanized anti-endoglin antibody VK1VH1 and humanized/deimmunized anti-endoglin antibodies VK1AAVH1R, VK1AAVH1Q and VK1AAVKVH1A2.

| Anti-endoglin Antibody | $k_a$ (×10$^4$) | $k_d$ (×10$^{-5}$) | $K_D$ (×10$^{-10}$) | Chi$^2$ (×10$^{-2}$) |
|---|---|---|---|---|
| VK1AAVH1R | 6.40 | 3.41 | 5.33 | 6.84 |
| VK1VH1 | 4.19 | 3.46 | 8.25 | 5.53 |
| Chimeric | 5.47 | 3.28 | 6.00 | 6.78 |
| VK1AAVH1Q | 3.56 | 3.03 | 8.50 | 7.07 |
| VK1AAVH1A2 | 4.60 | 3.25 | 7.06 | 5.52 |

Example 3

Antibody Avidity and Number of Available Epitopes on Endoglin-Expressing Cells

Antibody avidity and number of available epitopes on endoglin-expressing cells can be assessed utilizing Scatchard plot analyses using standard protocols.

Briefly, Scatchard plot analyses of direct binding of radiolabeled humanized anti-endoglin antibodies to endoglin-expressing KM-3 leukemia cells and sub-confluent proliferating HUVECs are carried out. The purified anti-endoglin antibodies are individually radiolabeled with $^{125}$I using Iodo-Gen and according to standard methods known to those skilled in the art. The radiolabeled humanized anti-endoglin antibodies are assayed for the mean number of iodine atoms per IgG molecule. Titration experiments are carried out using a fixed amount (0.1 μg) of each $^{125}$I-labeled mAb and 2-fold serial increments of endoglin-expressing HUVEC cells to determine antigen-binding activity. Analysis of Scatchard plot of binding data is carried out according to known methods. An equilibrium constant and an average maximal number of mAb bound/cell are estimated by this analysis.

Example 4

Western Blot Assay for Anti-Endoglin Antibody Activity

The ability of humanized anti-endoglin antibodies to modify intracellular signaling in proliferating endothelial cells that express CD105 can be assayed via western blots to detect the phosphorylation of the proteins involved in the CD105 signaling pathway.

Western blot analyses are performed to identify phosphorylated Smad1/5/8 or Smad2/3 according to known western blotting techniques in untransfected endothelial cells. Primary antibodies against phosphorylated Smad1, Smad2, Smad5, Id1 (Santa Cruz) and endoglin are utilized to detect molecules in samples. Detection is performed by enhanced chemoluminescence (ECL).

Example 5

Inhibition of HUVEC Growth and $^3$H-Thymidine Incorporation Assay

A number of assays are available to assess inhibition of cell growth.

In one example, the HUVEC cell line E6/E7 P3-17 was cultured in EBM2 media with supplements (Lonza-Clonetics) containing 5% fetal calf serum. Cells were cultured in 75-cm$^2$ flasks (Falcon, Becton-Dickinson, Franklin Lakes, N.J.) in a CO$_2$ incubator at 37° C. under subconfluent conditions. Cells are detached by incubating with Hanks' balanced salt solution with 15 mM EDTA in 25 mM HEPES buffer, pH=7.3, at 37° C. for 15 min. After washing twice with ice-cold PBS, cells are re-suspended in endothelial cell growth medium at a concentration of 25,000 cells/mL. In additional experiments, human umbilical vein endothelial cells (HUVECs) are suspended and cultured in an endothelial cell growth medium free of FBS and bovine brain extracts. A 200 µl aliquot of cell suspension containing 2,500 cells is seeded to each well of 96-well culture plates. Cells are cultured at 37° C. in a CO$_2$ incubator overnight before 100 ug/mL of humanized anti-endoglin antibody VK1AAVH1A2 or, control IgG or PBS are added in triplicate. Culture plates are kept in the incubator for 72 hr, during which fresh media and humanized anti-endoglin antibody, control IgG or PBS are replaced every 24 hr. $^3$H-thymidine (1 µCi) is added into each well and the plates are incubated for 20 hr. Cells are washed with PBS followed by treatment with 100 µl/well trypsin-EDTA (0.05% trypsin, 0.53 mM EDTA) at 37° C. for 15 min. Cells are harvested onto glass fiber filters (Wallac Printed FiltermatA) using Harvester 96 (TOMTEC, Hamden, Conn.) and $^3$H-radioactivity is determined in a Trilux 1540 MicroBeta Liquid Scintillation and Luminescence Counter (Wallac, Turku, Finland). In a second example, the cells used were a primary culture of HUVEC cells, HUVEC 2517C, Humanized TRC105 antibody inhibited the growth of the HUVEC cell line E6/E7 and the primary HUVEC culture, HUVEC 2517C derived from a single donor, compared to antibody control and PBS (Table 3).

TABLE 3

Inhibition of human endothelial cell growth by humanized/ deimmunized anti-endoglin antibody VK1AAVH1A2. E6/E7 cells

| Condition | Mean counts per minute | Standard deviation | % Inhibition versus PBS |
| --- | --- | --- | --- |
| PBS | 18320 | 173 | — |
| Control IgG | 18061 | 172 | 0.9 |
| Chimeric | 14452 | 1348 | 20.7 |
| Humanized/deimmiunized anti-endoglin antibody VK1AAVH1A2 | 14025 | 983 | 23.1 |

Example 6

Assay for Inhibition of Cell Migration by Anti-Endoglin Antibodies

Migration (chemokinesis) as a measure of cell proliferation and activation is measured using a Boyden chamber.

Briefly, cell migration is assessed as follows: a Costar nucleopore filter (8 mm pore) is coated with fibronectin overnight at 4° C. The chamber is washed with phosphate-buffered saline (PBS) and the lower chamber was filled with DMEM with or without serum and with or without TGF-β3. Cells are trypsinized and suspended at a final concentration of 50,000 cells/ml in DMEM with anti-endoglin antibody. A 150 µl aliquot of the cell suspension is added to the upper chamber and incubated at 37° C. After 16 hrs, the cells are washed and the upper surface is wiped to remove the non-migrating cells. The membranes are fixed in methanol, washed with water, stained and the numbers of cells present on the lower surface are counted.

Example 7

ADCC Assay for Humanized/Deimmunized Anti-Endoglin Antibodies

The anti-endoglin antibodies described herein can be assessed with respect to their ability to bind to IL-2 activated natural killer (NK) cells and to induce antibody dependent cell-mediated cytotoxicity (ADCC) of HUVECs using, for example, the following protocols.

NK Isolation and Generation of IL-2 Activated NK Cells

PBMC are isolated and allowed to rest for 24 hrs at 4° C. in RPMI with 10% FBS. PBMC are then placed in RPMI with 2% FBS (Total Volume=50 mL), and 10 mL of the cell suspension are plated in a petri dish. PBMC are incubated for 2 hrs at 37° C. and the non-adherent cells are collected. NK cells are cultured at 8×10$^6$/mL with 1000 U/mL IL-2 for 48 hrs, followed by normal culturing for 5-8 days before use in an ADCC assay.

Cytotoxicity and ADCC Assays

NK cells are scraped from the culture and collected in a 50 mL conical tube. Cells are washed once with RPMI Complete media and spun at 1200 rpm for 10 minutes. NK cells are then resuspended in 5 mL RPMI Complete media and counted. Prior to performing the assay, the NK cell count is normalized to an effector: target ratio of 10:1. Normalized NK cells are plated and 10 µL of anti-endoglin antibody is added into designated wells and incubated for 30 minutes at 37° C. Control samples include untreated or control-antibody treated cell populations. All samples and controls are tested in quintuplicate.

Target cells of interest are collected (HUVEC cells), washed, spun at 1200 rpm for 10 minutes, and re-suspended in 5 mL RPMI Complete media. Target cells are washed again and re-suspended in Serum Free RPMI to a final concentration of 1×10$^6$ cells/mL. Target cells are then labeled with a final concentration of 5 ug/mL Calcein AM for 1 hr at 37° C., followed by two washes with RPMI Complete media. Target cells are then re-suspended and added to the NK cell wells. The target cell/NK cell combination is incubated at 37° C. for 4 hours. After incubation, the plates are spun at 1200 rpm for 5 minutes and cells are washed and resuspended in DPBS. The fluorescence is read using Excitation/Emission of 450/530 nm and the emission is a measure of the cell killing mediated by the antibodies. The mean fluorescence intensity and standard deviation are calculated and used to calculate % ADCC according the following formula:

$$\% \text{ ADCC} = 100\% * [(f_{sample} - f_{media}) - (f_{isotype\ control} - f_{Triton})],$$

where:

$f_{sample}$=mean fluorescence in wells containing anti-endoglin antibody $f_{media}$=mean fluorescence in wells containing media without antibody $f_{isotype\ control}$=mean fluorescence in wells containing isotype control IgG $f_{Triton}$=mean fluorescence in wells containing Triton detergent (to lyse target cells)

Humanized/deimmunized antibody VK1AAVH1A2 demonstrated dose dependent ADCC of HUVECs that was significantly greater than isotype control antibody (Table 4).

TABLE 4

ADCC of humanized/deimmunized anti-endoglin antibody VK1AAVH1A2 versus isotype matched control IgG on HUVEC cells.

| Test Condition | ADCC of HUVECs (%) | Standard Deviation |
|---|---|---|
| Isotype Control (2 ug/mL) | 3.4 | 4.7 |
| VK1AAVH1A2 (0.4 ug/mL) | 14.6 | 2.1 |
| VK1AAVH1A2 (0.08 ug/mL) | 14.6 | 2.1 |
| VK1AAVH1A2 (0.016 ug/mL) | 12.6 | 4.1 |
| VK1AAVH1A2 (0.0032 ug/mL) | 8.4 | 4.1 |
| VK1AAVH1A2 (0.00064 ug/mL) | 7.6 | 2.0 |

Example 8

Effect of Humanized/Deimmunized Anti-Endoglin Antibodies on a Murine Model of Choroidal Neovascularization The effect of humanized/deimmunized anti-endoglin antibodies can be assessed in a murine model of choroidal neovascularization.

Briefly, 4 to 5 week old C57BL/6 mice are anesthetized with ketamine hydrochloride (100 mg/kg) and the pupils dilated with 1% tropicamide (Alcon Laboratories, Inc Fort Worth, Tex.). Three burns of a 532-nm diode laser photocoagulation (75-pm spot size, 01-second duration, 120 mW) are delivered to each retina using the slit lamp delivery system of a photocoagulator (OcuLight; Iridex, Mountain View, Calif.) and a handheld cover slip as a contact lens. Burns are performed in the 9, 12 and 3 o'clock positions of the posterior pole of the retina. Production of a bubble at the time of lasering, which indicates rupture of Bruch's membrane, is an important factor in obtaining choroidal neovascularization (CNV); thus only burns in which a bubble is produced are included in the study.

Four independent experiments are performed to investigate the effect of intraocular injections on day 0 after rupture of Bruch's membrane. Mice in Group 1 are given an intraocular injection of about 0.5 to about 5 µg of a anti-endoglin antibody or antigen-binding fragment in 1 µL of PBS in one eye and 1 µL of PBS in the fellow eye. Group 2 mice are given an intraocular injection of about 1.5 to about 10 µg of anti-endoglin antibody or antigen-binding fragment in 1 µL of PBS in one eye and 1 µL of PBS in the fellow eye. Group 3 mice are given an intraocular injection of about 5 to about 25 µg of anti-endoglin antibody or antigen-binding fragment in one eye and 1 µL of PBS in the fellow eye. Group 4 receive PBS in both eyes.

After 14 days, mice are anesthetized and perfused with fluorescein-labeled dextran ($2\times10^6$ average molecular weight, Sigma-Aldrich) and choroidal flat mounts are prepared. Briefly, the eyes are removed, fixed for 1 hour in 10% phosphate-buffered formalin, and the cornea and lens are removed. The entire retina is carefully dissected from the eyecup, radial cuts are made from the edge of the eyecup to the equator in all four quadrants, and the retina is flat-mounted in aqueous mounting medium (Aquamount; BDH, Poole, UK). Flat mounts are examined by fluorescence microscopy (Axioskop; Carl Zeiss Meditec, Thornwood, N.Y.), and the images are digitized with a three charge-coupled device (CCD) color video camera (1K-TU40A, Toshiba, Tokyo, Japan). Frame grabber image-analysis software is used to measure the area of each CNV lesion. Statistical comparisons are made using ANOVA with Dunnett's correction for multiple comparisons.

Example 9

Anti-Angiogenic Therapy of Preformed Human Breast Cancer Tumors in Human Skin Grafted into SCID Mice The effect of the humanized/deimmunized anti-endoglin antibodies described herein can be assessed with respect to their anti-angiogenic effect on preformed human breast cancer tumors grown in human skin grafted into SCID mice.

Briefly, MCF-7 cells ($8\times10^6$ cells in 0.1 ml PBS) are transplanted intradermally into human full-thickness skin grafted into SCID mice when the grafts showed no signs of inflammation, contraction or rejection. The mice are left untreated until distinct palpable tumors (3 to 6 mm in diameter in most cases) appear. Mice with distinct tumors are divided into groups for the therapeutic studies. Humanized/deimmunized anti-endoglin monoclonal antibody (mAb) and an isotype-matched control IgG are diluted with sterile PBS containing mouse serum albumin (0.05% final concentration). For the antibody therapy, 1 to 20 mg/kg anti-endoglin antibody or control IgG is intravenously (i.v.) administered via the tail vein of mice. The administration is given every two to three days.

During the treatment, mice are monitored daily for tumor size and morbidity. Mice are weighed twice a week using an electronic balance (OHAUS™ Model GT210). Tumor size is measured three times a week using an electronic caliper (PRO-MAX 6 inch caliper; Fowler Co., Newton, Mass.) connected to a computer using OptoDemo™ software (Fowler Co.). The measured tumor diameters are converted to tumor volumes using the following formula: V=length×width×height×pi/6. Statistical analysis of the data for the comparison of different groups of mice is carried out using Student's t-test.

Example 10

Mouse Model of Ovarian Cancer

To determine the ability of humanized/deimmunized anti-endoglin antibodies, or antigen-binding fragments thereof, to treat ovarian cancer, an ovarian cancer cell line can be used in SCID or nude mice.

Briefly, ovarian cancer cells are implanted into SCID or nude mice to generate ovarian tumors. Groups of mice bearing established tumors are treated by i.v. administration of escalating doses (starting at 1.8 mg/kg body weight) of humanized/deimmunized anti-endoglin antibody or control IgG. The treatment is performed 2 or 3 times per week. A VEGF inhibitor and/or other anticancer agent may be used in some or all groups. The mice are monitored and tumor growth is measured 2 or 3 times per week.

Example 11

Mouse Model of Colorectal Cancer

To determine the ability of humanized/deimmunized anti-endoglin antibodies, or antigen-binding fragments thereof, to treat colorectal cancer, a colorectal cancer cell line can be used in SCID, nude or immunocompetent mice.

Briefly, colorectal cancer cells are implanted into SCID, nude or immunocompetent mice to generate colorectal tumors. Groups of mice bearing established tumors are treated by i.v. administration of escalating doses (starting at 1.8 mg/kg body weight) of humanized/deimmunized anti-endoglin antibody or control IgG. The treatment is performed 2 or 3 times per week. A VEGF inhibitor and/or other anticancer agent may be used in some or all groups. The mice are monitored and tumor growth is measured 2 or 3 times per week. Tumors may be imaged by standard imaging test, including PET and ultrasound. Treated tumors may be explanted to assess intracellular signaling pathways or vascularity by immunohistochemistry.

Example 12

Mouse Model of Kidney Cancer

To determine the ability of humanized/deimmunized anti-endoglin antibodies or antigen-binding fragments thereof to treat kidney cancer, a kidney cancer cell line is used in SCID or nude mice.

Briefly, kidney cancer cells are implanted into SCID or nude mice to generate kidney tumors. Groups of mice bearing established tumors are treated by i.v. administration of escalating doses (starting at 1.8 µg/g body weight) of humanized/deimmunized anti-endoglin antibody or control IgG. The treatment is performed at 3-day intervals for the first three injections and at a 7-day interval for the fourth injection. A VEGF inhibitor and/or other anticancer agent may be used in some or all groups. The mice are monitored and tumor growth is measured via sacrifice of animals on a weekly basis.

Example 13

Mouse Model of Myeloma

To determine the ability of humanized/deimmunized anti-endoglin antibodies or antigen-binding fragments thereof to treat myeloma, a myeloma cell line is used in SCID or nude mice.

Briefly, myeloma cancer cells are implanted into SCID or nude mice to generate myeloma tumors. Groups of mice bearing established tumors are treated by i.v. administration of escalating doses (starting at 1.8 mg/kg body weight) of humanized/deimmunized anti-endoglin antibody or control IgG. The treatment is performed 2 or 3 times per week. A VEGF inhibitor and/or other anticancer agent may be used in some or all groups. The mice are monitored and tumor growth is measured 2 or 3 times per week.

Example 14

Mouse Model of Sarcoma

To determine the ability of humanized/deimmunized anti-endoglin antibodies or antigen-binding fragments thereof to treat sarcoma, a sarcoma cell line is used in SCID or nude mice.

Briefly, sarcoma cancer cells are implanted into SCID or nude mice to generate sarcoma tumors. Groups of mice bearing established tumors are treated by i.v. administration of escalating doses (starting at 1.8 mg/kg body weight) of humanized/deimmunized anti-endoglin antibody or control IgG. The treatment is performed 2 or 3 times per week. A VEGF inhibitor and/or other anticancer agent may be used in some or all groups. The mice are monitored and tumor growth is measured 2 or 3 times per week.

Example 15

Mouse Model of Breast Cancer

To determine the ability of a humanized/deimmunized anti-endoglin antibody to treat breast cancer, a breast cancer cell line is used in SCID or nude mice.

Briefly, breast cancer cells are implanted into SCID or nude mice to generate breast tumors. Groups of mice bearing established tumors are treated by i.v. administration of escalating doses (starting at 1.8 mg/kg body weight) of a humanized/deimmunized anti-endoglin antibody. Control animals are administered a control IgG. The treatment is performed 2 or 3 times per week. A VEGF inhibitor and/or other anticancer agent may be used in some or all groups. The mice are monitored and tumor growth is measured 2 to 3 times per week.

Example 16

Clinical Trial of Combination Therapy for Colorectal Cancer

This example describes a randomized, blinded, placebo-controlled, multicenter, Phase 2 study designed to provide a preliminary assessment of the safety and efficacy of a humanized/deimmunized anti-endoglin antibody in patients with colorectal cancer. Approximately about 100-about 800 patients are enrolled, with about 50-about 400 patients being assigned to a treatment group and about 50-about 400 patients assigned to a placebo group. The trial will consist of the administration of intravenous repeating doses of humanized/deimmunized anti-endoglin antibody at about 0.1-about 20 mg/kg or placebo every one, two or three weeks for 6-10 cycles. A VEGF inhibitor and/or other anticancer agent may be used in all groups. The time frame of the study is estimated at about 6 months to about 5 years, with continued therapy for responders as indicated at the end of the initial study. Additional outcome measures are as follows:

Primary outcome measure: overall response rate. One goal of the study is to demonstrate an increase progression-free survival by 35% with humanized/deimmunized anti-endoglin antibody.

Secondary outcome measures that can be assessed include overall response rate, duration of response, overall survival, serious and non-serious adverse events. For example, a treatment may prevent progression of the disease (i.e., stasis) or may result in an improvement. Alternately, or in addition, other goals can be measured with respect to one or more of the following: decreased tumor burden, decreased vascularity, reduced side effects, decreased adverse reactions, and/or increased patient compliance.

Example 17

Clinical Trial of Combination Therapy for Myeloma

This example describes a randomized, blinded, placebo-controlled, multicenter, Phase 2 study designed to provide a preliminary assessment of the safety and efficacy of combining humanized/deimmunized anti-endoglin antibody with bortezomib in patients with myeloma. Approximately about 100-about 800 patients are enrolled, with about 50-about 400 patients being assigned to a treatment group and about 50-about 400 patients assigned to a placebo group. The trial will consist of the administration of intravenous repeating doses of humanized/deimmunized anti-endoglin antibody at about 1-about 20 mg/kg or placebo every one, two or three weeks combined with bortezomib at about 1.3 mg/kg weekly. The time frame of the study is estimated at about 6 months to about 5 years, with continued therapy for responders as indicated at the end of the initial study. Additional outcome measures are as follows:

Primary outcome measure: overall response rate. One goal of the study is to demonstrate an increase overall response rate from about 40% with bortezomib plus placebo to about 60% (or more) with bortezomib plus humanized/deimmunized anti-endoglin antibody.

Secondary outcome measures that can be assessed include duration of response, progression free survival, overall survival, serious and non-serious adverse events. For example, a treatment may prevent progression of the disease (i.e., stasis) or may result in an improvement. Alternately, or in addition, other goals can be measured with respect to one or more of the following: decreased tumor burden, decreased vascularity, reduced side effects, decreased adverse reactions, and/or increased patient compliance.

Example 18

Clinical Trial of Combination Therapy for Kidney Cancer

This example describes a randomized, blinded, placebo-controlled, multicenter, Phase 2 study designed to provide a preliminary assessment of the safety and efficacy of combining humanized/deimmunized anti-endoglin antibody with sunitinib (Sutent®) in patients with renal cell cancer (kidney cancer). Approximately about 100-about 800 patients are enrolled, with about 50-about 400 patients being assigned to a treatment group and about 50-about 400 patients assigned to a placebo group. The trial will consist of the administration of intravenous repeating doses of humanized/deimmunized anti-endoglin antibody at about 0.1-about 20 mg/kg or placebo every one, two or three weeks combined with sunitinib at about 5-about 50 mg administered daily for 4 weeks, with 2 weeks off prior to repeating the 4 week dosage cycle. The time frame of the study is estimated at about 6 months-about 5 years, with continued therapy for responders as indicated at the end of the initial study. Additional outcome measures are as follows:

Primary outcome measure: progression-free survival. One goal of the study is to demonstrate an increase in progression free survival from about 9-13 months in the sunitinib plus placebo arm to about 14-18 months (or more) in the sunitinib plus humanized/deimmunized anti-endoglin antibody arm.

Secondary outcome measures that can be assessed include response rate, duration of response, time to tumor progression, overall survival, serious and non-serious adverse events. For example, a treatment may prevent progression of the disease (i.e., stasis) or may result in an improvement. Alternately, or in addition, other goals can be measured with respect to one or more of the following: decreased tumor burden, decreased vascularity, reduced side effects, decreased adverse reactions, and/or increased patient compliance.

Example 19

Clinical Trial of Combination Therapy for Hepatocellular Cancer

This example describes a randomized, blinded, placebo-controlled, multicenter, Phase 2 study designed to provide a preliminary assessment of the safety and efficacy of combining humanized/deimmunized anti-endoglin antibody with sorafenib (NEXAVAR®) in patients with hepatocellular cancer (liver cancer). Approximately about 100-about 800 patients are enrolled, with about 50-about 400 patients being assigned to a treatment group and about 50-about 400 patients assigned to a placebo group. The trial will consist of the administration of intravenous repeating doses of humanized/deimmunized anti-endoglin antibody at about 0.1-about 20 mg/kg or placebo every one, two or three weeks combined with sorafenib at about 400 mg daily for 3-6 cycles or until progression. The time frame of the study is estimated at about 6 months to about 5 years, with continued therapy for responders as indicated at the end of the initial study. Additional outcome measures are as follows:

Primary outcome measures: progression-free survival. One goal of the study is to demonstrate an increase in progression free survival from about 3-9 months in the sorafenib plus placebo arm to about 6-12 months (or more) in the sorafenib plus humanized/deimmunized anti-endoglin antibody arm.

Secondary outcome measures that can be assessed include duration of response, time to tumor progression, overall survival, serious and non-serious adverse events. For example, a treatment may prevent progression of the disease (i.e., stasis) or may result in an improvement. Alternately, or in addition, other goals can be measured with respect to one or more of the following: decreased tumor burden, decreased vascularity, reduced side effects, decreased adverse reactions, and/or increased patient compliance.

Example 20

Clinical Trial of Combination Therapy for Kidney Cancer

This example describes a randomized, blinded, placebo-controlled, multicenter, Phase 2 study designed to provide a preliminary assessment of the safety and efficacy of combining humanized/deimmunized anti-endoglin antibody with bevacizumab (AVASTIN®) in patients with renal cell cancer (kidney cancer). Approximately about 100-about 800 patients are enrolled, with about 50-about 400 patients being assigned to a treatment group and about 50-about 400 patients assigned to a placebo group. The trial will consist of the administration of intravenous repeating doses of humanized/deimmunized anti-endoglin antibody at about 0.1-about 20 mg/kg or placebo every one, two or three weeks combined with bevacizumab at about 7.5, about 10, or about 15 mg/kg administered intravenously every two weeks. The time frame of the study is estimated at about 6 months to about 5 years, with continued therapy for positive responders as indicated at the end of the initial study. Additional outcome measures are as follows:

Primary outcome measure: progression-free survival. One goal of the study is to demonstrate an increase in progression free survival from about 8-12 months in the bevacizumab plus placebo arm to about 13-18 months (or more) in the bevacizumab plus humanized/deimmunized anti-endoglin antibody arm.

Secondary outcome measures that can be assessed include overall response rate, duration of response, time to tumor progression, overall survival, serious and non-serious adverse events. For example, a treatment may prevent progression of the disease (i.e., stasis) or may result in an improvement. Alternately, or in addition, other goals can be measured with respect to one or more of the following:

decreased tumor burden, decreased vascularity, reduced side effects, decreased adverse reactions, and/or increased patient compliance.

Example 21

Clinical Trial of Combination Therapy for Ovarian Cancer

This example describes a randomized, blinded, placebo-controlled, multicenter, Phase 2 study designed to provide a preliminary assessment of the safety and efficacy of combining humanized/deimmunized anti-endoglin antibody with Doxil® in patients with ovarian cancer. Approximately about 100-about 800 patients are enrolled, with about 50-about 400 patients being assigned to a treatment group and about 50-about 400 patients assigned to a placebo group. The trial will consist of the administration of intravenous repeating doses of humanized/deimmunized anti-endoglin antibody at about 0.1-about 20 mg/kg or placebo every one, two or four weeks combined with Doxil at about 5 to about 50 mg/m² administered once every 4 weeks The time frame of the study is estimated at 6 months to about 5 years, with continued therapy for responders as indicated at the end of the initial study. Additional outcome measures are as follows:

Primary outcome measure: progression-free survival. One goal of the study is to demonstrate an increase in progression free survival from about 3-6 months in the Doxil® plus placebo arm to about 4-12 months (or more) in the Doxil® plus humanized/deimmunized anti-endoglin antibody arm.

Secondary outcome measures that can be assessed include duration of response, time to tumor progression, overall survival, serious and non-serious adverse events. For example, a treatment may prevent progression of the disease (i.e., stasis) or may result in an improvement. Alternately, or in addition, other goals can be measured with respect to one or more of the following: decreased tumor burden, decreased vascularity, reduced side effects, decreased adverse reactions, and/or increased patient compliance.

Example 22

Clinical Trial of Platinum Based Combination Therapy for Ovarian Cancer

This example describes a randomized, blinded, placebo-controlled, multicenter, Phase 2 study designed to provide a preliminary assessment of the safety and efficacy of combining humanized/deimmunized anti-endoglin antibody with platinum based chemotherapy in patients with ovarian cancer. Approximately about 100-about 800 patients are enrolled, with about 50-about 400 patients being assigned to a treatment group and about 50-about 400 patients assigned to a placebo group. The trial will consist of the administration of intravenous repeating doses of humanized/deimmunized anti-endoglin antibody at about 0.1-about 20 mg/kg or placebo every one, two or three weeks combined with a platinum based chemotherapy regimen (e.g., carboplatin and paclitaxel) by intravenous infusion with courses repeating throughout the study. The time frame of the study is estimated at about 6 months-about 5 years, with continued therapy for responders as indicated at the end of the initial study. Additional outcome measures are as follows:

Primary outcome measure: progression-free survival. One goal of the study is to demonstrate an increase in progression free survival from about 12-18 months in the topotecan plus placebo arm to about 12-24 months (or more) in platinum-based chemotherapy plus humanized/deimmunized anti-endoglin antibody arm.

Secondary outcome measures that can be assessed include duration of response, time to tumor progression, overall survival, serious and non-serious adverse events. For example, a treatment may prevent progression of the disease (i.e., stasis) or may result in an improvement. Alternately, or in addition, other goals can be measured with respect to one or more of the following: decreased tumor burden, decreased vascularity, reduced side effects, decreased adverse reactions, and/or increased patient compliance.

Example 23

Use of Anti-Endoglin Antibodies for the Treatment of Diabetic Retinopathy

Study Design

To evaluate the biologic activity of multiple intravitreal injections of humanized/deimmunized anti-endoglin antibodies in patients with center-involving clinically significant diabetic macular edema (DME) and to report any associated adverse events, a single-center, open-label, dose-escalating pilot study is initiated. Patients with DME involving the center of the macula and best-corrected visual acuity (BCVA) in the study eye between 20/40 and 20/400 are enrolled.

Study Treatment

Eligible patients are randomly assigned in a 1:1 ratio to receive three intravitreal injections of humanized/deimmunized anti-endoglin antibodies (about 0.25 to 2.5 mg per each injection) administered monthly and observations are continued until month 24. Primary end points are the frequency and severity of ocular and systemic adverse events. Secondary end points are 1) best corrected visual assessment as assessed with the Early Treatment Diabetic Retinopathy Study (ETDRS) chart, with the use of standardized refraction and testing protocol at a starting test distance of 2 m and 2) measurement of retinal thickness by optical coherence tomography. The evaluating physician is unaware of the patient's treatment assignment; the physician who administers the injection is aware of the patient's treatment assignment regarding humanized/deimmunized anti-endoglin antibody or sham treatment but is unaware of the dose of humanized/deimmunized anti-endoglin antibody. Other personnel at each study site (except for those assisting with injections), patients, and personnel at the central reading center are unaware of the patient's treatment assignment.

Efficacy and Safety Analyses

Efficacy analyses are performed on an intention-to-treat basis among all patients with the use of a last-observation-carried-forward method for missing data. For all pairwise comparisons, the statistical model is adjusted for baseline score for visual acuity (<55 letters vs. ≥55 letters). Between-group comparisons for dichotomous end points are performed with the use of the Cochran chi-square test. Change from baseline visual acuity is analyzed with the use of analysis-of-variance models. For end points for lesion characteristics, analysis-of-covariance models adjusting for the baseline value are used. The Hochberg-Bonferroni multiple-comparison procedure is used to adjust for the two pairwise treatment comparisons for the primary end point. Safety analyses include all treated patients.

Conclusion

Humanized anti-endoglin antibodies will be a well-tolerated therapy for patients with DME. This pilot study demonstrates that humanized/deimmunized anti-endoglin antibody therapy has the potential to maintain or improve best corrected visual acuity and reduce retinal thickness in patients with center-involved clinically significant DME.

Example 24

Clinical Trial of Anti-Endoglin Antibodies and Age-Related Macular Degeneration

Study Design

At multiple sites in the United States, patients are enrolled in a 2-year, prospective, randomized, double-blind, sham-controlled study of the safety and efficacy of repeated intravitreal injections of humanized/deimmunized anti-endoglin antibodies among patients with choroidal neovascularization associated with age-related macular degeneration. Primary efficacy analysis is performed at 12 months. The primary efficacy end point is the proportion of patients who had lost fewer than 15 letters (approximately 3 lines) from baseline visual acuity, as assessed with the Early Treatment Diabetic Retinopathy Study (ETDRS) chart, with the use of standardized refraction and testing protocol at a starting test distance of 2 m. The eligibility of lesions is confirmed by an independent central reading center with the use of standardized criteria and trained graders who are unaware of patients' treatment assignments. Patients provide written informed consent before determination of their full eligibility. Screening may last as long as 28 days.

To be included in the study, patients must be at least 50 years old; have a best corrected visual acuity of 20/40 to 20/320 (Snellen equivalent determined with the use of an ETDRS chart); have primary or recurrent choroidal neovascularization associated with age-related macular degeneration, involving the foveal center; have a type of lesion that had been assessed with the use of fluorescein angiography and fundus photography as minimally classic or occult with no classic choroidal neovascularization; have a maximum lesion size of 12 optic-disk areas (1 optic-disk area equals 2.54 $mm^2$ on the basis of 1 optic-disk diameter of 1.8 mm), with neovascularization composing 50% or more of the entire lesion; and have presumed recent progression of disease, as evidenced by observable blood, recent vision loss, or a recent increase in a lesion's greatest linear diameter of 10% or more. There are no exclusion criteria regarding preexisting cardiovascular, cerebrovascular, or peripheral vascular conditions.

First Study

Fifty to 500 patients (50 to 500 eyes) with AMD will participated in the study at multiple sites. Eligible patients are randomly assigned in a 1:1:1 ratio to receive humanized/deimmunized anti-endoglin antibodies at a dose of about 0.25 mg to 2.5 mg or a sham injection monthly (within 23 to 37 days) for 2 years (24 injections) in one eye. The evaluating physician is unaware of the patient's treatment assignment; the physician who administers the injection is aware of the patient's treatment assignment regarding humanized/deimmunized anti-endoglin antibody or sham treatment but is unaware of the dose of humanized/deimmunized anti-endoglin antibody. Other personnel at each study site (except for those assisting with injections), patients, and personnel at the central reading center are unaware of the patient's treatment assignment. Intervention therapy (e.g., Verteporfin photodynamic therapy) is allowed if the choroidal neovascularization in the study eye becomes predominantly classic.

As the first step of treatment, the patients are to receive a full ophthalmic examination to establish a baseline of ocular health. The ophthalmic examination includes indirect ophthalmoscopy, slit-lamp biomicroscopy, peripheral retinal examination, intraocular pressure measurements, visual acuity (unaided and best corrected) symptomatology, fundus photography, fluorescein angiography, optical coherence tomography, electroretinography and A-scan measurements.

Following the preliminary examination, an intravitreal injection as described above is given to a patient's affected eye manifesting AMD. If both eyes are affected, they may be treated separately. The eye to be treated is injected with an ophthalmic solution.

After treatment, the patients' eyes are to be examined on days one (1), two (2), seven (7), fifteen (15), thirty (30) and sixty (60) and every month thereafter for 2 years. Because of the possibility of reoccurrence, the patients should return for periodic examinations on a monthly basis thereafter. On each examination day the patient is monitored for vitreous liquefaction. Additionally, the patients are monitored for posterior vitreous detachments using indirect ophthalmoscopy with scleral depression. Finally, the extent of AMD presented by the patients is continuously monitored through periodic retinal examinations, optical coherence tomography and fluorescein angiograms to monitor for the presence of subretinal fluid, blood, exudates, RPE detachment, cystic retinal changes, or the presence of grayish green subretinal neovascular membrane. Additional treatments may be required if indicia of reoccurring neovascularization are observed. Additional treatments may be given on weekly or monthly basis. In a preferred embodiment, an initial treatment is followed by subsequent treatments between 1-6 months apart.

Efficacy analyses are performed on an intention-to-treat basis among all patients with the use of a last-observation-carried-forward method for missing data. For all pairwise comparisons, the statistical model is adjusted for baseline score for visual acuity (<55 letters vs. ≥55 letters) and subtype of choroidal neovascularization (minimally classic vs. occult with no classic disease). Between-group comparisons for dichotomous end points are performed with the use of the Cochran chi-square test. Change from baseline visual acuity is analyzed with the use of analysis-of-variance models. For end points for lesion characteristics, analysis-of-covariance models adjusting for the baseline value are used. The Hochberg-Bonferroni multiple-comparison procedure is used to adjust for the two pairwise treatment comparisons for the primary end point. Safety analyses include all treated patients.

Second Study

Patients manifesting age-related macular degeneration are treated according to the methods of the First Study (see above) with an intravitreal injection of (1) humanized/deimmunized anti-endoglin antibody alone, (2) ranibizumab alone, (3) humanized/deimmunized anti-endoglin antibody in combination with ranibizumab in the same composition or different compositions or (4) control antibody to reduce or prevent the development of neovascularization, macular disease, and retinal damage.

Conclusion

Humanized/deimmunized anti-endoglin antibodies will be a well-tolerated therapy for patients with AMD. This clinical trial demonstrates that humanized/deimmunized anti-endoglin antibody therapy has the potential to maintain or improve best corrected visual acuity and reduce choroidal neovascularization in patients with AMD. Further, humanized/deimmunized anti-endoglin antibodies will demonstrate superior activity compared to ranibizumab and the combination of humanized/deimmunized anti-endoglin antibodies and ranibizumab therapy and will demonstrate increased activity versus either antibody alone.

Example 25

Systemic Toxicology in Cynomolgus Monkeys

Cynomolgus monkeys are utilized in a study to address the systemic toxicology of humanized/deimmunized anti-endoglin antibodies.

Briefly, monkeys are dosed weekly for three weeks with 10.0 mg/kg, 30.0 mg/kg or 100.0 mg/kg of the humanized/deimmunized anti-endoglin antibody. Placebo animals are dosed on the same schedule with an appropriate solution in the absence of antibody. The doses are administered as an intravenous bolus over 30 to 60 minutes and at least six animals are dosed at each dose level. Toxicology is assessed via one or more of the following indications: body weight measurements, basic physiologic clinical measurements, serial serum chemistry, hematologic evaluations and histopathological evaluations.

Example 26

Systemic Toxicology in Combination with Bevacizumab in Cynomolgus Monkeys

Cynomolgus monkeys are utilized in a study to address the systemic toxicology of humanized/deimmunized anti-endoglin antibodies in combination with ranibizumab (LUCENTIS®).

Briefly, monkeys are dosed weekly for three weeks with 10.0 mg/kg, 30.0 mg/kg or 100.0 mg/kg of the humanized/deimmunized anti-endoglin antibody in combination with about 10 mg/kg to 100 mg/kg of bevacizumab. Other animals receive either humanized/deimmunized anti-endoglin antibody or bevacizumab alone. Placebo animals are dosed on the same schedule with an appropriate solution in the absence of antibody. The doses are administered as an intravenous bolus over 30 to 60 minutes and at least six animals are dosed at each dose level. Toxicology is assessed via one or more of the following indications: body weight measurements, basic physiologic clinical measurements, serial serum chemistry, hematologic evaluations and histopathological evaluations.

Example 27

Regional Toxicology Study in Cynomolgus Monkeys

Cynomolgus monkeys are utilized in a study to address the regional toxicology of humanized/deimmunized anti-endoglin antibodies.

Briefly, monkeys are dosed by intravitreal injection weekly for six weeks with 0.25, 1.25 and 2.5 mg of humanized/deimmunized anti-endoglin antibody. Placebo animals are dosed on the same schedule with an appropriate solution in the absence of antibody. The doses are administered as intravitreal injections and at least six animals are dosed at each dose level. Toxicology is assessed via one or more of the following indications: body weight measurements, basic physiologic clinical measurements, serial serum chemistry, hematologic evaluations and histopathological evaluations.

Combination Regional Toxicology Study

Cynomolgus monkeys are utilized in a study to address the toxicology of humanized/deimmunized anti-endoglin antibodies in combination with ranibizumab (LUCENTIS®) when given by intravitreal injection.

Briefly, monkeys are dosed by intravitreal injection weekly for six weeks with 0.25, 1.25 and 2.5 mg of humanized/deimmunized anti-endoglin antibody and 0.5 mg of ranibizumab (LUCENTIS®). Other animals receive either antibody alone, at the same dose and schedule. Placebo animals are dosed on the same schedule with an appropriate solution in the absence of antibody. The doses are administered as intravitreal injections and at least six animals are dosed at each dose level. Toxicology is assessed via one or more of the following indications: body weight measurements, basic physiologic clinical measurements, serial serum chemistry, hematologic evaluations and histopathological evaluations.

Example 28

Sprouting Assays

Angiogenesis can be tested in a three-dimensional in vitro model of sprouting. HUVECs are isolated from umbilical cords and grown in M199 supplemented with 10% fetal bovine serum (FBS) (GIBCO, Carlsbad, Calif.) and endothelial cell growth supplement (ECGS) (BD Biosciences, Bedford, Mass.) at 3° C. and 5% $CO_2$, Passage 2 to 4 HUVEC are used for all experiments (Passage 0 being the primary culture). Lung fibroblasts (LF) are routinely grown in DMEM (GIBCO, Carlsbad, Calif.) supplemented with 10% FBS at 37° C. and 5% $CO_2$ and used between P10 and P15. Other fibroblast lines, obtainable from ATCC, can also be used.

Preparing the Cells

HUVEC and fibroblasts are expanded in M199/10% FBS/Pen-Strep (1:100) 1 to 2 days before beading. For HUVEC, medium is switched to EGM-2 (Clonetics, Walkersville, Md.) the day before beading. For fibroblasts, medium is switched to EGM-2 the day before embedding. Beading requires approximately 400 HUVEC per bead. Fibroblasts are used at 20,000 cells per well for a 24-well plate. Ninety-six-well plates can also be used with quantities scaled accordingly.

Cytodex 3 Bead Preparation

Cytodex 3 microcarrier beads, for example, can be used in the assay (Amersham Pharmacia Biotech, Piscataway, N.J.).

Dry beads (0.5 g) are hydrated and swollen in 50 ml PBS (pH=7.4) for at least 3 hours at room temperature (RT) in a 50-ml tube and placed it on a rocker.

The beads are allowed to settle (about 15 min). The supernatant is discarded and the beads are washed for a few minutes in fresh PBS (50 ml).

The wash PBS is discarded and replaced with fresh PBS:

The bead suspension is placed in a siliconized glass bottle (from e.g., Windshield Wiper or Sigrnacote). The beads are sterilized by autoclaving for 15 min at 115° C. and then stored at 4° C.

Reagents

Fibrinogen Solution

A fibrinogen solution is made by dissolving 2 mg/ml fibrinogen in DPBS in a 37° C. waterbath. The solution is then mixed by inverting the tube rather than vortexing. The percentage of clottable protein can be determined and adjusted accordingly. The solution is then passed through a 0.22-µm filter to sterilize.

Aprotinin

Lyophilized aprotinin can be reconstituted at 4 U/ml in DI water and sterile filtered. Aliquots of 1 ml each are made and stored at −20° C.

Thrombin

Thrombin is reconstituted in sterile water at 50 U/ml. Aliquots of 0.5 ml are made and stored at −20° C.

Coating the Beads with HUVEC (Day 1)

HUVEC cells are trypsinized. Beads are allowed to settle (do not centrifuge), the supernatant is aspirated, and the beads are briefly washed in 1 ml of warm EGM-2 medium.

Beads (2500) are mixed with 1×10⁶ HUVEC in 1.5 ml of warm EGM-2 medium in a FACS tube and placed vertically in the incubator. (This will be enough for approximately 10 wells; scale up if needed).

The mixture is incubated for 4 hours at 37° C., inverting and mixing the tube every 20 min. (beads should look like mini golf balls after beading which indicates sufficient coating for sprouting).

After 4 hours, the coated beads are transferred to a T25 tissue culture flask (Falcon, Bedford, Mass.) and incubated overnight in 5 ml of EGM-2 medium at 37° C. and 5% $CO_2$.

Embedding Coated Beads in Fibrin Gel (Day 0)

A 2.0 mg/ml fibrinogen solution is prepared as described above and 0.15 Units/ml of aprotinin are added to the fibrinogen solution.

Coated beads are transferred to a 15 mL conical tube and the beads are allowed to settle.

Beads are resuspended in 1 ml of EGM-2 medium and transferred to a 1.5-ml centrifuge tube. The beads are washed three times with 1 ml of EGM-2 medium, mixing by pipetting up and down slowly with a P1000 pipette. The beads are counted on a coverslip and resuspended in a fibrinogen solution at a concentration of 500 beads/ml.

Thrombin (0.625 Units/ml) is added to each well of a 24-well plate. The fibrinogen/bead suspension (0.5 ml) to each well changing the pipette tip for each well.

The thrombin and the fibrinogen/beads are mixed by pipetting up and down gently about four to five times; avoid creating bubbles in the fibrin gel. Control samples either are treated in the absence of antibodies or one or more control antibodies. Test samples are treated with anti-endoglin antibodies alone, anti-VEGF antibodies alone, or a combination thereof. Multiple concentrations of agents can be tested. The fibrinogen/bead solution is allowed to clot for 5 minutes at room temperature and then at 37° C./5% $CO_2$ for 15 min. It is important that the plate not be disturbed during the first 5 min of clotting to minimize shearing fibrin, which can result in reduced sprouting.

EGM-2 (1 mL) is added to each well in a drop-wise fashion. Lung fibroblasts are seeded on top of the clot at a concentration of 20,000 cells/well. Replace culture medium with fresh EGM-2 medium every other day until desired growth is achieved.

When the fibrin gel is formed, tiny bubbles may be present in the gel; they will disappear in 3 to 4 days. Sprouting should be apparent between day 2 and 4. Lumen formation begins around day 4 to 5 and sprouts continue to elongate. Newly formed tubes begin to branch around day 4 to 6. By day 6 to 7, the microvessel-like structures begin to anastomose with adjoining tubes; increasing the number of beads per well results in earlier anastomosis. Sprouting distance is measured by standard techniques.

Example 29

Immunocytochemistry of Angiogenic Sprouts In Vitro

For endothelial cell (EC) nuclei staining, fibrin gels are washed twice with 1×PBS and then fixed overnight in 2% paraformaldehyde. After two more washes with 1×PBS, gels are then stained with 4',6-diamidino-2-phenylindole (DAPI) (Sigma, St. Louis, Mo.).

For immunostaining, lung fibroblasts (LF) are first removed through a brief treatment of the gels with 10× trypsin. Digestion is stopped with serum as soon as all fibroblasts are removed. Gels are then extensively washed with HBSS, 1× (Cellgro, Herndon, Va.). Cultures are then fixed for 10 minutes in 10% formalin and permeabilized with 0.5% Triton X-100 for 5 minutes. Non-specific binding is blocked with a solution of 5% BSA in PBS for 2 hours.

Primary antibodies are used at a 1/100 dilution in blocking buffer and incubated overnight at 4° C. After extensive washing, bound antibody is detected by species-specific Alexa Fluor 488-conjugated or Alexa Fluor 568-conjugated secondary antibodies at a 1/1000 dilution (Molecular Probes, Carlsbad, Calif.). Isotype-specific non-binding antibodies are used as a control. If high background occurs, the concentration of primary or secondary antibody can be reduced and, if necessary, incubation and/or washing times can be increased. F-actin is stained with TRITC-phalloidin (Sigma, St. Louis, Mo.) at a concentration of 0.2 µM.

Phase-contrast and fluorescent images are captured on an IX70 Olympus microscope coupled with a digital camera. Fluorescent Z-series image stacks are captured on a two-photon Carl Zeiss MicroImaging LSM 510 Meta microscope and compiled into three-dimensional renderings with Metamorph software (Universal Imaging Corporation, Downingtown Pa.). Thus, expression of various markers can be readily detected.

Fluorescent optical image stacks along the z-axis of the cultures can be captured to create 3D representations of the vessels. The nuclei are stained by DAPI (green), and vessel walls are stained for vimentin (orange). Wide, hollow lumens are clearly visible, surrounded by a single layer of endothelial cells. These images confirm that the lumens present in the in vitro assay are intercellular and not intracellular slits as is often seen in Matrigel assays. Furthermore, it can be confirmed that the HUVECs are polarized, in that they have an apical membrane, facing the lumen, and a basal membrane, apposed to a collagen IV-rich basement membrane and the fibrin gel.

Example 30

Suppression of Choroidal Neovascularization in Cynomolgus Monkeys

The effect of compositions described herein on laser-induced choroidal neovascularization is evaluated in adult cynomolgus monkeys.

In this experiment, (1) humanized/deimmunized anti-endoglin antibody alone, (2) anti-VEGF antibody alone, (3) humanized/deimmunized anti-endoglin antibody in combination with anti-VEGF antibody in the same composition or different compositions or (4) control antibody is administered by intravenous or intravitreal injection. Each animal receives nine or ten laser burns to each retina, and the development of active choroidal neovascular lesions is assessed by fluorescein angiography, once before the initiation of treatment and 15, 20 and 29 days post-laser treatment. Compositions are administered intravenously once per week, beginning one week before laser injury. Intravitreal injections are made once every two weeks beginning one week before laser, or once, two weeks following laser, at which time active CNV lesions have already formed. Control animals receive weekly intravenous or biweekly intravitreal injections of placebo, beginning one week before laser.

CNV lesions are visualized by fluorescein angiography and graded according to standard procedures.

Example 31

Inhibition of Injury-Induced Corneal Neovascularization

Corneal neovascularization is induced in male C57BL/6 mice by intrastromal placement of 3 nylon sutures, or by chemical injury (NaOH) and mechanical debridement of the corneal epithelium. Multiple experiments are conducted in which (1) humanized/deimmunized anti-endoglin antibody alone, (2) anti-VEGF antibody alone, (3) humanized/deimmunized anti-endoglin antibody in combination with anti-VEGF antibody alone in the same composition or different compositions or (4) control antibody is administered intraperitoneally once or at multiple time points immediately before or following injury.

The growth of corneal neovessels is evaluated by slit-lamp microscopy and histological evaluation. The vasculature is labeled with an endothelial cell specific fluorescein-conjugated lectin, and neovascularization is evaluated in corneal flat-mounts, as well as in cross sections using PECAM immunohistochemistry. The presence of corneal edema is evaluated, using slit lamp microscopy, and corneal thickness is measured in cross-sections; increases in corneal thickness reflect the amount of edema. The numbers of polymorphonuclear leukocytes (PMN) and macrophages are determined by staining cross-sections with HEMA-3 or rat anti-mouse F4/80 monoclonal antibody, respectively.

Example 32

Identification of T-Cell Epitopes in Humanized Anti-Endoglin Antibodies

Sequences of humanized variable regions were tested by iTope™ analysis. Humanized variable region sequences were divided into overlapping 9-15 mer peptides. The variable region sequences were analyzed for promiscuous high affinity binding to human MHC class II (potential T cell epitopes) using iTope™, an in silico analytic tool that determines the affinity of peptides for MHC Class II by computational analysis. Sequences with the lowest frequencies of potential T cell epitopes from the iTope™ analysis are identified as leads for generation of a humanized antibody. The selected humanized variable region sequences may redesigned through inclusion of mutations in order to remove potential T cell epitopes. Mutations are designed using iTope™ to reduce or eliminate MHC class II binding. Alternatively, germline human sequences can be substituted at sites of potential T cell epitopes or alternative sequences may be substituted.

FIGS. 19-23 present the predicted binding of 9 mer peptides for the humanized anti-endoglin antibody containing the light chain HuVK_v0 and the heavy chain HuVH_v0, noted in FIG. 4.

Example 33

Design of Anti-CD105 Humanized/Deimmunized Antibodies

This example describes the design of therapeutic monoclonal, humanized-deimmunized antibodies targeting human CD105 that exhibit reduced immunogenicity.

The promiscuous high affinity MHC class II binding sequences identified using iTope™ (see Example 31) were further analyzed by iTope™ in order to identify amino acid substitutions at key MHC class II pocket positions that would reduce or eliminate peptide binding to MHC class II. Since all the sequences overlapped CDRs, consideration was also given to the CDR location of the changes (potential antigen contact residues) and the physicochemical characteristics of the original and replacement amino acids. TCR contact residues and residues outside the main binding groove involved in the stabilization of peptide/MHC class II-TCR interactions were also considered for replacement.

In VHV1, a 9-mer peptide lying completely within CDR2 and starting at residue 51 was identified as a promiscuous high affinity MHC class II binding peptide. The most successful method for elimination of MHC class II binding is to target the first amino acid of the 9-mer (the pocket 1 or p1 position) where removal of the hydrophobic side-chain or replacement with a hydrophilic side-chain eliminates MHC class II binding. However, this type of radical amino acid replacement may not always be successful in retaining antibody affinity, hence secondary pocket positions (p4, p6, p7 or p9), alone or in combination, were also assessed. iTope™ analysis revealed that targeting the p4 position of this peptide by changing K52b to Q or R is predicted to significantly reduce MHC class II binding while replacement of I51 at p1 with A is predicted to remove binding entirely (Table 5).

TABLE 5

Analysis of the effect of substitutions on the immunogenic region of VHV1 using iTope ™.

| Sequence | B1*0101 | B1*0102 | B1*1501 | B1*1502 | B1*0301 | B1*0305 | B1*0306 | B1*0309 | B1*0401 | B*0405 |
|---|---|---|---|---|---|---|---|---|---|---|
| WVGEIRSKASNHAT | X | X | X | O |  |  | X |  | X | X |
| WVGEIRSQASNHAT |  | X |  |  |  |  |  |  | X |  |
| WVGEIRSRASNHAT |  |  |  |  |  |  |  |  | X |  |
| WVGEARSKASNHAT |  |  |  |  |  |  |  |  |  |  |
| Sequence | B*0404 | B*0405 | B*0408 | B1*0410 | B1*0421 | B1*1101 | B1*1102 | B1*1104 | B1*1107 | B1*1114 |
| WVGEIRSKASNHAT | X | X | X | X | X | X | X | X | O | X |
| WVGEIRSQASNHAT | O | X |  | X | X |  |  |  |  |  |
| WVGEIRSRASNHAT |  | X |  | X | X |  |  |  |  |  |
| WVGEARSKASNHAT |  |  |  |  |  |  |  |  |  |  |

TABLE 5-continued

Analysis of the effect of substitutions on the immunogenic region of VHV1 using iTope ™.

| Sequence | B1*1120 | B1*1128 | B1*1301 | B1*1304 | B1*1307 | B1*1321 | B1*0701 | B1*0801 | B1*0802 | B1*0804 |
|---|---|---|---|---|---|---|---|---|---|---|
| WVGE<u>IRSKASNHA</u>T | X | O | X | X | X | O | O | X | X | X |
| WVGE<u>IRSQASNHA</u>T |  |  |  | X |  | O | O |  |  |  |
| WVGE<u>IRSRASNHA</u>T |  |  |  |  |  | O |  |  |  |  |
| WVGEA<u>RSKASNHA</u>T |  |  |  |  |  |  |  |  |  |  |

| Sequence | B1*0806 | B1*0813 | B1*0817 | B5*0101 | Total Alleles Binding | High Affinity |
|---|---|---|---|---|---|---|
| WVGE<u>IRSKASNHA</u>T | X | X | X |  | 31 | 26 |
| WVGE<u>IRSQASNHA</u>T | O |  | O |  | 11 | 6 |
| WVGE<u>IRSRASNHA</u>T | O |  |  |  | 6 | 4 |
| WVGEA<u>RSKASNHA</u>T |  |  |  |  | 0 | 0 |

The core 9-mer peptide is underlined in the "sequence" column and substitutions are highlighted in bold type.
Flanking residues are not underlined.
The predicted binding of each core 9-mer peptide to each MHC class II alleles is indicated by "O" if the binding score was 0.55-0.6 and "X" if the binding score was >0.6.
The numbers of MHC class II alleles predicted to bind are shown in the "total" and "high affinity" columns.
Table 5 discloses SEQ ID NOS 106-109, respectively, in order of appearance.

Crystal structures of antibody/antigen complexes suggest that I51 may infrequently contact with antigen; however a radical change of I to A (a substitution for disrupting a p1 anchor position) at this position could affect the overall conformation of the CDR. Therefore, relatively conservative changes at K52b (p4 anchor position) were also included since this residue is solvent exposed but may not contact antigen. Finally, additional mutations lying outside the CDR were also designed (G49 to A or S) to assess the destabilizing effect on peptide/MHC class II/TCR interactions. Table 6 lists the humanized and humanized/deimmunized variant VH regions that were constructed; the SEQ ID NOS for the corresponding nucleotide and amino acid sequences are indicated next to the constructs.

TABLE 6

| Construct Name | Parental Sequence | Amino Acid Substitutions | SEQ ID NO |
|---|---|---|---|
| VH1 | VHV1 | N/A | 42 |
| VH2 | VHV2 | N/A | 43 |
| VK1 | VKV1 | N/A | 4 |
| VK2 | VKV2 | N/A | 5 |
| VH1A2 | VHV1 | I51A | 89 |
| VH1Q | VHV1 | K52bQ | 90 |
| VH1R | VHV1 | K52bR | 91 |
| VH1S | VHV1 | G49S | 92 |
| VH1A | VHV1 | G49A | 88 |
| VK2AA | VKV2 | V19A + I48A | 94 |

TABLE 6-continued

| Construct Name | Parental Sequence | Amino Acid Substitutions | SEQ ID NO |
|---|---|---|---|
| VK2AS | VKV2 | V19A + T51S | 95 |
| VK2SA | VKV2 | T22S + I48A | 96 |
| VK2SS | VKV2 | T22S + T51S | 97 |
| VK1AA | VKV1 | V19A + I48A | 93 |
| VK1AS | VKV1 | V19A + T51S | 102 |
| VK1SA | VKV1 | T22S + I48A | 103 |
| VK1SS | VKV1 | T22S + T51S | 100 |

Two promiscuous high affinity MHC class II binding peptides were identified in VKV2 and VKV1. The first, with a p1 anchor at V19, partially overlaps CDR1 and the second, with a p1 anchor at I48, overlaps CDR2. Both p1 anchors lie outside the CDRs and were targeted by mutation to A, which may completely remove MHC class II binding (Table 7). However, both these residues may be involved in the maintenance of the conformations of CDRs 1 and 2; therefore, additional mutations were designed that significantly reduced MHC class II binding (Table 7). In both cases, p4 residues were targeted by mutation of T to S. T22S also lies outside the CDR and is less likely to affect CDR conformation than V19A. T51 lies inside CDR2; however evidence from crystal structures of antibodies complexed with antigen suggests that this residue rarely contacts antigen. Table 6 lists the humanized and humanized/deimmunized VK regions that were constructed.

TABLE 7

Analysis of the effect of substitutions on the immunogenic regions of VKV2 or VKV1 using iTope ™.

| Sequence | B1*0101 | B1*0102 | B1*1501 | B1*1502 | B1*0301 | B1*0305 | B1*0306 | B1*0309 | B1*0401 | B*0405 |
|---|---|---|---|---|---|---|---|---|---|---|
| DRVTITCRASSSV | O | | | X | X | X | X | O | O | O |
| DRVTISCRASSSV | | | | | X | X | X | X | | |
| DRATITCRASSSV | | | | | | | | | | |
| PWIYATSNLASGV | O | X | X | O | | | O | | X | X |
| PWIYASSNLASGV | | | | | | | O | | X | |
| PWAYATSNLASGV | | | | | | | | | | |

| Sequence | B*0404 | B*0405 | B*0408 | B1*0410 | B1*0421 | B1*1101 | B1*1102 | B1*1104 | B1*1107 | B1*1114 |
|---|---|---|---|---|---|---|---|---|---|---|
| DRVTITCRASSSV | | | | | O | X | X | X | X | X |
| DRVTISCRASSSV | | | | | | | | | X | |
| DRATITCRASSSV | | | | | | | | | | |
| PWIYATSNLASGV | X | X | X | X | X | X | O | X | | |
| PWIYASSNLASGV | O | | O | | X | | | | | |
| PWAYATSNLASGV | | | | | | | | | | |

| Sequence | B1*1120 | B1*1128 | B1*1301 | B1*1304 | B1*1307 | B1*1321 | B1*0701 | B1*0801 | B1*0802 | B1*0804 |
|---|---|---|---|---|---|---|---|---|---|---|
| DRVTITCRASSSV | X | X | X | X | X | X | | X | X | X |
| DRVTISCRASSSV | | | | | | | | | | |
| DRATITCRASSSV | | | | | | | | | | |
| PWIYATSNLASGV | | X | O | | X | X | X | | | X |
| PWIYASSNLASGV | | X | O | | | | | | | |
| PWAYATSNLASGV | | | | | | | | | | |

| Sequence | B1*0806 | B1*0813 | B1*0817 | B5*0101 | Total Alleles Binding | High Affinity |
|---|---|---|---|---|---|---|
| DRVTITCRASSSV | X | X | O | O | 27 | 20 |
| DRVTISCRASSSV | | | | | 5 | 5 |
| DRATITCRASSSV | | | | | 0 | 0 |
| PWIYATSNLASGV | | | O | O | 23 | 16 |
| PWIYASSNLASGV | | | | | 7 | 3 |
| PWAYATSNLASGV | | | | | 0 | 0 |

The core 9-mer peptide is underlined in the "sequence" column and substitutions are highlighted in bold type.
Flanking residues are not underlined.
The predicted binding of each core 9-mer peptide to each MHC class II alleles is indicated by "O" if the binding score was 0.55-0.6 and "X" if the binding score was >0.6.
The numbers of MHC class II alleles predicted to bind are shown in the "total" and "high affinity" columns.
Table 7 discloses SEQ ID NOS 110-115, respectively, in order of appearance.

Example 34

This example describes a method of screening anti-endoglin antibodies for T-cell epitopes. The interaction between MHC, polypeptide and T cell receptor (TCR) provides the structural basis for the antigen specificity of T cell recognition. T cell proliferation assays test the binding of polypeptides processed from antibodies to MHC and the recognition of MHC/polypeptide complexes by the TCR. In vitro T cell proliferation assays of the present example, involve the stimulation of peripheral blood mononuclear cells (PBMCs), containing antigen presenting cells (APCs) and T cells. Stimulation is conducted in vitro using intact anti-endoglin antibodies. Stimulated T cell proliferation is measured using $^3$H-thymidine ($^3$H-Thy) and the presence of incorporated $^3$H-Thy is assessed using scintillation counting of washed fixed cells.

All humanized and humanized/deimmunized VH and VK region genes were synthesized using a series of overlapping oligonucleotides that were annealed, ligated and PCR amplified to give full length synthetic V regions. The assembled variants were then cloned directly into Antitope Ltd.'s pANT expression vector system for IgG1 heavy chains and kappa light chains.

Purification of Antibodies

Anti-endoglin antibodies were purified from the supernatants of mammalian cultures by protein A chromatography. Buffer exchange and protein concentration was done using PBS pH=7.4. Anti-endoglin antibody was further purified by size exclusion chromatography using a Sephacryl S200 column (GE Healthcare, AMersham, UK). The major peak is collected, filter sterilized and shown to have endotoxin levels<5 EU/mg using an Endosafe-PTS (Charles River, Margate, UK). The purified antibodies are stored at 4 degrees Celsius. Final concentrations were determined by UV absorption using calculated molar extinction coefficients, where A280 1.0=1.62 mg/mL. Each antibody was then diluted to 100 ug/mL in AIMV culture medium.

Preparation and Selection of Donor PBMC

Peripheral Blood Mononuclear cells (PBMC) are isolated from healthy community donor buffy coats (from blood drawn within 24 hours) which are obtained from the UK National Blood Transfusion Service (Addenbrooke's Hospital, Cambridge, UK) according to approval granted by Addenbrooke's Hospital Local Research Ethics Committee. PBMC are isolated from buffy coats by Lymphoprep (Axis-shield, Dundee, Scotland) density centrifugation and CD8+ T cells are depleted using CD8+RossetteSep™ (StemCell Technologies, Inc.). Donors are characterized by identifying HLA-DR haplotypes using a Biotest HLA SSP-PCR based tissue-typing kit (Biotest, Landsteinerstraβe, Denmark). T cell responses to a control antigen, Keyhole Limpet Haemocyanin (KLH) (Pierce, Rockford, Ill., USA) are determined for a positive control. PBMC were then frozen and stored in liquid nitrogen until required. When required for use, cells are thawed rapidly in a water bath at 37° C. before transferring to 10 ml pre-warmed AIM V medium.

A cohort of 20 donors is selected to best represent the number and frequency of HLA-DR allotypes expressed in the world population. Analysis of the allotypes expressed in the cohort against those expressed in the world population revealed that coverage of >80% is achieved and that all major HLA-DR alleles (individual allotypes with a frequency>5% expressed in the world population) are well represented. A summary of donor haplotypes is provided in FIG. 23, and a comparison of the frequency of donor allotypes used in the study versus those present in the world population is made.

PBMCs from each donor are thawed, counted and viability assessed. Cells were revived and resuspended in AIMV culture medium to 4-6×10$^6$ PBMC/mL. For each donor, bulk cultures were established in which a total of 1 mL proliferation cell stock was added to a 24-well plate. A total of 1 mL of each diluted test sample was added to the PBMC to give a final concentration of 50 ug/mL per antibody sample. For each donor, a positive control (cells incubated with 100 ug/mL KLH) and a negative control (cells incubated with culture media only) were also included. For the first 4 donors, an additional control was included to test for modulation of T cell responses by the test samples, where test sample and KLH were added to the PBMC. Comparison of these samples with KLH alone can be used to assess the effects of the test samples on proliferation. Cultures were incubated for a total of 8 days at 37 degrees Celsius with 5% carbon dioxide. On days 5, 6. 7 and 8, the cells in each well are gently resuspended and three 100 uL aliquots are transferred to individual wells of a round bottom 96 well plate. The cultures are pulsed with 1 μCi $^3$[H]-Thy (Perkin Elmer, Waltham, Mass.) in 100 uL AIMV culture medium and incubated for a further 18 hours before harvesting onto filter mats using a TomTec Mach III cell harvester. Counts per minute (cpm) for each well are determined by Meltilex™ (Perkin Elmer®, Waltham, Mass., USA) scintillation counting on a Microplate Beta Counter (Perkin Elmer®, Waltham, Mass., USA) in paralux, low background counting mode.

Results are expressed as stimulation indices, where the stimulation index (SI) is derived by division of the proliferation score (e.g. counts per minute of radioactivity) measured to the test anti-endoglin antibody by the score measured in cells not contacted with a test anti-endoglin antibody. All basal cpm for the control wells are above the minimum threshold for the assay of 150 cpm.

For proliferation assays, an empirical threshold of a stimulation index (SI) equal to or greater than 2 (SI≥2) has been previously established whereby samples inducing proliferative responses above this threshold are deemed positive (where included, borderline Sis ≥1.90 are highlighted). Extensive assay development and previous studies have shown that this is the minimum signal to noise threshold allowing maximum sensitivity without detecting large numbers of false positive responses. Positive responses are defined by the following statistical and empirical thresholds:

1. Significance (p<0.05) of the response by comparing cpm of test wells against medium control wells using unpaired two sample student's t-test.
2. Stimulation index greater than 2 (SI≥2), where SI=mean of test wells (cpm)/mean medium control wells (cpm).

In addition, intra-assay variation is assessed by calculating the coefficient of variance and standard deviation (SD) of the raw data from replicate cultures.

Results for the EpiScreen time course proliferation assay with the anti-endoglin antibodies are shown in FIG. 24 and summarized in tabular form (Table 8). The chimeric antibody stimulated responses in 4 of 20 donors (20% of the study cohort) and, although two of the donor responses were borderline (1.92 and 1.95 for donors 11 and 17, respectively), they were significantly different from background (p<0.05). The humanized antibody VK1VH1 stimulated responses in 2 of 20 donors (10% of the study cohort) including one borderline response (1.91 for donor 20) that was significantly different from background (p<0.05). It is noteworthy that donors 11 and 20 responded to both of these antibodies suggesting that there could be a shared T cell epitope. In contrast, none of the donors in the study cohort responded positively to the deimmunized anti-endoglin antibody VK1AA VH1A2. Results with the control antigen KLH show that there was a good correlation between positive and negative results, indicating a high level of reproducibility in the assay.

TABLE 8

T cells stimulation, as a measure of immunogenicity, induced culture with anti-endoglin antibodies and KLH, where "P*" indicate borderline stimulation above baseline and "P" indicates a stimulation index greater than 2.

| Donor No | Chimeric | VK1VH1 | VK1AA VH1A2 | KLH | Basal CPM |
|---|---|---|---|---|---|
| 1 | | | | P | 7456 |
| 2 | | | | P* | 2272 |
| 3 | | | | P | 3943 |
| 4 | | | | P | 2827 |
| 5 | | | | P | 2029 |
| 6 | | | | P | 1918 |
| 7 | | | | | 3870 |
| 8 | | | | P | 3110 |
| 9 | | | | P | 1242 |
| 10 | | | | | 6042 |
| 11 | P* | P | | P | 1696 |
| 12 | | | | P | 3275 |
| 13 | | | | P | 4644 |
| 14 | | | | P | 1993 |
| 15 | | | | P | 2727 |
| 16 | | | | P | 1781 |
| 17 | P* | | | P | 3681 |
| 18 | | | | P | 893 |
| 19 | P | | | P | 1705 |
| 20 | P | P* | | P | 2901 |
| Positive Responses: | 4(20%) | 2(10%) | 0(0%) | 92 | |

Example 35

EpiScreen™ T Cell Epitope Mapping

EpiScreen™ is an ex vivo technology for measurement of T cell epitopes in whole antibodies or for mapping the sequence location of such T cell epitopes as described in more detail below.

EpiScreen Donor Selection

Peripheral Blood Mononuclear cells (PBMC) are isolated from healthy community donor buffy coats (from blood drawn within 24 hours) which are obtained from the UK National Blood Transfusion Service (Addenbrooke's Hospital, Cambridge, UK) according to approval granted by Addenbrooke's Hospital Local Research Ethics Committee. PBMC are isolated from buffy coats by Lymphoprep (Axisshield, Dundee, Scotland) density centrifugation and CD8+ T cells are depleted using CD8+RossetteSep™ (StemCell Technologies, Inc.). Donors are characterized by identifying HLA-DR haplotypes using a Biotest HLA SSP-PCR based tissue-typing kit (Biotest, Landsteinerstraβe, Denmark). T cell responses to a control antigen, e.g., Keyhole Limpet Haemocyanin (KLH) (Pierce, Rockford, USA) are also determined for a positive control. A cohort of 54 donors is selected to best represent the number and frequency of HLA-DR allotypes expressed in the world population. Analysis of the allotypes expressed in the cohort against those expressed in the world population revealed that coverage of >80% is achieved and that all major HLA-DR alleles (individual allotypes with a frequency>5% expressed in the world population) are well represented. A summary of donor haplotypes is provided, and a comparison of the frequency of donor allotypes used in the study versus those present in the world population is made.

Donor details and haplotypes. Donor responses (SI) to KLH are tested in two independent experiments. Test 1 is performed on freshly isolated PBMC and an antibody is the re-test in the current study. Responses that did not produce the same result (i.e., positive or negative) in both tests are highlighted. Donors with very low basal cpm (<150 cpm) are excluded from the analysis.

EpiScreen Analysis: Proliferation Assays

EpiScreen™ is used to test overlapping peptides derived from the sequence of chimeric, humanized and humanized/deimmunized antibodies. Overlapping peptides are designed. A series of 128×15-mer peptides overlapping by 12 amino acids are synthesized together with 1×14-mer and 1×11-mer and used to stimulate peripheral blood mononuclear cells (PBMC) derived from a cohort of 51 healthy donors using EpiScreen™ T cell epitope mapping. Individual peptides are tested in replicate cultures and responses are assessed using T cell proliferation assays to identify the precise location of epitopes. PBMC from each donor are thawed, counted and assessed for viability. Cells are revived in room temperature AIM V culture medium (Invitrogen, Carlsbad, Calif.) before adjusting the cell density to $2.5 \times 10^6$ PBMC/ml (proliferation cell stock). Peptides are dissolved in DMSO (Sigma-Aldrich, St Louis, Mo., USA) to a final concentration of 10 mM. Peptide culture stocks are then prepared by diluting into AIM V culture medium to a final concentration of 5 µM. For each peptide and each donor, sextuplicate cultures are established by adding 100 µl of the peptide culture stocks to 100 µl of proliferation cell stock in a flat bottomed 96 well plate. Both positive and negative control cultures are also established in sextuplicate. A total of 9×96 well plates are used for each donor, and each plate is sufficient to test 15 peptides with one negative control (carrier alone) in sextuplicate. On the final plate, a positive control is added.

Cultures are incubated for a total of 6 days before adding 0.5 µCi $^3$[H]-Thymidine (Perkin Elmer®, Waltham, Mass., USA) to each well. Cultures are incubated for a further 18 hours before harvesting onto filter mats using a TomTec Mach III cell harvester. Counts per minute (cpm) for each well are determined by Meltilex™ (Perkin Elmer®, Waltham, Mass., USA) scintillation counting on a Microplate Beta Counter (Perkin Elmer®, Waltham, Mass., USA) in paralux, low background counting mode.

For proliferation assays, an empirical threshold of a stimulation index (SI) equal to or greater than 2 (SI≥2) has been previously established whereby samples inducing proliferative responses above this threshold are deemed positive (where included, borderline SIs≥1.90 are highlighted). Extensive assay development and previous studies have shown that this is the minimum signal to noise threshold allowing maximum sensitivity without detecting large numbers of false positive responses. Positive responses are defined by the following statistical and empirical thresholds:

1. Significance (p<0.05) of the response by comparing cpm of test wells against medium control wells using unpaired two sample student's t-test.
2. Stimulation index greater than 2 (SI≥2), where SI=mean of test wells (cpm)/mean medium control wells (cpm).

In addition, intra-assay variation is assessed by calculating the coefficient of variance and standard deviation (SD) of the raw data from replicate cultures.

Proliferation assays are set up in sextuplicate cultures ("non adjusted data"). To ensure that intra assay variability is low, data is also analyzed after removing the maximum and minimum cpm values ("adjusted data") and the SI of donor responses are compared using both data sets. Details of donor SIs from both adjusted and non-adjusted data sets are prepared. T cell epitopes are identified by calculating the average frequency of responses to all peptides in the study+ 2×SD (background response rate). Any peptide(s) that induced proliferation above this threshold is considered to contain a T cell epitope.

In Silico iTope™ Analysis of Peptides

The sequences of peptides that are positive in the proliferation assay are analyzed using Antitope's predictive iTope™ software. This software predicts favorable interactions between amino acid side chains of the peptide and specific binding pockets within the MHC class II binding groove. The location of key binding residues is determined by generating 10-mer peptides that overlapped by one amino acid spanning the long peptide sequence. Each 10-mer is tested against Antitope's database of MHC class II allotypes and scored based on their fit and interactions with the MHC class II molecules. Peptides that produced a high binding score against a large number of alleles are considered to contain the core 9 mer.

Identification of T Cell Epitopes

All peptides identified using the EpiScreen™ Analysis described above are successfully synthesized for testing against 51 healthy donors (54 donors are originally selected; donors may be excluded from the analysis due to low basal cpm, i.e., below the cut off value of 150 cpm). Positive responses are defined by donors that produced a significant (p<0.05) response with a SI≥2 to any given peptide. Borderline responses (a significant (p<0.05) response with an SI≥1.90) are also included. The outputs from non-adjusted and adjusted data analyses are compared to ensure that intra-assay variability is low and that positive responses are not the result of spurious proliferation in individual wells. The results from each analysis showed little difference between the methods; consequently, the T cell epitope map is compiled using the adjusted data analysis. Donor stimulation indices from both non-adjusted and adjusted analyses are prepared. T cell epitopes are identified by calculating the average frequency of the responses to all peptides in the study plus twice the standard deviation (termed 'background response rate'). This is calculated to be 5.6% and is the equivalent of inducing a positive response in three or more donors. Peptides inducing proliferative responses above this threshold are considered to contain a T cell epitope.
Immunogenicity Testing of Lead Variants Using EpiScreen™

Lead variants are purified and compared against the wild-type polypeptide using EpiScreen™ time course T cell assays. A large number of healthy donors representing the world population according to expression of HLA allotypes are selected from a donor library as described above. Donors are stimulated with each protein in separate bulk cultures containing 2-4×10$^6$ CD8$^+$ T cell depleted PBMC. Replicate samples (of T blasts) are removed from bulk cultures on days 5-8, and proliferation along with IL-2 secretion (ELISPOT) is assessed. To further validate the assessment between wild type and variants, the study cohort is supplemented with responding donors from the EpiScreen™ T cell epitope mapping study (provided sufficient numbers of CD8$^+$ T cell depleted PBMC remain).

In order to confirm loss of immunogenicity in lead variants, an analysis of T cell immunogenicity by EpiScreen™ time course T cell assays is undertaken as follows:
(i) Buffy coats from healthy donors (with >80% DRB1 allotypic coverage for world population) are used to isolate PBMC which contain physiological levels of APC and CD4$^+$ T cells;
(ii) Each donor is tested against positive control antigens including keyhole limpet haemocyanin (a potent neoantigen);
(iii) CD8$^+$ T cells are depleted to exclude the detection of MHC class I restricted T cell responses;
(iv) Lead variants and wild-type polypeptides are compared against each other to evaluate relative capacity to activate T cells CD4$^+$ T cells;
( -continued Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys
            100                 105

<210> SEQ ID NO 2
<211> LENGTH: 107
<212> TYPE: PRT
<213> ORGANISM: Homo sapiens

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 3
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
            20                  25                  30

His Trp Tyr Gln Gln Lys Pro Gly Lys Ala Pro Lys Leu Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 4
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Ser Tyr Met
            20                  25                  30

His Trp Tyr Gln Gln Lys Pro Gly Lys Ala Pro Lys Pro Trp Ile Tyr
            35                  40                  45

Ala Thr Ser Asn Leu Ala Ser Gly Val Pro Ser Arg Phe Ser Gly Ser
        50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 5
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Ile Gln Leu Thr Gln Ser Pro Ser Ser Leu Ser Ala Ser Val Gly
1               5                   10                  15

Asp Arg Val Thr Ile Thr Cys Arg Ala Ser Ser Val Ser Tyr Met
            20                  25                  30

His Trp Tyr Gln Gln Lys Pro Gly Lys Ala Pro Lys Pro Trp Ile Tyr
            35                  40                  45

Ala Thr Ser Asn Leu Ala Ser Gly Val Pro Ser Arg Phe Ser Gly Ser
        50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 6
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 7
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 7

Asp Ile Gln Leu Thr Gln Ser Pro Ser Ser Leu Ser Ala Ser Val Gly
1               5                   10                  15

Asp Arg Val Thr Ile Thr Cys
            20

<210> SEQ ID NO 8
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 9
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asp Ile Val Met Thr Gln Ser Pro Ser Ser Leu Ser Ala Ser Val Gly
1               5                   10                  15

Asp Arg Val Thr Ile Thr Cys
            20

<210> SEQ ID NO 10
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asp Ile Gln Met Ser Gln Ser Pro Ser Ser Leu Ser Ala Ser Val Gly
1               5                   10                  15

Asp Arg Val Thr Ile Thr Cys
            20

<210> SEQ ID NO 11
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Ile Val Met Ser Gln Ser Pro Ser Ser Leu Ser Ala Ser Val Gly
1               5                   10                  15

Asp Arg Val Thr Ile Thr Cys
            20

<210> SEQ ID NO 12
<211> LENGTH: 23
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Ile Val Leu Thr Gln Ser Pro Ser Ser Leu Ser Ala Ser Val Gly
1               5                   10                  15

Asp Arg Val Thr Ile Thr Cys
            20

<210> SEQ ID NO 13
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp Ile Val Leu Ser Gln Ser Pro Ser Ser Leu Ser Ala Ser Val Gly
1               5                   10                  15

Asp Arg Val Thr Ile Thr Cys
            20

<210> SEQ ID NO 14
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asp Ile Gln Leu Ser Gln Ser Pro Ser Ser Leu Ser Ala Ser Val Gly
1               5                   10                  15

Asp Arg Val Thr Ile Thr Cys
            20

<210> SEQ ID NO 15
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Ile Val Met Thr Gln Ser Pro Ser Ser Leu Ser Ala Ser Val Gly
1               5                   10                  15

Asp Arg Val Thr Ile Thr Cys
            20

<210> SEQ ID NO 16
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Ile Gln Leu Thr Gln Ser Pro Ser Ser Leu Ser Ala Ser Val Gly
1               5                   10                  15
```

Asp Arg Val Thr Ile Thr Cys
            20

<210> SEQ ID NO 17
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gln Ile Gln Met Ser Gln Ser Pro Ser Ser Leu Ser Ala Ser Val Gly
1               5                   10                  15

Asp Arg Val Thr Ile Thr Cys
            20

<210> SEQ ID NO 18
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Ile Val Leu Thr Gln Ser Pro Ser Ser Leu Ser Ala Ser Val Gly
1               5                   10                  15

Asp Arg Val Thr Ile Thr Cys
            20

<210> SEQ ID NO 19
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Ile Gln Leu Ser Gln Ser Pro Ser Ser Leu Ser Ala Ser Val Gly
1               5                   10                  15

Asp Arg Val Thr Ile Thr Cys
            20

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Trp Tyr Gln Gln Lys Pro Gly Lys Ala Pro Lys Leu Leu Ile Tyr
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Trp Tyr Gln Gln Lys Pro Gly Lys Ala Pro Lys Pro Trp Ile Tyr
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Trp Tyr Gln Gln Lys Pro Gly Lys Ala Pro Lys Pro Leu Ile Tyr
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Trp Tyr Gln Gln Lys Pro Gly Lys Ala Pro Lys Leu Trp Ile Tyr
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Trp Phe Gln Gln Lys Pro Gly Lys Ala Pro Lys Leu Leu Ile Tyr
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Trp Phe Gln Gln Lys Pro Gly Lys Ala Pro Lys Pro Leu Ile Tyr
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Trp Phe Gln Gln Lys Pro Gly Lys Ala Pro Lys Leu Trp Ile Tyr
1               5                   10                  15

<210> SEQ ID NO 27
<211> LENGTH: 15
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 27

Trp Phe Gln Gln Lys Pro Gly Lys Ala Pro Lys Pro Trp Ile Tyr
1               5                   10                  15

<210> SEQ ID NO 28
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 29
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gly Val Pro Ser Arg Phe Ser Gly Ser Gly Ser Gly Thr Asp Tyr Thr
1               5                   10                  15

Leu Thr Ile Ser Ser Leu Gln Pro Glu Asp Phe Ala Thr Tyr Tyr Cys
            20                  25                  30

<210> SEQ ID NO 30
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gly Val Pro Val Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 31
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gly Val Pro Ala Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 32
<211> LENGTH: 32

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gly Val Pro Val Arg Phe Ser Gly Ser Gly Ser Gly Thr Asp Tyr Thr
1               5                   10                  15

Leu Thr Ile Ser Ser Leu Gln Pro Glu Asp Phe Ala Thr Tyr Tyr Cys
            20                  25                  30

<210> SEQ ID NO 33
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gly Val Pro Ala Arg Phe Ser Gly Ser Gly Ser Gly Thr Asp Tyr Thr
1               5                   10                  15

Leu Thr Ile Ser Ser Leu Gln Pro Glu Asp Phe Ala Thr Tyr Tyr Cys
            20                  25                  30

<210> SEQ ID NO 34
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gly Val Pro Ser Arg Phe Ser Gly Ser Gly Ser Gly Thr Ser Phe Thr
1               5                   10                  15

Leu Thr Ile Ser Ser Leu Gln Pro Glu Asp Phe Ala Thr Tyr Tyr Cys
            20                  25                  30

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Phe Gly Gly Gly Thr Lys Val Glu Ile Lys
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Phe Gly Ala Gly Thr Lys Val Glu Ile Lys
1               5                   10

<210> SEQ ID NO 37
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Phe Gly Gly Gly Thr Lys Val Glu Leu Lys
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Phe Gly Ala Gly Thr Lys Val Glu Leu Lys
1               5                   10

<210> SEQ ID NO 39
<211> LENGTH: 118
<212> TYPE: PRT
<213> ORGANISM: Mus sp.

<400> SEQUENCE: 39

Glu Val Lys Leu Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Arg Ser Lys Ala Ser Asn His Ala Thr Tyr Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Ser Leu Arg Ala Glu Asp Thr Gly Ile Tyr
                85                  90                  95

Tyr Cys Thr Arg Trp Arg Arg Phe Phe Asp Ser Trp Gly Gln Gly Thr
            100                 105                 110

Thr Leu Thr Val Ser Ser
        115

<210> SEQ ID NO 40
<211> LENGTH: 115
<212> TYPE: PRT
<213> ORGANISM: Homo sapiens

<400> SEQUENCE: 40

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80
```

```
Leu Tyr Leu Gln Met Asn Ser Leu Lys Thr Glu Asp Thr Ala Val Tyr
                85                  90                  95

Tyr Cys Thr Thr Tyr Phe Asp Tyr Trp Gly Gln Gly Thr Leu Val Thr
            100                 105                 110

Val Ser Ser
        115

<210> SEQ ID NO 41
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Trp Val
        35                  40                  45

Gly Glu Ile Arg Ser Lys Ala Ser Asn His Ala Thr Tyr Tyr Ala Glu
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Trp Arg Arg Phe Phe Asp Ser Trp Gly Gln Gly Thr
            100                 105                 110

Leu Val Thr Val Ser Ser
        115

<210> SEQ ID NO 42
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Trp Val
        35                  40                  45

Gly Glu Ile Arg Ser Lys Ala Ser Asn His Ala Thr Tyr Tyr Ala Glu
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Arg Trp Arg Arg Phe Phe Asp Ser Trp Gly Gln Gly Thr
            100                 105                 110

Leu Val Thr Val Ser Ser
        115
```

<210> SEQ ID NO 43
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Trp Val
        35                  40                  45

Ala Glu Ile Arg Ser Lys Ala Ser Asn His Ala Thr Tyr Tyr Ala Glu
    50                  55                  60

Ser Val Lys Gly Arg Phe Thr Ile Ser Arg Asp Asp Ser Lys Asn Thr
65                  70                  75                  80

Val Tyr Leu Gln Met Asn Ser Leu Lys Thr Glu Asp Thr Ala Val Tyr
                85                  90                  95

Tyr Cys Thr Arg Trp Arg Arg Phe Phe Asp Ser Trp Gly Gln Gly Thr
            100                 105                 110

Leu Val Thr Val Ser Ser
        115

<210> SEQ ID NO 44
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser
            20                  25                  30

<210> SEQ ID NO 45
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Trp Val Arg Gln Ala Pro Gly Lys Gly Leu Glu Trp Val Gly
1               5                   10

<210> SEQ ID NO 46
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Trp Val Arg Gln Ala Pro Gly Lys Gly Leu Glu Trp Val Ala

```
<210> SEQ ID NO 47
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Arg Phe Thr Ile Ser Arg Asp Asp Ser Lys Asn Thr Leu Tyr Leu Gln
1               5                   10                  15
Met Asn Ser Leu Lys Thr Glu Asp Thr Ala Val Tyr Tyr Cys Thr Thr
            20                  25                  30

<210> SEQ ID NO 48
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Arg Phe Thr Ile Ser Arg Asp Asp Ser Lys Asn Thr Val Tyr Leu Gln
1               5                   10                  15
Met Asn Ser Leu Lys Thr Glu Asp Thr Ala Val Tyr Tyr Cys Thr Arg
            20                  25                  30

<210> SEQ ID NO 49
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Arg Phe Thr Ile Ser Arg Asp Asp Ser Lys Asn Thr Val Tyr Leu Gln
1               5                   10                  15
Met Asn Ser Leu Lys Thr Glu Asp Thr Ala Val Tyr Tyr Cys Thr Thr
            20                  25                  30

<210> SEQ ID NO 50
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Arg Phe Thr Ile Ser Arg Asp Asp Ser Lys Ser Thr Leu Tyr Leu Gln
1               5                   10                  15
Met Asn Ser Leu Lys Thr Glu Asp Thr Ala Val Tyr Tyr Cys Thr Thr
            20                  25                  30

<210> SEQ ID NO 51
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 51

Arg Phe Thr Ile Ser Arg Asp Asp Ser Lys Asn Arg Leu Tyr Leu Gln
1               5                   10                  15

Met Asn Ser Leu Lys Thr Glu Asp Thr Ala Val Tyr Tyr Cys Thr Thr
                20                  25                  30

<210> SEQ ID NO 52
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Arg Phe Thr Ile Ser Arg Asp Asp Ser Lys Asn Thr Leu Tyr Leu Gln
1               5                   10                  15

Met Ile Ser Leu Lys Thr Glu Asp Thr Ala Val Tyr Tyr Cys Thr Thr
                20                  25                  30

<210> SEQ ID NO 53
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Arg Phe Thr Ile Ser Arg Asp Asp Ser Lys Asn Thr Leu Tyr Leu Gln
1               5                   10                  15

Met Arg Phe Thr Ile Ser Arg Asp Asp Ser Ile Tyr Tyr Cys Thr Thr
                20                  25                  30

<210> SEQ ID NO 54
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Arg Phe Thr Ile Ser Arg Asp Asp Ser Lys Asn Thr Leu Tyr Leu Gln
1               5                   10                  15

Met Arg Phe Thr Ile Ser Arg Asp Asp Ser Leu Tyr Tyr Cys Thr Thr
                20                  25                  30

<210> SEQ ID NO 55
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Arg Phe Thr Ile Ser Arg Asp Asp Ser Lys Asn Thr Leu Tyr Leu Gln
1               5                   10                  15

Met Asn Ser Leu Lys Thr Glu Asp Thr Ala Val Tyr Tyr Cys Thr Gly
                20                  25                  30

<210> SEQ ID NO 56
<211> LENGTH: 11
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Trp Gly Gln Gly Thr Leu Val Thr Val Ser Ser
1               5                   10

<210> SEQ ID NO 57
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Trp Gly Gln Gly Thr Thr Val Thr Val Ser Ser
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Trp Gly Gln Gly Thr Leu Leu Thr Val Ser Ser
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Trp Gly Gln Gly Thr Leu Val Thr Val Ser Ala
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Trp Gly Gln Gly Thr Thr Val Thr Val Ser Ala
1               5                   10

<210> SEQ ID NO 61
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Trp Gly Gln Gly Thr Leu Leu Thr Val Ser Ala
```

```
1               5                   10

<210> SEQ ID NO 62
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Trp Gly Gln Gly Thr Thr Leu Thr Val Ser Ser
1               5                   10

<210> SEQ ID NO 63
<211> LENGTH: 10
<212> TYPE: PRT
<213> ORGANISM: Mus sp.

<400> SEQUENCE: 63

Arg Ala Ser Ser Ser Val Ser Tyr Met His
1               5                   10

<210> SEQ ID NO 64
<211> LENGTH: 7
<212> TYPE: PRT
<213> ORGANISM: Mus sp.

<400> SEQUENCE: 64

Ala Thr Ser Asn Leu Ala Ser
1               5

<210> SEQ ID NO 65
<211> LENGTH: 9
<212> TYPE: PRT
<213> ORGANISM: Mus sp.

<400> SEQUENCE: 65

Gln Gln Trp Ser Ser Asn Pro Leu Thr
1               5

<210> SEQ ID NO 66
<211> LENGTH: 5
<212> TYPE: PRT
<213> ORGANISM: Mus sp.

<400> SEQUENCE: 66

Asp Ala Trp Met Asp
1               5

<210> SEQ ID NO 67
<211> LENGTH: 19
<212> TYPE: PRT
<213> ORGANISM: Mus sp.

<400> SEQUENCE: 67

Glu Ile Arg Ser Lys Ala Ser Asn His Ala Thr Tyr Tyr Ala Glu Ser
1               5                   10                  15

Val Lys Gly

<210> SEQ ID NO 68
<211> LENGTH: 7
<212> TYPE: PRT
<213> ORGANISM: Mus sp.
```

<400> SEQUENCE: 68

Trp Arg Arg Phe Phe Asp Ser
1               5

<210> SEQ ID NO 69
<211> LENGTH: 107
<212> TYPE: PRT
<213> ORGANISM: Homo sapiens

<400> SEQUENCE: 69

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 70
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Met
            20                  25                  30

His Trp Tyr Gln Gln Lys Pro Gly Gln Ala Pro Arg Leu Leu Ile Tyr
        35                  40                  45

Ala Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 71
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Val Ser Tyr Met
            20                  25                  30

His Trp Tyr Gln Gln Lys Pro Gly Gln Ala Pro Arg Pro Trp Ile Tyr
        35                  40                  45

Ala Thr Ser Asn Leu Ala Ser Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 72
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Val Ser Tyr Met
            20                  25                  30

His Trp Tyr Gln Gln Lys Pro Gly Gln Ala Pro Arg Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 73
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

```
Tyr Cys Thr Arg Tyr Phe Asp Tyr Trp Gly Gln Gly Thr Leu Val Thr
                100                 105                 110

Val Ser Ser
        115

<210> SEQ ID NO 74
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asp Ala
            20                  25                  30

Trp Met Asp Trp Val Arg Gln Ala Ser Gly Lys Gly Leu Glu Trp Val
        35                  40                  45

Gly Glu Ile Arg Ser Lys Ala Ser Asn His Ala Thr Tyr Tyr Ala Glu
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg Trp Arg Arg Phe Phe Asp Ser Trp Gly Gln Gly Thr
                100                 105                 110

Leu Val Thr Val Ser Ser
        115

<210> SEQ ID NO 75
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asp Ala
            20                  25                  30

Trp Met Asp Trp Val Arg Gln Ala Ser Gly Lys Gly Leu Glu Trp Val
        35                  40                  45

Ala Glu Ile Arg Ser Lys Ala Ser Asn His Ala Thr Tyr Tyr Ala Glu
    50                  55                  60

Ser Val Lys Gly Arg Phe Thr Ile Ser Arg Asp Asp Ser Lys Asn Thr
65                  70                  75                  80

Val Tyr Leu Gln Met Asn Ser Leu Lys Thr Glu Asp Thr Ala Val Tyr
                85                  90                  95

Tyr Cys Thr Arg Trp Arg Arg Phe Phe Asp Ser Trp Gly Gln Gly Thr
                100                 105                 110

Leu Val Thr Val Ser Ser
        115

<210> SEQ ID NO 76
```

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Trp Gly Gln Gly Thr Leu Val Thr Val Ser Ser
1               5                   10

<210> SEQ ID NO 77
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Trp Gly Arg Gly Thr Leu Val Thr Val Ser Ser
1               5                   10

<210> SEQ ID NO 78
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Trp Gly Gln Gly Thr Met Val Thr Val Ser Ser
1               5                   10

<210> SEQ ID NO 79
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Trp Gly Gln Gly Thr Thr Val Thr Val Ser Ser
1               5                   10

<210> SEQ ID NO 80
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Phe Gly Gln Gly Thr Lys Val Glu Ile Lys
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81
```

```
Phe Gly Gln Gly Thr Lys Leu Glu Ile Lys
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Phe Gly Pro Gly Thr Lys Val Asp Ile Lys
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Phe Gly Gly Gly Thr Lys Val Glu Ile Lys
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Phe Gly Gln Gly Thr Arg Leu Glu Ile Lys
1               5                   10

<210> SEQ ID NO 85
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 85

His His His His His His
1               5

<210> SEQ ID NO 86
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Asp or Gln
<220> FEATURE:
<221> NAME/KEY: MOD_RES
<222> LOCATION: (3)..(3)
<223> OTHER INFORMATION: Gln or Val
<220> FEATURE:
<221> NAME/KEY: MOD_RES
<222> LOCATION: (4)..(4)
<223> OTHER INFORMATION: Met or Leu
```

```
<220> FEATURE:
<221> NAME/KEY: MOD_RES
<222> LOCATION: (5)..(5)
<223> OTHER INFORMATION: Thr or Ser
<220> FEATURE:
<221> NAME/KEY: MOD_RES
<222> LOCATION: (35)..(35)
<223> OTHER INFORMATION: Tyr or Phe
<220> FEATURE:
<221> NAME/KEY: MOD_RES
<222> LOCATION: (45)..(45)
<223> OTHER INFORMATION: Pro or Leu
<220> FEATURE:
<221> NAME/KEY: MOD_RES
<222> LOCATION: (46)..(46)
<223> OTHER INFORMATION: Trp or Leu
<220> FEATURE:
<221> NAME/KEY: MOD_RES
<222> LOCATION: (59)..(59)
<223> OTHER INFORMATION: Ser, Val or Ala
<220> FEATURE:
<221> NAME/KEY: MOD_RES
<222> LOCATION: (69)..(69)
<223> OTHER INFORMATION: Asp or Ser
<220> FEATURE:
<221> NAME/KEY: MOD_RES
<222> LOCATION: (70)..(70)
<223> OTHER INFORMATION: Tyr or Phe
<220> FEATURE:
<221> NAME/KEY: MOD_RES
<222> LOCATION: (99)..(99)
<223> OTHER INFORMATION: Gly or Ala
<220> FEATURE:
<221> NAME/KEY: MOD_RES
<222> LOCATION: (105)..(105)
<223> OTHER INFORMATION: Ile or Leu

<400> SEQUENCE: 86

Xaa Ile Xaa Xaa Xaa Gln Ser Pro Ser Ser Leu Ser Ala Ser Val Gly
1               5                   10                  15

Asp Arg Val Thr Ile Thr Cys Arg Ala Ser Ser Val Ser Tyr Met
            20                  25                  30

His Trp Xaa Gln Gln Lys Pro Gly Lys Ala Pro Lys Xaa Xaa Ile Tyr
        35                  40                  45

Ala Thr Ser Asn Leu Ala Ser Gly Val Pro Xaa Arg Phe Ser Gly Ser
50                  55                  60

Gly Ser Gly Thr Xaa Xaa Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                85                  90                  95

Phe Gly Xaa Gly Thr Lys Val Glu Xaa Lys
            100                 105

<210> SEQ ID NO 87
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (49)..(49)
<223> OTHER INFORMATION: Gly or Ala
<220> FEATURE:
<221> NAME/KEY: MOD_RES
<222> LOCATION: (79)..(79)
<223> OTHER INFORMATION: Asn or Ser
<220> FEATURE:
<221> NAME/KEY: MOD_RES
<222> LOCATION: (80)..(80)
```

```
<223> OTHER INFORMATION: Thr or Arg
<220> FEATURE:
<221> NAME/KEY: MOD_RES
<222> LOCATION: (81)..(81)
<223> OTHER INFORMATION: Leu or Val
<220> FEATURE:
<221> NAME/KEY: MOD_RES
<222> LOCATION: (86)..(86)
<223> OTHER INFORMATION: Asn or Ile
<220> FEATURE:
<221> NAME/KEY: MOD_RES
<222> LOCATION: (95)..(95)
<223> OTHER INFORMATION: Val, Ile or Leu
<220> FEATURE:
<221> NAME/KEY: MOD_RES
<222> LOCATION: (100)..(100)
<223> OTHER INFORMATION: Arg, Thr or Gly
<220> FEATURE:
<221> NAME/KEY: MOD_RES
<222> LOCATION: (113)..(113)
<223> OTHER INFORMATION: Leu or Thr
<220> FEATURE:
<221> NAME/KEY: MOD_RES
<222> LOCATION: (114)..(114)
<223> OTHER INFORMATION: Val or Leu
<220> FEATURE:
<221> NAME/KEY: MOD_RES
<222> LOCATION: (118)..(118)
<223> OTHER INFORMATION: Ser or Ala

<400> SEQUENCE: 87

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Trp Val
        35                  40                  45

Xaa Glu Ile Arg Ser Lys Ala Ser Asn His Ala Thr Tyr Tyr Ala Glu
    50                  55                  60

Ser Val Lys Gly Arg Phe Thr Ile Ser Arg Asp Asp Ser Lys Xaa Xaa
65                  70                  75                  80

Xaa Tyr Leu Gln Met Xaa Ser Leu Lys Thr Glu Asp Thr Ala Xaa Tyr
                85                  90                  95

Tyr Cys Thr Xaa Trp Arg Arg Phe Phe Asp Ser Trp Gly Gln Gly Thr
            100                 105                 110

Xaa Xaa Thr Val Ser Xaa
        115

<210> SEQ ID NO 88
<211> LENGTH: 118
<212> TYPE: PRT
<213> ORGANISM: Artificial Sequence
<220> FEATURE:
<223> OTHER INFORMATION: Description of Artificial Sequence: Synthetic
      VH_v1(A) polypeptide

<400> SEQUENCE: 88

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Trp Val
        35                  40                  45

Ala Glu Ile Arg Ser Lys Ala Ser Asn His Ala Thr Tyr Tyr Ala Glu
    50                  55                  60
```

```
Ser Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Arg Trp Arg Arg Phe Phe Asp Ser Trp Gly Gln Gly Thr
                100                 105                 110

Leu Val Thr Val Ser Ser
        115

<210> SEQ ID NO 89
<211> LENGTH: 118
<212> TYPE: PRT
<213> ORGANISM: Artificial Sequence
<220> FEATURE:
<223> OTHER INFORMATION: Description of Artificial Sequence: Synthetic
      VH_v1(A2) polypeptide

<400> SEQUENCE: 89

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
                20                  25                  30

Trp Met Asp Trp Val Arg Gln Ala Pro Gly Lys Gly Leu Glu Trp Val
            35                  40                  45

Gly Glu Ala Arg Ser Lys Ala Ser Asn His Ala Thr Tyr Tyr Ala Glu
    50                  55                  60

Ser Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Arg Trp Arg Arg Phe Phe Asp Ser Trp Gly Gln Gly Thr
                100                 105                 110

Leu Val Thr Val Ser Ser
        115

<210> SEQ ID NO 90
<211> LENGTH: 118
<212> TYPE: PRT
<213> ORGANISM: Artificial Sequence
<220> FEATURE:
<223> OTHER INFORMATION: Description of Artificial Sequence: Synthetic
      VH_v1(Q) polypeptide

<400> SEQUENCE: 90

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
                20                  25                  30

Trp Met Asp Trp Val Arg Gln Ala Pro Gly Lys Gly Leu Glu Trp Val
            35                  40                  45

Gly Glu Ile Arg Ser Gln Ala Ser Asn His Ala Thr Tyr Tyr Ala Glu
    50                  55                  60

Ser Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Arg Trp Arg Arg Phe Phe Asp Ser Trp Gly Gln Gly Thr
                100                 105                 110
```

Leu Val Thr Val Ser Ser
        115

<210> SEQ ID NO 91
<211> LENGTH: 118
<212> TYPE: PRT
<213> ORGANISM: Artificial Sequence
<220> FEATURE:
<223> OTHER INFORMATION: Description of Artificial Sequence: Synthetic
      VH_v1(R) polypeptide

<400> SEQUENCE: 91

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Trp Val
        35                  40                  45

Gly Glu Ile Arg Ser Arg Ala Ser Asn His Ala Thr Tyr Tyr Ala Glu
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Arg Trp Arg Arg Phe Phe Asp Ser Trp Gly Gln Gly Thr
            100                 105                 110

Leu Val Thr Val Ser Ser
        115

<210> SEQ ID NO 92
<211> LENGTH: 118
<212> TYPE: PRT
<213> ORGANISM: Artificial Sequence
<220> FEATURE:
<223> OTHER INFORMATION: Description of Artificial Sequence: Synthetic
      VH_v1(S) polypeptide

<400> SEQUENCE: 92

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Trp Val
        35                  40                  45

Ser Glu Ile Arg Ser Lys Ala Ser Asn His Ala Thr Tyr Tyr Ala Glu
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Arg Trp Arg Arg Phe Phe Asp Ser Trp Gly Gln Gly Thr
            100                 105                 110

Leu Val Thr Val Ser Ser
        115

<210> SEQ ID NO 93
<211> LENGTH: 106
<212> TYPE: PRT
<213> ORGANISM: Artificial Sequence
<220> FEATURE:

<223> OTHER INFORMATION: Description of Artificial Sequence: Synthetic
      VK_v1(AA) polypeptide

<400> SEQUENCE: 93

Asp Ile Gln Met Thr Gln Ser Pro Ser Ser Leu Ser Ala Ser Val Gly
1               5                   10                  15

Asp Arg Ala Thr Ile Thr Cys Arg Ala Ser Ser Val Ser Tyr Met
            20                  25                  30

His Trp Tyr Gln Gln Lys Pro Gly Lys Ala Pro Lys Pro Trp Ala Tyr
        35                  40                  45

Ala Thr Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 94
<211> LENGTH: 106
<212> TYPE: PRT
<213> ORGANISM: Artificial Sequence
<220> FEATURE:
<223> OTHER INFORMATION: Description of Artificial Sequence: Synthetic
      VK_v2(AA) polypeptide

<400> SEQUENCE: 94

Asp Ile Gln Leu Thr Gln Ser Pro Ser Ser Leu Ser Ala Ser Val Gly
1               5                   10                  15

Asp Arg Ala Thr Ile Thr Cys Arg Ala Ser Ser Val Ser Tyr Met
            20                  25                  30

His Trp Tyr Gln Gln Lys Pro Gly Lys Ala Pro Lys Pro Trp Ala Tyr
        35                  40                  45

Ala Thr Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 95
<211> LENGTH: 106
<212> TYPE: PRT
<213> ORGANISM: Artificial Sequence
<220> FEATURE:
<223> OTHER INFORMATION: Description of Artificial Sequence: Synthetic
      VK_v2(AA) polypeptide

<400> SEQUENCE: 95

Asp Ile Gln Leu Thr Gln Ser Pro Ser Ser Leu Ser Ala Ser Val Gly
1               5                   10                  15

Asp Arg Ala Thr Ile Thr Cys Arg Ala Ser Ser Val Ser Tyr Met
            20                  25                  30

His Trp Tyr Gln Gln Lys Pro Gly Lys Ala Pro Lys Pro Trp Ile Tyr
        35                  40                  45

Ala Ser Ser Asn Leu Ala Ser Gly Val Pro Ser Arg Phe Ser Gly Ser

```
                50                  55                  60
Gly Ser Gly Thr Asp Tyr Thr Leu Thr Ile Ser Ser Leu Gln Pro Glu
 65                  70                  75                  80

Asp Phe Ala Thr Tyr Tyr Cys Gln Gln Trp Ser Ser Asn Pro Leu Thr
                 85                  90                  95

Phe Gly Gly Gly Thr Lys Val Glu Ile Lys
                100                 105

<210> SEQ ID NO 96
<211> LENGTH: 106
<212> TYPE: PRT
<213> ORGANISM: Artificial Sequence
<220> FEATURE:
<223> OTHER INFORMATION: Description of Artificial Sequence: Synthetic
      VK_v2(SA) polypeptide

<400> SEQUENCE: 96

Asp Ile Gln Leu Thr Gln Ser Pro Ser Ser Leu Ser Ala Ser Val Gly
 1               5                  10                  15

Asp Arg Val Thr Ile Ser Cys Arg Ala Ser Ser Ser Val Ser Tyr Met
                 20                  25                  30

His Trp Tyr Gln Gln Lys Pro Gly Lys Ala Pro Lys Pro Trp Ala Tyr
                 35                  40                  45

Ala Thr Ser Asn Leu Ala Ser Gly Val Pro Ser Arg Phe Ser Gly Ser
 50                  55                  60

Gly Ser Gly Thr Asp Tyr Thr Leu Thr Ile Ser Ser Leu Gln Pro Glu
 65                  70                  75                  80

Asp Phe Ala Thr Tyr Tyr Cys Gln Gln Trp Ser Ser Asn Pro Leu Thr
                 85                  90                  95

Phe Gly Gly Gly Thr Lys Val Glu Ile Lys
                100                 105

<210> SEQ ID NO 97
<211> LENGTH: 106
<212> TYPE: PRT
<213> ORGANISM: Artificial Sequence
<220> FEATURE:
<223> OTHER INFORMATION: Description of Artificial Sequence: Synthetic
      VK_v2(SS) polypeptide

<400> SEQUENCE: 97

Asp Ile Gln Leu Thr Gln Ser Pro Ser Ser Leu Ser Ala Ser Val Gly
 1               5                  10                  15

Asp Arg Val Thr Ile Ser Cys Arg Ala Ser Ser Ser Val Ser Tyr Met
                 20                  25                  30

His Trp Tyr Gln Gln Lys Pro Gly Lys Ala Pro Lys Pro Trp Ile Tyr
                 35                  40                  45

Ala Ser Ser Asn Leu Ala Ser Gly Val Pro Ser Arg Phe Ser Gly Ser
 50                  55                  60

Gly Ser Gly Thr Asp Tyr Thr Leu Thr Ile Ser Ser Leu Gln Pro Glu
 65                  70                  75                  80

Asp Phe Ala Thr Tyr Tyr Cys Gln Gln Trp Ser Ser Asn Pro Leu Thr
                 85                  90                  95

Phe Gly Gly Gly Thr Lys Val Glu Ile Lys
                100                 105

<210> SEQ ID NO 98
<211> LENGTH: 330
<212> TYPE: PRT
```

<213> ORGANISM: Artificial Sequence
<220> FEATURE:
<223> OTHER INFORMATION: Description of Artificial Sequence: Synthetic
      IgG1(m3)_constant_region polypeptide

<400> SEQUENCE: 98

| | | | | | | | | | | | | | | |
|---|---|---|---|---|---|---|---|---|---|---|---|---|---|---|
| Ala | Ser | Thr | Lys | Gly | Pro | Ser | Val | Phe | Pro | Leu | Ala | Pro | Ser | Ser | Lys |
| 1 | | | | 5 | | | | | 10 | | | | | 15 | |
| Ser | Thr | Ser | Gly | Gly | Thr | Ala | Ala | Leu | Gly | Cys | Leu | Val | Lys | Asp | Tyr |
| | | | 20 | | | | | 25 | | | | | 30 | | |
| Phe | Pro | Glu | Pro | Val | Thr | Val | Ser | Trp | Asn | Ser | Gly | Ala | Leu | Thr | Ser |
| | | | 35 | | | | 40 | | | | | 45 | | | |
| Gly | Val | His | Thr | Phe | Pro | Ala | Val | Leu | Gln | Ser | Ser | Gly | Leu | Tyr | Ser |
| | 50 | | | | | 55 | | | | | 60 | | | | |
| Leu | Ser | Ser | Val | Val | Thr | Val | Pro | Ser | Ser | Ser | Leu | Gly | Thr | Gln | Thr |
| 65 | | | | | 70 | | | | | 75 | | | | | 80 |
| Tyr | Ile | Cys | Asn | Val | Asn | His | Lys | Pro | Ser | Asn | Thr | Lys | Val | Asp | Lys |
| | | | | 85 | | | | | 90 | | | | | 95 | |
| Arg | Val | Glu | Pro | Lys | Ser | Cys | Asp | Lys | Thr | His | Thr | Cys | Pro | Pro | Cys |
| | | | 100 | | | | | 105 | | | | | 110 | | |
| Pro | Ala | Pro | Glu | Leu | Leu | Gly | Gly | Pro | Ser | Val | Phe | Leu | Phe | Pro | Pro |
| | | | 115 | | | | | 120 | | | | | 125 | | |
| Lys | Pro | Lys | Asp | Thr | Leu | Met | Ile | Ser | Arg | Thr | Pro | Glu | Val | Thr | Cys |
| | 130 | | | | | 135 | | | | | 140 | | | | |
| Val | Val | Val | Asp | Val | Ser | His | Glu | Asp | Pro | Glu | Val | Lys | Phe | Asn | Trp |
| 145 | | | | | 150 | | | | | 155 | | | | | 160 |
| Tyr | Val | Asp | Gly | Val | Glu | Val | His | Asn | Ala | Lys | Thr | Lys | Pro | Arg | Glu |
| | | | | 165 | | | | | 170 | | | | | 175 | |
| Glu | Gln | Tyr | Asn | Ser | Thr | Tyr | Arg | Val | Val | Ser | Val | Leu | Thr | Val | Leu |
| | | | 180 | | | | | 185 | | | | | 190 | | |
| His | Gln | Asp | Trp | Leu | Asn | Gly | Lys | Glu | Tyr | Lys | Cys | Lys | Val | Ser | Asn |
| | | | 195 | | | | | 200 | | | | | 205 | | |
| Lys | Ala | Leu | Pro | Ala | Pro | Ile | Glu | Lys | Thr | Ile | Ser | Lys | Ala | Lys | Gly |
| | 210 | | | | | 215 | | | | | 220 | | | | |
| Gln | Pro | Arg | Glu | Pro | Gln | Val | Tyr | Thr | Leu | Pro | Pro | Ser | Arg | Glu | Glu |
| 225 | | | | | 230 | | | | | 235 | | | | | 240 |
| Met | Thr | Lys | Asn | Gln | Val | Ser | Leu | Thr | Cys | Leu | Val | Lys | Gly | Phe | Tyr |
| | | | | 245 | | | | | 250 | | | | | 255 | |
| Pro | Ser | Asp | Ile | Ala | Val | Glu | Trp | Glu | Ser | Asn | Gly | Gln | Pro | Glu | Asn |
| | | | 260 | | | | | 265 | | | | | 270 | | |
| Asn | Tyr | Lys | Thr | Thr | Pro | Pro | Val | Leu | Asp | Ser | Asp | Gly | Ser | Phe | Phe |
| | | | 275 | | | | | 280 | | | | | 285 | | |
| Leu | Tyr | Ser | Lys | Leu | Thr | Val | Asp | Lys | Ser | Arg | Trp | Gln | Gln | Gly | Asn |
| | 290 | | | | | 295 | | | | | 300 | | | | |
| Val | Phe | Ser | Cys | Ser | Val | Met | His | Glu | Ala | Leu | His | Asn | His | Tyr | Thr |
| 305 | | | | | 310 | | | | | 315 | | | | | 320 |
| Gln | Lys | Ser | Leu | Ser | Leu | Ser | Pro | Gly | Lys | | | | | | |
| | | | | 325 | | | | | 330 | | | | | | |

<210> SEQ ID NO 99
<211> LENGTH: 107
<212> TYPE: PRT
<213> ORGANISM: Artificial Sequence
<220> FEATURE:
<223> OTHER INFORMATION: Description of Artificial Sequence: Synthetic
      CK_constant_region polypeptide -continued

<400> SEQUENCE: 99

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 100
<211> LENGTH: 106
<212> TYPE: PRT
<213> ORGANISM: Artificial Sequence
<220> FEATURE:
<223> OTHER INFORMATION: Description of Artificial Sequence: Synthetic
      97 with L4M polypeptide

<400> SEQUENCE: 100

Asp Ile Gln Met Thr Gln Ser Pro Ser Ser Leu Ser Ala Ser Val Gly
1               5                   10                  15

Asp Arg Val Thr Ile Ser Cys Arg Ala Ser Ser Ser Val Ser Tyr Met
            20                  25                  30

His Trp Tyr Gln Gln Lys Pro Gly Lys Ala Pro Lys Pro Trp Ile Tyr
        35                  40                  45

Ala Ser Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 101
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Asp Ile Gln Leu Thr Gln Ser Pro Ser Ser Leu Ser Pro Trp Ile Tyr
1               5                   10                  15

Ala Thr Ser Asn Leu Ala Ser Tyr Thr Leu Thr Ile Ser Ser Leu Gln
            20                  25                  30

<210> SEQ ID NO 102
<211> LENGTH: 106
<212> TYPE: PRT
<213> ORGANISM: Artificial Sequence
<220> FEATURE:
<223> OTHER INFORMATION: Description of Artificial Sequence: Synthetic 95 with L4M polypeptide

<400> SEQUENCE: 102

Asp Ile Gln Met Thr Gln Ser Pro Ser Ser Leu Ser Ala Ser Val Gly
1               5                   10                  15

Asp Arg Ala Thr Ile Thr Cys Arg Ala Ser Ser Val Ser Tyr Met
            20                  25                  30

His Trp Tyr Gln Gln Lys Pro Gly Lys Ala Pro Lys Pro Trp Ile Tyr
        35                  40                  45

Ala Ser Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 103
<211> LENGTH: 106
<212> TYPE: PRT
<213> ORGANISM: Artificial Sequence
<220> FEATURE:
<223> OTHER INFORMATION: Description of Artificial Sequence: Synthetic
      96 with L4M polypeptide

<400> SEQUENCE: 103

Asp Ile Gln Met Thr Gln Ser Pro Ser Ser Leu Ser Ala Ser Val Gly
1               5                   10                  15

Asp Arg Val Thr Ile Ser Cys Arg Ala Ser Ser Val Ser Tyr Met
            20                  25                  30

His Trp Tyr Gln Gln Lys Pro Gly Lys Ala Pro Lys Pro Trp Ala Tyr
        35                  40                  45

Ala Thr Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 104
<211> LENGTH: 12
<212> TYPE: PRT
<213> ORGANISM: Influenza A virus

<400> SEQUENCE: 104

Pro Lys Tyr Val Lys Gln Asn Thr Leu Lys Leu Ala
1               5                   10

<210> SEQ ID NO 105
<211> LENGTH: 15
<212> TYPE: PRT
<213> ORGANISM: Unknown
<220> FEATURE:
<223> OTHER INFORMATION: Description of Unknown: Chlamydia
      HSP 60 peptide

<400> SEQUENCE: 105

Lys Val Val Asp Gln Ile Lys Lys Ile Ser Lys Pro Val Gln His
1               5                   10                  15

<210> SEQ ID NO 106
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Trp Val Gly Glu Ile Arg Ser Lys Ala Ser Asn His Ala Thr
1               5                   10

<210> SEQ ID NO 107
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Trp Val Gly Glu Ile Arg Ser Gln Ala Ser Asn His Ala Thr
1               5                   10

<210> SEQ ID NO 108
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Trp Val Gly Glu Ile Arg Ser Arg Ala Ser Asn His Ala Thr
1               5                   10

<210> SEQ ID NO 109
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Trp Val Gly Glu Ala Arg Ser Lys Ala Ser Asn His Ala Thr
1               5                   10

<210> SEQ ID NO 110
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Asp Arg Val Thr Ile Thr Cys Arg Ala Ser Ser Ser Val
1               5                   10

<210> SEQ ID NO 111
<211> LENGTH: 13
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 111

Asp Arg Val Thr Ile Ser Cys Arg Ala Ser Ser Ser Val
1               5                   10

<210> SEQ ID NO 112
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Asp Arg Ala Thr Ile Thr Cys Arg Ala Ser Ser Ser Val
1               5                   10

<210> SEQ ID NO 113
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Pro Trp Ile Tyr Ala Thr Ser Asn Leu Ala Ser Gly Val
1               5                   10

<210> SEQ ID NO 114
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Pro Trp Ile Tyr Ala Ser Ser Asn Leu Ala Ser Gly Val
1               5                   10

<210> SEQ ID NO 115
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Pro Trp Ala Tyr Ala Thr Ser Asn Leu Ala Ser Gly Val
1               5                   10

<210> SEQ ID NO 116
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (49)..(49)
<223> OTHER INFORMATION: Gly, Ala or Ser
<220> FEATURE:
<221> NAME/KEY: MOD_RES
<222> LOCATION: (51)..(51)

<223> OTHER INFORMATION: Ala or Ile
<220> FEATURE:
<221> NAME/KEY: MOD_RES
<222> LOCATION: (54)..(54)
<223> OTHER INFORMATION: Lys, Gln or Arg
<220> FEATURE:
<221> NAME/KEY: MOD_RES
<222> LOCATION: (81)..(81)
<223> OTHER INFORMATION: Leu or Val

<400> SEQUENCE: 116

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Trp Val
        35                  40                  45

Xaa Glu Xaa Arg Ser Xaa Ala Ser Asn His Ala Thr Tyr Tyr Ala Glu
    50                  55                  60

Ser Val Lys Gly Arg Phe Thr Ile Ser Arg Asp Asp Ser Lys Asn Thr
65                  70                  75                  80

Xaa Tyr Leu Gln Met Asn Ser Leu Lys Thr Glu Asp Thr Ala Val Tyr
                85                  90                  95

Tyr Cys Thr Arg Trp Arg Arg Phe Phe Asp Ser Trp Gly Gln Gly Thr
            100                 105                 110

Leu Val Thr Val Ser Ser
            115

<210> SEQ ID NO 117
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (19)..(19)
<223> OTHER INFORMATION: Ala or Val
<220> FEATURE:
<221> NAME/KEY: MOD_RES
<222> LOCATION: (22)..(22)
<223> OTHER INFORMATION: Thr or Ser
<220> FEATURE:
<221> NAME/KEY: MOD_RES
<222> LOCATION: (47)..(47)
<223> OTHER INFORMATION: Ala or Ile
<220> FEATURE:
<221> NAME/KEY: MOD_RES
<222> LOCATION: (50)..(50)
<223> OTHER INFORMATION: Thr or Ser

<400> SEQUENCE: 117

Asp Ile Gln Met Thr Gln Ser Pro Ser Ser Leu Ser Ala Ser Val Gly
1               5                   10                  15

Asp Arg Xaa Thr Ile Xaa Cys Arg Ala Ser Ser Ser Val Ser Tyr Met
            20                  25                  30

His Trp Tyr Gln Gln Lys Pro Gly Lys Ala Pro Lys Pro Trp Xaa Tyr
        35                  40                  45

Ala Xaa Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr

-continued

```
                    85                  90                  95
Phe Gly Gly Gly Thr Lys Val Glu Ile Lys
                100                 105

<210> SEQ ID NO 118
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Trp Val Ala Glu Ile Arg Ser Lys Ala Ser Asn Val Tyr Leu Gln Met
1               5                   10                  15

Asn Ser Leu Lys Val Tyr Tyr Cys Thr Arg Trp Arg Arg Phe Phe Asp
            20                  25                  30

Ser Trp
```

What is claimed is:

1. A method of treating an ocular condition that is choroidal neovascularization (CNV), diabetic nephropathy, non-diabetic retinopathy, sub-retinal neovascularization, proliferative vitreoretinopathy, or a neovascular glaucoma in a subject in need thereof, comprising administering to the subject a composition comprising an antibody or antigen-binding fragment thereof, that binds endoglin, wherein the antibody or antigen-binding fragment thereof comprises a heavy chain variable region having an amino acid sequence set forth as SEQ ID NO: 89 and a light chain variable region having an amino acid sequence set forth as SEQ ID NO: 93.

2. The method of claim 1, wherein the ocular condition is choroidal neovascularization.

3. The method of claim 1, wherein the ocular condition is diabetic nephropathy.

4. The method of claim 1, wherein the ocular condition is non-diabetic retinopathy.

5. The method of claim 1, wherein the ocular condition is sub-retinal neovascularization.

6. The method of claim 1, wherein the ocular condition is proliferative vitreoretinopathy.

7. The method of claim 1, wherein the ocular condition is a neovascular glaucoma.

8. A method of treating choroidal neovascularization (CNV) in a subject in need thereof, comprising administering to the subject a composition comprising an antibody or antigen-binding fragment thereof, that binds endoglin, wherein the antibody or antigen-binding fragment thereof comprises a heavy chain variable region having the amino acid sequence set forth as SEQ ID NO: 89 and a light chain variable region having the amino acid sequence set forth as SEQ ID NO: 93, wherein: said heavy chain variable region further comprises one or more modifications selected from the group consisting of a substitution of glycine (G) by alanine (A) or serine (S) at position 49; a substitution of alanine (A) by isoleucine (I) at position 51; a substitution of lysine (K) by arginine (R) or asparagine (Q) at position 54, a substitution of leucine (L) by valine (V) at position 81 utilizing the Kabat numbering system; and the light chain variable region further comprises one or more modifications selected from the group consisting of a substitution of methionine (M) by leucine (L) at position 4; a substitution of alanine (A) by valine (V) at position 19; a substitution of threonine (T) by serine (S) at position 22; a substitution of alanine (A) by isoleucine (I) at position 48; and a substitution of threonine (T) by serine (S) at position 51 utilizing the Kabat numbering system.

9. The method of claim 8, comprising a heavy chain variable region having an amino acid sequence set forth as SEQ ID NO: 88, 89, 90, 91 or 92; and a light chain variable region having an amino acid sequence set forth as SEQ ID NO: 93, 94, 95, 96, 97, 100, 102, or 103.

10. The method of claim 8, wherein the ocular condition is choroidal neovascularization.

11. The method of claim 8, wherein the ocular condition is diabetic nephropathy.

12. The method of claim 8, wherein the ocular condition is non-diabetic retinopathy.

13. The method of claim 8, wherein the ocular condition is sub-retinal neovascularization.

14. The method of claim 8, wherein the ocular condition is proliferative vitreoretinopathy.

15. The method of claim 8, wherein the ocular condition is a neovascular glaucoma.

16. A method of treating a chronic inflammatory disease in a subject in need thereof, comprising administering to the subject a composition comprising an antibody or antigen-binding fragment thereof, that binds endoglin, wherein the antibody or antigen-binding fragment thereof comprises a heavy chain variable region having an amino acid sequence set forth as SEQ ID NO: 89 and a light chain variable region having an amino acid sequence set forth as SEQ ID NO: 93.

17. The method of claim 16, wherein the chronic inflammatory disease is an inflammatory bowel disease (IBD).

18. The method of claim 17, wherein the inflammatory bowel disease is Crohn's disease.

19. The method of claim 17, wherein the inflammatory bowel disease is ulcerative colitis.

20. A method of treating a chronic inflammatory disease in a subject in need thereof, comprising administering to the subject a composition comprising an antibody or antigen-binding fragment thereof, that binds endoglin, wherein the antibody or antigen-binding fragment thereof comprises a heavy chain variable region having the amino acid sequence set forth as SEQ ID NO: 89 and a light chain variable region having the amino acid sequence set forth as SEQ ID NO: 93, wherein: said heavy chain variable region further comprises one or more modifications selected from the group consisting of a substitution of glycine (G) by alanine (A) or serine (S) at position 49; a substitution of alanine (A) by isoleucine (I) at position 51; a substitution of lysine (K) by arginine (R) or asparagine (Q) at position 54, a substitution of leucine (L) by valine (V) at position 81 utilizing the Kabat numbering system; and the light chain variable region further comprises one or more modifications selected from the group consisting of a substitution of methionine (M) by leucine (L) at position 4; a substitution of alanine (A) by valine (V) at position 19; a substitution of threonine (T) by serine (S) at position 22; a substitution of alanine (A) by isoleucine (I) at position 48; and a substitution of threonine (T) by serine (S) at position 51 utilizing the Kabat numbering system.

21. The method of claim 20, comprising a heavy chain variable region having an amino acid sequence set forth as SEQ ID NO: 88, 89, 90, 91 or 92; and a light chain variable region having an amino acid sequence set forth as SEQ ID NO: 93, 94, 95, 96, 97, 100, 102, or 103.

22. The method of claim 20, wherein the chronic inflammatory disease is an inflammatory bowel disease (IBD).

23. The method of claim 22, wherein the inflammatory bowel disease is Crohn's disease.

24. The method of claim 22, wherein the inflammatory bowel disease is ulcerative colitis.

* * * * *

UNITED STATES PATENT AND TRADEMARK OFFICE
CERTIFICATE OF CORRECTION

PATENT NO. : 9,518,122 B2
APPLICATION NO. : 14/838006
DATED : December 13, 2016
INVENTOR(S) : Charles Theuer et al.

It is certified that error appears in the above-identified patent and that said Letters Patent is hereby corrected as shown below:

Column 213, Line 63, Claim 8, please delete "utilizing the Kabat numbering system"

Column 214, Line 25-26, Claim 8, please delete "utilizing the Kabat numbering system"

Column 215, Line 3-4, Claim 20, please delete "utilizing the Kabat numbering system"

Column 215, Line 11-12, Claim 20, please delete "utilizing the Kabat numbering system"

Signed and Sealed this
Twenty-ninth Day of August, 2017

Joseph Matal
*Performing the Functions and Duties of the*
*Under Secretary of Commerce for Intellectual Property and*
*Director of the United States Patent and Trademark Office*